(12) United States Patent
Poulos et al.

(10) Patent No.: US 11,293,038 B2
(45) Date of Patent: Apr. 5, 2022

(54) PRODUCTION OF CANNABINOIDS IN YEAST

(71) Applicant: Librede Inc., Sherman Oaks, CA (US)

(72) Inventors: Jason L. Poulos, Los Angeles, CA (US); Anthony N. Farina, Pasadena, CA (US)

(*) Notice: Subject to any disclaimer, the term of this patent is extended or adjusted under 35 U.S.C. 154(b) by 0 days.

(21) Appl. No.: 16/679,637

(22) Filed: Nov. 11, 2019

(65) Prior Publication Data

US 2020/0071732 A1    Mar. 5, 2020

Related U.S. Application Data

(63) Continuation-in-part of application No. 16/539,436, filed on Aug. 13, 2019, now Pat. No. 10,954,534, which is a continuation-in-part of application No. 16/122,702, filed on Sep. 5, 2018, now Pat. No. 10,392,635, which is a continuation of application No. 15/815,651, filed on Nov. 16, 2017, now Pat. No. 10,093,949, which is a continuation of application No. 14/795,816, filed on Jul. 9, 2015, now Pat. No. 9,822,384.

(60) Provisional application No. 62/024,099, filed on Jul. 14, 2014.

(51) Int. Cl.
| | |
|---|---|
| *C12P 7/42* | (2006.01) |
| *C12N 9/00* | (2006.01) |
| *C12N 9/88* | (2006.01) |
| *C12N 9/10* | (2006.01) |
| *C12N 1/20* | (2006.01) |
| *C12N 15/00* | (2006.01) |
| *C12N 1/14* | (2006.01) |
| *C12N 15/81* | (2006.01) |

(52) U.S. Cl.
CPC .............. *C12P 7/42* (2013.01); *C12N 9/1029* (2013.01); *C12N 9/1085* (2013.01); *C12N 9/88* (2013.01); *C12N 9/93* (2013.01); *C12N 15/81* (2013.01); *C12Y 203/01206* (2015.07); *C12Y 205/01* (2013.01); *C12Y 504/99* (2013.01); *C12Y 602/01* (2013.01)

(58) Field of Classification Search
CPC ...... C12N 9/1085; C12N 9/88; C12N 9/1029; C12N 15/81; C12P 7/42
See application file for complete search history.

*Primary Examiner* — Yong D Pak
(74) *Attorney, Agent, or Firm* — Carr & Ferrell LLP

(57) ABSTRACT

Exemplary embodiments provided herein include genetically engineering microorganisms, such as yeast or bacteria, to produce cannabinoids by inserting genes that produce the appropriate enzymes for the metabolic production of a desired compound.

1 Claim, 8 Drawing Sheets

Specification includes a Sequence Listing.

Librede's Pathway from Glucose to CBD

SEQUENCE LISTING

```
<160> NUMBER OF SEQ ID NOS: 124

<210> SEQ ID NO 1
<211> LENGTH: 7969
<212> TYPE: DNA
<213> ORGANISM: Artificial Sequence
<220> FEATURE:
<223> OTHER INFORMATION: Codon Optimized

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcgggctgg  cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctctag tacactctat atttttttat gcctcggtaa tgattttcat     360
```

```
tttttttttt ccccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggttttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg cgcgtggag     840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcattttc ttgaaagctt tgcagaggct agcagaatta    1020
ccctccacgt tgattgtctg cgaggcaaga atgatcatca ccgtagtgag agtgcgttca    1080
aggctcttgc ggttgccata agagaagcca cctcgcccaa tggtaccaac gatgttccct    1140
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320
cctttttcct ttttgctttt tctttttttt tctcttgaac tcgacggatc tatgcggtgt    1380
gaaataccgc acagatgcgt aaggagaaaa taccgcatca ggaaattgta acgttaata    1440
ttttgttaaa attcgcgtta aattttttgtt aaatcagctc atttttttaac caataggccg    1500
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt ttttggggt     1680
cgaggtgccg taaagcacta aatcggaacc ctaaagggag ccccgatttt agagcttgac    1740
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa aggggatgt gctgcaaggc    1980
gattaagttg ggtaacgcca gggttttccc agtcacgacg ttgtaaaacg acggccagtg    2040
agcgcgcgta atacgactca ctataggcg aattgggtac cggccgcaaa ttaaagcctt    2100
cgagcgtccc aaaaccttct caagcaaggt tttcagtata atgttacatg cgtacacgcg    2160
tctgtacaga aaaaaagaa aaatttgaaa tataaataac gttcttaata ctaacataac    2220
tataaaaaaa taaatagggga cctagacttc aggttgtcta actccttcct tttcggttag    2280
agcggatgtg gggggagggc gtgaatgtaa gcgtgacata actaattaca tgactcgagg    2340
tcgactcatt cgaaatgact gaattgttgt ctcaaaactc ttctcatgat cttgtttgtt    2400
gcagttctag gtaaggatga caatgggaca actctagtaa ctttgaataa tgggttcaat    2460
ttcttttgca aacccaagtt aaaggataat ctcaattggt tcaaatcaat ggttgtgtcg    2520
tttgaatcct tcaatacgaa aaatatgacc aattgttctg gaccaccacc caaaggtgga    2580
acaccaatag cagtggtttc aaaaactctg tcatctactt cattacagac tctttcgatt    2640
tcgatagaac taatttgat accaccgatg ttcatagtgt catcggctct accgtgtgca    2700
tggtagtaac cgttagaggt caattcgaaa atgtcaccat gtcttctcaa tacttcacca    2760
```

```
ttcaaggttg gcatacccct gaaatagaca tcgtgatgat taccgtttaa caatgttttt    2820
gaggcaccaa acataacagg acctaatgcc aattcaccga tacctggctt attttaggc     2880 attgggtaac cgttcttatc taatatgtac aaggtgcaac ccatacattg ggatgaaaaa    2940
gaacttaaag attgagcttg caaaaatgaa ccagcagaaa aagcaccacc gatttctgta    3000
ccaccacaca tttctataac tggcttgtag ttagctctac ccattaacca caaatattcg    3060
tctacattag aggcttcacc ggatgaagaa aagcatctta tggtggacca atcgtaacct    3120
gaaacacaat ttgtggattt ccatgatctt acaatagatg gtacgacacc caacattgtg    3180
acctttgcat cttgaacaaa tttagcgaaa ccagagacta aaggactacc gttgtacaag    3240
gcaatagatg caccatttaa caaactagca taaaccaacc aaggacccat catccaaccc    3300
aaattagttg gccatactat aacgtcacct tttctaatat ccaaatgaga ccaaccatca    3360
gcagcagcct tcaatggggt ggcttgtgtc caaggaattg cttttggttc acctgtagta    3420
ccactggaga ataagatgtt agtataagca tcaacaggtt gttctctggc agtaaactcg    3480 cagttttaa actccttggc tctttctaaa aagtaatccc aagatatgtc accatctctc     3540
aattctgcac caatgttaga accactacaa gggataacta ttgccattgg ggatttagct    3600
tcaactactc ttgaatacaa tggtattctc tttttacctc tgatgatgtg atcttgtgtg    3660
aaaattgcct tagctttgga taatctcaat ctagttgaga tttcaggggc ggaaaatgaa    3720
tctgctatag agacaactac gtaaccagcc aatactatgg ccaaatatat aacaacagca    3780
tcaacatgca ttggcatatc gatggctatt gcacaacctt tttctaaacc catttcttcc    3840
aatgcataac caaccaacca aactctcttt ctcaattgat ctaatgtcaa cttattcaaa    3900
ggcaagtcat cgttaccctc gtctctccaa acgatcatag tatcgttcaa tttcttattg    3960
gagtttacgt tcaagcaatt tttagctgag ttcaagtaac caccaggtaa ccattcagaa    4020
ccacctgggt tgttgatgtc atctcttctc aagatacatt ctgggtcctt agagaaacta    4080
attttcattt catccatcaa tactgttctc caatagactt cagggtttct aacagaaaat    4140
tcttggaagt gagaaaaaga agaaattgga tctttgtact ttacacccaa aaattcttta    4200
cctctctttt ccaacaaagc acccaaatta gttgacttga cttttcagg gtctggaatc     4260 caagcaggtg gggctggacc gaaatccttg tagcaaccat aaaacaacat ttggtgtaag    4320
gagaaaggca atctggtga caagatatgg ttagcgatgt tgatccaagt ttgaggggtt     4380
gcagcaccat aattacaaac gatttctgcc aatctaccat gtaatgtttc tgctacttct    4440
gaggtgatac ccaatgcgat gaaatctgag gcaacgactg aatccaagga cttatagttt    4500
ttacccatac tagttctaga tccgtcgaaa ctaagttctt ggtgttttaa aactaaaaaa    4560
aagactaact ataaagtag aatttaagaa gtttaagaaa tagatttaca gaattacaat     4620
caatacctac cgtctttata tacttattag tcaagtaggg gaataatttc agggaactgg    4680
tttaaacctt tttttcagc ttttttccaaa tcagagagag cagaaggtaa tagaaggtgt    4740
aagaaaatga gatagataca tgcgtgggtc aattgccttg tgtcatcatt tactccaggc    4800
aggttgcatc actccattga ggttgtgccc gttttttgcc tgtttgtgcc ctgttctctg    4860
tagttgcgct aagagaatgg acctatgaac tgatggttgg tgaagaaaac aatatttgg     4920 tgctgggatt cttttttttt ctggatgcca gcttaaaaag cgggctccat tatatttagt    4980
ggatgccagg aataaacctg ttcacccaag caccatcagt gttatatatt ctgtgtaacc    5040 cgcccctat tttggcatgt acgggttaca gcagaattaa aaggctaatt ttttgactaa     5100
```

```
ataaagttag gaaaatcact actattaatt atttacgtat tctttgaaat ggcagtattg    5160
ataatgataa actcgagagc tccagctttt gttcccttta gtgagggtta attgcgcgct    5220
tggcgtaatc atggtcatag ctgtttcctg tgtgaaattg ttatccgctc acaattccac    5280
acaacatagg agccggaagc ataaagtgta aagcctgggg tgcctaatga gtgaggtaac    5340
tcacattaat tgcgttgcgc tcactgcccg ctttccagtc gggaaacctg tcgtgccagc    5400
tgcattaatg aatcggccaa cgcgcgggga gaggcggttt gcgtattggg cgctcttccg    5460
cttcctcgct cactgactcg ctgcgctcgg tcgttcggct gcggcgagcg gtatcagctc    5520
actcaaaggc ggtaatacgg ttatccacag aatcagggga taacgcagga aagaacatgt    5580
gagcaaaagg ccagcaaaag gccaggaacc gtaaaaaggc cgcgttgctg gcgttttttcc    5640 ataggctccg ccccccctgac gagcatcaca aaaatcgacg ctcaagtcag aggtggcgaa    5700
acccgacagg actataaaga taccaggcgt ttccccctgg aagctccctc gtgcgctctc    5760
ctgttccgac cctgccgctt accggatacc tgtccgcctt tctcccttcg ggaagcgtgg    5820
cgctttctca tagctcacgc tgtaggtatc tcagttcggt gtaggtcgtt cgctccaagc    5880
tgggctgtgt gcacgaaccc cccgttcagc ccgaccgctg cgccttatcc ggtaactatc    5940
gtcttgagtc caacccggta agacacgact tatcgccact ggcagcagcc actggtaaca    6000
ggattagcag agcgaggtat gtaggcggtg ctacagagtt cttgaagtgg tggcctaact    6060
acggctacac tagaaggaca gtatttggta tctgcgctct gctgaagcca gttaccttcg    6120
gaaaaagagt tggtagctct tgatccggca acaaaccac cgctggtagc ggtggttttt    6180
ttgtttgcaa gcagcagatt acgcgcagaa aaaaaggatc tcaagaagat cctttgatct    6240
tttctacggg gtctgacgct cagtggaacg aaaactcacg ttaagggatt ttggtcatga    6300
gattatcaaa aaggatcttc acctagatcc ttttaaatta aaaatgaagt tttaaatcaa    6360
tctaaagtat atatgagtaa acttggtctg acagttacca atgcttaatc agtgaggcac    6420
ctatctcagc gatctgtcta tttcgttcat ccatagttgc ctgactcccc gtcgtgtaga    6480
taactacgat acgggagggc ttaccatctg gccccagtgc tgcaatgata ccgcgagacc    6540
cacgctcacc ggctccagat ttatcagcaa taaaccagcc agccggaagg gccgagcgca    6600
gaagtggtcc tgcaacttta tccgcctcca tccagtctat taattgttgc cgggaagcta    6660
gagtaagtag ttcgccagtt aatagtttgc gcaacgttgt tgccattgct acaggcatcg    6720
tggtgtcacg ctcgtcgttt ggtatggctt cattcagctc cggttcccaa cgatcaaggc    6780
gagttacatg atcccccatg ttgtgcaaaa aagcggttag ctccttcggt cctccgatcg    6840
ttgtcagaag taagttggcc gcagtgttat cactcatggt tatggcagca ctgcataatt    6900
ctcttactgt catgccatcc gtaagatgct tttctgtgac tggtgagtac tcaaccaagt    6960
cattctgaga atagtgtatg cggcgaccga gttgctcttg cccggcgtca atacgggata    7020
ataccgcgcc acatagcaga actttaaaag tgctcatcat tggaaaacgt tcttcggggc    7080
gaaaactctc aaggatctta ccgctgttga gatccagttc gatgtaaccc actcgtgcac    7140
ccaactgatc ttcagcatct tttactttca ccagcgtttc tgggtgagca aaaacaggaa    7200
ggcaaaatgc cgcaaaaaag gaataagggc gacacggaa atgttgaata ctcatactct    7260
tcctttttca atattattga agcatttatc agggttattg tctcatgagc ggatacatat    7320
ttgaatgtat ttagaaaaat aaacaaatag gggttccgcg cacatttccc cgaaaagtgc    7380 cacctggtc cttttcatca cgtgctataa aaataattat aatttaaatt ttttaatata    7440
aatatataaa ttaaaaatag aaagtaaaaa aagaaattaa agaaaaaata gttttgtttt    7500
```

```
tccgaagatg taaaagactc taggggatc gccaacaaat actaccttt atcttgctct    7560 tcctgctctc aggtattaat gccgaattgt ttcatcttgt ctgtgtagaa gaccacacac   7620
gaaaatcctg tgattttaca ttttacttat cgttaatcga atgtatatct atttaatctg   7680
cttttcttgt ctaataaata tatatgtaaa gtacgctttt tgttgaaatt ttttaaacct   7740
ttgtttattt ttttttcttc attccgtaac tcttctacct tctttattta ctttctaaaa   7800
tccaaataca aaacataaaa ataaataaac acagagtaaa ttcccaaatt attccatcat   7860
taaaagatac gaggcgcgtg taagttacag gcaagcgatc cgtcctaaga aaccattatt   7920
atcatgacat taacctataa aaataggcgt atcacgaggc cctttcgtc              7969

<210> SEQ ID NO 2
<211> LENGTH: 10004
<212> TYPE: DNA
<213> ORGANISM: Artificial Sequence
<220> FEATURE:
<223> OTHER INFORMATION: Codon Optimized

<400> SEQUENCE: 2
tcgcgcgttt cggtgatgac ggtgaaaacc tctgacacat gcagctcccg gagacggtca     60
cagcttgtct gtaagcggat gccgggagca gacaagcccg tcagggcgcg tcagcgcgtg    120
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctttca attcatcatt tttttttat tctttttttt gatttcggtt    360
tctttgaaat tttttgatt cggtaatctc cgaacagaag gaagaacgaa ggaaggagca    420
cagacttaga ttggtatata tacgcatatg tagtgttgaa gaaacatgaa attgcccagt    480
attcttaacc caactgcaca gaacaaaaac ctgcaggaaa cgaagataaa tcatgtcgaa    540
agctacatat aaggaacgtg ctgctactca tcctagtcct gttgctgcca agctatttaa    600
tatcatgcac gaaaagcaaa caaacttgtg tgcttcattg gatgttcgta ccaccaagga    660
attactggag ttagttgaag cattaggtcc caaaatttgt ttactaaaaa cacatgtgga    720
tatcttgact gattttttcca tggagggcac agttaagccg ctaaaggcat atccgccaa    780 gtacaatttt ttactcttcg aagacagaaa atttgctgac attggtaata cagtcaaatt    840
gcagtactct gcgggtgtat acagaatagc agaatgggca gacattacga atgcacacgg    900
tgtggtgggc ccaggtattg ttagcggttt gaagcaggcg gcagaagaag taacaaagga    960
acctagaggc cttttgatgt tagcagaatt gtcatgcaag ggctccctat ctactggaga   1020
atatactaag ggtactgttg acattgcgaa gagcgacaaa gattttgtta tcggctttat   1080
tgctcaaaga gacatgggtg gaagagatga aggttacgat tggttgatta tgacacccgg   1140
tgtgggttta gatgacaagg gagacgcatt gggtcaacag tatagaaccg tggatgatgt   1200
ggtctctaca ggatctgaca ttattattgt tggaagagga ctatttgcaa agggaaggga   1260
tgctaaggta gagggtgaac gttacagaaa agcaggctgg gaagcatatt tgagaagatg   1320
cggccagcaa aactaatgac accgattatt taaagctgca gcatacgata tatatacatg   1380
tgtatatatg tataccctatg aatgtcagta agtatgtata cgaacagtat gatactgaag   1440
atgacaaggt aatgcatcat tctatacgtg tcattctgaa cgaggcgcgc tttccttttt   1500
tctttttgct ttttctttt ttttctcttg aactcgacgg atctatgcgg tgtgaaatac   1560
```

```
cgcacagatg cgtaaggaga aaataccgca tcaggaaatt gtaaacgtta atattttgtt    1620
aaaattcgcg ttaaattttt gttaaatcag ctcattttt  aaccaatagg ccgaaatcgg    1680
caaaatccct tataaatcaa agaatagac  cgagatag gg ttgagtgttg ttccagtttg    1740
gaacaagagt ccactattaa agaacgtgga ctccaacgtc aaagggcgaa aaaccgtcta    1800
tcagggcgat ggcccactac gtgaaccatc accctaatca agttttttgg ggtcgaggtg    1860
ccgtaaagca ctaaatcgga accctaaagg gagcccccga tttagagctt gacggggaaa    1920
gccggcgaac gtggcgagaa aggaagggaa gaaagcgaaa ggagcgggcg ctagggcgct    1980
ggcaagtgta gcggtcacgc tgcgcgtaac caccacaccc gccgcgctta atgcgccgct    2040
acagggcgcg tcgcgccatt cgccattcag gctgcgcaac tgttgggaag ggcgatcggt    2100
gcgggcctct tcgctattac gccagctggc gaaaggggga tgtgctgcaa ggcgattaag    2160
ttgggtaacg ccagggtttt cccagtcacg acgttgtaaa acgacggcca gtgagcgcgc    2220
gtaatacgac tcactatagg gcgaattggg taccggccgc aaattaaagc cttcgagcgt    2280
cccaaaacct tctcaagcaa ggttttcagt ataatgttac atgcgtacac gcgtctgtac    2340
agaaaaaaaa gaaaaatttg aaatataaat aacgttctta atactaacat aactataaaa    2400
aaataaatag ggacctagac ttcaggttgt ctaactcctt ccttttcggt tagagcggat    2460 gtgggggag  ggcgtgaatg taagcgtgac ataactaatt acatgactcg aggtcgactt    2520
acttgtcatc gtcatctttg tagtcaatat cgtggtcttt atagtcaccg tcatgatcct    2580
tgtaatcctt tgatctcttg tagaccttat tcaagaaagc tgtcaaaacg tcggctttaa    2640
aacctcttga ttcatcaact tgactaatct ttgcctttaa gtctttagcg atggattctt    2700
cgtattcatg gtacaattgt tcaatcttca aatcattaaa aatttcttta cactttgctt    2760
cagcaactga gtccttttta ccgtagtttt catccaaagt ctttctttgt tcggcagatg    2820
ctaattccaa agccttgtta ataacccaac tgcacttatt gtcttgaata tctgtaccga    2880
ttttacctat ttgttctgga gtaccgaaac agtctaagta gtcatcttgg atttggaagt    2940
attcacccaa aggtatcaaa acatctcttg cttgcttcaa gtcttttca tcagtaatac     3000 cagctacgta catagccaag gcgactggca aatagaagga gtaataagca gtttcaaagg    3060
tgacgatgaa tgaatgtttc ttcaaggaaa actttgacaa gtcaacttta tcttcaggtg    3120
cagttatcaa atccatcaat tgacccaatt ctgtttggaa agtaacttcg tggataatt     3180 cggtaatatc gatgtagtac ttttcgtttc tgaaatgtga cttcaacaat ttatagatag    3240
cggcttccaa cataaaagca tcatttatgg ctatttcacc aacttctgga actttgtacc    3300
agcatggttg acctcttctt gttatagact tatccatcat gtcatcggca accaaaaagt    3360
atgcttgcaa caattcaata caccaaccca agatagcgac ctttcgtat  tcttcttgac    3420 ctaattgttc aacggttttg ttagacaaga tagcataagt atcaactaca ctcaaacctc    3480
tattcaattt accacctgga gtattgtagt ttaaagagtg agcataccaa tcgcaggctt    3540
ctttaggcat accataagct aacaaactag cgttcaattc ttcaactaac tttgggaata    3600
cgttcaagaa tctttctctt cttatttcct tttctgaagc cataggacct ggattttctt    3660
caacgtcacc acatgttaac aaagaacctc taccttcttc gaaatgactg aattgttgtc    3720
tcaaaactct tctcatgatc ttgtttgttg cagttctagg taaggatgac aatgggacaa    3780
ctctagtaac tttgaataat gggttcaatt tcttttgcaa acccaagtta aaggataatc    3840
tcaattggtt caaatcaatg gttgtgtcgt ttgaatcctt caatacgaaa aatatgacca    3900
attgttctgg accaccaccc aaaggtggaa caccaatagc agtggtttca aaaactctgt    3960
```

```
catctacttc attacagact ctttcgattt cgatagaact aattttgata ccaccgatgt    4020
tcatagtgtc atcggctcta ccgtgtgcat ggtagtaacc gttagaggtc aattcgaaaa    4080
tgtcaccatg tcttctcaat acttcaccat tcaaggttgg catacccttg aaatagacat    4140
cgtgatgatt accgtttaac aatgtttttg aggcaccaaa cataacagga cctaatgcca    4200
attcaccgat acctggctta tttttaggca ttgggtaacc gttcttatct aatatgtaca    4260
aggtgcaacc catacattgg gatgaaaaag aacttaaaga ttgagcttgc aaaaatgaac    4320
cagcagaaaa agcaccaccg atttctgtac caccacacat ttctataact ggcttgtagt    4380
tagctctacc cattaaccac aaatattcgt ctacattaga ggcttcaccg gatgaagaaa    4440
agcatcttat ggtggaccaa tcgtaacctg aaacacaatt tgtggatttc catgatctta    4500
caatagatgg tacgacaccc aacattgtga cctttgcatc ttgaacaaat ttagcgaaac    4560
cagagactaa aggactaccg ttgtacaagg caatagatgc accatttaac aaactagcat    4620
aaaccaacca aggacccatc atccaaccca aattagttgg ccatactata acgtcacctt    4680
ttctaatatc caaatgagac caaccatcag cagcagcctt caatggggtg gcttgtgtcc    4740
aaggaattgc ttttggttca cctgtagtac cactggagaa taagatgtta gtataagcat    4800
caacaggttg ttctctggca gtaaactcgc agttttaaa ctccttggct ctttctaaaa     4860
agtaatccca agatatgtca ccatctctca attctgcacc aatgttagaa ccactacaag    4920
ggataactat tgccattggg gatttagctt caactactct tgaatacaat ggtattctct    4980
ttttacctct gatgatgtga tcttgtgtga aaattgcctt agctttggat aatctcaatc    5040
tagttgagat ttcaggggcg gaaaatgaat ctgctataga gacaactacg taaccagcca    5100
atactatggc caaatatata acaacagcat caacatgcat tggcatatcg atggctattg    5160
cacaaccttt ttctaaaccc atttcttcca atgcataacc aaccaaccaa actctctttc    5220
tcaattgatc taatgtcaac ttattcaaag gcaagtcatc gttaccctcg tctctccaaa    5280
cgatcatagt atcgttcaat ttcttattgg agtttacgtt caagcaattt ttagctgagt    5340
tcaagtaacc accaggtaac cattcagaac cacctgggtt gttgatgtca tctcttctca    5400
agatacattc tgggtcctta gagaaactaa ttttcatttc atccatcaat actgttctcc    5460
aatagacttc agggtttcta acagaaaatt cttggaagtg agaaaaagaa gaaattggat    5520
ctttgtactt tacacccaaa aattctttac ctctcttttc caacaaagca cccaaattag    5580
ttgacttgac ttttcaggg tctggaatcc aagcaggtgg ggctggaccg aaatccttgt     5640
agcaaccata aaacaacatt tggtgtaagg agaaaggcaa atctggtgac aagatatggt    5700
tagcgatgtt gatccaagtt tgaggggttg cagcaccata attacaaacg atttctgcca    5760
atctaccatg taatgtttct gctacttctg aggtgatacc caatgcgatg aaatctgagg    5820
caacgactga atccaaggac ttatagtttt taccoatact agttctagat ccgtcgaaac    5880
taagttcttg gtgtttaaa actaaaaaaa agactaacta taaagtagaa atttaagaag     5940
tttaagaaat agatttacag aattacaatc aatacctacc gtctttatat acttattagt    6000
caagtagggg aataatttca gggaactggt ttaaaccttt ttttcagct ttttccaaat     6060 cagagagagc agaaggtaat agaaggtgta agaaaatgag atagatacat gcgtgggtca    6120
attgccttgt gtcatcattt actccaggca ggttgcatca ctccattgag gttgtgcccg    6180
ttttttgcct gtttgtgccc tgttctctgt agttgcgcta agagaatgga cctatgaact    6240
gatggttggt gaagaaaaca atattttggt gctgggattc tttttttttc tggatgccag    6300
```

```
cttaaaaagc gggctccatt atatttagtg gatgccagga ataaacctgt tcacccaagc    6360
accatcagtg ttatatattc tgtgtaaccc gcccccctatt ttggcatgta cgggttacag    6420
cagaattaaa aggctaattt tttgactaaa taaagttagg aaaatcacta ctattaatta    6480
tttacgtatt cttttgaaatg gcagtattga taatgataaa ctcgagagct ccagcttttg    6540
ttcagttgat tgtatgcttg gtatagcttg aaatattgtg cagaaaaaga aacaaggaag    6600
aaagggaacg agaacaatga cgaggaaaca aaagattaat aattgcaggt ctatttatac    6660
ttgatagcaa gacagcaaac ttttttttat ttcaaattca gtaactggaa aggaaggccg    6720
tataccgttg ctcattagag agtagtgtgc gtgaatgaag gaaggaaaaa gtttcgtgtg    6780
cttcgagata cccctcatca gctctggaac aacgacatct gttggtgctg tctttgtcgt    6840
taattttttc ctttagtgtc ttccatcatt tttttgtcat tgcggatatg gtgagacaac    6900 aacggggag agagaaaaga aaaaaaaga aaagaagttg catgcgccta ttattacttc    6960
aatagatggc aaatgcaaaa agggtagtga aacttcgata tgatgatggc tatcaagtct    7020
agggctacag tattagttcg ttatgtacca ccatcaatga ggcagtgtaa ttggtgtagt    7080
cttgtttagc ccattatgtc ttgtctggta tctgttctat tgtatatctc ccctccgcca    7140
cctacatgtt agggagacca acgaaggtat tataggaatc ccgatgtatg ggtttggttg    7200
ccagaaaaga ggaagtccat attgtacacc cggaacaac aaaaggatgc gcgcttggcg    7260
taatcatggt catagctgtt tcctgtgtga aattgttatc cgctcacaat tccacacaac    7320
ataggagccg gaagcataaa gtgtaaagcc tggggtgcct aatgagtgag gtaactcaca    7380
ttaattgcgt tgcgctcact gcccgctttc cagtcgggaa acctgtcgtg ccagctgcat    7440
taatgaatcg gccaacgcgc ggggagaggc ggtttgcgta ttgggcgctc ttccgcttcc    7500
tcgctcactg actcgctgcg ctcggtcgtt cggctgcggc gagcggtatc agctcactca    7560
aaggcggtaa tacggttatc cacagaatca ggggataacg caggaaagaa catgtgagca    7620
aaaggccagc aaaaggccag gaaccgtaaa aaggccgcgt tgctggcgtt tttccatagg    7680
ctccgccccc ctgacgagca tcacaaaaat cgacgctcaa gtcagaggtg gcgaaacccg    7740
acaggactat aaagatacca ggcgtttccc cctggaagct ccctcgtgcg ctctcctgtt    7800
ccgaccctgc cgcttaccgg atacctgtcc gcctttctcc cttcgggaag cgtggcgctt    7860
tctcatagct cacgctgtag gtatctcagt tcggtgtagg tcgttcgctc caagctgggc    7920
tgtgtgcacg aaccccccgt tcagcccgac cgctgcgcct tatccggtaa ctatcgtctt    7980
gagtccaacc cggtaagaca cgacttatcg ccactggcag cagccactgg taacaggatt    8040
agcagagcga ggtatgtagg cggtgctaca gagttcttga agtggtggcc taactacggc    8100
tacactagaa ggacagtatt tggtatctgc gctctgctga agccagttac cttcggaaaa    8160
agagttggta gctcttgatc cggcaaacaa accaccgctg gtagcggtgg tttttttgtt    8220
tgcaagcagc agattacgcg cagaaaaaaa ggatctcaag aagatccttt gatcttttct    8280
acggggtctg acgctcagtg gaacgaaaac tcacgttaag ggattttggt catgagatta    8340
tcaaaaagga tcttcaccta gatcctttta aattaaaaat gaagttttaa atcaatctaa    8400
agtatatatg agtaaacttg gtctgacagt taccaatgct taatcagtga ggcacctatc    8460
tcagcgatct gtctatttcg ttcatccata gttgcctgac tccccgtcgt gtagataact    8520
acgatacggg agggcttacc atctggcccc agtgctgcaa tgataccgcg agacccacgc    8580
tcaccggctc cagatttatc agcaataaac cagccagccg aagggccga gcgcagaagt    8640 ggtcctgcaa cttttatccgc ctccatccag tctattaatt gttgccggga agctagagta    8700
```

```
agtagttcgc cagttaatag tttgcgcaac gttgttgcca ttgctacagg catcgtggtg      8760
tcacgctcgt cgtttggtat ggcttcattc agctccggtt cccaacgatc aaggcgagtt      8820
acatgatccc ccatgttgtg caaaaaagcg gttagctcct tcggtcctcc gatcgttgtc      8880
agaagtaagt tggccgcagt gttatcactc atggttatgg cagcactgca taattctctt      8940
actgtcatgc catccgtaag atgctttttct gtgactggtg agtactcaac caagtcattc      9000
tgagaatagt gtatgcggcg accgagttgc tcttgcccgg cgtcaatacg ggataatacc      9060
gcgccacata gcagaacttt aaaagtgctc atcattggaa aacgttcttc ggggcgaaaa      9120
ctctcaagga tcttaccgct gttgagatcc agttcgatgt aacccactcg tgcacccaac      9180
tgatcttcag catcttttac tttcaccagc gtttctgggt gagcaaaaac aggaaggcaa      9240
aatgccgcaa aaaagggaat aagggcgaca cggaaatgtt gaatactcat actcttcctt      9300
tttcaatatt attgaagcat ttatcagggt tattgtctca tgagcggata catatttgaa      9360
tgtatttaga aaaataaaca aataggggtt ccgcgcacat ttccccgaaa agtgccacct      9420
gggtcctttt catcacgtgc tataaaaata attataattt aaattttttta atataaatat      9480
ataaattaaa aatagaaagt aaaaaagaa attaaagaaa aatagtttt tgttttccga      9540
agatgtaaaa gactctaggg ggatcgccaa caaatactac cttttatctt gctcttcctg      9600
ctctcaggta ttaatgccga attgtttcat cttgtctgtg tagaagacca cacgaaaa      9660
tcctgtgatt ttacatttta cttatcgtta atcgaatgta tatctattta atctgctttt      9720
cttgtctaat aaatatatat gtaaagtacg cttttttgttg aaatttttta aacctttgtt      9780
tatttttttt tcttcattcc gtaactcttc taccttcttt atttactttc taaaatccaa      9840
atacaaaaca taaaataaa taacacaga gtaaattccc aaattattcc atcattaaaa      9900
gatacgaggc gcgtgtaagt tacaggcaag cgatccgtcc taagaaacca ttattatcat      9960
gacattaacc tataaaaata ggcgtatcac gaggcccttt cgtc                     10004
```

<210> SEQ ID NO 3
<211> LENGTH: 9508
<212> TYPE: DNA
<213> ORGANISM: Artificial Sequence
<220> FEATURE:
<223> OTHER INFORMATION: Codon Optimized

<400> SEQUENCE: 3

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgcgtg       120
ttggcgggtg tcggggctgg cttaactatg cggcatcaga gcagattgta ctgagagtgc       180
accataaatt cccgttttaa gagcttggtg agcgctagga gtcactgcca ggtatcgttt       240
gaacacggca ttagtcaggg aagtcataac acagtccttt cccgcaattt tctttttcta       300
ttactcttgg cctcctaacg acattactat atatataata taggaagcat ttaatagaca       360
gcatcgtaat atatgtgtac tttgcagtta tgacgccaga tggcagtagt ggaagatatt       420
ctttattgaa aaatagcttg tcaccttacg tacaatcttg atccggagct tttctttttt       480
tgccgattaa gaattaattc ggtcgaaaaa agaaaaggag agggcaaga gggagggcat       540
tggtgactat tgagcacgtg agtatacgtg attaagcaca caaaggcagc ttggagtatg       600
tctgttatta atttcacagg tagttctggt ccattggtga agtttgcgg cttgcagagc       660
acagaggccg cagaatgtgc tctagattcc gatgctgact tgctgggtat tatatgtgtg       720
```

| | |
|---|---|
| cccaatagaa agagaacaat tgacccggtt attgcaagga aaatttcaag tcttgtaaaa | 780 |
| gcatataaaa atagttcagg cactccgaaa tacttggttg gcgtgtttcg taatcaacct | 840 |
| aaggaggatg ttttggctct ggtcaatgat tacggcattg atatcgtcca actgcatgga | 900 |
| gatgagtcgt ggcaagaata ccaagagttc ctcggtttgc cagttattaa agactcgta | 960 |
| tttccaaaag actgcaacat actactcagt gcagcttcac agaaacctca ttcgtttatt | 1020 |
| cccttgtttg attcagaagc aggtgggaca ggtgaacttt tggattggaa ctcgatttct | 1080 |
| gactggggttg gaaggcaaga gagccccgaa agcttacatt ttatgttagc tggtggactg | 1140 |
| acgccagaaa atgttggtga tgcgcttaga ttaaatggcg ttattggtgt tgatgtaagc | 1200 |
| ggaggtgtgg agacaaatgg tgtaaaagac tctaacaaaa tagcaaattt cgtcaaaaat | 1260 |
| gctaagaaat agtgacaccg attatttaaa gctgcagcat acgatatata tacatgtgta | 1320 |
| tatatgtata cctatgaatg tcagtaagta tgtatacgaa cagtatgata ctgaagatga | 1380 |
| caaggtaatg catcattcta tacgtgtcat tctgaacgag gcgcgctttc cttttttctt | 1440 |
| tttgcttttt cttttttttt ctcttgaact cgacggatct atgcggtgtg aaataccgca | 1500 |
| cagatgcgta aggagaaaat accgcatcag gaaattgtaa acgttaatat tttgttaaaa | 1560 |
| ttcgcgttaa attttttgtta aatcagctca tttttttaacc aataggccga aatcggcaaa | 1620 |
| atcccttata aatcaaaaga atagaccgag atagggttga gtgttgttcc agtttggaac | 1680 |
| aagagtccac tattaaagaa cgtggactcc aacgtcaaag ggcgaaaaac cgtctatcag | 1740 |
| ggcgatggcc cactacgtga accatcaccc taatcaagtt ttttggggtc gaggtgccgt | 1800 |
| aaagcactaa atcggaaccc taaagggagc ccccgattta gagcttgacg gggaaagccg | 1860 |
| gcgaacgtgg cgagaaagga agggaagaaa gcgaaaggag cgggcgctag ggcgctggca | 1920 |
| agtgtagcgg tcacgctgcg cgtaaccacc acacccgccg cgcttaatgc gccgctacag | 1980 |
| ggcgcgtcgc gccattcgcc attcaggctg cgcaactgtt gggaagggcg atcggtgcgg | 2040 |
| gcctcttcgc tattacgcca gctggcgaaa ggggatgtg ctgcaaggcg attaagttgg | 2100 |
| gtaacgccag ggttttccca gtcacgacgt tgtaaaacga cggccagtga gcgcgcgtaa | 2160 |
| tacgactcac tatagggcga attgggtacc ggccgcaaat taaagccttc gagcgtccca | 2220 |
| aaaccttctc aagcaaggtt ttcagtataa tgttacatgc gtacacgcgt ctgtacagaa | 2280 |
| aaaaagaaa aatttgaaat ataaataacg ttcttaatac taacataact ataaaaaaat | 2340 |
| aaatagggac ctagacttca ggttgtctaa ctccttcctt ttcggttaga gcggatgtgg | 2400 |
| ggggagggcg tgaatgtaag cgtgacataa ctaattacat gactcgaggt cgacttacaa | 2460 |
| atcttcttca cttattaatt tttgttcgtg gtggtgaggt ggcaaggtg ggatggattg | 2520 |
| ttcgtttctg aaaagttgt tagggtcggc tttagtcttt actttaacta atctgttgaa | 2580 |
| atttttacca aagtactttt caccccaaat tcttgcttgt gtatagttat ttggagattc | 2640 |
| agggttagtt ttacctaagt ccaaatctct gtagttcaaa tatgccaatc ttgggttttg | 2700 |
| actaacgtaa ggtgtagtga agttgtaaac ggatctgacc cagttgatat gcttttcgtt | 2760 |
| atcttcttgc ttttcccatg aggctgtgta ccataattca tacatgatac cagctctgtg | 2820 |
| aggaaatggt atggctgatt cagatatttc ttccataata ccaccgtatg gatacaaaac | 2880 |
| gtacatgccg acacctacat cttcttcgta caacttttcc aatatcttga ccattgcagt | 2940 |
| ttcagggatt ggtttcttaa cgtagtccaa tttaatagaa aaagcggtct ttttaccagc | 3000 |
| ggatctatcc aacaagattt cctttttgaa gttagcggtg ttgaagttta caacacctga | 3060 |
| atagaagatg gttgtgtcta tccaagaaaa ttccttgcaa tctgtctttt taatacccaa | 3120 |

```
ttctgggaat gacttattca tcaaatcaac caaagaatct acaccaccat ggaaaattga   3180
agaaaaataa ccgtgaacag tggtcttatt tttaccatgg ttatctgtaa tattttagt    3240 gatgaaatgg gtcatcaaaa ccaagtcctt atcgtacttg taagcgatgt tttgccactt   3300
attaaacaac ttaccaaac cgtggatttc catgttcttt ttgacagaga aaatagtact    3360
tttggaagga acagcgacta acttaatttt ccaagcggca atgataccga aattttcacc   3420
accaccacct cttatggccc aaaacaaatc ttcacccata gactttctgt ccaaaacttt   3480
accatctacg ttaaccaaat gggcgtctat aatattatct gcagctaaac cgtagtttct   3540
catcaatgca ccataaccac caccagaaaa gtgaccaccg acacctactg ttggacagta   3600
accaccaggg aaagaaaagt tttcattctt ttcgttgatc cagtagtaaa cttcacccaa   3660
ggtggcacct gcttctaccc atgctgtttg actgtgaacg tcgatcttta tggaatgcat   3720
atttctcaaa tcgactacaa cgaatggaac ttgtgagatg taagacatgc cttctgcatc   3780
atgaccacct gatctagttc tgatttgcaa acctactttc ttagagcaca atatagaagc   3840
ttgaatgtga ctaacattgg aaggtgtaac aatgactaaa ggttttggtg tagtgtcaga   3900
agtgaatctc aaattttgga tggtactgtt caaaacggac atgtacaatt gatcatgttg   3960
agtatatata aactttgggt tagcagggtt gtttgggatg tattcggaga aacacttcaa   4020
aaagttttct tgtggatttg cgatggagat ttggatgttg aaggacaaga agaagaagat   4080
tattttacag acgaaccaga agagaatgc ggagcagttc ataggacctg gattttcttc    4140
aacgtcacca caggtcaaca aagaacctct accttcaata aaaacgtata ccaaatattc   4200
agcgtagtac aatttccaca taaactcgta gaatcttcta cctgcttcag ggtcataatt   4260
tgtcaaagcg aaatctctag tttgcaagat caaccagaaa gccaagatgg catgtgacaa   4320
caacataacg ttagaattaa aggcttgtgg ccaaatgata cctgccaaaa tggctgcgac   4380
gtaacttaac aaaacgatac cggagcagaa caaagtcaaa tttcttgaac cgtacttaga   4440
agccaaggta ctaataccga actttgtgtc accttcaacg tcagaggcat ccttgatcaa   4500
ggctaatgca gaacccatac ttttcatgaa tgccaacaaa aatgtgaatg aaggtctcaa   4560
ttcgaatggc aaacctaaag cagctcttga agcgtagtag aaggtgaagt ttgtgatgat   4620
atgagctaag aaattcaaca aaaaggcagt actagggttt tgtttccatc taaaaggtgg   4680
tacgaaatag acaataccac cgaagatacc gaaacgtaa ccgaagatgt acaatggacc    4740
acccttcatt ttaattgtga tgatcaaacc gaacaaggct actatgatag acatgatcca   4800
tgcagtattg acgatatt cacctgaagc caaaggcaaa tctggtttgt taattctgtc     4860
gatgtgcaaa tcgtatattt gattaattgt agtggtgaat gaagcgatgc acaagatggc   4920
aactaaaaag aaaaatgcct tgaacatcaa ggaccatgaa attaagttag tgttatgcaa   4980
caattcttta ccgaataaac cgcatgcaca agaagtaaaa gcgattatgg tgtatggtct   5040
ttgcaacttc caacatgctt taccgaagtt caaaatttt gtggcaacag agtgattatc     5100
actttcaggt ggttcagttt gatttgtagt tgcagctctg atagagttct tagctataga   5160
caaactttcg gagcacttat tttgtaagtg aaggacttg gttgaacaat gttttgatgg     5220
aaagttgttg taagagtact taataggtgt ctttggatgt ctgtaacaca acaatgatgt   5280
ttttggattg ttgttgtgag gattcaataa ggtatgatag ttagtttgga aggagaaagt   5340
acagacggat gataaaccca tactagttct agatccgtcg aaactaagtt cttggtgttt   5400
taaaactaaa aaaagactaa ctataaaag tagaatttaa gaagtttaag aaatagattt      5460
```

```
acagaattac aatcaatacc taccgtctttt atatacttat tagtcaagta ggggaataat    5520
ttcagggaac tggtttaaac cttttttttc agcttttttcc aaatcagaga gagcagaagg    5580
taatagaagg tgtaagaaaa tgagatagat acatgcgtgg gtcaattgcc ttgtgtcatc    5640
atttactcca ggcaggttgc atcactccat tgaggttgtg cccgtttttt gcctgtttgt    5700
gccctgttct ctgtagttgc gctaagagaa tggacctatg aactgatggt tggtgaagaa    5760
aacaatattt tggtgctggg attctttttt tttctggatg ccagcttaaa aagcgggctc    5820
cattatattt agtggatgcc aggaataaac ctgttcaccc aagcaccatc agtgttatat    5880
attctgtgta acccgccccc tattttggca tgtacgggtt acagcagaat taaaaggcta    5940 atttttttgac taaataaagt taggaaaatc actactatta attatttacg tattctttga    6000
aatggcagta ttgataatga taaactcgag agctccagct tttgttcagt tgattgtatg    6060
cttggtatag cttgaaatat tgtgcagaaa aagaaacaag gaagaaaggg aacgagaaca    6120
atgacgagga aacaaaagat taataattgc aggtctattt atacttgata gcaagacagc    6180
aaactttttt ttatttcaaa ttcaagtaac tggaaggaag gccgtatacc gttgctcatt    6240
agagagtagt gtgcgtgaat gaaggaagga aaaagtttcg tgtgcttcga gatacccctc    6300
atcagctctg gaacaacgac atctgttggt gctgtctttg tcgttaattt tttcctttag    6360
tgtcttccat catttttttg tcattgcgga tatggtgaga caacaacggg ggagagagaa    6420
aagaaaaaaa aagaaaagaa gttgcatgcg cctattatta cttcaataga tggcaaatgg    6480
aaaaagggta gtgaaacttc gatatgatga tggctatcaa gtctagggct acagtattag    6540
ttcgttatgt accaccatca atgaggcagt gtaattggtg tagtcttgtt tagcccatta    6600
tgtcttgtct ggtatctgtt ctattgtata tctcccctcc gccacctaca tgttagggag    6660
accaacgaag gtattatagg aatcccgatg tatgggtttg gttgccagaa aagaggaagt    6720
ccatattgta cacccggaaa caacaaaagg atgcgcgctt ggcgtaatca tggtcatagc    6780
tgtttcctgt gtgaaattgt tatccgctca caattccaca caacatagga gccggaagca    6840
taaagtgtaa agcctggggt gcctaatgag tgaggtaact cacattaatt gcgttgcgct    6900
cactgcccgc tttccagtcg ggaaacctgt cgtgccagct gcattaatga atcggccaac    6960
gcgcggggag aggcggtttg cgtattgggc gctcttccgc ttcctcgctc actgactcgc    7020
tgcgctcggt cgttcggctg cggcgagcgg tatcagctca ctcaaaggcg gtaatacggt    7080
tatccacaga atcaggggat aacgcaggaa agaacatgtg agcaaaaggc cagcaaaagg    7140
ccaggaaccg taaaaaggcc gcgttgctgg cgtttttcca taggctccgc cccccctgacg    7200 agcatcacaa aaatcgacgc tcaagtcaga ggtggcgaaa cccgacagga ctataaagat    7260
accaggcgtt tccccctgga agctccctcg tgcgctctcc tgttccgacc ctgccgctta    7320
ccggatacct gtccgccttt ctcccttcgg gaagcgtggc gctttctcat agctcacgct    7380
gtaggtatct cagttcggtg taggtcgttc gctccaagct gggctgtgtg cacgaacccc    7440
ccgttcagcc cgaccgctgc gccttatccg gtaactatcg tcttgagtcc aacccggtaa    7500
gacacgactt atcgccactg gcagcagcca ctggtaacag gattagcaga gcgaggtatg    7560
taggcggtgc tacagagttc ttgaagtggt ggcctaacta cggctacact agaaggacag    7620
tatttggtat ctgcgctctg ctgaagccag ttaccttcgg aaaaagagtt ggtagctctt    7680
gatccggcaa acaaaccacc gctggtagcg gtggtttttt tgtttgcaag cagcagatta    7740
cgcgcagaaa aaaaggatct caagaagatc ctttgatctt ttctacgggg tctgacgctc    7800
agtggaacga aaactcacgt taagggattt tggtcatgag attatcaaaa aggatcttca    7860
```

```
cctagatcct tttaaattaa aaatgaagtt ttaaatcaat ctaaagtata tatgagtaaa    7920
cttggtctga cagttaccaa tgcttaatca gtgaggcacc tatctcagcg atctgtctat    7980
ttcgttcatc catagttgcc tgactccccg tcgtgtagat aactacgata cgggagggct    8040
taccatctgg ccccagtgct gcaatgatac cgcgagaccc acgctcaccg gctccagatt    8100
tatcagcaat aaaccagcca gccggaaggg ccgagcgcag aagtggtcct gcaactttat    8160
ccgcctccat ccagtctatt aattgttgcc gggaagctag agtaagtagt tcgcagtta    8220
atagtttgcg caacgttgtt gccattgcta caggcatcgt ggtgtcacgc tcgtcgtttg    8280
gtatggcttc attcagctcc ggttcccaac gatcaaggcg agttacatga tcccccatgt    8340
tgtgcaaaaa agcggttagc tccttcggtc ctccgatcgt tgtcagaagt aagttggccg    8400
cagtgttatc actcatggtt atggcagcac tgcataattc tcttactgtc atgccatccg    8460
taagatgctt ttctgtgact ggtgagtact caaccaagtc attctgagaa tagtgtatgc    8520
ggcgaccgag ttgctcttgc ccggcgtcaa tacgggataa taccgcgcca catagcagaa    8580
cttttaaaagt gctcatcatt ggaaaacgtt cttcggggcg aaaactctca aggatcttac    8640
cgctgttgag atccagttcg atgtaaccca ctcgtgcacc caactgatct tcagcatctt    8700
ttactttcac cagcgtttct gggtgagcaa aaacaggaag gcaaaatgcc gcaaaaaagg    8760
gaataagggc gacacggaaa tgttgaatac tcatactctt cctttttcaa tattattgaa    8820
gcatttatca gggttattgt ctcatgagcg gatacatatt tgaatgtatt tagaaaaata    8880
aacaaatagg ggttccgcgc acatttcccc gaaaagtgcc acctgggtcc ttttcatcac    8940
gtgctataaa aataattata atttaaattt tttaatataa atatataaat taaaaataga    9000
aagtaaaaaa agaaattaaa gaaaaaatag ttttgttttt ccgaagatgt aaaagactct    9060
aggggggatcg ccaacaaata ctacctttta tcttgctctt cctgctctca ggtattaatg    9120
ccgaattgtt tcatcttgtc tgtgtagaag accacacacg aaaatcctgt gattttacat    9180
tttacttatc gttaatcgaa tgtatatcta tttaatctgc ttttcttgtc taataaatat    9240
atatgtaaag tacgcttttt gttgaaattt tttaaacctt tgtttatttt ttttcttca    9300
ttccgtaact cttctacctt ctttatttac tttctaaaat ccaaatacaa aacataaaaa    9360
taaataaaca cagagtaaat tcccaaatta ttccatcatt aaaagatacg aggcgcgtgt    9420
aagttacagg caagcgatcc gtcctaagaa accattatta tcatgacatt aacctataaa    9480
aataggcgta tcacgaggcc ctttcgtc                                      9508
```

<210> SEQ ID NO 4
<211> LENGTH: 9505
<212> TYPE: DNA
<213> ORGANISM: Artificial Sequence
<220> FEATURE:
<223> OTHER INFORMATION: Codon Optimized

<400> SEQUENCE: 4

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgcgtg    120
ttggcgggtg tcgggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctaacg acattactat atatataata taggaagcat ttaatagaca    360
```

```
gcatcgtaat atatgtgtac tttgcagtta tgacgccaga tggcagtagt ggaagatatt      420
ctttattgaa aaatagcttg tcaccttacg tacaatcttg atccggagct tttcttttt       480 tgccgattaa gaattaattc ggtcgaaaaa agaaaaggag agggccaaga gggagggcat      540
tggtgactat tgagcacgtg agtatacgtg attaagcaca caaaggcagc ttggagtatg      600
tctgttatta atttcacagg tagttctggt ccattggtga agtttgcgg cttgcagagc       660 acagaggccg cagaatgtgc tctagattcc gatgctgact tgctgggtat tatatgtgtg     720
cccaatagaa agagaacaat tgacccggtt attgcaagga aaatttcaag tcttgtaaaa     780
gcatataaaa atagttcagg cactccgaaa tacttggttg gcgtgtttcg taatcaacct     840
aaggaggatg ttttggctct ggtcaatgat tacggcattg atatcgtcca actgcatgga     900
gatgagtcgt ggcaagaata ccaagagttc ctcggtttgc cagttattaa agactcgta     960 tttccaaaag actgcaacat actactcagt gcagcttcac agaaacctca ttcgtttatt    1020
cccttgtttg attcagaagc aggtgggaca ggtgaacttt tggattggaa ctcgatttct    1080
gactgggttg gaaggcaaga gagccccgaa agcttacatt ttatgttagc tggtggactg    1140
acgccagaaa atgttggtga tgcgcttaga ttaaatggcg ttattggtgt tgatgtaagc    1200
ggaggtgtgg agacaaatgg tgtaaaagac tctaacaaaa tagcaaattt cgtcaaaaat    1260
gctaagaaat agtgacaccg attatttaaa gctgcagcat acgatatata tacatgtgta    1320
tatatgtata cctatgaatg tcagtaagta tgtatacgaa cagtatgata ctgaagatga    1380
caaggtaatg catcattcta tacgtgtcat tctgaacgag gcgcgctttc cttttttctt    1440
tttgcttttt cttttttttt ctcttgaact cgacggatct atgcggtgtg aaataccgca    1500
cagatgcgta aggagaaaat accgcatcag gaaattgtaa acgttaatat tttgttaaaa    1560
ttcgcgttaa attttgtta aatcagctca ttttttaacc aataggccga atcggcaaa     1620 atcccttata aatcaaaaga atagaccgag atagggttga gtgttgttcc agtttggaac    1680
aagagtccac tattaaagaa cgtggactcc aacgtcaaag gcgaaaaac cgtctatcag     1740 ggcgatggcc cactacgtga accatcaccc taatcaagtt ttttgggtc gaggtgccgt     1800 aaagcactaa atcggaaccc taaagggagc ccccgattta gagcttgacg gggaaagccg    1860
gcgaacgtgg cgagaaagga agggaagaaa gcgaaaggag cgggcgctag gcgctggca     1920 agtgtagcgg tcacgctgcg cgtaaccacc acacccgccg cgcttaatgc gccgctacag    1980
ggcgcgtcgc gccattcgcc attcaggctg cgcaactgtt gggaagggcg atcggtgcgg    2040
gcctcttcgc tattacgcca gctggcgaaa ggggatgtg ctgcaaggcg attaagttgg     2100
gtaacgccag ggttttccca gtcacgacgt tgtaaaacga cggccagtga gcgcgcgtaa    2160
tacgactcac tatagggcga attgggtacc ggccgcaaat taaagccttc gagcgtccca    2220
aaaccttctc aagcaaggtt ttcagtataa tgttacatgc gtacacgcgt ctgtacagaa    2280 aaaaagaaa aatttgaaat ataaataacg ttcttaatac taacataact ataaaaaaat    2340
aaatagggac ctagacttca ggttgtctaa ctccttcctt ttcggttaga gcggatgtgg    2400
ggggagggcg tgaatgtaag cgtgacataa ctaattacat gactcgaggt cgacttacaa    2460
atcttcttca cttattaatt tttgttcgtg tctatgtcta ggtaaaggtg aatggattg     2520 ttcgtttcta aagaagttgt ttgggtcaac caatgtctta acctttacta atctatcgaa    2580 attttttaccg aagtattttt cacccccaaat tctagcttgg gtatagttgt taggattctt    2640
tggatcgtta ataccgatgt ccaaatctct gtagttcaaa tatgccaatc tagggttttt    2700
agaaacgtat ggagtcatga agttatagat gtttctaatc cagtttaagt gcttttcgtt    2760
```

| | |
|---|---|
| atcttcttgc ttttcccatg aacaaatgta ccacaattcg tataagatac cagctctatg | 2820 |
| aggaaatgga atggcagatt cactgatttc gtccattata ccaccgtatg gatacaaggc | 2880 |
| gtacatgcct gcaccaatat cttcttcgta caattttcct aagatttgga cgaaaactga | 2940 |
| ttcaggtatt ggcttttaa cgtagtctaa cttaatttta aaggcaccgt tttgacctgc | 3000 |
| ggatctatcc aataatattt ctttgttgaa gttgtctgta tcgtagttga caacacctga | 3060 |
| ataaagatg atggtgtcga tccaagacaa ttgtctacaa tcagttttct taatacctaa | 3120 |
| ttctggaaaa gacttattca tcaagtctac taaggaatcg acaccaccca agaaaactga | 3180 |
| agaaaagtat gtgtggatag cagtcttatt tttaccttgg ttatcggtga tgtttcttgt | 3240 |
| gatgaaatga gtcatcaaca acaagtcctt atcgtacttg tatgcgatgt tttgccactt | 3300 |
| attgaccaat ttaactaatt catggatttc cattatcttt ttgactgaga acatagtaga | 3360 |
| ctttggtact gcgactaatc ttatcttcca agcaactatg ataccgaatg attctgcacc | 3420 |
| accacctctc aaagcccaaa ataagtcttc acccatagac tttctatcca aaactttacc | 3480 |
| gtgaacattt accaaatgag cgtcgattat gttatcagcg gccaaaccgt agtttctcat | 3540 |
| taaaggacca taaccaccac caccaaaatg accacctgcg caaactgttg gacagtaacc | 3600 |
| agcagccaat gataagtttt cattcttttc gttaacccag tagtatactt cacccaatgt | 3660 |
| tgcaccagct tcaacccaag cagtttgtga gtgtacgtct atttttaattg atctcatgtt | 3720 |
| tctcaaatca acgataacga atggaacttg ggagatgtat gacatgcctt cactatcatg | 3780 |
| accaccggat ctagttctaa tttgcaaacc aaccttttta gaacataaga tagtaccttg | 3840 |
| gatgtgagat acatgactag gggttacaat gaccaaaggt tttggagtgg tatcagaagt | 3900 |
| gaatctcaaa ttatggattg tactgttcaa gacggacatg tacaatgggt tgttttgagt | 3960 |
| gtaaaccaac ttcaaattgg tggcgttatt aggtatgtat tgtgagaagc acttcaaaaa | 4020 |
| gttttctctt gggtttgcga tacttgtttg gatgttaaag gaaaagaaaa agaagatgat | 4080 |
| cttgcatacg aaccaaaagg agaaagttga acatttcata ggacctggat tttcttcaac | 4140 |
| gtcaccacag gtcaacaaag aacctctacc ttcaataaaa acgtatacca aatattcagc | 4200 |
| gtagtacaat ttccacataa actcgtagaa tcttctacct gcttcagggt cataatttgt | 4260 |
| caaagcgaaa tctctagttt gcaagatcaa ccagaaagcc aagatggcat gtgacaacaa | 4320 |
| cataacgtta gaattaaagg cttgtggcca aatgatacct gccaaaatgg ctgcgacgta | 4380 |
| acttaacaaa acgataccgg agcagaacaa agtcaaattt cttgaaccgt acttagaagc | 4440 |
| caaggtacta ataccgaact tgtgtcacc ttcaacgtca gaggcatcct tgatcaaggc | 4500 |
| taatgcagaa cccatacttt tcatgaatgc caacaaaaat gtgaatgaag gtctcaattc | 4560 |
| gaatggcaaa cctaaagcag ctcttgaagc gtagtagaag gtgaagtttg tgatgatatg | 4620 |
| agctaagaaa ttcaacaaaa aggcagtact agggttttgt ttccatctaa aaggtggtac | 4680 |
| ggaatagaca ataccaccga agataccgaa acagtaaccg aagatgtaca atggaccacc | 4740 |
| cttcattta attgtgatga tcaaaccgaa caaggctact atgatagaca tgatccatgc | 4800 |
| agtattgacg atatttcac ctgaagccaa aggcaaatct ggtttgttaa ttctgtcgat | 4860 |
| gtgcaaatcg tatatttgat taattgtagt ggtgaatgaa gcgatgcaca agatggcaac | 4920 |
| taaaagaaa aatgccttga acatcaagga ccatgaaatt aagttagtgt tatgcaacaa | 4980 |
| ttctttaccg aataaaccgc atgcacaaga agtaaaagcg attatggtgt atggtctttg | 5040 |
| caacttccaa catgctttac cgaagttcaa aattttgtg gcaacagagt gattatcact | 5100 |

```
ttcaggtggt tcagtttgat ttgtagttgc agctctgata gagttcttag ctatagacaa      5160
actttcggag cacttatttt gtaagtggaa ggacttggtt gaacaatgtt ttgatggaaa      5220
gttgttgtaa gagtacttaa taggtgtctt tggatgtctg taacacaaca atgatgtttt      5280
tggattgttg ttgtgaggat tcaataaggt atgatagtta gtttggaagg agaaagtaca      5340
gacggatgat aaacccatac tagttctaga tccgtcgaaa ctaagttctt ggtgttttaa      5400
aactaaaaaa aagactaact ataaaagtag aatttaagaa gtttaagaaa tagatttaca      5460
gaattacaat caatacctac cgtctttata tacttattag tcaagtaggg gaataatttc      5520
agggaactgg tttaaacctt ttttttcagc ttttttccaaa tcagagagag cagaaggtaa      5580
tagaaggtgt aagaaaatga gatagataca tgcgtgggtc aattgccttg tgtcatcatt      5640
tactccaggc aggttgcatc actccattga ggttgtgccc gttttttgcc tgtttgtgcc      5700
ctgttctctg tagttgcgct aagagaatgg acctatgaac tgatggttgg tgaagaaaac      5760
aatattttgg tgctgggatt cttttttttt ctggatgcca gcttaaaaag cgggctccat      5820
tatatttagt ggatgccagg aataaacctg ttcacccaag caccatcagt gttatatatt      5880
ctgtgtaacc cgcccctat tttggcatgt acgggttaca gcagaattaa aaggctaatt      5940
ttttgactaa ataagttag gaaaatcact actattaatt atttacgtat tctttgaaat      6000
ggcagtattg ataatgataa actcgagagc tccagctttt gttcagttga ttgtatgctt      6060
ggtatagctt gaaatattgt gcagaaaaag aaacaaggaa gaaagggaac gagaacaatg      6120
acgaggaaac aaaagattaa taattgcagg tctatttata cttgatagca agacagcaaa      6180 cttttttta tttcaaattc aagtaactgg aaggaaggcc gtataccgtt gctcattaga      6240
gagtagtgtg cgtgaatgaa ggaaggaaaa agtttcgtgt gcttcgagat accctcatc      6300 agctctggaa caacgacatc tgttggtgct gtctttgtcg ttaattttt cctttagtgt      6360 cttccatcat tttttgtca ttgcggatat ggtgagacaa caacggggga gagagaaaag      6420 aaaaaaaag aaaagaagtt gcatgcgcct attattactt caatagatgg caaatggaaa      6480
aagggtagtg aaacttcgat atgatgatgg ctatcaagtc tagggctaca gtattagttc      6540
gttatgtacc accatcaatg aggcagtgta attggtgtag tcttgtttag cccattatgt      6600
cttgtctggt atctgttcta ttgtatatct cccctccgcc acctacatgt tagggagacc      6660
aacgaaggta ttataggaat cccgatgtat gggtttggtt gccagaaaag aggaagtcca      6720
tattgtacac ccggaaacaa caaaaggatg cgcgcttggc gtaatcatgg tcatagctgt      6780
ttcctgtgtg aaattgttat ccgctcacaa ttccacacaa cataggagcc ggaagcataa      6840
agtgtaaagc ctggggtgcc taatgagtga ggtaactcac attaattgcg ttgcgctcac      6900
tgcccgcttt ccagtcggga aacctgtcgt gccagctgca ttaatgaatc ggccaacgcg      6960
cggggagagg cggtttgcgt attgggcgct cttccgcttc ctcgctcact gactcgctgc      7020
gctcggtcgt tcggctgcgg cgagcggtat cagctcactc aaaggcggta atacggttat      7080
ccacagaatc agggggataac gcaggaaaga acatgtgagc aaaaggccag caaaaggcca      7140
ggaaccgtaa aaaggccgcg ttgctggcgt ttttccatag gctccgcccc cctgacgagc      7200
atcacaaaaa tcgacgctca agtcagaggt ggcgaaaccc gacaggacta taaagatacc      7260
aggcgtttcc ccctggaagc tccctcgtgc gctctcctgt tccgaccctg ccgcttaccg      7320
gatacctgtc cgcctttctc ccttcgggaa gcgtggcgct ttctcatagc tcacgctgta      7380
ggtatctcag ttcggtgtag gtcgttcgct ccaagctggg ctgtgtgcac gaaccccccg      7440
ttcagcccga ccgctgcgcc ttatccggta actatcgtct tgagtccaac ccggtaagac      7500
```

```
acgacttatc gccactggca gcagccactg gtaacaggat tagcagagcg aggtatgtag    7560
gcggtgctac agagttcttg aagtggtggc ctaactacgg ctacactaga aggacagtat    7620
ttggtatctg cgctctgctg aagccagtta ccttcggaaa aagagttggt agctcttgat    7680
ccggcaaaca aaccaccgct ggtagcggtg gttttttttgt ttgcaagcag cagattacgc    7740
gcagaaaaaa aggatctcaa gaagatcctt tgatcttttc tacggggtct gacgctcagt    7800
ggaacgaaaa ctcacgttaa gggattttgg tcatgagatt atcaaaaagg atcttcacct    7860 agatccttttt aaattaaaaa tgaagtttta atcaatcta aagtatatat gagtaaactt    7920
ggtctgacag ttaccaatgc ttaatcagtg aggcacctat ctcagcgatc tgtctatttc    7980
gttcatccat agttgcctga ctccccgtcg tgtagataac tacgatacgg agggcttac    8040 catctggccc cagtgctgca atgataccgc gagacccacg ctcaccggct ccagatttat    8100
cagcaataaa ccagccagcc ggaagggccg agcgcagaag tggtcctgca actttatccg    8160
cctccatcca gtctattaat tgttgccggg aagctagagt aagtagttcg ccagttaata    8220
gtttgcgcaa cgttgttgcc attgctacag gcatcgtggt gtcacgctcg tcgtttggta    8280
tggcttcatt cagctccggt tcccaacgat caaggcgagt tacatgatcc cccatgttgt    8340
gcaaaaaagc ggttagctcc ttcggtcctc cgatcgttgt cagaagtaag ttggccgcag    8400
tgttatcact catggttatg gcagcactgc ataattctct tactgtcatg ccatccgtaa    8460
gatgcttttc tgtgactggt gagtactcaa ccaagtcatt ctgagaatag tgtatgcggc    8520
gaccgagttg ctcttgcccg gcgtcaatac gggataatac cgcgccacat agcagaactt    8580
taaaagtgct catcattgga aaacgttctt cggggcgaaa actctcaagg atcttaccgc    8640
tgttgagatc cagttcgatg taacccactc gtgcacccaa ctgatcttca gcatctttta    8700 cttttcaccag cgtttctggg tgagcaaaaa caggaaggca aaatgccgca aaaaagggaa    8760
taagggcgac acggaaatgt tgaatactca tactcttcct tttcaatat tattgaagca    8820 tttatcaggg ttattgtctc atgagcggat acatatttga atgtatttag aaaaataaac    8880
aaataggggt tccgcgcaca tttccccgaa aagtgccacc tgggtccttt tcatcacgtg    8940
ctataaaaat aattataatt taaatttttt aatataaata tataaattaa aaatagaaag    9000 taaaaaaga aattaaagaa aaaatagttt ttgttttccg aagatgtaaa agactctagg    9060
gggatcgcca acaaatacta cctttttatct tgctcttcct gctctcaggt attaatgccg    9120
aattgtttca tcttgtctgt gtagaagacc acacacgaaa atcctgtgat tttacatttt    9180
acttatcgtt aatcgaatgt atatctattt aatctgcttt tcttgtctaa taaatatata    9240
tgtaaagtac gcttttttgtt gaaatttttt aaacctttgt ttattttttt ttcttcattc    9300
cgtaactctc ctaccttctt tatttacttt ctaaaatcca aatacaaaac ataaaaataa    9360 ataacacag agtaaattcc caaattattc catcattaaa agatacgagg cgcgtgtaag    9420
ttacaggcaa gcgatccgtc ctaagaaacc attattatca tgacattaac ctataaaaat    9480
aggcgtatca cgaggccctt tcgtc                                         9505
```

<210> SEQ ID NO 5
<211> LENGTH: 8696
<212> TYPE: DNA
<213> ORGANISM: Artificial Sequence
<220> FEATURE:
<223> OTHER INFORMATION: Codon Optimized

<400> SEQUENCE: 5

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgcgtg   120
ttggcgggtg tcgggctgg cttaactatg cggcatcaga gcagattgta ctgagagtgc   180
accataaatt cccgttttaa gagcttggtg agcgctagga gtcactgcca ggtatcgttt   240
gaacacggca ttagtcaggg aagtcataac acagtccttt cccgcaattt tcttttttcta  300 ttactcttgg cctcctaact gtgggaatac tcaggtatcg taagatgcaa gagttcgaat   360
ctcttagcaa ccattatttt tttcctcaac ataacgagaa cacacagggg cgctatcgca   420
cagaatcaaa ttcgatgact ggaaattttt tgttaatttc agaggtcgcc tgacgcatat   480
acctttttca actgaaaaat tgggagaaaa aggaaaggtg agaggccgga accggctttt   540
catatagaat agagaagcgt tcatgactaa atgcttgcat cacaatactt gaagttgaca   600
atattattta aggacctatt gttttttcca ataggtggtt agcaatcgtc ttactttcta   660
acttttctta cctttacat ttcagcaata tatatatata tttcaaggat ataccattct   720
aatgtctgcc cctatgtctg cccctaagaa gatcgtcgtt ttgccaggtg accacgttgg   780
tcaagaaatc acagccgaag ccattaaggt tcttaaagct atttctgatg ttcgttccaa   840
tgtcaagttc gatttcgaaa atcatttaat tggtggtgct gctatcgatg ctacaggtgt   900
cccacttcca gatgaggcgc tggaagcctc caagaaggtt gatgccgttt tgttaggtgc   960
tgtgggtggt cctaaatggg gtaccggtag tgttagacct gaacaaggtt tactaaaaat  1020
ccgtaaagaa cttcaattgt acgccaactt aagaccatgt aactttgcat ccgactctct  1080
tttagactta tctccaatca agccacaatt tgctaaaggt actgacttcg ttgttgtcag  1140
agaattagtg ggaggtattt actttggtaa gagaaaggaa gacgatggtg atggtgtcgc  1200
ttgggatagt gaacaataca ccgttccaga agtgcaaaga atcacaagaa tggccgcttt  1260
catggcccta caacatgagc caccattgcc tatttggtcc ttggataaag ctaatgtttt  1320
ggcctcttca agattatgga gaaaaactgt ggaggaaacc atcaagaacg aattccctac  1380
attgaaggtt caacatcaat tgattgattc tgccgccatg atcctagtta agaacccaac  1440
ccacctaaat ggtattataa tcaccagcaa catgttggt gatatcatct ccgatgaagc  1500
ctccgttatc ccaggttcct tgggtttgtt gccatctgcg tccttggcct ctttgccaga  1560
caagaacacc gcatttggtt tgtacgaacc atgccacggt tctgctccag atttgccaaa  1620
gaataaggtt gaccctatcg ccactatctt gtctgctgca atgatgttga aattgtcatt  1680
gaacttgcct gaagaaggta aggccattga agatgcagtt aaaaaggttt tggatgcagg  1740
tatcagaact ggtgatttag gtggttccaa cagtaccacc gaagtcggtg atgctgtcgc  1800
cgaagaagtt aagaaaatcc ttgcttaatg acaccgatta tttaaagctg cagcatacga  1860
tatatataca tgtgtatata tgtataccta tgaatgtcag taagtatgta tacgaacagt  1920
atgatactga agatgacaag gtaatgcatc attctatacg tgtcattctg aacgaggcgc  1980
gctttccttt tttctttttg cttttctctt ttttttctct tgaactcgac ggatctatgc  2040
ggtgtgaaat accgcacaga tgcgtaagga gaaaataccg catcaggaaa ttgtaaacgt  2100
taatattttg ttaaaattcg cgttaaattt ttgttaaatc agctcatttt ttaaccaata  2160
ggccgaaatc ggcaaaatcc cttataaatc aaaagaatag accgagatag ggttgagtgt  2220
tgttccagtt tggaacaaga gtccactatt aagaacgtg gactccaacg tcaagggcg  2280 aaaaaccgtc tatcagggcg atggcccact acgtgaacca tcaccctaat caagtttttt  2340
ggggtcgagg tgccgtaaag cactaaatcg gaaccctaaa gggagccccc gatttagagc  2400
```

```
ttgacgggga aagccggcga acgtggcgag aaaggaaggg aagaaagcga aaggagcggg   2460
cgctagggcg ctggcaagtg tagcggtcac gctgcgcgta accaccacac ccgccgcgct   2520
taatgcgccg ctacagggcg cgtcgcgcca ttcgccattc aggctgcgca actgttggga   2580
agggcgatcg gtgcgggcct cttcgctatt acgccagctg gcgaaagggg gatgtgctgc   2640
aaggcgatta agttgggtaa cgccagggtt ttcccagtca cgacgttgta aaacgacggc   2700
cagtgagcgc gcgtaatacg actcactata gggcgaattg ggtaccggcc gcaaattaaa   2760
gccttcgagc gtcccaaaac cttctcaagc aaggttttca gtataatgtt acatgcgtac   2820
acgcgtctgt acagaaaaaa aagaaaaatt tgaaatataa ataacgttct taatactaac   2880
ataactataa aaaataaat agggacctag acttcaggtt gtctaactcc ttccttttcg   2940
gttagagcgg atgtgggggg agggcgtgaa tgtaagcgtg acataactaa ttacatgact   3000
cgaggtcgac ttatgcatag tctggaacat cgtaagggta cttcttgggg tgtaatcga    3060 agatcaacaa ttttttcccag aaggatctgt aaacgtcacc aaaaccaacg tgagctggat   3120
gaatgatgta atcttggata gtttcaactg attcgaaggt tacttcgaca atgtgtgtat   3180
aaccttcttc tttcttttgt gtaacgtctt taccccagta tacatctttc atagcaggta   3240
taatgttgac caaattaacg taggtcttga aaaattcttc cttttgagct tctgtgattt   3300
catctttaaa cttcaatact atcaaatgct tgacggccat aggacctggg ttttcttcaa   3360
cgtcaccaca agttaacaag gaacctctac cttcatattt aattggtact gatctgacaa   3420
ctactctttc gacggtcaaa ccaggaccga aaccaaataa gacaccccat tcaaaaccgt   3480
caccagtagt agatttaccc tcttctaatg atctctttct caattcatcc attacgaaca   3540
agacagtgga tgaagacatg ttaccgtgtt cagataaaac atgtctacta tctacaaact   3600 tttcttttctt caaatccaat ttttcttcaa ccttatccaa aatggcttta ccacctggat   3660
gtgttatcca gaaatagag ttccaatctg agatacctat aggagtgaat gcttctatca   3720
aacacttttc tatgttgtta gagattaaca ttggaacgtc tttgtgcaaa tcgaagatca   3780
aacctgcttc tcttatatga ccaccaattg taccttcaga attaggcaag atggtttgac   3840
ctgtactgac taattcaaat attggtctttt caccaacaga ttcgtcaggt tctgcaccaa   3900
caataacagc agcagcaccg tcaccgaaga tagcttgacc aactaacaat tccaagtcag   3960
aatcacttgg acctctaaac aagcaagcca taatgtcgca acaaacagct aatactctgg   4020 caccccttgtt gttttctgca atatccttag cgattctcaa aacagtacca ccaccgtagc   4080
aacctaattg atacatcatg actctcttaa cggatggtga caaacctaac aatttggcac   4140
agtggtagtc tgcaccaggc atatctgtag tagatgcact tgtaaaaatc aaatgagtga   4200 tcttttgactt tggttgaccc cattccttaa tggcttttgc acaagcatct ttacccaatt   4260
taggaacttc gacaactaac atgtcttgtc tggcatccaa tgtttgcatt tcgtgttcta   4320
ccaatcttgg attttgcttc aaatgttctt cgttcaagaa gcagtttctc tttctgatca   4380
tagacttatc acatattttt ctaaactttt ccttcaattg agtcatgtgt tcactcttgg   4440
taactctgaa gtaataatca ggaaattcat cttggatcaa tatgttttct gggttggctg   4500
tacctatggc taatacggag gcaggacctt cggctctcaa atggttcata ctagttctag   4560
atccgtcgaa actaagttct tggtgtttta aaactaaaaa aaagactaac tataaaagta   4620
gaatttaaga agtttaagaa atagatttac agaattacaa tcaataccta ccgtctttat   4680
atacttatta gtcaagtagg ggaataattt cagggaactg gtttaaacct tttttttcag   4740
```

```
cttttttccaa atcagagaga gcagaaggta atagaaggtg taagaaaatg agatagatac    4800
atgcgtgggt caattgcctt gtgtcatcat ttactccagg caggttgcat cactccattg    4860
aggttgtgcc cgttttttgc ctgtttgtgc cctgttctct gtagttgcgc taagagaatg    4920
gacctatgaa ctgatggttg gtgaagaaaa caatattttg gtgctgggat tcttttttt     4980 tctggatgcc agcttaaaaa gcgggctcca ttatatttag tggatgccag gaataaacct    5040
gttcacccaa gcaccatcag tgttatatat tctgtgtaac ccgccccta ttttggcatg     5100 tacgggttac agcagaatta aaaggctaat tttttgacta aataaagtta ggaaaatcac    5160
tactattaat tatttacgta ttctttgaaa tggcagtatt gataatgata aactcgagag    5220
ctccagcttt tgttcagttg attgtatgct tggtatagct tgaaatattg tgcagaaaaa    5280
gaaacaagga agaaagggaa cgagaacaat gacgaggaaa caaaagatta ataattgcag    5340
gtctatttat acttgatagc aagacagcaa acttttttt atttcaaatt caagtaactg      5400
gaaggaaggc cgtataccgt tgctcattag agagtagtgt gcgtgaatga aggaaggaaa    5460
aagtttcgtg tgcttcgaga taccctcat cagctctgga acaacgacat ctgttggtgc     5520
tgtctttgtc gttaattttt tcctttagtg tcttccatca ttttttttgtc attgcggata    5580 tggtgagaca acaacggggg agagagaaaa gaaaaaaaaa gaaagaagt tgcatgcgcc     5640 tattattact tcaatagatg gcaaatggaa aagggtagt gaaacttcga tatgatgatg     5700
gctatcaagt ctagggctac agtattagtt cgttatgtac caccatcaat gaggcagtgt    5760
aattggtgta gtcttgttta gcccattatg tcttgtctgg tatctgttct attgtatatc    5820 tccctccgc cacctacatg ttagggagac caacgaaggt attataggaa tcccgatgta     5880
tgggtttggt tgccagaaaa gaggaagtcc atattgtaca cccggaaaca acaaaaggat    5940
gcgcgcttgg cgtaatcatg gtcatagctg tttcctgtgt gaaattgtta ccgctcaca     6000 attccacaca acataggagc cggaagcata agtgtaaag cctggggtgc ctaatgagtg     6060
aggtaactca cattaattgc gttgcgctca ctgcccgctt ccagtcggg aaacctgtcg     6120 tgccagctgc attaatgaat cggccaacgc gcggggagag gcggtttgcg tattgggcgc    6180
tcttccgctt cctcgctcac tgactcgctg cgctcggtcg ttcggctgcg gcgagcggta    6240
tcagctcact caaaggcggt aatacggtta tccacagaat caggggataa cgcaggaaag    6300
aacatgtgag caaaaggcca gcaaaaggcc aggaaccgta aaaaggccgc gttgctggcg    6360 ttttccata ggctccgccc ccctgacgag catcacaaaa atcgacgctc aagtcagagg      6420
tggcgaaacc cgacaggact ataaagatac caggcgtttc ccctggaag ctccctcgtg     6480 cgctctcctg ttccgaccct gccgcttacc ggatacctgt ccgcctttct cccttcggga    6540
agcgtggcgc tttctcatag ctcacgctgt aggtatctca gttcggtgta ggtcgttcgc    6600
tccaagctgg gctgtgtgca cgaaccccc gttcagcccg accgctgcgc cttatccggt     6660
aactatcgtc ttgagtccaa cccggtaaga cacgacttat cgccactggc agcagccact    6720
ggtaacagga ttagcagagc gaggtatgta ggcggtgcta cagagttctt gaagtggtgg    6780
cctaactacg gctacactag aaggacagta tttggtatct gcgctctgct gaagccagtt    6840
accttcggaa aaagagttgg tagctcttga tccggcaaac aaaccaccgc tggtagcggt    6900 ggttttttg tttgcaagca gcagattacg cgcagaaaaa aaggatctca agaagatcct     6960
ttgatctttt ctacggggtc tgacgctcag tggaacgaaa actcacgtta agggattttg    7020
gtcatgagat tatcaaaaag gatcttcacc tagatccttt taaattaaaa atgaagtttt    7080
aaatcaatct aaagtatata tgagtaaact tggtctgaca gttaccaatg cttaatcagt    7140
```

-continued

```
gaggcaccta tctcagcgat ctgtctattt cgttcatcca tagttgcctg actcccgtc    7200 gtgtagataa ctacgatacg ggagggctta ccatctggcc ccagtgctgc aatgataccg    7260
cgagacccac gctcaccggc tccagattta tcagcaataa accagccagc cggaagggcc    7320
gagcgcagaa gtggtcctgc aactttatcc gcctccatcc agtctattaa ttgttgccgg    7380
gaagctagag taagtagttc gccagttaat agtttgcgca acgttgttgc cattgctaca    7440
ggcatcgtgg tgtcacgctc gtcgtttggt atggcttcat tcagctccgg ttcccaacga    7500
tcaaggcgag ttacatgatc ccccatgttg tgcaaaaaag cggttagctc cttcggtcct    7560
ccgatcgttg tcagaagtaa gttggccgca gtgttatcac tcatggttat ggcagcactg    7620
cataattctc ttactgtcat gccatccgta agatgctttt ctgtgactgg tgagtactca    7680
accaagtcat tctgagaata gtgtatgcgg cgaccgagtt gctcttgccc ggcgtcaata    7740
cgggataata ccgcgccaca tagcagaact ttaaaagtgc tcatcattgg aaaacgttct    7800
tcggggcgaa aactctcaag gatcttaccg ctgttgagat ccagttcgat gtaacccact    7860
cgtgcaccca actgatcttc agcatctttt actttcacca gcgtttctgg gtgagcaaaa    7920
acaggaaggc aaaatgccgc aaaaaaggga ataaggcga cacggaaatg ttgaatactc    7980
atactcttcc ttttcaata ttattgaagc atttatcagg gttattgtct catgagcgga    8040
tacatatttg aatgtattta gaaaaataaa caaataggggg ttccgcgcac atttccccga    8100
aaagtgccac ctgggtcctt ttcatcacgt gctataaaaa taattataat ttaaatttt    8160 taatataaat atataaatta aaaatagaaa gtaaaaaaag aaattaaaga aaaaatagtt    8220
tttgttttcc gaagatgtaa aagactctag ggggatcgcc aacaaatact acctttatc    8280 ttgctcttcc tgctctcagg tattaatgcc gaattgtttc atcttgtctg tgtagaagac    8340
cacacacgaa atcctgtga ttttacattt tacttatcgt taatcgaatg tatatctatt    8400
taatctgctt tcttgtcta ataaatatat atgtaaagta cgcttttgt tgaaattttt    8460 taaacctttg tttattttt tttcttcatt ccgtaactct tctaccttct ttatttactt    8520
tctaaaatcc aaatacaaaa cataaaaata aataaacaca gagtaaattc ccaaattatt    8580
ccatcattaa aagatacgag cgcgtgtaa gttacaggca agcgatccgt cctaagaaac    8640
cattattatc atgacattaa cctataaaaa taggcgtatc acgaggccct ttcgtc       8696
```

<210> SEQ ID NO 6
<211> LENGTH: 4322
<212> TYPE: DNA
<213> ORGANISM: Artificial Sequence
<220> FEATURE:
<223> OTHER INFORMATION: Codon Optimized

<400> SEQUENCE: 6

```
aggaaacgaa gataaatctc gagtttatca ttatcaatac tgccatttca aagaatacgt     60
aaataattaa tagtagtgat tttcctaact ttatttagtc aaaaaattag ccttttaatt    120
ctgctgtaac ccgtacatgc caaaataggg ggcgggttac acagaatata taacactgat    180
ggtgcttggg tgaacaggtt tattcctggc atccactaaa tataatggag cccgcttttt    240
aagctggcat ccagaaaaaa aaagaatccc agcaccaaaa tattgttttc ttcaccaacc    300
atcagttcat aggtccattc tcttagcgca actacagaga acagggcaca aacaggcaaa    360
aaacgggcac aacctcaatg gagtgatgca acctgcctgg agtaaatgat gacacaaggc    420
aattgaccca cgcatgtatc tatctcattt tcttacacct tctattacct tctgctctct    480
```

```
ctgatttgga aaaagctgaa aaaaaaggtt taaaccagtt ccctgaaatt attcccctac    540
ttgactaata agtatataaa gacggtaggt attgattgta attctgtaaa tctatttctt    600
aaacttctta aattctactt ttatagttag tctttttttt agttttaaaa caccaagaac    660
ttagtttcga cggatctaga actagtatgg gtaaaaacta taagtccttg gattcagtcg    720
ttgcctcaga tttcatcgca ttgggtatca cctcagaagt agcagaaaca ttacatggta    780
gattggcaga atcgtttgt aattatggtg ctgcaacccc tcaaacttgg atcaacatcg    840
ctaaccatat cttgtcacca gatttgcctt tctccttaca ccaaatgttg ttttatggtt    900
gctacaagga tttcggtcca gccccacctg cttggattcc agaccctgaa aaagtcaagt    960
caactaattt gggtgctttg ttggaaaaga gaggtaaaga attttttggt gtaaagtaca   1020
aagatccaat ttcttctttt tctcacttcc aagaattttc tgttagaaac cctgaagtct   1080
attggagaac agtattgatg gatgaaatga aaattagttt ctctaaggac ccagaatgta   1140
tcttgagaag agatgacatc aacaacccag gtggttctga atggttacct ggtggttact   1200
tgaactcagc taaaaattgc ttgaacgtaa actccaataa gaaattgaac gatactatga   1260
tcgtttggag agacgagggt aacgatgact tgccttttgaa taagttgaca ttagatcaat   1320
tgagaaagag agtttggttg gttggttatg cattggaaga aatgggttta gaaaaaggtt   1380
gtgcaatagc catcgatatg ccaatgcatg ttgatgctgt tgttatatat ttggccatag   1440
tattggctgg ttacgtagtt gtctctatag cagattcatt ttccgcccct gaaatctcaa   1500
ctagattgag attatccaaa gctaaggcaa ttttcacaca agatcacatc atcagaggta   1560
aaaagagaat accattgtat tcaagagtag ttgaagctaa atccccaatg gcaatagtta   1620
tcccttgtag tggttctaac attggtgcag aattgagaga tggtgacata tcttgggatt   1680 acttttaga aagagccaag gagtttaaaa actgcgagtt tactgccaga gaacaacctg   1740
ttgatgctta tactaacatc ttattctcca gtggtactac aggtgaacca aaagcaattc   1800
cttggacaca agccacccca ttgaaggctg ctgctgatgg ttggtctcat ttggatatta   1860
gaaaaggtga cgttatagta tggccaacta atttgggttg gatgatgggt ccttggttgg   1920
tttatgctag tttgttaaat ggtgcatcta ttgccttgta caacggtagt cctttagtct   1980
ctggtttcgc taaatttgtt caagatgcaa aggtcacaat gttgggtgtc gtaccatcta   2040
ttgtaagatc atgaaatcc acaaattgtg tttcaggtta cgattggtcc accataagat   2100
gcttttcttc atccggtgaa gcctctaatg tagacgaata tttgtggtta atgggtagag   2160
ctaactacaa gccagttata gaaatgtgtg gtggtacaga aatcggtggt gcttttctg   2220 ctggttcatt tttgcaagct caatctttaa gttcttttc atcccaatgt atgggttgca   2280
ccttgtacat attagataag aacgttaccc caatgcctaa aaataagcca ggtatcggtg   2340
aattggcatt aggtcctgtt atgtttggtg cctcaaaaac attgttaaac ggtaatcatc   2400
acgatgtcta tttcaagggt atgccaacct tgaatggtga agtattgaga agacatggtg   2460
acattttcga attgacctct aacggttact accatgcaca cggtagagcc gatgacacta   2520
tgaacatcgg tggtatcaaa attagttcta tcgaaatcga aagagtctgt aatgaagtag   2580 atgcagagt ttttgaaacc actgctattg gtgttccacc tttgggtggt ggtccagaac   2640
aattggtcat attttttcgta ttgaaggatt caaacgacac aaccattgat ttgaaccaat   2700
tgagattatc ctttaacttg ggttttgcaaa agaaattgaa cccattattc aaagttacta   2760
gagttgtccc attgtcatcc ttacctagaa ctgcaacaaa caagatcatg agaagagttt   2820
tgagacaaca attcagtcat ttcgaagaag gtagaggttc tttgttaaca tgtggtgacg   2880
```

```
ttgaagaaaa tccaggtcct atggcttcag aaaaggaaat aagaagagaa agattcttga    2940
acgtattccc aaagttagtt gaagaattga acgctagttt gttagcttat ggtatgccta    3000
aagaagcctg cgattggtat gctcactctt taaactacaa tactccaggt ggtaaattga    3060
atagaggttt gagtgtagtt gatacttatg ctatcttgtc taacaaaacc gttgaacaat    3120
taggtcaaga agaatacgaa aaggtcgcta tcttgggttg gtgtattgaa ttgttgcaag    3180 catactttt ggttgccgat gacatgatgg ataagtctat aacaagaaga ggtcaaccat    3240
gctggtacaa agttccagaa gttggtgaaa tagccataaa tgatgctttt atgttggaag    3300
ccgctatcta taaattgttg aagtcacatt tcagaaacga aaagtactac atcgatatta    3360
ccgaattatt ccacgaagtt actttccaaa cagaattggg tcaattgatg gatttgataa    3420
ctgcacctga agataaagtt gacttgtcaa agttttcctt gaagaaacat tcattcatcg    3480
tcacctttga aactgcttat tactccttct atttgccagt cgccttggct atgtacgtag    3540
ctggtattac tgatgaaaaa gacttgaagc aagcaagaga tgttttgata cctttggggtg    3600 aatacttcca atccaagat gactacttag actgtttcgg tactccagaa caaataggta    3660
aaatcggtac agatattcaa gacaataagt gcagttgggt tattaacaag ctttggaat    3720 tagcatctgc cgaacaaaga aagactttgg atgaaaacta cggtaaaaag gactcagttg    3780
ctgaagcaaa gtgtaagaaa atttttaatg atttgaagat tgaacaattg taccatgaat    3840
acgaagaatc catcgctaaa gacttaaagg caaagattag tcaagttgat gaatcaagag    3900
gttttaaagc cgacgttttg acagctttct tgaataaggt ctacaagaga tcaaaggatt    3960
acaaggatca tgacggtgac tataaagacc acgatattga ctacaaagat gacgatgaca    4020
agtaagtcga cctcgagtca tgtaattagt tatgtcacgc ttacattcac gccctccccc    4080
cacatccgct ctaaccgaaa aggaaggagt tagacaacct gaagtctagg tccctattta    4140
tttttttata gttatgttag tattaagaac gttattttata tttcaaattt ttcttttttt    4200
tctgtacaga cgcgtgtacg catgtaacat tatactgaaa accttgcttg agaaggtttt    4260
gggacgctcg aaggctttaa tttgcgtgac ataactaatt acatgacttg actgattttt    4320
cc                                                                  4322
```

<210> SEQ ID NO 7  
<211> LENGTH: 2522  
<212> TYPE: DNA  
<213> ORGANISM: Artificial Sequence  
<220> FEATURE:  
<223> OTHER INFORMATION: Codon Optimized

<400> SEQUENCE: 7

```
aggaaacgaa gataaatctc gagtttatca ttatcaatac tgccatttca aagaatacgt      60
aaataattaa tagtagtgat tttcctaact ttatttagtc aaaaaattag ccttttaatt     120
ctgctgtaac ccgtacatgc caaaataggg ggcgggttac acagaatata taacactgat     180
ggtgcttggg tgaacaggtt tattcctggc atccactaaa tataatggag cccgcttttt     240
aagctggcat ccagaaaaaa aagaatccc agcaccaaaa tattgttttc ttcaccaacc     300
atcagttcat aggtccattc tcttagcgca actacagaga cagggcaca aacaggcaaa     360 aaacgggcac aacctcaatg gagtgatgca acctgcctgg agtaaatgat gacacaaggc     420
aattgaccca cgcatgtatc tatctcattt tcttacacct tctattacct tctgctctct     480
ctgatttgga aaaagctgaa aaaaaaggtt taaaccagtt ccctgaaatt attcccctac     540
```

```
ttgactaata agtatataaa gacggtaggt attgattgta attctgtaaa tctatttctt       600
aaacttctta aattctactt ttatagttag tctttttttt agttttaaaa caccaagaac       660
ttagtttcga cggatctaga actagtatga accatttgag agccgaaggt cctgcctccg       720
tattagccat aggtacagcc aacccagaaa acatattgat ccaagatgaa tttcctgatt       780
attacttcag agttaccaag agtgaacaca tgactcaatt gaaggaaaag tttagaaaaa       840
tatgtgataa gtctatgatc agaaagagaa actgcttctt gaacgaagaa catttgaagc       900
aaaatccaag attggtagaa cacgaaatgc aaacattgga tgccagacaa gacatgttag       960
ttgtcgaagt tcctaaattg ggtaaagatg cttgtgcaaa agccattaag gaatggggtc      1020
aaccaaagtc aaagatcact catttgattt ttacaagtgc atctactaca gatatgcctg      1080
gtgcagacta ccactgtgcc aaattgttag gtttgtcacc atccgttaag agagtcatga      1140
tgtatcaatt aggttgctac ggtggtggta ctgttttgag aatcgctaag gatattgcag      1200
aaaacaacaa gggtgccaga gtattagctg tttgttgcga cattatggct tgcttgttta      1260
gaggtccaag tgattctgac ttggaattgt tagttggtca agctatcttc ggtgacggtg      1320
ctgctgctgt tattgttggt gcagaacctg acgaatctgt tggtgaaaga ccaatatttg      1380
aattagtcag tacaggtcaa accatcttgc ctaattctga aggtacaatt ggtggtcata      1440
taagagaagc aggtttgatc ttcgatttgc acaaagacgt tccaatgtta atctctaaca      1500
acatagaaaa gtgtttgata gaagcattca ctcctatagg tatctcagat tggaactcta      1560 tttttctggat aacacatcca ggtggtaaag ccatttgga taaggttgaa gaaaaattgg      1620
atttgaagaa agaaaagttt gtagatagta gacatgtttt atctgaacac ggtaacatgt      1680
cttcatccac tgtcttgttc gtaatggatg aattgagaaa gagatcatta aagagggta      1740 aatctactac tggtgacggt tttgaatggg gtgtcttatt tggtttcggt cctggtttga      1800
ccgtcgaaag agtagttgtc agatcagtac caattaaata tgaaggtaga ggttccttgt      1860
taacttgtgg tgacgttgaa gaaaacccag gtcctatggc cgtcaagcat ttgatagtat      1920
tgaagtttaa agatgaaatc acagaagctc aaaaggaaga attttttcaag acctacgtta      1980 atttggtcaa cattataccct gctatgaaag atgtatactg gggtaaagac gttacacaaa      2040
agaaagaaga aggttataca cacattgtcg aagtaaccct cgaatcagtt gaaactatcc      2100
aagattacat cattcatcca gctcacgttg gtttttggtga cgtttacaga tccttctggg      2160
aaaaattgtt gatcttcgat tacacccccaa gaaagtaccc ttacgatgtt ccagactatg      2220
cataagtcga cctcgagtca tgtaattagt tatgtcacgc ttacattcac gccctccccc      2280
cacatccgct ctaaccgaaa aggaaggagt tagacaacct gaagtctagg tccctattta      2340
tttttttata gttatgttag tattaagaac gttatttata tttcaaattt ttctttttttt      2400 tctgtacaga cgcgtgtacg catgtaacat tatactgaaa accttgcttg agaaggtttt      2460
gggacgctcg aaggctttaa tttgcgtgac ataactaatt acatgacttg actgattttt      2520
cc                                                                     2522
```

<210> SEQ ID NO 8
<211> LENGTH: 3887
<212> TYPE: DNA
<213> ORGANISM: Artificial Sequence
<220> FEATURE:
<223> OTHER INFORMATION: Codon Optimized

<400> SEQUENCE: 8

```
aggaaacgaa gataaatctc gagtttatca ttatcaatac tgccatttca aagaatacgt        60
```

```
aaataattaa tagtagtgat tttcctaact ttatttagtc aaaaaattag cctttttaatt    120 ctgctgtaac ccgtacatgc caaaatagqq qqcqqqttac acagaatata taacactgat    180
ggtgcttggg tgaacaggtt tattcctggc atccactaaa tataatggag cccgcttttt    240
aagctggcat ccagaaaaaa aaagaatccc agcaccaaaa tattgttttc ttcaccaacc    300
atcagttcat aggtccattc tcttagcgca actacagaga acagggcaca aacaggcaaa    360
aaacgggcac aacctcaatg gagtgatgca acctgcctgg agtaaatgat gacacaaggc    420
aattgaccca cgcatgtatc tatctcattt tcttacacct tctattacct tctgctctct    480
ctgatttgga aaaagctgaa aaaaaaggtt taaaccagtt ccctgaaatt attcccctac    540
ttgactaata agtatataaa gacggtaggt attgattgta attctgtaaa tctatttctt    600
aaacttctta aattctactt ttatagttag tcttttttttt agttttaaaa caccaagaac    660
ttagtttcga cggatctaga actagtatgg gtttatcatc cgtctgtact ttctccttcc    720
aaactaacta tcataccttg ttgaatcctc acaacaacaa tccaaaaaca tcattgttgt    780
gttacagaca tccaaagaca cctattaagt actcttacaa caacttttcca tcaaaacatt    840 gttcaaccaa gtccttccac ttacaaaata agtgctccga aagtttgtct atagctaaga    900
actctatcag agctgcaact acaaatcaaa ctgaaccacc tgaaagtgat aatcactctg    960
ttgccacaaa aattttgaac ttcggtaaag catgttggaa gttgcaaaga ccatacacca   1020
taatcgcttt tacttcttgt gcatgcggtt tattcggtaa agaattgttg cataacacta   1080
acttaatttc atggtccttg atgttcaagg catttttctt tttagttgcc atcttgtgca   1140
tcgcttcatt caccactaca attaatcaaa tatacgattt gcacatcgac agaattaaca   1200
aaccagattt gcctttggct tcaggtgaaa tatccgtcaa tactgcatgg atcatgtcta   1260
tcatagtagc cttgttcggt ttgatcatca caattaaaat gaagggtggt ccattgtaca   1320
tcttcggtta ctgtttcggt atcttcggtg gtattgtcta ttccgtacca cctttttagat   1380 ggaaacaaaa ccctagtact gccttttttgt tgaatttctt agctcatatc atcacaaact   1440
tcaccttcta ctacgcttca agagctgctt taggtttgcc attcgaattg agaccttcat   1500
tcacattttt gttggcattc atgaaaagta tgggttctgc attagccttg atcaaggatg   1560
cctctgacgt tgaaggtgac acaaagttcg gtattagtac cttggcttct aagtacggtt   1620
caagaaattt gactttgttc tgctccggta tcgttttgtt aagttacgtc gcagccattt   1680
tggcaggtat catttggcca caagccttta attctaacgt tatgttgttg tcacatgcca   1740
tcttggcttt ctggttgatc ttgcaaacta gagatttcgc tttgacaaat tatgaccctg   1800
aagcaggtag aagattctac gagtttatgt ggaaattgta ctacgctgaa tatttggtat   1860
acgtttttat tgaaggtaga ggttcttttgt tgacctgtgg tgacgttgaa gaaaatccag   1920
gtcctatgaa atgttcaact ttctcctttt ggttcgtatg caagatcatc ttcttttcct   1980
tttcctttaa catccaaaca agtatcgcaa acccaagaga aaacttttg aagtgcttct   2040 cacaatacat acctaataac gccaccaatt tgaagttggt ttacactcaa aacaacccat   2100
tgtacacgtc cgtcttgaac agtacaatcc ataatttgag attcacttct gataccactc   2160
caaaaccttt ggtcattgta acccctagtc atgtatctca catccaaggt actatcttat   2220
gttctaaaaa ggttggtttg caaattagaa ctagatccgg tggtcatgat agtgaaggca   2280
tgtcatacat ctcccaagtt ccattcgtta tcgttgattt gagaaacatg agatcaatta   2340
aaatagacgt acactcacaa actgcttggg ttgaagctgg tgcaacattg ggtgaagtat   2400
```

| | |
|---|---:|
| actactgggt taacgaaaag aatgaaaact tatcattggc tgctggttac tgtccaacag | 2460 |
| tttgcgcagg tggtcatttt ggtggtggtg gttatggtcc tttaatgaga aactacggtt | 2520 |
| tggccgctga taacataatc gacgctcatt tggtaaatgt tcacggtaaa gttttggata | 2580 |
| gaaagtctat gggtgaagac ttattttggg ctttgagagg tggtggtgca gaatcattcg | 2640 |
| gtatcatagt tgcttggaag ataagattag tcgcagtacc aaagtctact atgttctcag | 2700 |
| tcaaaaagat aatggaaatc catgaattag ttaaattggt caataagtgg caaaacatcg | 2760 |
| catacaagta cgataaggac ttgttgttga tgactcattt catcacaaga aacatcaccg | 2820 |
| ataaccaagg taaaaataag actgctatcc acacatactt tcttcagtt ttcttgggtg | 2880 |
| gtgtcgattc cttagtagac ttgatgaata agtcttttcc agaattaggt attaagaaaa | 2940 |
| ctgattgtag acaattgtct tggatcgaca ccatcatctt ttattcaggt gttgtcaact | 3000 |
| acgatacaga caacttcaac aaagaaatat tattggatag atccgcaggt caaaacggtg | 3060 |
| cctttaaaat taagtttagac tacgttaaaa agccaatacc tgaatcagtt ttcgtccaaa | 3120 |
| tcttagaaaa attgtacgaa gaagatattg gtgcaggcat gtacgccttg tatccatacg | 3180 |
| gtggtataat ggacgaaatc agtgaatctg ccattccatt tcctcataga gctggtatct | 3240 |
| tatacgaatt gtggtacatt tgttcatggg aaaagcaaga agataacgaa aagcacttaa | 3300 |
| actggattag aaacatctat aacttcatga ctccatacgt ttctaaaaac cctagattgg | 3360 |
| catatttgaa ctacagagat ttggacatcg gtattaacga tccaagaat cctaacaact | 3420 |
| atacccaagc tagaatttgg ggtgaaaaat acttcggtaa aaatttcgat agattagtaa | 3480 |
| aggttaagac attggttgac ccaaacaact tctttagaaa cgaacaatcc attccacctt | 3540 |
| tacctagaca tagacacgaa caaaaattaa taagtgaaga gatttgtaa gtcgacctcg | 3600 |
| agtcatgtaa ttagttatgt cacgcttaca ttcacgccct ccccccacat ccgctctaac | 3660 |
| cgaaaggaa ggagttagac aacctgaagt ctaggtccct atttattttt ttatagttat | 3720 |
| gttagtatta agaacgttat ttatatttca aatttttctt ttttttctgt acagacgcgt | 3780 |
| gtacgcatgt aacattatac tgaaaacctt gcttgagaag gttttgggac gctcgaaggc | 3840 |
| tttaatttgc gtgacataac taattacatg acttgactga ttttcc | 3887 |

<210> SEQ ID NO 9
<211> LENGTH: 8963
<212> TYPE: DNA
<213> ORGANISM: Artificial Sequence
<220> FEATURE:
<223> OTHER INFORMATION: Codon Optimized

<400> SEQUENCE: 9

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accataaacg acattactat atatataata taggaagcat ttaatagaca gcatcgtaat | 240 |
| atatgtgtac tttgcagtta tgacgccaga tggcagtagt ggaagatatt ctttattgaa | 300 |
| aaatagcttg tcaccttacg tacaatcttg atccggagct tttcttttt tgccgattaa | 360 |
| gaattaattc ggtcgaaaaa agaaaaggag agggccaaga gggagggcat tggtgactat | 420 |
| tgagcacgtg agtatacgtg attaagcaca caaaggcagc ttggagtatg tctgttatta | 480 |
| atttcacagg tagttctggt ccattggtga agtttgcgg cttgcagagc acagaggccg | 540 |
| cagaatgtgc tctagattcc gatgctgact tgctgggtat tatatgtgtg cccaatagaa | 600 |

```
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat tttttaacca ataggccgaa   1320
atcggcaaaa tcccttataa atcaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt ttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact ataggggcgaa ttgggtaccg gccgcaaatt aaagccttcg   1920
agcgtcccaa aaccttctca agcaaggttt tcagtataat gttacatgcg tacacgcgtc   1980
tgtacagaaa aaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacttacttg tcatcgtcat ctttgtagtc aatatcgtgg tctttatagt caccgtcatg   2220
atccttgtaa tcctttgatc tcttgtagac cttattcaag aaagctgtca aaacgtcggc   2280
tttaaaacct cttgattcat caacttgact aatctttgcc tttaagtctt tagcgatgga   2340
ttcttcgtat tcatggtaca attgttcaat cttcaaatca ttaaaatttt cttacacttt   2400
tgcttcagca actgagtcct ttttaccgta gttttcatcc aaagtctttc tttgttcggc   2460
agatgctaat tccaaagcct tgttaataac ccaactgcac ttattgtctt gaatatctgt   2520
accgatttta cctatttgtt ctggagtacc gaaacagtct aagtagtcat cttggatttg   2580
gaagtattca cccaaaggta tcaaaacatc tcttgcttgc ttcaagtctt tttcatcagt   2640
aataccagct acgtacatag ccaaggcgac tggcaaatag aaggagtaat aagcagtttc   2700
aaaggtgacg atgaatgaat gtttcttcaa ggaaaacttt gacaagtcaa ctttatcttc   2760
aggtgcagtt atcaaatcca tcaattgacc caattctgtt tggaaagtaa cttcgtggaa   2820
taattcggta atatcgatgt agtacttttc gtttctgaaa tgtgacttca acaatttata   2880
gatagcggct tccaacataa aagcatcatt tatggctatt tcaccaactt ctggaacttt   2940
```

```
gtaccagcat ggttgacctc ttcttgttat agacttatcc atcatgtcat cggcaaccaa      3000
aaagtatgct tgcaacaatt caatacacca acccaagata gcgacctttt cgtattcttc      3060
ttgacctaat tgttcaacgg ttttgttaga caagatagca taagtatcaa ctacactcaa      3120
acctctattc aatttaccac ctggagtatt gtagtttaaa gagtgagcat accaatcgca      3180
ggcttcttta ggcataccat aagctaacaa actagcgttc aattcttcaa ctaactttgg      3240
gaatacgttc aagaatcttt ctcttcttat ttccttttct gaagccatag gacctggatt      3300
ttcttcaacg tcaccacatg ttaacaaaga acctctacct tcttcgaaat gactgaattg      3360
ttgtctcaaa actcttctca tgatcttgtt tgttgcagtt ctaggtaagg atgacaatgg      3420
gacaactcta gtaactttga ataatgggtt caatttcttt tgcaaaccca agttaaagga      3480
taatctcaat tggttcaaat caatggttgt gtcgtttgaa tccttcaata cgaaaaatat      3540
gaccaattgt tctggaccac acccaaagg tggaacacca atagcagtgg tttcaaaaac       3600
tctgtcatct acttcattac agactctttc gatttcgata gaactaattt tgataccacc      3660
gatgttcata gtgtcatcgg ctctaccgtg tgcatggtag taaccgttag aggtcaattc      3720
gaaaatgtca ccatgtcttc tcaatacttc accattcaag gttggcatac ccttgaaata      3780
gacatcgtga tgattaccgt ttaacaatgt ttttgaggca ccaaacataa caggacctaa      3840
tgccaattca ccgatacctg gcttatttt aggcattggg taaccgttct tatctaatat       3900
gtacaaggtg caacccatac attgggatga aaagaactt aaagattgag cttgcaaaaa       3960
tgaaccagca gaaaagcac caccgatttc tgtaccacca cacatttcta taactggctt      4020
gtagttagct ctacccatta accacaaata ttcgtctaca ttagaggctt caccggatga      4080
agaaaagcat cttatggtgg accaatcgta acctgaaaca caatttgtgg atttccatga      4140
tcttacaata gatggtacga cacccaacat tgtgaccttt gcatcttgaa caaatttagc      4200
gaaaccagag actaaaggac taccgttgta caaggcaata gatgcaccat ttaacaaact      4260
agcataaacc aaccaaggac ccatcatcca acccaaatta gttggccata ctataacgtc      4320
acctttccta atatccaaat gagaccaacc atcagcagca gccttcaatg gggtggcttg      4380
tgtccaagga attgcttttg gttcacctgt agtaccactg gagaataaga tgttagtata      4440
agcatcaaca ggttgttctc tggcagtaaa ctcgcagttt ttaaactcct ggctctttc       4500 taaaaagtaa tcccaagata tgtcaccatc tctcaattct gcaccaatgt tagaaccact      4560
acaagggata actattgcca ttggggattt agcttcaact actcttgaat acaatggtat      4620
tctcttttta cctctgatga tgtgatcttg tgtgaaaatt gccttagctt tggataatct      4680
caatctagtt gagatttcag gggcggaaaa tgaatctgct atagagacaa ctacgtaacc      4740
agccaatact atggccaaat atataacaac agcatcaaca tgcattggca tatcgatggc      4800
tattgcacaa cctttttcta aacccatttc ttccaatgca taaccaacca accaaactct      4860
ctttctcaat tgatctaatg tcaacttatt caaaggcaag tcatcgttac cctcgtctct      4920
ccaaacgatc atagtatcgt tcaatttctt attggagttt acgttcaagc aatttttagc      4980
tgagttcaag taaccaccag gtaaccattc agaaccacct gggttgttga tgtcatctct      5040
tctcaagata cattctgggt ccttagagaa actaattttc atttcatcca tcaatactgt      5100
tctccaatag acttcagggt ttctaacaga aaattcttgg aagtgagaaa agaagaaat       5160 tggatctttg tactttacac ccaaaaattc tttacctctc ttttccaaca aagcacccaa      5220
attagttgac ttgactttt cagggtctgg aatccaagca ggtggggctg gaccgaaatc       5280
cttgtagcaa ccataaaaca acatttggtg taaggagaaa ggcaaatctg gtgacaagat      5340
```

```
atggttagcg atgttgatcc aagtttgagg ggttgcagca ccataattac aaacgatttc    5400
tgccaatcta ccatgtaatg tttctgctac ttctgaggtg atacccaatg cgatgaaatc    5460
tgaggcaacg actgaatcca aggacttata gttttttaccc atactagttc tagatccgtc    5520
gaaactaagt tcttggtgtt ttaaaactaa aaaaaagact aactataaaa gtagaattta    5580
agaagtttaa gaaatagatt tacagaatta caatcaatac ctaccgtctt tatatactta    5640
ttagtcaagt aggggaataa tttcagggaa ctggtttaaa ccttttttt cagcttttc    5700 caaatcagag agagcagaag gtaatagaag gtgtaagaaa atgagataga tacatgcgtg    5760
ggtcaattgc cttgtgtcat catttactcc aggcaggttg catcactcca ttgaggttgt    5820
gcccgttttt tgcctgtttg tgccctgttc tctgtagttg cgctaagaga atggacctat    5880
gaactgatgt ttggtgaaga aaacaatatt ttggtgctgg gattcttttt ttttctggat    5940
gccagcttaa aaagcgggct ccattatatt tagtggatgc caggaataaa cctgttcacc    6000
caagcaccat cagtgttata tattctgtgt aacccgcccc ctattttggc atgtacgggt    6060
tacagcagaa ttaaaaggct aattttttga ctaaataaag ttaggaaaat cactactatt    6120
aattatttac gtattctttg aaatggcagt attgataatg ataaactcga gagctccagc    6180
ttttgttccc tttagtgagg gttaattgcg cgcttggcgt aatcatggtc atagctgttt    6240
cctgtgtgaa attgttatcc gctcacaatt ccacacaaca taggagccgg aagcataaag    6300
tgtaaagcct ggggtgccta atgagtgagg taactcacat taattgcgtt gcgctcactg    6360
cccgctttcc agtcgggaaa cctgtcgtgc cagctgcatt aatgaatcgg ccaacgcgcg    6420
gggagaggcg gtttgcgtat tgggcgctct tccgcttcct cgctcactga ctcgctgcgc    6480
tcggtcgttc ggctgcggcg agcggtatca gctcactcaa aggcggtaat acggttatcc    6540
acagaatcag gggataacgc aggaaagaac atgtgagcaa aaggccagca aaaggccagg    6600
aaccgtaaaa aggccgcgtt gctggcgttt ttccataggc tccgcccccc tgacgagcat    6660
cacaaaaatc gacgctcaag tcagaggtgg cgaaacccga caggactata aagataccag    6720
gcgtttcccc ctggaagctc cctcgtgcgc tctcctgttc cgaccctgcc gcttaccgga    6780
tacctgtccg cctttctccc ttcgggaagc gtggcgcttt ctcatagctc acgctgtagg    6840
tatctcagtt cggtgtaggt cgttcgctcc aagctgggct gtgtgcacga accccccgtt    6900
cagcccgacc gctgcgcctt atccggtaac tatcgtcttg agtccaaccc ggtaagacac    6960
gacttatcgc cactggcagc agccactggt aacaggatta gcagagcgag gtatgtaggc    7020
ggtgctacag agttcttgaa gtggtggcct aactacggct acactagaag gacagtattt    7080
ggtatctgcg ctctgctgaa gccagttacc ttcggaaaaa gagttggtag ctcttgatcc    7140
ggcaaacaaa ccaccgctgg tagcggtggt ttttttgttt gcaagcagca gattacgcgc    7200
agaaaaaaag gatctcaaga agatcctttg atcttttcta cggggtctga cgctcagtgg    7260
aacgaaaact cacgttaagg gattttggtc atgagattat caaaaaggat cttcacctag    7320
atcctttaaa attaaaaatg aagttttaaa tcaatctaaa gtatatatga gtaaacttgg    7380
tctgacagtt accaatgctt aatcagtgag gcacctatct cagcgatctg tctatttcgt    7440
tcatccatag ttgcctgact ccccgtcgtg tagataacta cgatacggga gggcttacca    7500
tctggcccca gtgctgcaat gataccgcga gacccacgct caccggctcc agatttatca    7560
gcaataaacc agccagccgg aagggccgag cgcagaagtg gtcctgcaac tttatccgcc    7620
tccatccagt ctattaattg ttgccgggaa gctagagtaa gtagttcgcc agttaatagt    7680
```

```
ttgcgcaacg ttgttgccat tgctacaggc atcgtggtgt cacgctcgtc gtttggtatg      7740
gcttcattca gctccggttc ccaacgatca aggcgagtta catgatcccc catgttgtgc      7800
aaaaaagcgg ttagctcctt cggtcctccg atcgttgtca gaagtaagtt ggccgcagtg      7860
ttatcactca tggttatggc agcactgcat aattctctta ctgtcatgcc atccgtaaga      7920
tgcttttctg tgactggtga gtactcaacc aagtcattct gagaatagtg tatgcggcga      7980
ccgagttgct cttgcccggc gtcaatacgg gataataccg cgccacatag cagaacttta      8040
aaagtgctca tcattggaaa acgttcttcg gggcgaaaac tctcaaggat cttaccgctg      8100
ttgagatcca gttcgatgta acccactcgt gcacccaact gatcttcagc atcttttact      8160
ttcaccagcg tttctgggtg agcaaaaaca ggaaggcaaa atgccgcaaa aagggaata       8220 agggcgacac ggaaatgttg aatactcata ctcttccttt tcaatatta ttgaagcatt       8280 tatcagggtt attgtctcat gagcggatac atatttgaat gtatttagaa aaataaacaa      8340 atagggttc cgcgcacatt tccccgaaaa gtgccacctg gtccttttc atcacgtgct        8400 ataaaataa ttataattta aattttttaa tataaatata taaattaaaa atagaaagta       8460 aaaaagaaa ttaaagaaaa aatagttttt gttttccgaa gatgtaaaag actctagggg      8520
gatcgccaac aaatactacc ttttatcttg ctcttcctgc tctcaggtat taatgccgaa      8580
ttgtttcatc ttgtctgtgt agaagaccac acacgaaaat cctgtgattt tacattttac     8640
ttatcgttaa tcgaatgtat atctatttaa tctgcttttc ttgtctaata aatatatatg     8700
taaagtacgc ttttgttga aatttttaa acctttgttt atttttttt cttcattccg        8760 taactcttct accttcttta tttacttct aaaatccaa tacaaaacat aaaatataat        8820
aaacacagag taaattccca aattattcca tcattaaaag atacgaggcg cgtgtaagtt     8880
acaggcaagc gatccgtcct aagaaaccat tattatcatg acattaacct ataaaaatag     8940
gcgtatcacg aggcccttc gtc                                              8963
```

<210> SEQ ID NO 10
<211> LENGTH: 7163
<212> TYPE: DNA
<213> ORGANISM: Artificial Sequence
<220> FEATURE:
<223> OTHER INFORMATION: Codon Optimized

<400> SEQUENCE: 10

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
accataaacg acattactat atatataata taggaagcat ttaatagaca gcatcgtaat      240
atatgtgtac tttgcagtta tgacgccaga tggcagtagt ggaagatatt ctttattgaa      300
aaatagcttg tcaccttacg tacaatcttg atccggagct tttctttttt tgccgattaa      360
gaattaattc ggtcgaaaaa agaaaaggag agggccaaga gggagggcat tggtgactat      420
tgagcacgtg agtatacgtg attaagcaca caaaggcagc ttggagtatg tctgttatta     480
atttcacagg tagttctggt ccattggtga agtttgcgg cttgcagagc acagaggccg       540
cagaatgtgc tctagattcc gatgctgact tgctgggtat tatatgtgtg cccaatagaa       600
agagaacaat tgacccggtt attgcaagga aaatttcaag tcttgtaaaa gcatataaaa      660
atagttcagg cactccgaaa tacttggttg gcgtgtttcg taatcaacct aaggaggatg      720
ttttggctct ggtcaatgat tacggcattg atatcgtcca actgcatgga gatgagtcgt      780
```

```
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagcccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg ggaagggcga   1740
tcggtgcggg cctcttcgct attacgccag ctggcgaaag ggggatgtgc tgcaaggcga   1800
ttaagttggg taacgccagg ttttcccag tcacgacgtt gtaaaacgac ggccagtgag   1860
cgcgcgtaat acgactcact ataggggcgaa ttgggtaccg gccgcaaatt aaagccttcg   1920
agcgtcccaa aaccttctca agcaaggttt tcagtataat gttacatgcg tacacgcgtc   1980
tgtacagaaa aaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgaggtc   2160
gacttatgca tagtctggaa catcgtaagg gtactttctt ggggtgtaat cgaagatcaa   2220 caattttttcc cagaaggatc tgtaaacgtc accaaaacca acgtgagctg gatgaatgat   2280
gtaatcttgg atagtttcaa ctgattcgaa ggttacttcg acaatgtgtg tataaccttc   2340 ttctttctttt tgtgtaacgt ctttacccca gtatacatct ttcatagcag gtataatgtt   2400
gaccaaatta acgtaggtct tgaaaaattc ttccttttga gcttctgtga tttcatcttt   2460
aaacttcaat actatcaaat gcttgacggc cataggacct gggttttctt caacgtcacc   2520
acaagttaac aaggaacctc taccttcata tttaattggt actgatctga caactactct   2580
ttcgacggtc aaaccaggac cgaaaccaaa taagacaccc cattcaaaac cgtcaccagt   2640
agtagattta ccctcttcta atgatctctt tctcaattca tccattacga acaagacagt   2700
ggatgaagac atgttaccgt gttcagataa aacatgtcta ctatctacaa acttttcttt   2760
cttcaaatcc aattttcct caaccttatc caaaatggct ttaccacctg gatgtgttat   2820
ccagaaaata gagttccaat ctgagatacc tataggagtg aatgcttcta tcaaacactt   2880
ttctatgttg ttagagatta acattggaac gtctttgtgc aaatcgaaga tcaaacctgc   2940
ttctcttata tgaccaccaa ttgtaccttc agaattaggc aagatggttt gacctgtact   3000
gactaattca aatattggtc tttcaccaac agattcgtca ggttctgcac caacaataac   3060
agcagcagca ccgtcaccga agatagcttg accaactaac aattccaagt cagatcact   3120
```

```
tggacctcta aacaagcaag ccataatgtc gcaacaaaca gctaatactc tggcacccectt    3180 gttgttttct gcaatatcct tagcgattct caaaacagta ccaccaccgt agcaacctaa    3240
ttgatacatc atgactctct taacggatgg tgacaaacct aacaatttgg cacagtggta    3300
gtctgcacca ggcatatctg tagtagatgc acttgtaaaa atcaaatgag tgatctttga    3360
ctttggttga ccccattcct taatggcttt tgcacaagca tctttaccca atttaggaac    3420
ttcgacaact aacatgtctt gtctggcatc caatgtttgc atttcgtgtt ctaccaatct    3480
tggattttgc ttcaaatgtt cttcgttcaa gaagcagttt ctctttctga tcatagactt    3540
atcacatatt tttctaaact tttccttcaa ttgagtcatg tgttcactct tggtaactct    3600
gaagtaataa tcaggaaatt catcttggat caatatgttt tctgggttgg ctgtacctat    3660
ggctaatacg gaggcaggac cttcggctct caaatggttc atactagttc tagatccgtc    3720
gaaactaagt tcttggtgtt ttaaaactaa aaaaaagact aactataaaa gtagaattta    3780
agaagtttaa gaaatagatt tacagaatta caatcaatac ctaccgtctt tatatactta    3840
ttagtcaagt aggggaataa tttcagggaa ctggtttaaa ccttttttt cagcttttc      3900 caaatcagag agagcagaag gtaatagaag gtgtaagaaa atgagataga tacatgcgtg    3960
ggtcaattgc cttgtgtcat catttactcc aggcaggttg catcactcca ttgaggttgt    4020
gcccgttttt tgcctgtttg tgccctgttc tctgtagttg cgctaagaga atggacctat    4080
gaactgatgg ttggtgaaga aaacaatatt ttggtgctgg gattctttt ttttctggat      4140 gccagcttaa aaagcgggct ccattatatt tagtggatgc caggaataaa cctgttcacc    4200
caagcaccat cagtgttata tattctgtgt aacccgcccc ctattttggc atgtacgggt    4260
tacagcagaa ttaaaaggct aattttttga ctaaataaag ttaggaaaat cactactatt    4320
aattatttac gtattctttg aaatggcagt attgataatg ataaactcga gagctccagc    4380
ttttgttccc tttagtgagg gttaattgcg cgcttggcgt aatcatggtc atagctgttt    4440
cctgtgtgaa attgttatcc gctcacaatt ccacacaaca taggagccgg aagcataaag    4500
tgtaaagcct ggggtgccta atgagtgagg taactcacat taattgcgtt gcgctcactg    4560 cccgcttttcc agtcgggaaa cctgtcgtgc cagctgcatt aatgaatcgg ccaacgcgcg    4620
gggagaggcg gtttgcgtat tgggcgctct tccgcttcct cgctcactga ctcgctgcgc    4680
tcggtcgttc ggctgcggcg agcggtatca gctcactcaa aggcggtaat acggttatcc    4740
acagaatcag gggataacgc aggaaagaac atgtgagcaa aaggccagca aaaggccagg    4800
aaccgtaaaa aggccgcgtt gctggcgttt ttccataggc tccgcccccc tgacgagcat    4860
cacaaaaatc gacgctcaag tcagaggtgg cgaaacccga caggactata agataccag     4920 gcgtttcccc ctggaagctc cctcgtgcgc tctcctgttc cgaccctgcc gcttaccgga    4980
tacctgtccg cctttctccc ttcgggaagc gtggcgcttt ctcatagctc acgctgtagg    5040
tatctcagtt cggtgtaggt cgttcgctcc aagctgggct gtgtgcacga accccccgtt    5100
cagcccgacc gctgcgcctt atccggtaac tatcgtcttg agtccaaccc ggtaagacac    5160
gacttatcgc cactggcagc agccactggt aacaggatta gcagagcgag gtatgtaggc    5220
ggtgctacag agttcttgaa gtggtggcct aactacggct acactagaag gacagtattt    5280
ggtatctgcg ctctgctgaa gccagttacc ttcggaaaaa gagttggtag ctcttgatcc    5340
ggcaaacaaa ccaccgctgg tagcggtggt ttttttgttt gcaagcagca gattacgcgc    5400
agaaaaaaag gatctcaaga agatcctttg atcttttcta cggggtctga cgctcagtgg    5460
aacgaaaact cacgttaagg gattttggtc atgagattat caaaaaggat cttcacctag    5520
```

| | | | | |
|---|---|---|---|---|
| atcctttaa | attaaaaatg | aagttttaaa | tcaatctaaa | gtatatatga | gtaaacttgg | 5580 |
| tctgacagtt | accaatgctt | aatcagtgag | gcacctatct | cagcgatctg | tctatttcgt | 5640 |
| tcatccatag | ttgcctgact | ccccgtcgtg | tagataacta | cgatacggga | gggcttacca | 5700 |
| tctggcccca | gtgctgcaat | gataccgcga | gacccacgct | caccggctcc | agatttatca | 5760 |
| gcaataaacc | agccagccgg | aagggccgag | cgcagaagtg | gtcctgcaac | tttatccgcc | 5820 |
| tccatccagt | ctattaattg | ttgccgggaa | gctagagtaa | gtagttcgcc | agttaatagt | 5880 |
| ttgcgcaacg | ttgttgccat | tgctacaggc | atcgtggtgt | cacgctcgtc | gtttggtatg | 5940 |
| gcttcattca | gctccggttc | ccaacgatca | aggcgagtta | catgatcccc | catgttgtgc | 6000 |
| aaaaaagcgg | ttagctcctt | cggtcctccg | atcgttgtca | gaagtaagtt | ggccgcagtg | 6060 |
| ttatcactca | tggttatggc | agcactgcat | aattctctta | ctgtcatgcc | atccgtaaga | 6120 |
| tgcttttctg | tgactggtga | gtactcaacc | aagtcattct | gagaatagtg | tatgcggcga | 6180 |
| ccgagttgct | cttgcccggc | gtcaatacgg | gataataccg | cgccacatag | cagaacttta | 6240 |
| aaagtgctca | tcattggaaa | acgttcttcg | gggcgaaaac | tctcaaggat | cttaccgctg | 6300 |
| ttgagatcca | gttcgatgta | acccactcgt | gcacccaact | gatcttcagc | atcttttact | 6360 |
| ttcaccagcg | tttctgggtg | agcaaaaaca | ggaaggcaaa | atgccgcaaa | aagggaata | 6420 |
| agggcgacac | ggaaatgttg | aatactcata | ctcttccttt | ttcaatatta | ttgaagcatt | 6480 |
| tatcagggtt | attgtctcat | gagcggatac | atatttgaat | gtatttagaa | aaataaacaa | 6540 |
| ataggggttc | cgcgcacatt | tccccgaaaa | gtgccacctg | ggtccttttc | atcacgtgct | 6600 |
| ataaaaataa | ttataattta | aatttttttaa | tataaatata | taaattaaaa | atagaaagta | 6660 |
| aaaaagaaa | ttaaagaaaa | aatagttttt | gttttccgaa | gatgtaaaag | actctagggg | 6720 |
| gatcgccaac | aaatactacc | ttttatcttg | ctcttcctgc | tctcaggtat | taatgccgaa | 6780 |
| tgtttcatc | ttgtctgtgt | agaagaccac | acacgaaaat | cctgtgattt | tacatttac | 6840 |
| ttatcgttaa | tcgaatgtat | atctatttaa | tctgctttc | ttgtctaata | aatatatatg | 6900 |
| taaagtacgc | tttttgttga | atttttaa | accttgttt | atttttttt | cttcattccg | 6960 |
| taactcttct | accttcttta | tttactttct | aaaatccaaa | tacaaaacat | aaaaataaat | 7020 |
| aaacacagag | taaattccca | aattattcca | tcattaaaag | atacgaggcg | cgtgtaagtt | 7080 |
| acaggcaagc | gatccgtcct | aagaaaccat | tattatcatg | acattaacct | ataaaaatag | 7140 |
| gcgtatcacg | aggccctttc | gtc | | | | 7163 |

<210> SEQ ID NO 11
<211> LENGTH: 8710
<212> TYPE: DNA
<213> ORGANISM: Artificial Sequence
<220> FEATURE:
<223> OTHER INFORMATION: Codon Optimized

<400> SEQUENCE: 11

| | | | | |
|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgcgtg | 120 |
| ttggcgggtg | tcgggctgg | cttaactatg | cggcatcaga | gcagattgta | ctgagagtgc | 180 |
| accataaatt | cccgttttaa | gagcttggtg | agcgctagga | gtcactgcca | ggtatcgttt | 240 |
| gaacacggca | ttagtcaggg | aagtcataac | acagtccttt | cccgcaattt | tcttttctca | 300 |
| ttactcttgg | cctcctctag | tacactctat | atttttttat | gcctcggtaa | tgattttcat | 360 |

```
tttttttttt cccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggttttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt tggatgaggc actttccaga gcggtggtag    900
atctttcgaa caggccgtac gcagttgtcg aacttggttt gcaaagggag aaagtaggag    960
atctctcttg cgagatgatc ccgcatttt ttgaaagctt tgcagaggct agcagaatta   1020
ccctccacgt tgattgtctg cgaggcaaga atgatcatca ccgtagtgag agtgcgttca   1080
aggctcttgc ggttgccata agagaagcca cctcgcccaa tggtaccaac gatgttccct   1140
ccaccaaagg tgttcttatg tagtgacacc gattatttaa agctgcagca tacgatatat   1200
atacatgtgt atatatgtat acctatgaat gtcagtaagt atgtatacga acagtatgat   1260
actgaagatg acaaggtaat gcatcattct atacgtgtca ttctgaacga ggcgcgcttt   1320
ccttttttct ttttgctttt tctttttttt tctcttgaac tcgacggatc tatgcggtgt   1380
gaaataccgc acagatgcgt aaggagaaaa taccgcatca ggaaattgta aacgttaata   1440
ttttgttaaa attcgcgtta aattttgtt aaatcagctc attttttaac caataggccg   1500
aaatcggcaa aatcccttat aaatcaaaag aatagaccga gatagggttg agtgttgttc   1560
cagtttggaa caagagtcca ctattaaaga acgtggactc caacgtcaaa gggcgaaaaa   1620
ccgtctatca gggcgatggc ccactacgtg aaccatcacc ctaatcaagt tttttggggt   1680
cgaggtgccg taaagcacta aatcggaacc ctaaagggag cccccgattt agagcttgac   1740
ggggaaagcc ggcgaacgtg gcgagaaagg aagggaagaa agcgaaagga gcgggcgcta   1800
gggcgctggc aagtgtagcg gtcacgctgc gcgtaaccac cacacccgcc gcgcttaatg   1860
cgccgctaca gggcgcgtcg cgccattcgc cattcaggct gcgcaactgt tgggaagggc   1920
gatcggtgcg ggcctcttcg ctattacgcc agctggcgaa aggggatgt gctgcaaggc   1980
gattaagttg ggtaacgcca gggttttccc agtcacgacg ttgtaaaacg acggccagtg   2040
agcgcgcgta atacgactca ctataggcg aattgggtac cggccgcaaa ttaaagcctt   2100
cgagcgtccc aaaaccttct caagcaaggt tttcagtata atgttacatg cgtacacgcg   2160
tctgtacaga aaaaaagaa aaatttgaaa tataaataac gttcttaata ctaacataac   2220
tataaaaaaa taaatagggga cctagacttc aggttgtcta actccttcct tttcggttag   2280
agcggatgtg gggggagggc gtgaatgtaa gcgtgacata actaattaca tgactcgagg   2340
tcgacttaca aatcttcttc acttattaat ttttgttcgt gtctatgtct aggtaaaggt   2400
ggaatggatt gttcgtttct aaagaagttg tttgggtcaa ccaatgtctt aacctttact   2460
aatctatcga aatttttacc gaagtatttt tcaccccaaa ttctagcttg ggtatagttg   2520
ttaggattct ttggatcgtt aataccgatg tccaaatctc tgtagttcaa atatgccaat   2580
ctagggtttt tagaaacgta tggagtcatg aagttataga tgtttctaat ccagtttaag   2640
tgcttttcgt tatcttcttg ctttttcccat gaacaaatgt accacaattc gtataagata   2700
ccagctctat gaggaaatgg aatggcagat tcactgattt cgtccattat accaccgtat   2760
```

```
ggatacaagg cgtacatgcc tgcaccaata tcttcttcgt acaattttc taagatttgg    2820 acgaaaactg attcaggtat tggctttta acgtagtcta acttaatttt aaaggcaccg    2880
ttttgacctg cggatctatc caataatatt tctttgttga agttgtctgt atcgtagttg    2940
acaacacctg aataaaagat gatggtgtcg atccaagaca attgtctaca atcagttttc    3000
ttaataccta attctggaaa agacttattc atcaagtcta ctaaggaatc gacaccaccc    3060
aagaaaactg aagaaaagta tgtgtggata gcagtcttat ttttaccttg gttatcggtg    3120
atgtttcttg tgatgaaatg agtcatcaac aacaagtcct tatcgtactt gtatgcgatg    3180
ttttgccact tattgaccaa tttaactaat tcatggattt ccattatctt tttgactgag    3240
aacatagtag actttggtac tgcgactaat cttatcttcc aagcaactat gataccgaat    3300
gattctgcac caccacctct caaagcccaa aataagtctt cacccataga ctttctatcc    3360
aaaactttac cgtgaacatt taccaaatga gcgtcgatta tgttatcagc ggccaaaccg    3420
tagtttctca ttaaaggacc ataaccacca ccaccaaaat gacccctgc gcaaactgtt     3480 ggacagtaac cagcagccaa tgataagttt tcattctttt cgttaaccca gtagtatact    3540
tcacccaatg ttgcaccagc ttcaacccaa gcagtttgtg agtgtacgtc tattttaatt    3600
gatctcatgt ttctcaaatc aacgataacg aatggaactt gggagatgta tgacatgcct    3660
tcactatcat gaccaccgga tctagttcta atttgcaaac caaccttttt agaacataag    3720
atagtacctt ggatgtgaga tacatgacta ggggttacaa tgaccaaagg ttttggagtg    3780
gtatcagaag tgaatctcaa attatggatt gtactgttca agacggacat gtacaatggg    3840
ttgttttgag tgtaaaccaa cttcaaattg gtggcgttat taggtatgta ttgtgagaag    3900
cacttcaaaa agtttctct tgggtttgcg atacttgttt ggatgttaaa ggaaaagaaa     3960
aagaagatga tcttgcatac gaaccaaaag gagaaagttg aacatttcat aggacctgga    4020
ttttcttcaa cgtcaccaca ggtcaacaaa gaacctctac cttcaataaa aacgtatacc    4080
aaatattcag cgtagtacaa tttccacata aactcgtaga atcttctacc tgcttcaggg    4140
tcataatttg tcaaagcgaa atctctagtt tgcaagatca accagaaagc caagatggca    4200
tgtgacaaca acataacgtt agaattaaag gcttgtggcc aaatgatacc tgccaaaatg    4260
gctgcgacgt aacttaacaa aacgataccg gagcagaaca aagtcaaatt tcttgaaccg    4320
tacttagaag ccaaggtact aataccgaac tttgtgtcac cttcaacgtc agaggcatcc    4380
ttgatcaagg ctaatgcaga acccatactt tcatgaatg ccaacaaaaa tgtgaatgaa     4440
ggtctcaatt cgaatggcaa acctaaagca gctcttgaag cgtagtagaa ggtgaagttt    4500
gtgatgatat gagctaagaa attcaacaaa aaggcagtac tagggttttg tttccatcta    4560
aaaggtggta cggaatagac aataccaccg aagataccga aacagtaacc gaagatgtac    4620
aatggaccac ccttcatttt aattgtgatg atcaaaccga acaaggctac tatgatagac    4680
atgatccatg cagtattgac ggatatttca cctgaagcca aagcaaatc tggtttgtta     4740 attctgtcga tgtgcaaatc gtatatttga ttaattgtag tggtgaatga agcgatgcac    4800
aagatggcaa ctaaaaagaa aaatgccttg aacatcaagg accatgaaat taagttagtg    4860
ttatgcaaca attctttacc gaataaaccg catgcacaag aagtaaaagc gattatggtg    4920
tatggtcttt gcaacttcca acatgcttta ccgaagttca aatttttgt ggcaacagag     4980 tgattatcac tttcaggtgg ttcagtttga tttgtagttg cagctctgat agagttctta    5040
gctatagaca aactttcgga gcacttattt tgtaagtgga aggacttggt tgaacaatgt    5100
```

```
tttgatggaa agttgttgta agagtactta ataggtgtct ttggatgtct gtaacacaac    5160
aatgatgttt ttggattgtt gttgtgagga ttcaataagg tatgatagtt agtttggaag    5220
gagaaagtac agacggatga taaacccata ctagttctag atccgtcgaa actaagttct    5280
tggtgtttta aaactaaaaa aaagactaac tataaaagta gaatttaaga agtttaagaa    5340
atagatttac agaattacaa tcaatacctc ccgtctttat atacttatta gtcaagtagg    5400
ggaataattt cagggaactg gtttaaacct ttttttcag cttttccaa atcagagaga      5460 gcagaaggta atagaaggtg taagaaaatg agatagatac atgcgtgggt caattgcctt    5520
gtgtcatcat ttactccagg caggttgcat cactccattg aggttgtgcc cgttttttgc    5580
ctgtttgtgc cctgttctct gtagttgcgc taagagaatg gacctatgaa ctgatggttg    5640
gtgaagaaaa caatattttg gtgctgggat tcttttttt tctggatgcc agcttaaaaa     5700
gcgggctcca ttatatttag tggatgccag gaataaacct gttcacccaa gcaccatcag    5760
tgttatatat tctgtgtaac ccgccccta ttttggcatg tacgggttac agcagaatta    5820
aaaggctaat tttttgacta aataaagtta ggaaaatcac tactattaat tatttacgta    5880
ttctttgaaa tggcagtatt gataatgata aactcgagag ctccagcttt tgttcccttt    5940
agtgagggtt aattgcgcgc ttggcgtaat catggtcata gctgtttcct gtgtgaaatt    6000
gttatccgct cacaattcca cacaacatag gagccggaag cataaagtgt aaagcctggg    6060
gtgcctaatg agtgaggtaa ctcacattaa ttgcgttgcg ctcactgccc gctttccagt    6120
cgggaaacct gtcgtgccag ctgcattaat gaatcggcca acgcgcgggg agaggcggtt    6180
tgcgtattgg gcgctcttcc gcttcctcgc tcactgactc gctgcgctcg gtcgttcggc    6240
tgcggcgagc ggtatcagct cactcaaagg cggtaatacg gttatccaca gaatcagggg    6300
ataacgcagg aaagaacatg tgagcaaaag gccagcaaaa ggccaggaac cgtaaaaagg    6360
ccgcgttgct ggcgtttttc cataggctcc gccccctga cgagcatcac aaaaatcgac     6420
gctcaagtca gaggtggcga aacccgacag gactataaag ataccaggcg tttccccctg    6480
gaagctccct cgtgcgctct cctgttccga ccctgccgct taccggatac ctgtccgcct    6540
ttctcccttc gggaagcgtg gcgctttctc atagctcacg ctgtaggtat ctcagttcgg    6600
tgtaggtcgt tcgctccaag ctgggctgtg tgcacgaacc ccccgttcag cccgaccgct    6660
gcgccttatc cggtaactat cgtcttgagt ccaacccggt aagacacgac ttatcgccac    6720
tggcagcagc cactggtaac aggattagca gagcgaggta tgtaggcggt gctacagagt    6780
tcttgaagtg gtggcctaac tacggctaca ctagaaggac agtatttggt atctgcgctc    6840
tgctgaagcc agttaccttc ggaaaaagag ttggtagctc ttgatccggc aaacaaacca    6900
ccgctggtag cggtggtttt tttgtttgca agcagcagat tacgcgcaga aaaaaaggat    6960
ctcaagaaga tcctttgatc ttttctacgg ggtctgacgc tcagtggaac gaaaactcac    7020
gttaagggat tttggtcatg agattatcaa aaaggatctt cacctagatc cttttaaatt    7080
aaaaatgaag ttttaaatca atctaaagta tatatgagta aacttggtct gacagttacc    7140
aatgcttaat cagtgaggca cctatctcag cgatctgtct atttcgttca tccatagttg    7200
cctgactccc cgtcgtgtag ataactacga tacgggaggg cttaccatct ggccccagtg    7260
ctgcaatgat accgcgagac ccacgctcac cggctccaga tttatcagca ataaaccagc    7320
cagccggaag ggccgagcgc agaagtggtc ctgcaacttt atccgcctcc atccagtcta    7380
ttaattgttg ccgggaagct agagtaagta gttcgccagt taatagtttg cgcaacgttg    7440
ttgccattgc tacaggcatc gtggtgtcac gctcgtcgtt tggtatggct tcattcagct    7500
```

```
ccggttccca acgatcaagg cgagttacat gatcccccat gttgtgcaaa aaagcggtta   7560
gctccttcgg tcctccgatc gttgtcagaa gtaagttggc cgcagtgtta tcactcatgg   7620
ttatggcagc actgcataat tctcttactg tcatgccatc cgtaagatgc ttttctgtga   7680
ctggtgagta ctcaaccaag tcattctgag aatagtgtat gcggcgaccg agttgctctt   7740
gcccggcgtc aatacgggat aataccgcgc cacatagcag aactttaaaa gtgctcatca   7800
ttggaaaacg ttcttcgggg cgaaaactct caaggatctt accgctgttg agatccagtt   7860
cgatgtaacc cactcgtgca cccaactgat cttcagcatc ttttactttc accagcgttt   7920
ctgggtgagc aaaaacagga aggcaaaatg ccgcaaaaaa gggaataagg gcgacacgga   7980
aatgttgaat actcatactc ttccttttc aatattattg aagcatttat cagggttatt   8040
gtctcatgag cggatacata tttgaatgta tttagaaaaa taaacaaata ggggttccgc   8100
gcacatttcc ccgaaaagtg ccacctgggt ccttttcatc acgtgctata aaaataatta   8160
taatttaaat tttttaatat aaatatataa attaaaaata gaaagtaaaa aagaaatta    8220
aagaaaaaat agttttgtt ttccgaagat gtaaagact ctaggggat cgccaacaaa      8280
tactacctt tatcttgctc ttcctgctct caggtattaa tgccgaattg tttcatcttg    8340
tctgtgtaga agaccacaca cgaaaatcct gtgatttac attttactta tcgttaatcg    8400
aatgtatatc tatttaatct gcttttcttg tctaataaat atatatgaa agtacgcttt    8460
tgttgaaat tttttaaacc tttgtttatt ttttttcttc cattccgtaa ctcttctacc    8520
ttctttattt actttctaaa atccaaatac aaaacataaa aataaataaa cacagagtaa   8580
attcccaaat tattccatca ttaaaagata cgaggcgcgt gtaagttaca ggcaagcgat   8640
ccgtcctaag aaaccattat tatcatgaca ttaacctata aaaataggcg tatcacgagg   8700
cccttttcgtc                                                         8710
```

<210> SEQ ID NO 12
<211> LENGTH: 9617
<212> TYPE: DNA
<213> ORGANISM: Artificial Sequence
<220> FEATURE:
<223> OTHER INFORMATION: Codon Optimized

<400> SEQUENCE: 12

```
ttatcatgac attaacctat aaaaataggc gtatcacgag gccctttcgt ctcgcgcgtt     60
tcggtgatga cggtgaaaac ctctgacaca tgcagctccc ggagacggtc acagcttgtc    120
tgtaagcgga tgccgggagc agacaagccc gtcaggcgc gtcagcgggt gttggcgggt     180
gtcggggctg gcttaactat gcggcatcag agcagattgt actgagagtg caccacgctt    240
ttcaattcaa ttcatcattt tttttttatt cttttttttg atttcggttt ctttgaaatt    300
ttttttgattc ggtaatctcc gaacagaagg aagaacgaag gaaggagcac agacttagat    360
tggtatatat acgcatatgt agtgttgaag aaacatgaaa ttgcccagta ttcttaaccc    420
aactgcacag aacaaaaacc tgcaggaaac gaagataaat catgtcgaaa gctacatata    480
aggaacgtgc tgctactcat cctagtcctg ttgctgccaa gctatttaat atcatgcacg    540
aaaagcaaac aaacttgtgt gcttcattgg atgttcgtac caccaaggaa ttactggagt    600
tagttgaagc attaggtccc aaaatttgtt tactaaaaac acatgtggat atcttgactg    660
atttttccat ggagggcaca gttaagccgc taaaggcatt atccgccaag tacaattttt    720
tactcttcga agacagaaaa tttgctgaca ttggtaatac agtcaaattg cagtactctg    780
```

```
cgggtgtata cagaatagca gaatgggcag acattacgaa tgcacacggt gtggtgggcc      840
caggtattgt tagcggtttg aagcaggcgg cagaagaagt aacaaaggaa cctagaggcc      900
ttttgatgtt agcagaattg tcatgcaagg gctccctatc tactggagaa tatactaagg      960
gtactgttga cattgcgaag agcgacaaag attttgttat cggctttatt gctcaaagag     1020
acatgggtgg aagagatgaa ggttacgatt ggttgattat gacacccggt gtgggtttag     1080
atgacaaggg agacgcattg ggtcaacagt atagaaccgt ggatgatgtg gtctctacag     1140
gatctgacat tattattgtt ggaagaggac tatttgcaaa gggaagggat gctaaggtag     1200
agggtgaacg ttacagaaaa gcaggctggg aagcatattt gagaagatgc ggccagcaaa     1260
actaaaaaac tgtattataa gtaaatgcat gtatactaaa ctcacaaatt agagcttcaa     1320
tttaattata tcagttatta ccctgcggtg tgaaataccg cacagatgcg taaggagaaa     1380
ataccgcatc aggaaattgt aaacgttaat attttgttaa aattcgcgtt aaattttttgt    1440 taaatcagct catttttttaa ccaataggcc gaaatcggca aaatccctta taaatcaaaa    1500
gaatagaccg agataggggtt gagtgttgtt ccagtttgga acaagagtcc actattaaag    1560
aacgtggact ccaacgtcaa agggcgaaaa accgtctatc agggcgatgg cccactacgt     1620
gaaccatcac cctaatcaag ttttttgggg tcgaggtgcc gtaaagcact aaatcggaac     1680
cctaaaggga gccccgatt tagagcttga cggggaaagc cggcgaacgt ggcgagaaag      1740
gaagggaaga aagcgaaagg agcgggcgct agggcgctgg caagtgtagc ggtcacgctg     1800
cgcgtaacca ccacacccgc cgcgcttaat gcgccgctac agggcgcgtc gcgccattcg     1860
ccattcaggc tgcgcaactg ttgggaaggg cgatcggtgc gggcctcttc gctattacgc     1920
cagctggcga aggggggatg tgctgcaagg cgattaagtt gggtaacgcc agggttttcc     1980
cagtcacgac gttgtaaaac gacggccagt gaattgtaat acgactcact ataggggcgaa    2040 ttggagctct agtacggatt agaagccgcc gagcgggcga cagccctccg acggaagact     2100
ctcctccgtg cgtcctcgtc ttcaccggtc gcgttcctga acgcagatg tgcctcgcgc      2160 cgcactgctc cgaacaataa agattctaca atactagctt ttatggttat gaagaggaaa    2220
aattggcagt aacctggccc cacaaacctt caaattaacg aatcaaatta caaccatag     2280 gatgataatg cgattagttt tttagcctta tttctggggt aattaatcag cgaagcgatg    2340 attttttgatc tattaacaga tatataaatg gaaaagctgc ataaccactt taactaatac    2400
tttcaacatt ttcagtttgt attacttctt attcaaatgt cataaaagta tcaacaaaaa    2460
attgttaata tacctctata ctttaacgtc aaggagaaaa aaccccggat tctagaacta    2520
gtggatcccc catcatgaac catttgagag ccgaaggtcc tgcctccgta ttagccatag    2580
gtacagccaa cccagaaaac atattgatcc aagatgaatt tcctgattat tacttcagag    2640
ttaccaagag tgaacacatg actcaattga aggaaaagtt tagaaaaata tgtgataagt    2700
ctatgatcag aaagagaaac tgcttcttga cgaagaaca tttgaagcaa aatccaagat    2760
tggtagaaca cgaaatgcaa acattggatg ccagacaaga catgttagtt gtcgaagttc    2820
ctaaattggg taaagatgct tgtgcaaaag ccattaagga atggggtcaa ccaaagtcaa    2880
agatcactca tttgattttt acaagtgcat ctactacaga tatgcctggt gcagactacc    2940
actgtgccaa attgttaggt tgtcaccat ccgttaagag agtcatgatg tatcaattag    3000
gttgctacgg tggtggtact gttttgagaa tcgctaagga tattgcagaa acaacaagg     3060 gtgccagagt attagctgtt tgttgcgaca ttatggcttg cttgtttaga ggtccaagtg    3120
attctgactt ggaattgtta gttggtcaag ctatcttcgg tgacggtgct gctgctgtta    3180
```

```
ttgttggtgc agaacctgac gaatctgttg gtgaaagacc aatatttgaa ttagtcagta    3240
caggtcaaac catcttgcct aattctgaag gtacaattgg tggtcatata agagaagcag    3300
gtttgatctt cgatttgcac aaagacgttc caatgttaat ctctaacaac atagaaaagt    3360
gtttgataga agcattcact cctataggta tctcagattg gaactctatt ttctggataa    3420
cacatccagg tggtaaagcc attttggata aggttgaaga aaaattggat ttgaagaaag    3480
aaaagtttgt agatagtaga catgttttat ctgaacacgg taacatgtct tcatccactg    3540
tcttgttcgt aatggatgaa ttgagaaaga gatcattaga agagggtaaa tctactactg    3600
gtgacggttt tgaatggggt gtcttatttg gtttcggtcc tggtttgacc gtcgaaagag    3660
tagttgtcag atcagtacca attaaatatg aaggtagagg ttccttgtta acttgtggtg    3720
acgttgaaga aaacccaggt cctatggccg tcaagcattt gatagtattg aagtttaaag    3780
atgaaatcac agaagctcaa aaggaagaat ttttcaagac ctacgttaat ttggtcaaca    3840
ttatacctgc tatgaaagat gtatactggg gtaaagacgt tacacaaaag aaagaagaag    3900
gttatacaca cattgtcgaa gtaaccttcg aatcagttga aactatccaa gattacatca    3960
ttcatccagc tcacgttggt tttggtgacg tttacagatc cttctgggaa aaattgttga    4020
tcttcgatta caccccaaga aagttaaagc caaaataatg ataacgagaa taatatcaag    4080
aataccttag aacaacatcg acaacaacaa caggcatttt cggatatgag tcacgtggag    4140
tattccagaa ttacaaaatt ttttcaagaa caaccactgg agggatatac ccttttctct    4200
cacaggtctg cgccatgggt ttatcatccg tctgtacttt ctccttccaa actaactatc    4260
ataccttatt gaatcctcac aacaacaatc caaaaacatc attgttgtgt tacagacatc    4320
caaagacacc tattaagtac tcttacaaca actttccatc aaaacattgt tcaaccaagt    4380
ccttccactt acaaaataag tgctccgaaa gtttgtctat agctaagaac tctatcagag    4440
ctgcaactac aaatcaaact gaaccacctg aaagtgataa tcactctgtt gccacaaaaa    4500
ttttgaactt cggtaaagca tgttggaagt tgcaaagacc atacaccata atcgctttta    4560
cttcttgtgc atgcggttta ttcggtaaag aattgttgca taacactaac ttaatttcat    4620
ggtccttgat gttcaaggca ttttttcttt tagttgccat cttgtgcatc gcttcattca    4680
ccactacaat taatcaaata tacgatttgc acatcgacag aattaacaaa ccagatttgc    4740 cttttggcttc aggtgaaata tccgtcaata ctgcatggat catgtctatc atagtagcct    4800
tgttcggttt gatcatcaca attaaaatga agggtggtcc attgtacatc ttcggttact    4860
gtttcggtat cttcggtggt attgtctatt ccgtaccacc ttttagatgg aaacaaaacc    4920
ctagtactgc ctttttgttg aatttcttag ctcatatcat cacaaacttc accttctact    4980
acgcttcaag agctgcttta ggtttgccat tcgaattgag accttcattc acattttgt    5040 tggcattcat gaaaagtatg ggttctgcat tagccttgat caaggatgcc tctgacgttg    5100
aaggtgacac aaagttcggt attagtacct tggcttctaa gtacggttca agaaatttga    5160
ctttgttctg ctccggtatc gttttgttaa gttacgtcgc agccattttg gcaggtatca    5220
tttggccaca agccttttaat tctaacgtta tgttgttgtc acatgccatc ttggctttct    5280
ggttgatctt gcaaactaga gatttcgctt tgacaaatta tgaccctgaa gcaggtagaa    5340
gattctacga gttatgtgg aaattgtact acgctgaata tttggtatac gttttattg    5400 aaggtagagg ttcttgttg acctgtggtg acgttgaaga aaatccaggt cctatgaaat    5460
gttcaacttt ctccttttgg ttcgtatgca agatcatctt ctttttcttt tcctttaaca    5520
```

```
tccaaacaag tatcgcaaac ccaagagaaa acttttttgaa gtgcttctca caatacatac    5580
ctaataacgc caccaatttg aagttggttt acactcaaaa caacccattg tacatgtccg    5640
tcttgaacag tacaatccat aatttgagat tcacttctga taccactcca aaacctttgg    5700
tcattgtaac ccctagtcat gtatctcaca tccaaggtac tatcttatgt tctaaaaagg    5760
ttggtttgca aattagaact agatccggtg gtcatgatag tgaaggcatg tcatacatct    5820
cccaagttcc attcgttatc gttgatttga gaaacatgag atcaattaaa atagacgtac    5880
actcacaaac tgcttgggtt gaagctggtg caacattggg tgaagtatac tactgggtta    5940
acgaaaagaa tgaaaactta tcattggctg ctggttactg tccaacagtt tgcgcaggtg    6000
gtcattttgg tggtggtggt tatggtcctt aatgagaaa ctacggtttg ccgctgata    6060 acataatcga cgctcatttg gtaaatgttc acggtaaagt tttggataga agtctatgg    6120 gtgaagactt attttgggct ttgagaggtg gtggtgcaga atcattcggt atcatagttg    6180
cttggaagat aagattagtc gcagtaccaa agtctactat gttctcagtc aaaaagataa    6240
tggaaatcca tgaattagtt aaattggtca ataagtggca aaacatcgca tacaagtacg    6300
ataaggactt gttgttgatg actcatttca tcacaagaaa catcaccgat aaccaaggta    6360
aaaataagac tgctatccac acatactttt cttcagtttt cttgggtggt gtcgattcct    6420
tagtagactt gatgaataag tcttttccag aattaggtat taagaaaact gattgtagac    6480
aattgtcttg gatcgacacc atcatctttt attcaggtgt tgtcaactac gatacagaca    6540
acttcaacaa agaaatatta ttggatagat ccgcaggtca aaacggtgcc tttaaaatta    6600
agttagacta cgttaaaaag ccaatacctg aatcagtttt cgtccaaatc ttagaaaaat    6660
tgtacgaaga agatattggt gcaggcatgt acgccttgta tccatacggt ggtataatgg    6720
acgaaatcag tgaatctgcc attccatttc ctcatagagc tggtatctta tacgaattgt    6780
ggtacatttg ttcatgggaa aagcaagaag ataacgaaaa gcacttaaac tggattagaa    6840
acatctataa cttcatgact ccatacgttt ctaaaaaccc tagattggca tatttgaact    6900
acagagattt ggacatcggt attaacgatc caaagaatcc taacaactat acccaagcta    6960
gaatttgggg tgaaaaatac ttcggtaaaa atttcgatag attagtaaag gttaagacat    7020
tggttgaccc aaacaacttc tttagaaacg aacaatccat tccaccttta cctagacata    7080
gacactgatg ggctgcagga attcgatatc aagcttatcg ataccgtcga cctcgagtca    7140
tgtaattagt tatgtcacgc ttacattcac gccctccccc cacatccgct ctaaccgaaa    7200
aggaaggagt tagacaacct gaagtctagg tccctattta ttttttttata gttatgttag    7260 tattaagaac gttatttata tttcaaattt ttcttttttt tctgtacaga cgcgtgtacg    7320
catgtaacat tatactgaaa accttgcttg agaaggtttt gggacgctcg aaggctttaa    7380
tttgcggccg gtacccagct tttgttccct ttagtgaggg ttaattccga gcttggcgta    7440
atcatggtca tagctgtttc ctgtgtgaaa ttgttatccg ctcacaattc cacacaacat    7500
aggagccgga agcataaagt gtaaagcctg ggtgcctaa tgagtgaggt aactcacatt    7560
aattgcgttg cgctcactgc ccgctttcca gtcgggaaac ctgtcgtgcc agctgcatta    7620
atgaatcggc caacgcgcgg ggagaggcgg tttgcgtatt gggcgctctt ccgcttcctc    7680
gctcactgac tcgctgcgct cggtcgttcg gctgcggcga gcggtatcag ctcactcaaa    7740
ggcggtaata cggttatcca cagaatcagg ggataacgca ggaaagaaca tgtgagcaaa    7800
aggccagcaa aaggccagga accgtaaaaa ggccgcgttg ctggcgtttt tccataggct    7860
cggcccccct gacgagcatc acaaaaatcg acgctcaagt cagaggtggc gaaacccgac    7920
```

| | |
|---|---|
| aggactataa agataccagg cgttcccccc tggaagctcc ctcgtgcgct ctcctgttcc | 7980 |
| gaccctgccg cttaccggat acctgtccgc ctttctccct tcgggaagcg tggcgctttc | 8040 |
| tcaatgctca cgctgtaggt atctcagttc ggtgtaggtc gttcgctcca agctgggctg | 8100 |
| tgtgcacgaa ccccccgttc agcccgaccg ctgcgcctta ccggtaact atcgtcttga | 8160 |
| gtccaacccg gtaagacacg acttatcgcc actggcagca gccactggta acaggattag | 8220 |
| cagagcgagg tatgtaggcg gtgctacaga gttcttgaag tggtggccta actacggcta | 8280 |
| cactagaagg acagtatttg gtatctgcgc tctgctgaag ccagttacct tcggaaaaag | 8340 |
| agttggtagc tcttgatccg gcaaacaaac caccgctggt agcggtggtt tttttgtttg | 8400 |
| caagcagcag attacgcgca gaaaaaaagg atctcaagaa gatcctttga tcttttctac | 8460 |
| ggggtctgac gctcagtgga acgaaaactc acgttaaggg attttggtca tgagattatc | 8520 |
| aaaaaggatc ttcacctaga tccttttaaa ttaaaaatga agttttaaat caatctaaag | 8580 |
| tatatatgag taaacttggt ctgacagtta ccaatgctta atcagtgagg cacctatctc | 8640 |
| agcgatctgt ctatttcgtt catccatagt tgcctgactg cccgtcgtgt agataactac | 8700 |
| gatacgggag ggcttaccat ctggccccag tgctgcaatg ataccgcgag acccacgctc | 8760 |
| accggctcca gatttatcag caataaacca gccagccgga agggccgagc gcagaagtgg | 8820 |
| tcctgcaact ttatccgcct ccatccagtc tattaattgt tgccgggaag ctagagtaag | 8880 |
| tagttcgcca gttaatagtt tgcgcaacgt tgttgccatt gctacaggca tcgtggtgtc | 8940 |
| acgctcgtcg tttggtatgg cttcattcag ctccggttcc caacgatcaa ggcgagttac | 9000 |
| atgatccccc atgttgtgaa aaaaagcggt tagctccttc ggtcctccga tcgttgtcag | 9060 |
| aagtaagttg gccgcagtgt tatcactcat ggttatggca gcactgcata attctcttac | 9120 |
| tgtcatgcca tccgtaagat gcttttctgt gactggtgag tactcaacca agtcattctg | 9180 |
| agaatagtgt atgcggcgac cgagttgctc ttgcccggcg tcaatacggg ataataccgc | 9240 |
| gccacatagc agaactttaa aagtgctcat cattggaaaa cgttcttcgg ggcgaaaact | 9300 |
| ctcaaggatc ttaccgctgt tgagatccag ttcgatgtaa cccactcgtg cacccaactg | 9360 |
| atcttcagca tcttttactt tcaccagcgt ttctgggtga gcaaaaacag gaaggcaaaa | 9420 |
| tgccgcaaaa aagggaataa gggcgacacg gaaatgttga atactcatac tcttcctttt | 9480 |
| tcaatattat tgaagcattt atcagggtta ttgtctcatg agcggataca tatttgaatg | 9540 |
| tatttagaaa aataaacaaa taggggttcc gcgcacattt ccccgaaaag tgccacctga | 9600 |
| cgtctaagaa accatta | 9617 |

```
<210> SEQ ID NO 13
<211> LENGTH: 7879
<212> TYPE: DNA
<213> ORGANISM: Artificial Sequence
<220> FEATURE:
<223> OTHER INFORMATION: Codon Optimized

<400> SEQUENCE: 13
```

| | |
|---|---|
| aacctataaa aataggcgta tcacgaggcc ctttcgtctc gcgcgtttcg gtgatgacgg | 60 |
| tgaaaacctc tgacacatgc agctcccgga gacggtcaca gcttgtctgt aagcggatgc | 120 |
| cgggagcaga caagcccgtc agggcgcgtc agcgggtgtt ggcgggtgtc ggggctggct | 180 |
| taactatgcg gcatcagagc agattgtact gagagtgcac cacgcttttc aattcaattc | 240 |
| atcatttttt ttttattctt ttttttgatt tcggtttctt tgaaattttt ttgattcggt | 300 |

```
aatctccgaa cagaaggaag aacgaaggaa ggagcacaga cttagattgg tatatatacg    360
catatgtagt gttgaagaaa catgaaattg cccagtattc ttaacccaac tgcacagaac    420
aaaaacctgc aggaaacgaa gataaatcat gtcgaaagct acatataagg aacgtgctgc    480
tactcatcct agtcctgttg ctgccaagct atttaatatc atgcacgaaa agcaaacaaa    540
cttgtgtgct tcattggatg ttcgtaccac caaggaatta ctggagttag ttgaagcatt    600
aggtcccaaa atttgtttac taaaaacaca tgtggatatc ttgactgatt tttccatgga    660
gggcacagtt aagccgctaa aggcattatc cgccaagtac aatttttac tcttcgaaga     720 cagaaaattt gctgacattg gtaatacagt caaattgcag tactctgcgg gtgtatacag    780
aatagcagaa tgggcagaca ttacgaatgc acacggtgtg gtgggcccag gtattgttag    840
cggtttgaag caggcggcag aagaagtaac aaaggaacct agaggccttt tgatgttagc    900
agaattgtca tgcaagggct ccctatctac tggagaatat actaagggta ctgttgacat    960
tgcgaagagc gacaaagatt ttgttatcgg ctttattgct caaagagaca tgggtggaag   1020
agatgaaggt tacgattggt tgattatgac acccggtgtg ggtttagatg acaagggaga   1080
cgcattgggt caacagtata gaaccgtgga tgatgtggtc tctacaggat ctgacattat   1140
tattgttgga agaggactat ttgcaaaggg aagggatgct aaggtagagg gtgaacgtta   1200
cagaaaagca ggctgggaag catatttgag aagatgcggc cagcaaaact aaaaaactgt   1260
attataagta aatgcatgta tactaaactc acaaattaga gcttcaattt aattatatca   1320
gttattaccc tgcggtgtga ataccgcac agatgcgtaa ggagaaaata ccgcatcagg    1380
aaattgtaaa cgttaatatt ttgttaaaat tcgcgttaaa tttttgttaa atcagctcat   1440
tttttaacca ataggccgaa atcggcaaaa tcccttataa atcaaaagaa tagaccgaga   1500
tagggttgag tgttgttcca gtttggaaca agagtccact attaaagaac gtggactcca   1560
acgtcaaagg gcgaaaaacc gtctatcagg gcgatggccc actacgtgaa ccatcaccct   1620
aatcaagttt tttggggtcg aggtgccgta aagcactaaa tcggaacccct aaagggagcc   1680 cccgatttag agcttgacgg ggaaagccgg cgaacgtggc gagaaaggaa gggaagaaag   1740
cgaaaggagc gggcgctagg gcgctggcaa gtgtagcggt cacgctgcgc gtaaccacca   1800
cacccgccgc gcttaatgcg ccgctacagg gcgcgtcgcg ccattcgcca ttcaggctgc   1860
gcaactgttg gaagggcga tcggtgcggg cctcttcgct attacgccag ctggcgaagg   1920
ggggatgtgc tgcaaggcga ttaagttggg taacgccagg gttttcccag tcacgacgtt   1980
gtaaaacgac ggccagtgaa ttgtaatacg actcactata gggcgaattg agctctagt    2040 acggattaga agccgccgag cgggcgacag ccctccgacg gaagactctc ctccgtgcgt   2100
cctcgtcttc accggtcgcg ttcctgaaac gcagatgtgc ctcgcgccgc actgctccga   2160
acaataaaga ttctacaata ctagctttta tggttatgaa gaggaaaaat tggcagtaac   2220
ctggccccac aaaccttcaa attaacgaat caaattaaca accataggat gataatgcga   2280
ttagtttttt agccttattt ctggggtaat taatcagcga agcgatgatt tttgatctat   2340
taacagatat ataaatggaa aagctgcata accactttaa ctaatacttt caacattttc   2400
agtttgtatt acttcttatt caaatgtcat aaaagtatca acaaaaaatt gttaatatac   2460
ctctatactt taacgtcaag gagaaaaaac cccggattct agaactagtg gatcatgaac   2520
catttgagag ccgaaggtcc tgcctccgta ttagccatag gtacagccaa cccagaaaac   2580
atattgatcc aagatgaatt tcctgattat tacttcagag ttaccaagag tgaacacatg   2640
actcaattga aggaaaagtt tagaaaaata tgtgataagt ctatgatcag aaagagaaac   2700
```

```
tgcttcttga acgaagaaca tttgaagcaa aatccaagat tggtagaaca cgaaatgcaa    2760
acattggatg ccagacaaga catgttagtt gtcgaagttc ctaaattggg taaagatgct    2820
tgtgcaaaag ccattaagga atggggtcaa ccaaagtcaa agatcactca tttgattttt    2880
acaagtgcat ctactacaga tatgcctggt gcagactacc actgtgccaa attgttaggt    2940
ttgtcaccat ccgttaagag agtcatgatg tatcaattag gttgctacgg tggtggtact    3000
gttttgagaa tcgctaagga tattgcagaa aacaacaagg gtgccagagt attagctgtt    3060
tgttgcgaca ttatggcttg cttgtttaga ggtccaagtg attctgactt ggaattgtta    3120
gttggtcaag ctatcttcgg tgacggtgct gctgctgtta ttgttggtgc agaacctgac    3180
gaatctgttg gtgaaagacc aatatttgaa ttagtcagta caggtcaaac catcttgcct    3240
aattctgaag gtacaattgg tggtcatata agagaagcag gtttgatctt cgatttgcac    3300
aaagacgttc caatgttaat ctctaacaac atagaaaagt gtttgataga agcattcact    3360
cctataggta tctcagattg gaactctatt ttctggataa cacatccagg tggtaaagcc    3420
attttggata aggttgaaga aaaattggat ttgaagaaag aaaagtttgt agatagtaga    3480
catgttttat ctgaacacgg taacatgtct tcatccactg tcttgttcgt aatggatgaa    3540
ttgagaaaga gatcattaga agagggtaaa tctactactg gtgacggttt tgaatggggt    3600
gtcttatttg gtttcggtcc tggtttgacc gtcgaaagag tagttgtcag atcagtacca    3660
attaaatatg aaggtagagg ttccttgtta acttgtggtg acgttgaaga aaacccaggt    3720
cctatggccg tcaagcattt gatagtattg aagtttaaag atgaaatcac agaagctcaa    3780
aaggaagaat ttttcaagac ctacgttaat ttggtcaaca ttatacctgc tatgaaagat    3840
gtatactggg gtaaagacgt tacacaaaag aaagaagaag gttatacaca cattgtcgaa    3900
gtaaccttcg aatcagttga aactatccaa gattacatca ttcatccagc tcacgttggt    3960
tttggtgacg tttacagatc cttctgggaa aaattgttga tcttcgatta cacccccaaga    4020 aagtgataac gagaataata tcaagaatac cttagaacaa catcgacaac aacaacaggc    4080
attttcggat atgagtcacg tggagtattc cagaattaca aaattttttc aagaacaacc    4140
actgagggga tataccccttt tctctcacag gtctgcgcca tgggtttatc atccgtctgt    4200
actttctcct tccaaactaa ctatcatacc ttattgaatc ctcacaacaa caatccaaaa    4260
acatcattgt tgtgttacag acatccaaag acacctatta gtactctta caacaacttt    4320 ccatcaaaac attgttcaac caagtccttc cacttacaaa ataagtgctc cgaaagtttg    4380
tctatagcta agaactctat cagagctgca actacaaatc aaactgaacc acctgaaagt    4440
gataatcact ctgttgccac aaaaattttg aacttcggta agcatgttg gaagttgcaa    4500 agaccataca ccataatcgc ttttacttct tgtgcatgcg gtttattcgg taaagaattg    4560
ttgcataaca ctaacttaat ttcatggtcc ttgatgttca aggcattttt cttttagtt    4620 gccatcttgt gcatcgcttc attcaccact acaattaatc aaatatacga tttgcacatc    4680
gacagaatta acaaaccaga tttgcctttg gcttcaggtg aaatatccgt caatactgca    4740
tggatcatgt ctatcatagt agccttgttc ggtttgatca tcacaattaa aatgaagggt    4800
ggtccattgt acatcttcgg ttactgtttc ggtatcttcg tggtattgt ctattccgta    4860 ccacctttta gatggaaaca aaacccctagt actgcctttt tgttgaattt cttagctcat    4920
atcatcacaa acttcacctt ctactacgct tcaagagctg ctttaggttt gccattcgaa    4980
ttgagacctt cattcacatt tttgttggca ttcatgaaaa gtatgggttc tgcattagcc    5040
```

```
ttgatcaagg atgcctctga cgttgaaggt gacacaaagt tcggtattag taccttggct   5100
tctaagtacg gttcaagaaa tttgactttg ttctgctccg gtatcgtttt gttaagttac   5160
gtcgcagcca ttttggcagg tatcatttgg ccacaagcct ttaattctaa cgttatgttg   5220
ttgtcacatg ccatcttggc tttctggttg atcttgcaaa ctagagattt cgctttgaca   5280
aattatgacc ctgaagcagg tagaagattc tacgagttta tgtggaaatt gtactacgct   5340
gaatatttgg tatacgtttt tatttaacga taccgtcgac ctcgagtcat gtaattagtt   5400
atgtcacgct tacattcacg ccctcccccc acatccgctc taaccgaaaa ggaaggagtt   5460
agacaacctg aagtctaggt ccctatttat tttttatag ttatgttagt attaagaacg    5520
ttatttatat ttcaaatttt tctttttttt ctgtacagac gcgtgtacgc atgtaacatt   5580
atactgaaaa ccttgcttga aaggttttg ggacgctcga aggctttaat ttgcggccgg    5640
tacccagctt ttgttcccctt tagtgagggt taattccgag cttggcgtaa tcatggtcat   5700
agctgtttcc tgtgtgaaat tgttatccgc tcacaattcc acacaacata ggagccggaa   5760
gcataaagtg taaagcctgg ggtgcctaat gagtgaggta actcacatta attgcgttgc   5820
gctcactgcc cgctttccag tcgggaaacc tgtcgtgcca gctgcattaa tgaatcggcc   5880
aacgcgcggg gagaggcggt ttgcgtattg ggcgctcttc cgcttcctcg ctcactgact   5940
cgctgcgctc ggtcgttcgg ctgcggcgag cggtatcagc tcactcaaag gcggtaatac   6000
ggttatccac agaatcaggg gataacgcag gaaagaacat gtgagcaaaa ggccagcaaa   6060
aggccaggaa ccgtaaaaag gccgcgttgc tggcgttttt ccataggctc ggccccctg    6120
acgagcatca caaaaatcga cgctcaagtc agaggtggcg aaacccgaca ggactataaa   6180
gataccaggc gttccccct ggaagctccc tcgtgcgctc tcctgttccg accctgccgc    6240
ttaccggata cctgtccgcc tttctccctt cgggaagcgt ggcgctttct caatgctcac   6300
gctgtaggta tctcagttcg gtgtaggtcg ttcgctccaa gctgggctgt gtgcacgaac   6360
cccccgttca gcccgaccgc tgcgccttat ccggtaacta tcgtcttgag tccaacccgg   6420
taagacacga cttatcgcca ctggcagcag ccactggtaa caggattagc agagcgaggt   6480
atgtaggcgg tgctacagag ttcttgaagt ggtggcctaa ctacggctac actagaagga   6540
cagtatttgg tatctgcgct ctgctgaagc cagttacctt cggaaaaaga gttggtagct   6600
cttgatccgg caaacaaacc accgctggta gcggtggttt ttttgtttgc aagcagcaga   6660
ttacgcgcag aaaaaaagga tctcaagaag atcctttgat cttttctacg gggtctgacg   6720
ctcagtggaa cgaaaactca cgttaaggga ttttggtcat gagattatca aaaaggatct   6780
tcacctagat ccttttaaat taaaaatgaa gttttaaatc aatctaaagt atatatgagt   6840
aaacttggtc tgacagttac caatgcttaa tcagtgaggc acctatctca gcgatctgtc   6900
tatttcgttc atccatagtt gcctgactgc ccgtcgtgta gataactacg atacgggagg   6960
gcttaccatc tggccccagt gctgcaatga taccgcgaga cccacgctca ccggctccag   7020
atttatcagc aataaaccag ccagccggaa gggccgagcg cagaagtggt cctgcaactt   7080
tatccgcctc catccagtct attaattgtt gccgggaagc tagagtaagt agttcgccag   7140
ttaatagttt gcgcaacgtt gttgccattg ctacaggcat cgtggtgtca cgctcgtcgt   7200
ttggtatggc ttcattcagc tccggttccc aacgatcaag gcgagttaca tgatccccca   7260
tgttgtgaaa aaaagcggtt agctccttcg gtcctccgat cgttgtcaga agtaagttgg   7320
ccgcagtgtt atcactcatg gttatggcag cactgcataa ttctcttact gtcatgccat   7380
ccgtaagatg cttttctgtg actggtgagt actcaaccaa gtcattctga gaatagtgta   7440
```

```
tgcggcgacc gagttgctct tgcccggcgt caatacggga taataccgcg ccacatagca    7500
gaactttaaa agtgctcatc attggaaaac gttcttcggg gcgaaaactc tcaaggatct    7560
taccgctgtt gagatccagt tcgatgtaac ccactcgtgc acccaactga tcttcagcat    7620
cttttacttt caccagcgtt tctgggtgag caaaaacagg aaggcaaaat gccgcaaaaa    7680
agggaataag ggcgacacgg aaatgttgaa tactcatact cttcctttt caatattatt     7740 gaagcattta tcagggttat tgtctcatga gcggatacat atttgaatgt atttagaaaa    7800
ataaacaaat aggggttccg cgcacatttc cccgaaaagt gccacctgac gtctaagaaa    7860
ccattattat catgacatt                                                 7879

<210> SEQ ID NO 14
<211> LENGTH: 3353
<212> TYPE: DNA
<213> ORGANISM: Artificial Sequence
<220> FEATURE:
<223> OTHER INFORMATION: Codon Optimized

<400> SEQUENCE: 14
actagtatgg gtaaaaacta taagtccttg gattcagtcg ttgcctcaga tttcatcgca      60
ttgggtatca cctcagaagt agcagaaaca ttacatggta gattggcaga aatcgtttgt     120
aattatggtg ctgcaacccc tcaaacttgg atcaacatcg ctaaccatat cttgtcacca     180
gatttgcctt tctccttaca ccaaatgttg ttttatggtt gctacaagga tttcggtcca     240 gcccacctg cttggattcc agaccctgaa aaagtcaagt caactaattt gggtgctttg      300
ttggaaaaga gaggtaaaga atttttgggt gtaaagtaca aagatccaat ttcttctttt     360
tctcacttcc aagaatttc tgttagaaac cctgaagtct attggagaac agtattgatg     420
gatgaaatga aaattagttt ctctaaggac ccagaatgta tcttgagaag agatgacatc     480
aacaacccag gtggttctga atggttacct ggtggttact tgaactcagc taaaaattgc     540
ttgaacgtaa actccaataa gaaattgaac gatactatga tcgtttggag agacgagggt     600
aacgatgact tgcctttgaa taagttgaca ttagatcaat tgagaaagag agttggttg     660 gttggttatg cattggaaga atgggttta gaaaaaggtt gtgcaatagc catcgatatg     720
ccaatgcatg ttgatgctgt tgtttatatat ttggccatag tattggctgg ttacgtagtt     780
gtctctatag cagattcatt ttccgcccct gaaatctcaa ctagattgag attatccaaa     840
gctaaggcaa ttttcacaca agatcacatc atcagaggta aaagagaat accattgtat     900 tcaagagtag ttgaagctaa atccccaatg gcaatagtta tcccttgtag tggttctaac     960
attggtgcag aattgagaga tggtgacata tcttgggatt acttttaga aagagccaag     1020 gagtttaaaa actgcgagtt tactgccaga gaacaacctg ttgatgctta tactaacatc    1080
ttattctcca gtggtactac aggtgaacca aaagcaattc cttggacaca agccacccca    1140
ttgaaggctc tgctgatgg ttggtctcat ttggatatta gaaaggtga cgttatagta     1200 tggccaacta atttgggttg gatgatgggt ccttggttgg tttatgctag tttgttaaat    1260
ggtgcatcta ttgccttgta caacggtagt ccttttagtct ctggtttcgc taaatttgtt    1320
caagatgcaa aggtcacaat gttgggtgtc gtaccatcta ttgtaagatc atggaaatcc    1380
acaaattgtg tttcaggtta cgattggtcc accataagat gctttttcttc atccggtgaa    1440 gcctctaatg tagacgaata tttgtggtta atgggtagag ctaactacaa gccagtttata    1500 gaaatgtgtg gtggtacaga aatcggtggt gcttttttctg ctggttcatt tttgcaagct    1560
```

```
caatctttaa gttcttttc atcccaatgt atgggttgca ccttgtacat attagataag    1620
aacggttacc caatgcctaa aaataagcca ggtatcggtg aattggcatt aggtcctgtt    1680
atgtttggtg cctcaaaaac attgttaaac ggtaatcatc acgatgtcta tttcaagggt    1740
atgccaacct tgaatggtga agtattgaga agacatggtg acattttcga attgacctct    1800
aacggttact accatgcaca cggtagagcc gatgacacta tgaacatcgg tggtatcaaa    1860
attagttcta tcgaaatcga aagagtctgt aatgaagtag atgacagagt ttttgaaacc    1920
actgctattg gtgttccacc tttgggtggt ggtccagaac aattggtcat attttcgta    1980 ttgaaggatt caaacgacac aaccattgat ttgaaccaat tgagattatc ctttaacttg    2040
ggtttgcaaa agaaattgaa cccattattc aaagttacta gagttgtccc attgtcatcc    2100
ttacctagaa ctgcaacaaa caagatcatg agaagagttt tgagacaaca attcagtcat    2160
ttcgaagaag gtagaggttc tttgttaaca tgtggtgacg ttgaagaaaa tccaggtcct    2220
atggcttcag aaaaggaaat aagaagagaa agattcttga acgtattccc aaagttagtt    2280
gaagaattga acgctagttt gttagcttat ggtatgccta agaagcctg cgattggtat    2340 gctcactctt taaactacaa tactccaggt ggtaaattga atagaggttt gagtgtagtt    2400
gatacttatg ctatcttgtc taacaaaacc gttgaacaat taggtcaaga agaatacgaa    2460
aaggtcgcta tcttgggttg gtgtattgaa ttgttgcaag catacttttt ggttgccgat    2520
gacatgatgg ataagtctat aacaagaaga ggtcaaccat gctggtacaa agttccagaa    2580
gttggtgaaa tagccataaa tgatgctttt atgttggaag ccgctatcta taaattgttg    2640
aagtcacatt tcagaaacga aaagtactac atcgatatta ccgaattatt ccacgaagtt    2700
actttccaaa cagaattggg tcaattgatg gatttgataa ctgcacctga agataaagtt    2760
gacttgtcaa gtttttcctt gaagaaacat tcattcatcg tcacctttga aactgcttat    2820
tactccttct atttgccagt cgccttggct atgtacgtag ctggtattac tgatgaaaaa    2880
gacttgaagc aagcaagaga tgttttgata cctttgggtg aatacttcca aatccaagat    2940
gactacttag actgtttcgg tactccagaa caaataggta aaatcggtac agatattcaa    3000
gacaataagt gcagttgggt tattaacaag gctttggaat tagcatctgc cgaacaaaga    3060
aagactttgg atgaaaacta cggtaaaaag gactcagttg ctgaagcaaa gtgtaagaaa    3120 attttaatg atttgaagat tgaacaattg taccatgaat acgaagaatc catcgctaaa    3180
gacttaaagg caaagattag tcaagttgat gaatcaagag gttttaaagc cgacgttttg    3240
acagctttct tgaataaggt ctacaagaga tcaaaggatt acaaggatca tgacggtgac    3300
tataaagacc acgatattga ctacaaagat gacgatgaca agtaagcggc cgc           3353
```

<210> SEQ ID NO 15
<211> LENGTH: 1553
<212> TYPE: DNA
<213> ORGANISM: Artificial Sequence
<220> FEATURE:
<223> OTHER INFORMATION: Codon Optimized

<400> SEQUENCE: 15

```
actagtatga accatttgag agccgaaggt cctgcctccg tattagccat aggtacagcc      60
aacccagaaa acatatttgat ccaagatgaa tttcctgatt attacttcag agttaccaag    120
agtgaacaca tgactcaatt gaaggaaaag tttagaaaaa tatgtgataa gtctatgatc    180
agaaagagaa actgcttctt gaacgaagaa catttgaagc aaaatccaag attggtagaa    240
cacgaaatgc aaacattgga tgccagacaa gacatgttag ttgtcgaagt tcctaaattg    300
```

```
ggtaaagatg cttgtgcaaa agccattaag gaatggggtc aaccaaagtc aaagatcact      360
catttgattt ttacaagtgc atctactaca gatatgcctg gtgcagacta ccactgtgcc      420
aaattgttag gtttgtcacc atccgttaag agagtcatga tgtatcaatt aggttgctac      480
ggtggtggta ctgttttgag aatcgctaag gatattgcag aaaacaacaa gggtgccaga      540
gtattagctg tttgttgcga cattatggct tgcttgttta gaggtccaag tgattctgac      600
ttggaattgt tagttggtca agctatcttc ggtgacggtg ctgctgctgt tattgttggt      660
gcagaacctg acgaatctgt tggtgaaaga ccaatatttg aattagtcag tacaggtcaa      720
accatcttgc ctaattctga aggtacaatt ggtggtcata agagaagc aggtttgatc      780 ttcgatttgc acaaagacgt tccaatgtta atctctaaca acatagaaaa gtgtttgata      840
gaagcattca ctcctatagg tatctcagat tggaactcta ttttctggat aacacatcca      900
ggtggtaaag ccatttgga taaggttgaa gaaaaattgg atttgaagaa agaaaagttt      960
gtagatagta gacatgtttt atctgaacac ggtaacatgt cttcatccac tgtcttgttc     1020
gtaatggatg aattgagaaa gagatcatta gaagagggta atctactac tggtgacggt     1080 tttgaatggg gtgtcttatt tggtttcggt cctggtttga ccgtcgaaag agtagttgtc     1140
agatcagtac caattaaata tgaaggtaga ggttccttgt taacttgtgg tgacgttgaa     1200
gaaaacccag gtcctatggc cgtcaagcat ttgatagtat tgaagtttaa agatgaaatc     1260
acagaagctc aaaaggaaga attttcaag acctacgtta atttggtcaa cattataccct     1320 gctatgaaag atgtatactg gggtaaagac gttacacaaa agaaagaaga aggttataca     1380
cacattgtcg aagtaacctt cgaatcagtt gaaactatcc aagattacat cattcatcca     1440
gctcacgttg gttttggtga cgtttacaga tccttctggg aaaaattgtt gatcttcgat     1500 tacacccccaa gaaagtaccc ttacgatgtt ccagactatg cataagcggc cgc           1553
```

<210> SEQ ID NO 16
<211> LENGTH: 2918
<212> TYPE: DNA
<213> ORGANISM: Artificial Sequence
<220> FEATURE:
<223> OTHER INFORMATION: Codon Optimized

<400> SEQUENCE: 16

```
actagtatgg gtttatcatc cgtctgtact ttctccttcc aaactaacta tcatacctta       60
ttgaatcctc acaacaacaa tccaaaaaca tcattgttgt gttacagaca tccaaagaca      120
cctattaagt actcttacaa caactttcca tcaaaacatt gttcaaccaa gtccttccac      180
ttacaaaata gtgctccga agtttgtct atagctaaga actctatcag agctgcaact      240
acaaatcaaa ctgaaccacc tgaaagtgat aatcactctg ttgccacaaa aattttgaac      300
ttcggtaaag catgttggaa gttgcaaaga ccatacacca taatcgcttt tacttcttgt      360
gcatgcggtt tattcggtaa agaattgttg cataacacta acttaatttc atggtccttg      420
atgttcaagg catttttctt tttagttgcc atcttgtgca tcgcttcatt caccactaca      480
attaatcaaa tatacgattt gcacatcgac agaattaaca aaccagattt gcctttggct      540
tcaggtgaaa tatccgtcaa tactgcatgg atcatgtcta tcatagtagc cttgttcggt      600
ttgatcatca caattaaaat gaagggtggt ccattgtaca tcttcggtta ctgtttccgt      660 atcttccggtg gtattgtcta ttccgtacca ccttttagat ggaaacaaaa ccctagtact      720
gcctttttgt tgaatttctt agctcatatc atcacaaaact tcaccttcta ctacgcttca      780
```

```
agagctgctt taggtttgcc attcgaattg agaccttcat tcacattttt gttggcattc    840
atgaaaagta tgggttctgc attagccttg atcaaggatg cctctgacgt tgaaggtgac    900
acaaagttcg gtattagtac cttggcttct aagtacggtt caagaaattt gactttgttc    960
tgctccggta tcgttttgtt aagttacgtc gcagccattt tggcaggtat catttggcca   1020
caagccttta attctaacgt tatgttgttg tcacatgcca tcttggcttt ctggttgatc   1080
ttgcaaacta gagatttcgc tttgacaaat tatgaccctg aagcaggtag aagattctac   1140
gagtttatgt ggaaattgta ctacgctgaa tatttggtat acgtttttat tgaaggtaga   1200
ggttctttgt tgacctgtgg tgacgttgaa gaaaatccag gtcctatgaa atgttcaact   1260
ttctcctttt ggttcgtatg caagatcatc ttcttttttct tttcctttaa catccaaaca   1320
agtatcgcaa acccaagaga aaacttttttg aagtgcttct cacaatacat acctaataac   1380
gccaccaatt tgaagttggt ttacactcaa acaacccat tgtacatgtc cgtcttgaac   1440
agtacaatcc ataatttgag attcacttct gataccactc caaaaccttt ggtcattgta   1500 accctagtc atgtatctca catccaaggt actatcttat gttctaaaaa ggttggtttg   1560
caaattagaa ctagatccgg tggtcatgat agtgaaggca tgtcatacat ctcccaagtt   1620
ccattcgtta tcgttgattt gagaaacatg agatcaatta aaatagacgt acactcacaa   1680
actgcttggg ttgaagctgg tgcaacattg ggtgaagtat actactgggt aacgaaaag    1740 aatgaaaact tatcattggc tgctggttac tgtccaacag tttgcgcagg tggtcatttt   1800
ggtggtggtg gttatggtcc tttaatgaga aactacggtt tggccgctga taacataatc   1860
gacgctcatt tggtaaatgt tcacggtaaa gttttggata aaagtctat gggtgaagac   1920 ttattttggg ctttgagagg tggtggtgca gaatcattcg gtatcatagt tgcttggaag   1980
ataagattag tcgcagtacc aaagtctact atgttctcag tcaaaaagat aatggaaatc   2040
catgaattag ttaaattggt caataagtgg caaaacatcg catacaagta cgataaggac   2100
ttgttgttga tgactcattt catcacaaga aacataccg ataaccaagg taaaaataag   2160
actgctatcc acacatactt ttcttcagtt ttcttgggtg gtgtcgattc cttagtagac   2220
ttgatgaata agtcttttcc agaattaggt attaagaaaa ctgattgtag acaattgtct   2280
tggatcgaca ccatcatctt ttattcaggt gttgtcaact acgatacaga caacttcaac   2340
aaagaaatat tattggatag atccgcaggt caaaacggtg cctttaaaat taagttagac   2400
tacgttaaaa agccaatacc tgaatcagtt ttcgtccaaa tcttagaaaa attgtacgaa   2460
gaagatattg gtgcaggcat gtacgccttg tatccatacg tggtataat ggacgaaatc   2520 agtgaatctg ccattccatt tcctcataga gctggtatct tatacgaatt gtggtacatt   2580
tgttcatggg aaaagcaaga agataacgaa aagcacttaa actggattag aaacatctat   2640
aacttcatga ctccatacgt ttctaaaaac cctagattgg catatttgaa ctacagagat   2700
ttggacatcg gtattaacga tccaaagaat cctaacaact atacccaagc tagaatttgg   2760 ggtgaaaat acttcggtaa aaatttcgat agattagtaa aggttaagac attggttgac   2820
ccaaacaact tctttagaaa cgaacaatcc attccacctt tacctagaca tagacacgaa   2880
caaaaattaa taagtgaaga agatttgtaa gcggccgc                           2918
```

<210> SEQ ID NO 17
<211> LENGTH: 167
<212> TYPE: DNA
<213> ORGANISM: Artificial Sequence
<220> FEATURE:
<223> OTHER INFORMATION: Codon Optimized

<400> SEQUENCE: 17

```
agccaaaata atgataacga gaataatatc aagaatacct tagaacaaca tcgacaacaa      60
caacaggcat tttcggatat gagtcacgtg gagtattcca gaattacaaa attttttcaa     120
gaacaaccac tggagggata tacccttttc tctcacaggt ctgcgcc                   167
```

<210> SEQ ID NO 18
<211> LENGTH: 1518
<212> TYPE: DNA
<213> ORGANISM: Artificial Sequence
<220> FEATURE:
<223> OTHER INFORMATION: Codon Optimized

<400> SEQUENCE: 18

```
atggtttcca atcacttgtt tgacgcaatg agagccgctg cccctggtaa cgccccttc      60
ataagaatag ataatactag aacttggaca tacgatgacg cctttgcttt atctggtaga    120
atagcatcag ctatggatgc tttgggtatc agaccaggtg acagagtcgc agttcaagta    180
gaaaaatccg ctgaagcatt gatcttgtat ttggcttgtt tgagaagtgg tgcagtttat    240
ttgccattga atactgccta cacattagct gaattggatt acttcatagg tgacgcagaa    300
cctagattgg ttgtagtcgc ctcttcagcc agagctggtg tagaaacaat tgctaaacca    360
agaggtgcaa tagtcgaaac cttagatgct gctggttctg gtagtttgtt agatttggcc    420
agagacgaac ctgctgattt tgttgacgct tcaagatcag ccgatgactt agccgctatt    480
ttgtacacct ctggtactac aggtagatca aagggtgcta tgttgactca tggtaatttg    540
ttgtcaaacg cattaacctt gagagatttc tggagagtta ctgccggtga cagattaatc    600
cacgctttgc caattttca tactcacggt ttattcgttg ctaccaacgt aactttgtta    660
gcaggtgcct ccatgttctt gttgagtaag ttcgatccag aagaaatatt atctttgatg    720
cctcaagcta ctatgttgat gggtgtccca acattctacg ttagattgtt acaatcacct    780
agattagata agcaagctgt tgcaaacatc agattgttta tatccggtag tgctccattg    840
ttagcagaaa cccatactga atttcaagca agaacaggtc acgccatttt agaaagatac    900
ggtatgacag aaaccaatat gaacacttct aaccctatg aaggtaaaag aatagctggt    960
acagttggtt ttccattgcc tgatgtcaca gttagagtaa ccgacccagc cactggttta   1020
gctttgccac tgaacaaac tggtatgatc gaaattaaag gtccaaacgt ttttaagggt   1080
tactggagaa tgcctgaaaa gactgctgct gagtttactg ctgatggttt ctttatctct   1140
ggtgacttag gtaaaattga tagagacggt tatgtccata ttgttggtcg tggtaaagat   1200
ttggttatat ccggtggtta aacatctac cctaaggaag tagaaggtga aatagatcaa   1260
atcgaaggtg ttgtagaatc agctgtaata ggtgtcccac atcctgattt tggtgaaggt   1320
gttacagcag tcgttgtaag aaaaccaggt gctgcattag atgaaaaggc aattgtttct   1380
gccttacaag acagattggc tagatacaag caaccaaaga gaataatctt cgcagaagat   1440
ttgcctagaa atactatggg taaagtacaa aagaacatct tgagacaaca atacgccgac   1500
ttatacacca gaacctga                                                 1518
```

<210> SEQ ID NO 19
<211> LENGTH: 2092
<212> TYPE: DNA
<213> ORGANISM: Artificial Sequence
<220> FEATURE:
<223> OTHER INFORMATION: Codon Optimized

<400> SEQUENCE: 19

```
actagtatgg gtttatcatc cgtctgtact ttctccttcc aaactaacta tcataccttta      60
ttgaatcctc acaacaacaa tccaaaaaca tcattgttgt gttacagaca tccaaagaca     120
cctattaagt actcttacaa caactttcca tcaaaacatt gttcaaccaa gtccttccac     180
ttacaaaata agtgctccga aagtttgtct atagctaaga actctatcag agctgcaact     240
acaaatcaaa ctgaaccacc tgaaagtgat aatcactctg ttgccacaaa aattttgaac     300
ttcggtaaag catgttggaa gttgcaaaga ccatacacca taatcgcttt tacttcttgt     360
gcatgcggtt tattcggtaa agaattgttg cataacacta acttaatttc atggtcctat     420
gaactgctcc gcattctctt tctggttcgt ctgtaaaata atcttcttct tcttgtcctt     480
caacatccaa atctccatcg caaatccaca agaaaacttt ttgaagtgtt tctccgaata     540
catcccaaac aaccctgcta acccaaagtt tatatatact caacatgatc aattgtacat     600
gtccgttttg aacagtacca tccaaaattt gagattcact tctgacacta caccaaaacc     660
tttagtcatt gttacacctt ccaatgttag tcacattcaa gcttctatat tgtgctctaa     720
gaaagtaggt ttgcaaatca gaactagatc aggtggtcat gatgcagaag gcatgtctta     780
catctcacaa gttccattcg ttgtagtcga tttgagaaat atgcattcca taagatcga      840
cgttcacagt caaacagcat gggtagaagc aggtgccacc ttgggtgaag tttactactg     900
gatcaacgaa aagaatgaaa acttttcttt ccctggtggt tactgtccaa cagtaggtgt     960
cggtggtcac ttttctggtg gtggttatgg tgcattgatg agaaactacg gtttagctgc    1020
agataatatt atagacgccc atttggttaa cgtagatggt aaagtttttgg acagaaagtc    1080
tatgggtgaa gatttgtttt gggccataag aggtggtggt ggtgaaaatt cggtatcat     1140
tgccgcttgg aaaattaagt tagtcgctgt tccttccaaa agtactattt tctctgtcaa    1200
aaagaacatg gaaatccacg gtttggttaa gttgtttaat aagtggcaaa acatcgctta    1260
caagtacgat aaggacttgg ttttgatgac ccatttcatc actaaaaata ttacagataa    1320
ccatggtaaa aataagacca ctgttcacgg ttatttttct tcaatttttcc atggtggtgt    1380
agattctttg gttgatttga tgaataagtc attcccagaa ttgggtatta aaaagacaga    1440
ttgcaaggaa ttttcttgga tagacacaac catcttctat tcaggtgttg taaacttcaa    1500
caccgctaac ttcaaaaagg aaatcttgtt ggatagatcc gctggtaaaa agaccgcttt    1560
ttctattaaa ttggactacg ttaagaaacc aatccctgaa actgcaatgg tcaagatatt    1620
ggaaaagttg tacgaagaag atgtaggtgt cggcatgtac gttttgtatc catacggtgg    1680
tattatggaa gaaatatctg aatcagccat accatttcct cacagagctg gtatcatgta    1740
tgaattatgg tacacagcct catgggaaaa gcaagaagat aacgaaaagc atatcaactg    1800
ggtcagatcc gtttacaact tcactacacc ttacgttagt caaaacccaa gattggcata    1860
tttgaactac agagatttgg acttaggtaa aactaaccct gaatctccaa ataactatac    1920
acaagcaaga atttggggtg aaaagtactt tggtaaaaat ttcaacagat tagttaaagt    1980
aaagactaaa gccgacccta caacttttt cagaaacgaa caatccatcc acctttgcc     2040
acctcaccac cacgaacaaa aattaataag tgaagaagat ttgtaagtcg ac            2092
```

<210> SEQ ID NO 20
<211> LENGTH: 7904
<212> TYPE: DNA
<213> ORGANISM: Artificial Sequence
<220> FEATURE:
<223> OTHER INFORMATION: Codon Optimized

<400> SEQUENCE: 20

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatcga ctacgtcgta aggccgtttc tgacagagta aaattcttga gggaactttc     240
accattatgg gaaatggttc aagaaggtat tgacttaaac tccatcaaat ggtcaggtca     300
ttgagtgttt tttatttgtt gtattttttt tttttagag aaaatcctcc aatatcaaat      360
taggaatcgt agtttcatga ttttctgtta cacctaactt tttgtgtggt gccctcctcc     420
ttgtcaatat taatgttaaa gtgcaattct ttttccttat cacgttgagc cattagtatc     480
aatttgctta cctgtattcc tttactatcc tccttttttct ccttcttgat aaatgtatgt    540
agattgcgta tatagtttcg tctaccctat gaacatattc cattttgtaa tttcgtgtcg     600
tttctattat gaatttcatt tataaagttt atgtacaaat atcataaaaa aagagaatct     660
ttttaagcaa ggattttctt aacttcttcg gcgacagcat caccgacttc ggtggtactg     720
ttggaaccac ctaaatcacc agttctgata cctgcatcca aaacctttt aactgcatct      780
tcaatggcct taccttcttc aggcaagttc aatgacaatt tcaacatcat tgcagcagac     840
aagatagtgg cgatagggtc aaccttattc tttggcaaat ctggagcaga accgtggcat     900
ggttcgtaca aaccaaatgc ggtgttcttg tctggcaaag aggccaagga cgcagatggc     960
aacaaaccca aggaacctgg gataacggag gcttcatcgg agatgatatc accaaacatg    1020
ttgctggtga ttataatacc atttaggtgg gttgggttct taactaggat catggcggca    1080
gaatcaatca attgatgttg aaccttcaat gtagggaatt cgttcttgat ggtttcctcc    1140
acagttttc tccataatct tgaagaggcc aaaacattag ctttatccaa ggaccaaata     1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt accttagca     1380
aattgtggct tgattggaga taagtctaaa agagagtcgg atgcaaagtt acatggtctt    1440
aagttggcgt acaattgaag ttcttttacgg atttttagta aaccttgttc aggtctaaca    1500
ctaccggtac cccatttagg accacccaca gcacctaaca aaacggcatc aaccttcttg    1560
gaggcttcca gcgcctcatc tggaagtggg cacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa acgacgatc     1740
ttcttagggg cagacatagg ggcagacatt agaatgtat atccttgaaa tatatatata    1800
tattgctgaa atgtaaaagg taagaaaagt tagaaagtaa gacgattgct aaccacctat    1860
tggaaaaaac aataggtcct taaataatat tgtcaacttc aagtattgtg atgcaagcat    1920
ttagtcatga acgcttctct attctatatg aaaagccggt tccggcctct caccttccct    1980
ttttctccca atttttcagt tgaaaaaggt atatgcgtca ggcgacctct gaaattaaca    2040
aaaaatttcc agtcatcgaa tttgattctg tgcgatagcg cccctgtgtg ttctcgttat    2100
gttgaggaaa aaaataatgg ttgctaagag attcgaactc ttgcatctta cgatacctga    2160
gtattcccac agttaactgc ggtcaagata tttcttgaat caggcgcctt agaccgctcg    2220
gccaaacaac caattacttg ttgagaaata gagtataatt atcctataaa tataacgttt    2280
```

```
ttgaacacac atgaacaagg aagtacagga caattgattt tgaagagaat gtggattttg    2340
atgtaattgt tgggattcca ttttaataa  ggcaataata ttaggtatgt ggatatacta    2400
gaagttctcc tcgagggtcg atatgcggtg tgaaataccg cacagatgcg taaggagaaa    2460
ataccgcatc aggaaattgt aaacgttaat attttgttaa aattcgcgtt aaattttgt     2520 taaatcagct catttttaa  ccaataggcc gaaatcggca aaatcccta taaatcaaaa     2580 gaatagaccg atatagggtt gagtgttgtt ccagtttgga acaagagtcc actattaaag    2640
aacgtggact ccaacgtcaa agggcgaaaa accgtctatc agggcgatgg cccactacgt    2700
gaaccatcac cctaatcaag ttttttgggg tcgaggtgcc gtaaagcact aaatcggaac    2760
cctaaaggga gcccccgatt tagagcttga cggggaaagc cggcgaacgt ggcgagaaag    2820
gaagggaaga aagcgaaagg agcggcgct  agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga agggggatg  tgctgcaagg cgattaagtt gggtaacgcc agggttttcc    3060
cagtcacgac gttgtaaaac gacggccagt gaattgtaat acgactcact atagggcgaa    3120
ttggagctct agtacggatt agaagccgcc gagcgggcga cagccctccg acggaagact    3180
ctcctccgtg cgtcctcgtc ttcaccggtc gcgttcctga aacgcagatg tgcctcgcgc    3240
cgcactgctc cgaacaataa agattctaca atactagctt ttatggttat gaagaggaaa    3300
aattggcagt aacctggccc cacaaacctt caaattaacg aatcaaatta acaaccatag    3360
gatgataatg cgattagttt tttagcctta tttctggggt aattaatcag cgaagcgatg    3420 attttttgatc tattaacaga tatataaatg gaaaagctgc ataaccactt taactaatac    3480
tttcaacatt ttcagtttgt attacttctt attcaaatgt cataaaagta tcaacaaaaa    3540
attgttaata tacctctata ctttaacgtc aaggagaaaa aaccccggat tctagaacta    3600
gtggatcccc catcacaagt ttgtacaaaa aagctgaacg agaaacgtaa aatgatataa    3660
atatcaatat attaaattag attttgcata aaaaacagac tacataatac tgtaaaacac    3720
aacatatcca gtcactatgg cggccgcatt aggcacccca ggctttacac tttatgcttc    3780
cggctcgtat aatgtgtgga ttttgagtta ggatccgtcg agattttcag gagctaagga    3840
agctaaaatg gagaaaaaaa tcactggata taccaccgtt gatatatccc aatggcatcg    3900
taaagaacat tttgaggcat ttcagtcagt tgctcaatgt acctataacc agaccgttca    3960
gctggatatt acggcctttt taagaccgt  aaagaaaaat aagcacaagt tttatccggc    4020
ctttattcac attcttgccc gcctgatgaa tgctcatccg gaattccgta tggcaatgaa    4080
agacggtgag ctggtgatat gggatagtgt tcacccttgt tacaccgttt tccatgagca    4140
aactgaaacg ttttcatcgc tctggagtga ataccacgac gatttccggc agtttctaca    4200
catatattcg caagatgtgg cgtgttacgg tgaaaacctg gcctatttcc ctaaagggtt    4260
tattgagaat atgtttttcg tctcagccaa tccctgggtg agtttcacca gttttgattt    4320
aaacgtggcc aatatggaca acttcttcgc cccgttttc  accatgggca aatattatac    4380
gcaaggcgac aaggtgctga tgccgctggc gattcaggtt catcatgccg tctgtgatgg    4440
cttccatgtc ggcagaatgc ttaatgaatt acaacagtac tgcgatgagt ggcagggcgg    4500
ggcgtaaacg ccgcgtggat ccggcttact aaaagccaga taacagtatg cgtatttgcg    4560
cgctgatttt tgcggtataa gaatatatac tgatatgtat acccgaagta tgtcaaaaag    4620
aggtatgcta tgaagcagcg tattacagtg acagttgaca gcgacagcta tcagttgctc    4680
```

```
aaggcatata tgatgtcaat atctccggtc tggtaagcac aaccatgcag aatgaagccc      4740
gtcgtctgcg tgccgaacgc tggaaagcgg aaaatcagga agggatggct gaggtcgccc      4800
ggtttattga aatgaacggc tcttttgctg acgagaacag gggctggtga aatgcagttt      4860
aaggtttaca cctataaaag agagagccgt tatcgtctgt tgtggatgt acagagtgat       4920 attattgaca cgcccgggcg acggatggtg atcccctgg ccagtgcacg tctgctgtca       4980
gataaagtct cccgtgaact ttacccggtg gtgcatatcg gggatgaaag ctggcgcatg      5040
atgaccaccg atatggccag tgtgccggtc tccgttatcg ggaagaagt ggctgatctc       5100 agccaccgcg aaaatgacat caaaaacgcc attaacctga tgttctgggg aatataaatg      5160
tcaggctccc ttatacacag ccagtctgca ggtcgaccat agtgactgga tatgttgtgt     5220
tttacagtat tatgtagtct gttttttatg caaaatctaa tttaatatat tgatatttat     5280
atcattttac gtttctcgtt cagctttctt gtacaaagtg gtgatgggct gcaggaattc    5340
gatatcaagc ttatcgatac cgtcgacctc gagtcatgta attagttatg tcacgcttac    5400
attcacgccc tccccccaca tccgctctaa ccgaaaagga aggagttaga caacctgaag    5460
tctaggtccc tatttatttt tttatagtta tgttagtatt aagaacgtta tttatatttc    5520 aaattttct ttttttttctg tacagacgcg tgtacgcatg taacattata ctgaaaacct     5580
tgcttgagaa ggttttggga cgctcgaagg ctttaatttg cggccggtac ccagcttttg    5640
ttccctttag tgagggttaa ttccgagctt ggcgtaatca tggtcatagc tgtttcctgt    5700
gtgaaattgt tatccgctca caattccaca acatagga gccggaagca taaagtgtaa     5760 agcctgggt gcctaatgag tgaggtaact cacattaatt gcgttgcgct cactgcccgc    5820
tttccagtcg ggaaacctgt cgtgccagct gcattaatga atcggccaac gcgcggggag    5880
aggcggtttg cgtattgggc gctcttccgc ttcctcgctc actgactcgc tgcgctcggt    5940
cgttcggctg cggcgagcgg tatcagctca ctcaaaggcg gtaatacggt tatccacaga    6000 atcagggat aacgcaggaa agaacatgtg agcaaaaggc cagcaaaagg ccaggaaccg    6060
taaaaaggcc gcgttgctgg cgttttttcca taggctcggc cccctgacg agcatcacaa    6120 aaatcgacgc tcaagtcaga ggtggcgaaa cccgacagga ctataaagat accaggcgtt    6180 ccccctgga agctccctcg tgcgctctcc tgttccgacc ctgccgctta ccggatacct    6240
gtccgccttt ctcccttcgg gaagcgtggc gctttctcaa tgctcacgct gtaggtatct    6300
cagttcggtg taggtcgttc gctccaagct gggctgtgtg cacgaacccc ccgttcagcc    6360
cgaccgctgc gccttatccg gtaactatcg tcttgagtcc aacccggtaa gacacgactt    6420
atcgccactg gcagcagcca ctggtaacag gattagcaga gcgaggtatg taggcggtgc    6480
tacagagttc ttgaagtggt ggcctaacta cggctacact agaaggacag tatttggtat    6540
ctgcgctctg ctgaagccag ttaccttcgg aaaaagagtt ggtagctctt gatccggcaa    6600
acaaaccacc gctggtagcg gtggtttttt tgtttgcaag cagcagatta cgcgcagaaa    6660
aaaaggatct caagaagatc ctttgatctt ttctacgggg tctgacgctc agtggaacga    6720
aaactcacgt taagggattt tggtcatgag attatcaaaa aggatcttca cctagatcct    6780
tttaaattaa aaatgaagtt ttaaatcaat ctaaagtata tatgagtaaa cttggtctga    6840
cagttaccaa tgcttaatca gtgaggcacc tatctcagcg atctgtctat ttcgttcatc    6900
catagttgcc tgactgcccg tcgtgtagat aactacgata cgggagggct taccatctgg    6960
ccccagtgct gcaatgatac cgcgagaccc acgctcaccg gctccagatt tatcagcaat    7020
```

| | |
|---|---|
| aaaccagcca gccggaaggg ccgagcgcag aagtggtcct gcaactttat ccgcctccat | 7080 |
| ccagtctatt aattgttgcc gggaagctag agtaagtagt tcgccagtta atagtttgcg | 7140 |
| caacgttgtt gccattgcta caggcatcgt ggtgtcacgc tcgtcgtttg gtatggcttc | 7200 |
| attcagctcc ggttcccaac gatcaaggcg agttacatga tcccccatgt tgtgaaaaaa | 7260 |
| agcggttagc tccttcggtc ctccgatcgt tgtcagaagt aagttggccg cagtgttatc | 7320 |
| actcatggtt atggcagcac tgcataattc tcttactgtc atgccatccg taagatgctt | 7380 |
| ttctgtgact ggtgagtact caaccaagtc attctgagaa tagtgtatgc ggcgaccgag | 7440 |
| ttgctcttgc ccggcgtcaa tacgggataa taccgcgcca catagcagaa ctttaaaagt | 7500 |
| gctcatcatt ggaaaacgtt cttcggggcg aaaactctca aggatcttac cgctgttgag | 7560 |
| atccagttcg atgtaaccca ctcgtgcacc caactgatct tcagcatctt ttactttcac | 7620 |
| cagcgtttct gggtgagcaa aaacaggaag gcaaaatgcc gcaaaaaagg gaataagggc | 7680 |
| gacacggaaa tgttgaatac tcatactctt cctttttcaa tattattgaa gcatttatca | 7740 |
| gggttattgt ctcatgagcg gatacatatt tgaatgtatt tagaaaaata aacaaatagg | 7800 |
| ggttccgcgc acatttcccc gaaaagtgcc acctgacgtc taagaaacca ttattatcat | 7860 |
| gacattaacc tataaaaata ggcgtatcac gaggccctttc cgtc | 7904 |

<210> SEQ ID NO 21
<211> LENGTH: 6773
<212> TYPE: DNA
<213> ORGANISM: Artificial Sequence
<220> FEATURE:
<223> OTHER INFORMATION: Codon Optimized

<400> SEQUENCE: 21

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accacgcttt tcaattcaat tcatcatttt ttttttattc tttttttttga tttcggtttc | 240 |
| tttgaaattt ttttgattcg gtaatctccg aacagaagga agaacgaagg aaggagcaca | 300 |
| gacttagatt ggtatatata cgcatatgta gtgttgaaga acatgaaat tgcccagtat | 360 |
| tcttaaccca actgcacaga acaaaaacct gcaggaaacg aagataaatc atgtcgaaag | 420 |
| ctacatataa ggaacgtgct gctactcatc ctagtcctgt tgctgccaag ctatttaata | 480 |
| tcatgcacga aaagcaaaca aacttgtgtg cttcattgga tgttcgtacc accaaggaat | 540 |
| tactggagtt agttgaagca ttaggtccca aaatttgttt actaaaaaca catgtggata | 600 |
| tcttgactga ttttccatg gagggcacag ttaagccgct aaaggcatta tccgccaagt | 660 |
| acaatttttt actcttcgaa gacagaaaat tgctgacat tggtaataca gtcaaattgc | 720 |
| agtactctgc gggtgtatac agaatagcag aatgggcaga cattacgaat gcacacggtg | 780 |
| tggtgggccc aggtattgtt agcggtttga agcaggcggc agaagaagta acaaaggaac | 840 |
| ctagaggcct tttgatgtta gcagaattgt catgcaaggg ctccctatct actggagaat | 900 |
| atactaaggg tactgttgac attgcgaaga gcgacaaaga ttttgttatc ggctttattg | 960 |
| ctcaaagaga catgggtgga agagatgaag gttacgattg gttgattatg acacccggtg | 1020 |
| tgggtttaga tgacaaggga gacgcattgg gtcaacagta tagaaccgtg gatgatgtgg | 1080 |
| tctctacagg atctgacatt attattgttg gaagaggact atttgcaaag ggaagggatg | 1140 |
| ctaaggtaga gggtgaacgt tacagaaaag caggctggga agcatatttg agaagatgcg | 1200 |

```
gccagcaaaa ctaaaaaact gtattataag taaatgcatg tatactaaac tcacaaatta      1260
gagcttcaat ttaattatat cagttattac cctgcggtgt gaaataccgc acagatgcgt      1320
aaggagaaaa taccgcatca ggaaattgta acgttaata ttttgttaaa attcgcgtta       1380
aatttttgtt aaatcagctc attttttaac caataggccg aaatcggcaa aatcccttat      1440
aaatcaaaag aatagaccga datagggttg agtgttgttc cagtttggaa caagagtcca      1500
ctattaaaga acgtggactc caacgtcaaa gggcgaaaaa ccgtctatca gggcgatggc      1560
ccactacgtg aaccatcacc ctaatcaagt tttttgggt cgaggtgccg taaagcacta       1620
aatcggaacc ctaaagggag cccccgattt agagcttgac ggggaaagcc ggcgaacgtg      1680
gcgagaaagg aagggaagaa agcgaaagga gcgggcgcta gggcgctggc aagtgtagcg      1740
gtcacgctgc gcgtaaccac cacacccgcc gcgcttaatg cgccgctaca gggcgcgtcg      1800
cgccattcgc cattcaggct gcgcaactgt tgggaagggc gatcggtgcg ggcctcttcg      1860
ctattacgcc agctggcgaa ggggggatgt gctgcaaggc gattaagttg ggtaacgcca      1920
gggttttccc agtcacgacg ttgtaaaacg acggccagtg aattgtaata cgactcacta      1980
tagggcgaat tggagctcta gtacggatta gaagccgccg agcgggcgac agccctccga      2040
cggaagactc tcctccgtgc gtcctcgtct tcaccggtcg cgttcctgaa acgcagatgt      2100
gcctcgcgcc gcactgctcc gaacaataaa gattctacaa tactagcttt tatggttatg      2160
aagaggaaaa attggcagta acctggcccc acaaaccttc aaattaacga atcaaattaa      2220
caaccatagg atgataatgc gattagtttt ttagccttat ttctggggta attaatcagc      2280
gaagcgatga ttttttgatct attaacagat atataaatgg aaaagctgca taaccacttt      2340
aactaatact ttcaacattt tcagtttgta ttacttctta ttcaaatgtc ataaaagtat      2400
caacaaaaaa ttgttaatat acctctatac tttaacgtca aggagaaaaa accccggatt      2460
ctagaactag tggatccccc atcacaagtt tgtacaaaaa agctgaacga gaaacgtaaa      2520
atgatataaa tatcaatata ttaaattaga ttttgcataa aaaacagact acataatact      2580
gtaaaacaca acatatccag tcactatggc ggccgcatta ggcacccag gctttacact      2640 ttatgcttcc ggctcgtata atgtgtggat tttgagttag gatccgtcga gattttcagg      2700
agctaaggaa gctaaaatgg agaaaaaaat cactggatat accaccgttg atatatccca      2760
atggcatcgt aaagaacatt tgaggcatt tcagtcagtt gctcaatgta cctataacca      2820
gaccgttcag ctggatatta cggccttttt aaagaccgta agaaaaata agcacaagtt      2880 ttatccggcc tttattcaca ttcttgcccg cctgatgaat gctcatccgg aattccgtat      2940
ggcaatgaaa gacggtgagc tggtgatatg gatagtgtt caccttgtt acaccgtttt      3000 ccatgagcaa actgaaacgt tttcatcgct ctggagtgaa taccacgacg atttccggca      3060
gtttctacac atatattcgc aagatgtggc gtgttacggt gaaaacctgg cctatttccc      3120
taaagggttt attgagaata tgttttcgt ctcagccaat ccctgggtga gtttcaccag      3180
ttttgattta acgtggcca atatggacaa cttcttcgcc cccgttttca ccatgggcaa      3240
atattatacg caaggcgaca aggtgctgat gccgctggcg attcaggttc atcatgccgt      3300
ctgtgatggc ttccatgtcg gcagaatgct taatgaatta acagtact gcgatgagtg      3360 gcagggcggg gcgtaaacgc gcgtggatc cggcttacta aaagccagat aacagtatgc      3420
gtatttgcgc gctgattttt gcggtataag aatatatact gatatgtata cccgaagtat      3480
gtcaaaaaga ggtatgctat gaagcagcgt attacagtga cagttgacag cgacagctat      3540
```

-continued

```
cagttgctca aggcatatat gatgtcaata tctccggtct ggtaagcaca accatgcaga      3600
atgaagcccg tcgtctgcgt gccgaacgct ggaaagcgga aaatcaggaa gggatggctg      3660
aggtcgcccg gtttattgaa atgaacggct cttttgctga cgagaacagg ggctggtgaa      3720
atgcagttta aggtttacac ctataaaaga gagagccgtt atcgtctgtt tgtggatgta      3780
cagagtgata ttattgacac gcccgggcga cggatggtga tcccctggc cagtgcacgt       3840 ctgctgtcag ataaagtctc ccgtgaactt tacccggtgg tgcatatcgg ggatgaaagc      3900
tggcgcatga tgaccaccga tatggccagt gtgccggtct ccgttatcgg ggaagaagtg     3960
gctgatctca gccaccgcga aaatgacatc aaaaacgcca ttaacctgat gttctgggga     4020
atataaatgt caggctccct tatacacagc cagtctgcag gtcgaccata gtgactggat     4080
atgttgtgtt ttacagtatt atgtagtctg ttttttatgc aaaatctaat ttaatatatt     4140
gatatttata tcattttacg tttctcgttc agctttcttg tacaaagtgg tgatgggctg     4200
caggaattcg atatcaagct tatcgatacc gtcgacctcg agtcatgtaa ttagttatgt     4260
cacgcttaca ttcacgccct ccccccacat ccgctctaac cgaaaggaa ggagttagac       4320 aacctgaagt ctaggtccct atttattttt ttatagttat gttagtatta agaacgttat     4380
ttatatttca aatttttctt tttttctgt acagacgcgt gtacgcatgt aacattatac      4440
tgaaaacctt gcttgagaag gttttgggac gctcgaaggc tttaatttgc ggccggtacc     4500
cagcttttgt tccctttagt gagggttaat tccgagcttg gcgtaatcat ggtcatagct     4560
gtttcctgtg tgaaattgtt atccgctcac aattccacac aacataggag ccggaagcat     4620
aaagtgtaaa gcctggggtg cctaatgagt gaggtaactc acattaattg cgttgcgctc     4680
actgcccgct ttccagtcgg gaaacctgtc gtgccagctg cattaatgaa tcggccaacg     4740
cgcggggaga ggcggtttgc gtattgggcg ctcttccgct tcctcgctca ctgactcgct     4800
gcgctcggtc gttcggctgc ggcgagcggt atcagctcac tcaaaggcgg taatacggtt     4860
atccacagaa tcaggggata acgcaggaaa gaacatgtga gcaaaaggcc agcaaaaggc     4920
caggaaccgt aaaaaggccg cgttgctggc gtttttccat aggctcggcc cccctgacga     4980
gcatcacaaa aatcgacgct caagtcagag gtggcgaaac ccgacaggac tataaagata     5040
ccaggcgttc ccccctggaa gctccctcgt gcgctctcct gttccgaccc tgccgcttac     5100
cggatacctg tccgcctttc tcccttcggg aagcgtggcg ctttctcaat gctcacgctg     5160
taggtatctc agttcggtgt aggtcgttcg ctccaagctg ggctgtgtgc acgaaccccc     5220
cgttcagccc gaccgctgcg ccttatccgg taactatcgt cttgagtcca acccggtaag     5280
acacgactta tcgccactgg cagcagccac tggtaacagg attagcagag cgaggtatgt     5340
aggcggtgct acagagttct tgaagtggtg gcctaactac ggctacacta aaggacagt      5400 atttggtatc tgcgctctgc tgaagccagt taccttcgga aaaagagttg gtagctcttg     5460
atccggcaaa caaaccaccg ctggtagcgg tggttttttt gtttgcaagc agcagattac     5520
gcgcagaaaa aaaggatctc aagaagatcc tttgatcttt tctacggggt ctgacgctca     5580
gtggaacgaa aactcacgtt aagggatttt ggtcatgaga ttatcaaaaa ggatcttcac     5640
ctagatcctt ttaaattaaa aatgaagttt taaatcaatc taaagtatat atgagtaaac     5700
ttggtctgac agttaccaat gcttaatcag tgaggcacct atctcagcga tctgtctatt     5760
tcgttcatcc atagttgcct gactccccgt cgtgtagata actacgatac gggagggctt     5820
accatctggc cccagtgctg caatgatacc gcgagaccca cgctcaccgg ctccagattt     5880
atcagcaata aaccagccag ccggaagggc cgagcgcaga agtggtcctg caactttatc     5940
```

-continued

```
cgcctccatc cagtctatta attgttgccg ggaagctaga gtaagtagtt cgccagttaa      6000
tagtttgcgc aacgttgttg ccattgctac aggcatcgtg gtgtcacgct cgtcgtttgg      6060
tatggcttca ttcagctccg gttcccaacg atcaaggcga gttacatgat cccccatgtt      6120
gtgaaaaaaa gcggttagct ccttcggtcc tccgatcgtt gtcagaagta agttggccgc      6180
agtgttatca ctcatggtta tggcagcact gcataattct cttactgtca tgccatccgt      6240
aagatgcttt tctgtgactg gtgagtactc aaccaagtca ttctgagaat agtgtatgcg      6300
gcgaccgagt tgctcttgcc cggcgtcaat acgggataat accgcgccac atagcagaac      6360
tttaaaagtg ctcatcattg gaaaacgttc ttcgggggcga aaactctcaa ggatcttacc      6420
gctgttgaga tccagttcga tgtaacccac tcgtgcaccc aactgatctt cagcatcttt      6480
tactttcacc agcgtttctg ggtgagcaaa acaggaagg caaatgccg caaaaaggg       6540 aataagggcg acacggaaat gttgaatact catactcttc cttttcaat attattgaag      6600 catttatcag ggttattgtc tcatgagcgg atacatattt gaatgtattt agaaaaataa      6660
acaaataggg gttccgcgca catttccccg aaaagtgcca cctgacgtct aagaaaccat      6720
tattatcatg acattaacct ataaaaatag gcgtatcacg aggccctttc gtc             6773
```

<210> SEQ ID NO 22
<211> LENGTH: 7690
<212> TYPE: DNA
<213> ORGANISM: Artificial Sequence
<220> FEATURE:
<223> OTHER INFORMATION: Codon Optimized

<400> SEQUENCE: 22

```
ttatcatgac attaacctat aaaaataggc gtatcacgag gccctttcgt ctcgcgcgtt        60
tcggtgatga cggtgaaaac ctctgacaca tgcagctccc ggagacggtc acagcttgtc       120
tgtaagcgga tgccgggagc agacaagccc gtcagggcgc gtcagcgggt gttggcgggt       180 gtcgggctg gcttaactat gcggcatcag agcagattgt actgagagtg caccacgctt       240
ttcaattcaa ttcatcattt ttttttatt ctttttttg atttcggttt cttgaaatt        300 tttttgattc ggtaatctcc gaacagaagg aagaacgaag gaaggagcac agacttagat       360
tggtatatat acgcatatgt agtgttgaag aaacatgaaa ttgcccagta ttcttaaccc       420
aactgcacag aacaaaaacc tgcaggaaac gaagataaat catgtcgaaa gctacatata       480
aggaacgtgc tgctactcat cctagtcctg ttgctgccaa gctatttaat atcatgcacg       540
aaaagcaaac aaacttgtgt gcttcattgg atgttcgtac caccaaggaa ttactggagt       600
tagttgaagc attaggtccc aaaatttgtt tactaaaaac acatgtggat atcttgactg       660 attttttccat ggagggcaca gttaagccgc taaaggcatt atccgccaag tacaattttt       720
tactcttcga agacagaaaa tttgctgaca ttggtaatac agtcaaattg cagtactctg       780
cgggtgtata cagaatagca gaatgggcag acattacgaa tgcacacggt gtggtgggcc       840
caggtattgt tagcggtttg aagcaggcgg cagaagaagt aacaaaggaa cctagaggcc       900
ttttgatgtt agcagaattg tcatgcaagg ctccctatc tactggagaa tatactaagg       960
gtactgttga cattgcgaag agcgacaaag attttgttat cggctttatt gctcaaagag      1020
acatgggtgg aagagatgaa ggttacgatt ggttgattat gacacccggt gtgggtttag      1080 atgcaaggg agacgcattg gtcaacagt atagaaccgt ggatgatgtg gtctctacag      1140
gatctgacat tattattgtt ggaagaggac tatttgcaaa gggaagggat gctaaggtag      1200
```

```
agggtgaacg ttacagaaaa gcaggctggg aagcatattt gagaagatgc ggccagcaaa    1260
actaaaaaac tgtattataa gtaaatgcat gtatactaaa ctcacaaatt agagcttcaa    1320
tttaattata tcagttatta ccctgcggtg tgaaataccg cacagatgcg taaggagaaa    1380
ataccgcatc aggaaattgt aaacgttaat attttgttaa aattcgcgtt aaattttttgt   1440 taaatcagct cattttttaa ccaataggcc gaaatcggca aaatccctta taaatcaaaa    1500
gaatagaccg agatagggtt gagtgttgtt ccagtttgga acaagagtcc actattaaag    1560
aacgtggact ccaacgtcaa agggcgaaaa accgtctatc agggcgatgg cccactacgt    1620
gaaccatcac cctaatcaag ttttttgggg tcgaggtgcc gtaaagcact aaatcggaac    1680
cctaagggga gcccccgatt tagagcttga cggggaaagc cggcgaacgt ggcgagaaag    1740
gaagggaaga aagcgaaagg agcgggcgct agggcgctgg caagtgtagc ggtcacgctg    1800
cgcgtaacca ccacacccgc cgcgcttaat gcgccgctac agggcgcgtc gcgccattcg    1860
ccattcaggc tgcgcaactg ttgggaaggg cgatcggtgc gggcctcttc gctattacgc    1920
cagctggcga aggggggatg tgctgcaagg cgattaagtt gggtaacgcc agggttttcc    1980
cagtcacgac gttgtaaaac gacggccagt gaattgtaat acgactcact atagggcgaa    2040
ttggagctct agtacggatt agaagccgcc gagcgggcga cagccctccg acggaagact    2100
ctcctccgtg cgtcctcgtc ttcaccggtc gcgttcctga aacgcagatg tgcctcgcgc    2160
cgcactgctc cgaacaataa agattctaca atactagctt ttatggttat gaagaggaaa    2220
aattggcagt aacctggccc cacaaacctt caaattaacg aatcaaatta acaaccatag    2280
gatgataatg cgattagttt tttagcctta tttctggggt aattaatcag cgaagcgatg    2340 attttgatc tattaacaga tatataaatg gaaaagctgc ataaccactt taactaatac     2400
tttcaacatt ttcagtttgt attacttctt attcaaatgt cataaaagta tcaacaaaaa    2460
attgttaata tacctctata ctttaacgtc aaggagaaaa aaccccggat tctagaacta    2520
gtggatcccc catcatggtt tccaatcact tgtttgacgc aatgagagcc gctgcccctg    2580
gtaacgcccc tttcataaga atagataata ctagaacttg gacatacgat gacgcctttg    2640
ctttatctgg tagaatagca tcagctatgg atgctttggg tatcagacca ggtgacagag    2700
tcgcagttca agtagaaaaa tccgctgaag cattgatctt gtatttggct tgtttgagaa    2760
gtggtgcagt ttatttgcca ttgaatactg cctacacatt agctgaattg gattacttca    2820
taggtgacgc agaacctaga ttggttgtag tcgcctcttc agccagagct ggtgtagaaa    2880
caattgctaa accaagaggt gcaatagtcg aaacctttaga tgctgctggt tctggtagtt    2940
tgttagattt ggccagagac gaacctgctg attttgttga cgcttcaaga tcagccgatg    3000
acttagccgc tattttgtac acctctggta ctacaggtag atcaaagggt gctatgttga    3060
ctcatggtaa tttgttgtca aacgcattaa ccttgagaga tttctggaga gttactgccg    3120
gtgacagatt aatccacgct ttgccaattt tcatactca cggtttattc gttgctacca    3180
acgtaacttt gttagcaggt gcctccatgt tcttgttgag taagttcgat ccagaagaaa    3240
tattatcttt gatgcctcaa gctactatgt tgatgggtgt cccaacattc tacgttagat    3300
tgttacaatc acctagatta gataagcaag ctgttgcaaa catcagattg tttatatccg    3360
gtagtgctcc attgttagca gaaacccata ctgaatttca agcaagaaca ggtcacgcca    3420
ttttagaaag atacggtatg acagaaacca atatgaacac ttctaaccct tatgaaggta    3480
aaagaatagc tggtacagtt ggttttccat tgcctgatgt cacagttaga gtaaccgacc    3540
cagccactgg tttagctttg ccacctgaac aaactggtat gatcgaaatt aaaggtccaa    3600
```

```
acgtttttaa gggttactgg agaatgcctg aaaagactgc tgctgagttt actgctgatg    3660
gtttctttat ctctggtgac ttaggtaaaa ttgatagaga cggttatgtc catattgttg    3720
gtcgtggtaa agatttggtt atatccggtg gttataacat ctaccctaag gaagtagaag    3780
gtgaaataga tcaaatcgaa ggtgttgtag aatcagctgt aataggtgtc ccacatcctg    3840
attttggtga aggtgttaca gcagtcgttg taagaaaacc aggtgctgca ttagatgaaa    3900
aggcaattgt ttctgcctta caagacagat tggctagata caagcaacca aagagaataa    3960
tcttcgcaga agatttgcct agaaatacta tgggtaaagt acaaaagaac atcttgagac    4020
aacaatacgc cgacttatac accagaaccg aaggtagagg ttctttgtta acatgtggtg    4080
acgttgaaga aaatccaggt cctatggctt cagaaaagga ataagaaga gaaagattct    4140 tgaacgtatt cccaaagtta gttgaagaat gaacgctag tttgttagct tatggtatgc    4200
ctaaagaagc ctgcgattgg tatgctcact ctttaaacta caatactcca ggtggtaaat    4260
tgaatagagg tttgagtgta gttgatactt atgctatctt gtctaacaaa accgttgaac    4320
aattaggtca agaagaatac gaaaaggtcg ctatcttggg ttggtgtatt gaattgttgc    4380
aagcatactt tttggttgcc gatgacatga tggataagtc tataacaaga agaggtcaac    4440
catgctggta caaagttcca gaagttggtg aaatagccat aaatgatgct tttatgttgg    4500
aagccgctat ctataaattg ttgaagtcac atttcagaaa cgaaaagtac tacatcgata    4560
ttaccgaatt attccacgaa gttactttcc aaacagaatt gggtcaattg atggatttga    4620
taactgcacc tgaagataaa gttgacttgt caaagttttc cttgaagaaa cattcattca    4680
tcgtcacctt tgaaactgct tattactcct tctatttgcc agtcgccttg gctatgtacg    4740
tagctggtat tactgatgaa aaagacttga agcaagcaag agatgttttg atacctttgg    4800
gtgaatactt ccaaatccaa gatgactact tagactgttt cggtactcca gaacaaatag    4860
gtaaaatcgg tacagatatt caagacaata agtgcagttg ggttattaac aaggctttgg    4920
aattagcatc tgccgaacaa agaaagactt tggatgaaaa ctacggtaaa aaggactcag    4980
ttgctgaagc aaagtgtaag aaaattttta atgatttgaa gattgaacaa ttgtaccatg    5040
aatacgaaga atccatcgct aaagacttaa aggcaaagat tagtcaagtt gatgaatcaa    5100
gaggttttaa agccgacgtt ttgacagctt tcttgaataa ggtctacaag agatcaaagt    5160
gatgggctgc aggaattcga tatcaagctt atcgataccg tcgacctcga gtcatgtaat    5220
tagttatgtc acgcttacat tcacgccctc cccccacatc cgctctaacc gaaaaggaag    5280
gagttagaca acctgaagtc taggtccctat tttatttttt tatagttatg ttagtattaa    5340
gaacgttatt tatatttcaa attttctttt tttttctgta cagacgcgtg tacgcatgta    5400
acattatact gaaaaccttg cttgagaagg ttttgggacg ctcgaaggct taatttgcg    5460 gccggtaccc agcttttgtt cccttttagtg agggttaatt ccgagcttgg cgtaatcatg    5520
gtcatagctg tttcctgtgt gaaattgtta tccgctcaca attccacaca ataggagc    5580 cggaagcata aagtgtaaag cctggggtgc ctaatgagtg aggtaactca cattaattgc    5640
gttgcgctca ctgcccgctt tccagtcggg aaacctgtcg tgccagctgc attaatgaat    5700
cggccaacgc gcggggagag cggtttgcg tattgggcgc tcttccgctt cctcgctcac    5760
tgactcgctg cgctcggtcg ttcggctgcg gcgagcggta tcagctcact caaaggcggt    5820
aatacggtta tccacagaat cagggggataa cgcaggaaag aacatgtgag caaaaggcca    5880
gcaaaaggcc aggaaccgta aaaaggccgc gttgctggcg ttttccata ggctccggccc    5940
```

```
ccctgacgag catcacaaaa atcgacgctc aagtcagagg tggcgaaacc cgacaggact    6000
ataaagatac caggcgttcc ccctggaag ctccctcgtg cgctctcctg ttccgaccct    6060
gccgcttacc ggatacctgt ccgcctttct cccttcggga agcgtggcgc tttctcaatg    6120
ctcacgctgt aggtatctca gttcggtgta ggtcgttcgc tccaagctgg gctgtgtgca    6180
cgaacccccc gttcagcccg accgctgcgc cttatccggt aactatcgtc ttgagtccaa    6240
cccggtaaga cacgacttat cgccactggc agcagccact ggtaacagga ttagcagagc    6300
gaggtatgta ggcggtgcta cagagttctt gaagtggtgg cctaactacg gctacactag    6360
aaggacagta tttggtatct gcgctctgct gaagccagtt accttcggaa aaagagttgg    6420
tagctcttga tccggcaaac aaaccaccgc tggtagcggt ggtttttttg tttgcaagca    6480
gcagattacg cgcagaaaaa aaggatctca agaagatcct ttgatctttt ctacggggtc    6540
tgacgctcag tggaacgaaa actcacgtta agggattttg gtcatgagat tatcaaaaag    6600
gatcttcacc tagatccttt taaattaaaa atgaagtttt aaatcaatct aaagtatata    6660
tgagtaaact tggtctgaca gttaccaatg cttaatcagt gaggcaccta tctcagcgat    6720
ctgtctattt cgttcatcca tagttgcctg actgcccgtc gtgtagataa ctacgatacg    6780
ggagggctta ccatctggcc ccagtgctgc aatgataccg cgagacccac gctcaccggc    6840
tccagattta tcagcaataa accagccagc cggaagggcc gagcgcagaa gtggtcctgc    6900
aactttatcc gcctccatcc agtctattaa ttgttgccgg gaagctagag taagtagttc    6960
gccagttaat agtttgcgca acgttgttgc cattgctaca ggcatcgtgg tgtcacgctc    7020
gtcgtttggt atggcttcat tcagctccgg ttcccaacga tcaaggcgag ttacatgatc    7080
ccccatgttg tgaaaaaag cggttagctc cttcggtcct ccgatcgttg tcagaagtaa    7140
gttggccgca gtgttatcac tcatggttat ggcagcactg cataattctc ttactgtcat    7200
gccatccgta agatgctttt ctgtgactgg tgagtactca accaagtcat tctgagaata    7260
gtgtatgcgg cgaccgagtt gctcttgccc ggcgtcaata cgggataata ccgcgccaca    7320
tagcagaact ttaaaagtgc tcatcattgg aaaacgttct cggggcgaaa actctcaag     7380 gatcttaccg ctgttgagat ccagttcgat gtaacccact cgtgcaccca actgatcttc    7440
agcatctttt actttcacca gcgtttctgg gtgagcaaaa acaggaaggc aaaatgccgc    7500
aaaaaaggga ataagggcga cacggaaatg ttgaatactc atactcttcc ttttcaata    7560 ttattgaagc atttatcagg gttattgtct catgagcgga tacatatttg aatgtattta    7620
gaaaaataaa caaatagggg ttccgcgcac atttccccga aaagtgccac ctgacgtcta    7680
agaaaccatt                                                           7690
```

<210> SEQ ID NO 23
<211> LENGTH: 2163
<212> TYPE: DNA
<213> ORGANISM: Artificial Sequence
<220> FEATURE:
<223> OTHER INFORMATION: Codon Optimized

<400> SEQUENCE: 23

```
atgggtaaaa actataagtc cttggattca gtcgttgcct cagatttcat cgcattgggt      60
atcacctcag aagtagcaga acattacat ggtagattgg cagaaatcgt tgtaattat      120 ggtgctgcaa cccctcaaac ttggatcaac atcgctaacc atatcttgtc accagatttg     180
cctttctcct tacaccaaat gttgttttat ggttgctaca aggatttcgg tccagcccca     240
cctgcttgga ttccagaccc tgaaaaagtc aagtcaacta atttgggtgc tttgttggaa     300
```

```
aagagaggta aagaattttt gggtgtaaag tacaaagatc caatttcttc tttttctcac    360
ttccaagaat tttctgttag aaaccctgaa gtctattgga gaacagtatt gatggatgaa    420
atgaaaatta gtttctctaa ggacccagaa tgtatcttga aagagatga catcaacaac     480
ccaggtggtt ctgaatggtt acctggtggt tacttgaact cagctaaaaa ttgcttgaac    540
gtaaactcca ataagaaatt gaacgatact atgatcgttt ggagagacga gggtaacgat    600
gacttgcctt tgaataagtt gacattagat caattgagaa agagagtttg gttggttggt    660
tatgcattgg aagaaatggg tttagaaaaa ggttgtgcaa tagccatcga tatgccaatg    720
catgttgatg ctgttgttat atatttggcc atagtattgg ctggttacgt agttgtctct    780
atagcagatt cattttccgc ccctgaaatc tcaactagat tgagattatc caaagctaag    840
gcaattttca caagatca catcatcaga ggtaaaaaga gaataccatt gtattcaaga     900
gtagttgaag ctaaatcccc aatggcaata gttatccctt gtagtggttc taacattggt    960
gcagaattga gagatggtga catatcttgg gattactttt tagaaagagc caaggagttt   1020
aaaaactgcg agtttactgc cagagaacaa cctgttgatg cttatactaa catcttattc   1080
tccagtggta ctacaggtga accaaaagca attccttgga cacaagccac cccattgaag   1140
gctgctgctg atggttggtc tcatttggat attagaaaag gtgacgttat agtatggcca   1200
actaatttgg gttggatgat gggtccttgg ttggttatg ctagtttgtt aaatggtgca   1260
tctattgcct tgtacaacgg tagtccttta gtctctggtt tcgctaaatt tgttcaagat   1320
gcaaaggtca aatgttggg tgtcgtacca tctattgtaa gatcatggaa atccacaaat   1380
tgtgtttcag gttacgattg gtccaccata agatgctttt cttcatccgg tgaagcctct   1440
aatgtagacg aatatttgtg gttaatgggt agagctaact acaagccagt tatagaaatg   1500
tgtggtggta cagaaatcgg tggtgctttt tctgctggtt catttttgca agctcaatct   1560
ttaagttctt tttcatccca atgtatgggt tgcaccttgt acatattaga taagaacggt   1620
tacccaatgc ctaaaaataa gccaggtatc ggtgaattgg cattaggtcc tgttatgttt   1680
ggtgcctcaa aaacattgtt aaacggtaat catcacgatg tctatttcaa gggtatgcca   1740
accttgaatg gtgaagtatt gagaagacat ggtgacattt cgaattgac ctctaacggt   1800
tactaccatg cacacggtag agccgatgac actatgaaca tcggtggtat caaaattagt   1860
tctatcgaaa tcgaaagagt ctgtaatgaa gtagatgaca gagttttga aaccactgct   1920
attggtgttc cacctttggg tggtggtcca gaacaattgg tcatatttt cgtattgaag   1980
gattcaaacg acacaaccat tgatttgaac caattgagat tatcctttaa cttgggtttg   2040
caaaagaaat tgaacccatt attcaaagtt actagagttg tcccattgtc atccttacct   2100
agaactgcaa caaacaagat catgagaaga gttttgagac aacaattcag tcatttcgaa   2160
tga                                                                 2163

<210> SEQ ID NO 24
<211> LENGTH: 1059
<212> TYPE: DNA
<213> ORGANISM: Artificial Sequence
<220> FEATURE:
<223> OTHER INFORMATION: Codon Optimized

<400> SEQUENCE: 24
atggcttcag aaaaggaaat aagaagagaa agattcttga acgtattccc aaagttagtt     60
gaagaattga acgctagttt gttagcttat ggtatgccta aagaagcctg cgattggtat    120
```

```
gctcactctt taaactacaa tactccaggt ggtaaattga atagaggttt gagtgtagtt      180
gatacttatg ctatcttgtc taacaaaacc gttgaacaat taggtcaaga agaatacgaa      240
aaggtcgcta tcttgggttg gtgtattgaa ttgttgcaag catactttt ggttgccgat       300 gacatgatgg ataagtctat aacaagaaga ggtcaaccat gctggtacaa agttccagaa      360
gttggtgaaa tagccataaa tgatgctttt atgttggaag ccgctatcta taaattgttg      420
aagtcacatt tcagaaacga aaagtactac atcgatatta ccgaattatt ccacgaagtt      480
actttccaaa cagaattggg tcaattgatg gatttgataa ctgcacctga agataaagtt      540
gacttgtcaa agttttcctt gaagaaacat tcattcatcg tcacctttga aactgcttat      600
tactccttct atttgccagt cgccttggct atgtacgtag ctggtattac tgatgaaaaa      660
gacttgaagc aagcaagaga tgttttgata cctttgggtg aatacttcca aatccaagat      720
gactacttag actgtttcgg tactccagaa caaataggta aaatcggtac agatattcaa      780
gacaataagt gcagtgggt tattaacaag gctttggaat tagcatctgc cgaacaaaga       840
aagactttgg atgaaaacta cggtaaaaag gactcagttc tgaagcaaa gtgtaagaaa       900 attttttaatg atttgaagat tgaacaattg taccatgaat acgaagaatc catcgctaaa     960
gacttaaagg caaagattag tcaagttgat gaatcaagag ttttaaagc cgacgttttg      1020 acagctttct tgaataaggt ctacaagaga tcaaagtag                           1059
```

<210> SEQ ID NO 25
<211> LENGTH: 1158
<212> TYPE: DNA
<213> ORGANISM: Artificial Sequence
<220> FEATURE:
<223> OTHER INFORMATION: Codon Optimized

<400> SEQUENCE: 25

```
atgaaccatt tgagagccga aggtcctgcc tccgtattag ccataggtac agccaaccca      60
gaaaacatat tgatccaaga tgaatttcct gattattact tcagagttac caagagtgaa     120
cacatgactc aattgaagga aaagtttaga aaaatatgtg ataagtctat gatcagaaag     180
agaaactgct tcttgaacga gaacatttg aagcaaaatc caagattggt agaacacgaa      240
atgcaaacat tggatgccag acaagacatg ttagttgtcg aagttcctaa attgggtaaa     300
gatgcttgtg caaaagccat taaggaatgg ggtcaaccaa agtcaaagat cactcatttg     360 attttttacaa gtgcatctac tacagatatg cctggtgcag actaccactg tgccaaattg     420
ttaggtttgt caccatccgt taagagagtc atgatgtatc aattaggttg ctacggtggt     480
ggtactgttt tgagaatcgc taaggatatt gcagaaaaca caagggtgc cagagtatta     540 gctgtttgtt gcgacattat ggcttgcttg tttagaggtc caagtgattc tgacttggaa     600
ttgttagttg gtcaagctat cttcggtgac ggtgctgctg ctgttattgt tggtgcagaa      660
cctgacgaat ctgttggtga aagaccaata tttgaattag tcagtacagg tcaaaccatc     720
ttgcctaatt ctgaaggtac aattggtggt catataagag aagcaggttt tgatcttcgat    780 ttgcacaaag acgttccaat gttaatctct aacaacatag aaaagtgttt gataagaagca    840 ttcactccta taggtatctc agattggaac tctatttcct ggataacaca tccaggtggt      900 aaagccatt tggataaggt tgaagaaaaa ttggatttga gaaagaaaaa gtttgtagat      960
agtagacatg ttttatctga acacggtaac atgtcttcat ccactgtctt gttcgtaatg    1020
gatgaattga gaaagagatc attagaagag ggtaaatcta ctactggtga cggttttgaa   1080
tggggtgtct tatttggttt cggtcctggt ttgaccgtcg aaagagtagt tgtcagatca   1140
```
gtaccaatta aatattag                                                  1158

<210> SEQ ID NO 26
<211> LENGTH: 315
<212> TYPE: DNA
<213> ORGANISM: Artificial Sequence
<220> FEATURE:
<223> OTHER INFORMATION: Codon Optimized

<400> SEQUENCE: 26
atggccgtca agcatttgat agtattgaag tttaaagatg aaatcacaga agctcaaaag    60
gaagaatttt tcaagaccta cgttaatttg gtcaacatta tacctgctat gaaagatgta   120
tactggggta agacgttac acaaaagaaa gaagaaggtt atacacacat tgtcgaagta   180
accttcgaat cagttgaaac tatccaagat tacatcattc atccagctca cgttggtttt   240
ggtgacgttt acagatcctt ctgggaaaaa ttgttgatct tcgattacac cccaagaaag   300
ttaaagccaa aataa                                                    315

<210> SEQ ID NO 27
<211> LENGTH: 1188
<212> TYPE: DNA
<213> ORGANISM: Artificial Sequence
<220> FEATURE:
<223> OTHER INFORMATION: Codon Optimized

<400> SEQUENCE: 27
atgggtttat catccgtctg tactttctcc ttccaaacta actatcatac cttattgaat    60
cctcacaaca caatccaaa acatcattg ttgtgttaca gacatccaaa gacacctatt   120
aagtactctt acaacaactt tccatcaaaa cattgttcaa ccaagtcctt ccacttacaa   180
aataagtgct ccgaaagttt gtctatagct aagaactcta tcagagctgc aactacaaat   240
caaactgaac cacctgaaag tgataatcac tctgttgcca caaaaatttt gaacttcggt   300
aaagcatgtt ggaagttgca aagaccatac accataatcg cttttacttc ttgtgcatgc   360
ggtttattcg gtaaagaatt gttgcataac actaacttaa tttcatggtc cttgatgttc   420
aaggcatttt tcttttttagt tgccatcttg tgcatcgctt cattcaccac tacaattaat   480
caaatatacg atttgcacat cgacagaatt aacaaaccag atttgccttt ggcttcaggt   540
gaaatatccg tcaatactgc atggatcatg tctatcatag tagccttgtt cggtttgatc   600
atcacaatta aaatgaaggg tggtccattg tacatcttcg ttactgttt cggtatcttc   660
ggtggtattg tctattccgt accacctttt agatggaaac aaaacccctag tactgccttt   720
ttgttgaatt tcttagctca tatcatcaca aacttcacct tctactacgc ttcaagagct   780
gctttaggtt tgccattcga attgagacct tcattccat ttttgttggc attcatgaaa   840
agtatgggtt ctgcattagc cttgatcaag gatgcctctg acgttgaagg tgacacaaag   900
ttcggtatta gtaccttggc ttctaagtac ggttcaagaa atttgacttt gttctgctcc   960
ggtatcgttt tgttaagtta cgtcgcagcc attttggcag gtatcatttg ccacaagcc   1020
tttaattcta cgttatgtt gttgtcacat gccatcttgg cttctggtt gatcttgcaa   1080
actagagatt tcgctttgac aaaattatgac cctgaagcag gtagaagatt ctacgagttt   1140
atgtggaaat tgtactacgc tgaatatttg gtatacgttt ttattttag                1188

<210> SEQ ID NO 28
<211> LENGTH: 1635
<212> TYPE: DNA

<213> ORGANISM: Artificial Sequence
<220> FEATURE:
<223> OTHER INFORMATION: Codon Optimized

<400> SEQUENCE: 28

```
atgaaatgtt caactttctc cttttggttc gtatgcaaga tcatcttctt tttcttttcc      60
tttaacatcc aaacaagtat cgcaaaccca agagaaaact ttttgaagtg cttctcacaa     120
tacataccta ataacgccac caatttgaag ttggtttaca ctcaaaacaa cccattgtac     180
atgtccgtct tgaacagtac aatccataat ttgagattca cttctgatac cactccaaaa     240
cctttggtca ttgtaaccc tagtcatgta tctcacatcc aaggtactat cttatgttct      300
aaaaaggttg gtttgcaaat tagaactaga tccggtggtc atgatagtga aggcatgtca     360
tacatctccc aagttccatt cgttatcgtt gatttgagaa acatgagatc aattaaaata     420
gacgtacact cacaaactgc ttgggttgaa gctggtgcaa cattgggtga agtatactac     480
tgggttaacg aaaagaatga aaacttatca ttggctgctg ttactgtcc aacagtttgc      540
gcaggtggtc atttggtgg tggtggttat ggtcctttaa tgagaaacta cggtttggcc     600
gctgataaca taatcgacgc tcatttggta aatgttcacg gtaaagtttt ggatagaaag     660
tctatgggtg aagacttatt tgggctttg agaggtggtg gtgcagaatc attcggtatc      720
atagttgctt ggaagataag attagtcgca gtaccaaagt ctactatgtt ctcagtcaaa     780
aagataatgg aaatccatga attagttaaa ttggtcaata agtggcaaaa catcgcatac     840
aagtacgata aggacttgtt gttgatgact catttcatca aagaaacat caccgataac      900
caaggtaaaa ataagactgc tatccacaca tactttttctt cagttttctt gggtggtgtc     960
gattccttag tagacttgat gaataagtct tttccagaat taggtattaa gaaaactgat    1020
tgtagacaat tgtcttggat cgacaccatc atctttatt caggtgttgt caactacgat    1080
acagacaact tcaacaaaga aatattattg gatagatccg caggtcaaaa cggtgccttt    1140
aaaattaagt tagactacgt taaaaagcca atacctgaat cagttttcgt ccaaatctta    1200
gaaaaattgt acgaagaaga tattggtgca ggcatgtacg ccttgtatcc atacggtggt    1260
ataatggacg aaatcagtga atctgccatt ccatttcctc atagagctgg tatcttatac    1320
gaattgtggt acatttgttc atgggaaaag caagaagata acgaaaagca cttaaactgg    1380
attagaaaca tctataactt catgactcca tacgtttcta aaaaccctag attggcatat    1440
ttgaactaca gagatttgga catcggtatt aacgatccaa agaatcctaa caactatacc    1500
caagctagaa tttggggtga aaaatacttc ggtaaaaatt tcgatagatt agtaaaggtt    1560
aagacattgg ttgacccaaa caacttcttt agaaacgaac aatccattcc acctttacct    1620
agacatagac actga                                                    1635
```

<210> SEQ ID NO 29
<211> LENGTH: 1638
<212> TYPE: DNA
<213> ORGANISM: Artificial Sequence
<220> FEATURE:
<223> OTHER INFORMATION: Codon Optimized

<400> SEQUENCE: 29

```
atgaactgct ccgcattctc tttctggttc gtctgtaaaa taatcttctt cttcttgtcc      60
ttcaacatcc aaatctccat cgcaaatcca caagaaaact ttttgaagtg tttctccgaa     120
tacatcccaa caaccctgc taacccaaag tttatatata ctcaacatga tcaattgtac      180
atgtccgttt tgaacagtac catccaaaat ttgagattca cttctgacac tacaccaaaa     240
```

```
cctttagtca ttgttacacc ttccaatgtt agtcacattc aagcttctat attgtgctct    300
aagaaagtag gtttgcaaat cagaactaga tcaggtggtc atgatgcaga aggcatgtct    360
tacatctcac aagttccatt cgttgtagtc gatttgagaa atatgcattc cataaagatc    420
gacgttcaca gtcaaacagc atgggtagaa gcaggtgcca ccttgggtga agtttactac    480
tggatcaacg aaaagaatga aaacttttct ttccctggtg gttactgtcc aacagtaggt    540
gtcggtggtc acttttctgg tggtggttat ggtgcattga tgagaaacta cggtttagct    600
gcagataata ttatagacgc ccatttggtt aacgtagatg gtaaagtttt ggacagaaag    660
tctatgggtg aagatttgtt ttgggccata agaggtggtg gtggtgaaaa tttcggtatc    720
attgccgctt ggaaaattaa gttagtcgct gttccttcca aaagtactat tttctctgtc    780
aaaaagaaca tggaaatcca cggtttggtt aagttgttta ataagtggca aaacatcgct    840
tacaagtacg ataaggactt ggttttgatg acccatttca tcactaaaaa tattacagat    900
aaccatggta aaaataagac cactgttcac ggttattttt cttcaatttt ccatggtggt    960
gtagattctt tggttgattt gatgaataag tcattcccag aattgggtat taaaaagaca   1020
gattgcaagg aatttttcttg gatagacaca accatcttct attcaggtgt tgtaaacttc   1080
aacaccgcta acttcaaaaa ggaaatcttg ttggatagat ccgctggtaa aaagaccgct   1140
tttttctatta aattggacta cgttaagaaa ccaatccctg aaactgcaat ggtcaagata   1200
ttggaaaagt tgtacgaaga agatgtaggt gtcggcatgt acgttttgta tccatacggt   1260
ggtattatgg aagaaatatc tgaatcagcc ataccatttc ctcacagagc tggtatcatg   1320
tatgaattat ggtacacagc ctcatgggaa aagcaagaag ataacgaaaa gcatatcaac   1380
tgggtcagat ccgtttacaa cttcactaca ccttacgtta gtcaaaaccc aagattggca   1440
tatttgaact acagagattt ggacttaggt aaaaactaacc ctgaatctcc aaataactat   1500
acacaagcaa gaatttgggg tgaaaagtac tttggtaaaa atttcaacag attagttaaa   1560
gtaaagacta agccgaccccc taacaacttt ttcagaaacg aacaatccat cccacctttg   1620
ccacctcacc accactaa                                                 1638

<210> SEQ ID NO 30
<211> LENGTH: 960
<212> TYPE: DNA
<213> ORGANISM: Artificial Sequence
<220> FEATURE:
<223> OTHER INFORMATION: Codon Optimized

<400> SEQUENCE: 30
atggctaatc aaacagaacc tccagaatct aatacgaaat atagtgtagt taccaaaatc     60
ctaagttttg gccacacttg ttggaaattg cagagaccgt atactttcat tggagtgatt    120
agttgcgcct gtggattgtt cggtagagag ttattccata atactaattt gctatcatgg    180
tctctgatgt tgaaagcttt cagctcattg atggtaatac tgtcagtgaa tctatgtacc    240
aatatcataa accagatcac tgacctggac atagacagaa tcaataagcc ggacttgcca    300
ttggcgagcg gggaaaatgtc cattgaaaca gcatggatta tgagtattat agttgcacta    360
actggattga tacttacgat aaagcttaat tgcggcccctt tgtttatatc tctatattgt    420
gtcagcatac tagtcggggc actatattca gtaccgccat tcagatggaa gcaaaatccc    480
aataccgcat tctcaagtta ttttatggga ctggtgatcg tcaattttac ctgctattac    540
gcaagcaggg ccgcctttgg actgccattc gagatgtcac ccccgttcac attcattctt    600
```

```
gcctttgtca agtcaatggg tagcgcactt tttttgtgta aagatgtctc tgacattgaa      660
ggagattcta agcacggtat atctacccct gcgacgaggt atggagcaaa aaacattact      720
ttcctttgct caggaatcgt actgctaacc tacgtaagcg cgatattggc tgcgattatt      780
tggccacaag ccttcaagtc caacgtgatg ctgttgagtc acgcaaccct ggccttttgg      840
cttatctttc agactagaga gttcgcgtta actaattaca atccagaggc agggaggaag      900
ttttacgagt tcatgtggaa gctgcactac gctgaatact tagtctatgt atttatatag      960
```

<210> SEQ ID NO 31
<211> LENGTH: 960
<212> TYPE: DNA
<213> ORGANISM: Artificial Sequence
<220> FEATURE:
<223> OTHER INFORMATION: Codon Optimized

<400> SEQUENCE: 31

```
atggctaatc aaacagaacc tccagaatct aatacgaaat atagtgtagt taccaaaatc       60
ctaagttttg gccacacttg ttggaaattg cagagaccgt atactttcat tggagtgatt      120
agttgcgcct gtggattgtt cggtagagag ttattccata atactaattt gctatcatgg      180
tctctgatgt tgaaagcttt cagctcattg atggtaaatc tgtcagtgaa tctatgtacc      240
aatatcataa accagatcac tgacctggac atagacagaa tcaataagcc ggacttgcca      300
ttggcgagcg ggggaaatgtc cattgaaaca gcatggatta tgagtattat agttgcacta      360
actggattga tacttacgat aaagcttaat tgcggccctt tgtttatatc tctatattgt      420
gtcagcatac tagtcggggc actatattca gtaccgccat tcagatggaa gcaaaatccc      480
aataccgcat tctcaagtta ttttatggga ctggtgatcg tcaattttac ctgctattac      540
gcaagcaggg ccgcctttgg actgccattc gagatgtcac ccccgttcac attcattctt      600
gcctttgtca agtcaatggg tagcgcactt tttttgtgta aagatgtctc tgacattgaa      660
ggagattcta agcacggtat atctacccct gcgacgaggt atggagcaaa aaacattact      720
ttcctttgct caggaatcgt actgctaacc tacgtaagcg cgatattggc tgcgattatt      780
tggccacaag ccttcaagtc caacgtgatg ctgttgagtc acgcaaccct ggccttttgg      840
cttatctttc agactagaga gttcgcgtta actaattaca atccagaggc agggaggaag      900
ttttacgagt tcatgtggaa gctgcactac gctgaatact tagtctatgt atttatatag      960
```

<210> SEQ ID NO 32
<211> LENGTH: 1023
<212> TYPE: DNA
<213> ORGANISM: Artificial Sequence
<220> FEATURE:
<223> OTHER INFORMATION: Codon Optimized

<400> SEQUENCE: 32

```
atgagattcc catctatttt cactgctgtt tgttcgctg cttcttctgc tttggctgct       60
ccagttgcta atcaaacaga acctccagaa tctaatacga aatatagtgt agttaccaaa      120
atcctaagtt ttggccacac ttgttggaaa ttgcagagac cgtatacttt cattggagtg      180
attagttgcg cctgtggatt gttcggtaga gagttattcc ataatactaa tttgctatca      240
tggtctctga tgttgaaagc tttcagctca ttgatggtaa tactgtcagt gaatctatgt      300
accaatatca taaaccagat cactgacctg gacatagaca gaatcaataa gccggacttg      360
ccattggcga gcgggggaaat gtccattgaa acagcatgga ttatgagtat tatagttgca      420
ctaactggat tgatacttac gataaagctt aattgcggcc ctttgtttat atctctatat      480
```

| | | |
|---|---|---|
| tgtgtcagca tactagtcgg ggcactatat tcagtaccgc cattcagatg gaagcaaaat | 540 |
| cccaataccg cattctcaag ttattttatg ggactggtga tcgtcaattt tacctgctat | 600 |
| tacgcaagca gggccgcctt tggactgcca ttcgagatgt cacccccgtt cacattcatt | 660 |
| cttgcctttg tcaagtcaat gggtagcgca ctttttttgt gtaaagatgt ctctgacatt | 720 |
| gaaggagatt ctaagcacgg tatatctacc cttgcgacga ggtatggagc aaaaaacatt | 780 |
| actttccttt gctcaggaat cgtactgcta acctacgtaa gcgcgatatt ggctgcgatt | 840 |
| atttggccac aagccttcaa gtccaacgtg atgctgttga gtcacgcaac cctggccttt | 900 |
| tggcttatct ttcagactag agagttcgcg ttaactaatt acaatccaga ggcagggagg | 960 |
| aagttttacg agttcatgtg gaagctgcac tacgctgaat acttagtcta tgtatttata | 1020 |
| tag | 1023 |

<210> SEQ ID NO 33
<211> LENGTH: 6025
<212> TYPE: DNA
<213> ORGANISM: Artificial Sequence
<220> FEATURE:
<223> OTHER INFORMATION: Codon Optimized

<400> SEQUENCE: 33

| | | |
|---|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accacgcttt tcaattcaat tcatcatttt ttttttattc ttttttttga tttcggtttc | 240 |
| tttgaaattt ttttgattcg gtaatctccg aacagaagga agaacgaagg aaggagcaca | 300 |
| gacttagatt ggtatatata cgcatatgta gtgttgaaga acatgaaat tgcccagtat | 360 |
| tcttaaccca actgcacaga acaaaaacct gcaggaaacg aagataaatc atgtcgaaag | 420 |
| ctacatataa ggaacgtgct gctactcatc ctagtcctgt tgctgccaag ctatttaata | 480 |
| tcatgcacga aaagcaaaca aacttgtgtg cttcattgga tgttcgtacc accaaggaat | 540 |
| tactggagtt agttgaagca ttaggtccca aaatttgttt actaaaaaca catgtggata | 600 |
| tcttgactga tttttccatg gagggcacag ttaagccgct aaaggcatta tccgccaagt | 660 |
| acaatttttt actcttcgaa gacagaaaat ttgctgacat ggtaataca gtcaaattgc | 720 |
| agtactctgc gggtgtatac agaatagcag aatgggcaga cattacgaat gcacacggtg | 780 |
| tggtgggccc aggtattgtt agcggtttga agcaggcggc agaagaagta acaaaggaac | 840 |
| ctagaggcct tttgatgtta gcagaattgt catgcaaggg ctccctatct actggagaat | 900 |
| atactaaggg tactgttgac attgcgaaga gcgacaaaga ttttgttatc ggctttattg | 960 |
| ctcaaagaga catgggtgga agagatgaag gttacgattg gttgattatg acacccggtg | 1020 |
| tgggtttaga tgacaaggga gacgcattgg gtcaacagta taaccgtgat gatgtgg | 1080 |
| tctctacagg atctgacatt attattgttg gaagaggact atttgcaaag gaagggatg | 1140 |
| ctaaggtaga gggtgaacgt tacagaaaag caggctggga agcatatttg agaagatgcg | 1200 |
| gccagcaaaa ctaaaaaact gtattataag taaatgcatg tatactaaac tcacaaatta | 1260 |
| gagcttcaat ttaattatat cagttattac cctgcggtgt gaaataccgc acagatgcgt | 1320 |
| aaggagaaaa taccgcatca ggaaattgta acgttaata ttttgttaaa attcgcgtta | 1380 |
| aatttttgtt aaatcagctc attttttaac caataggccg aaatcggcaa aatcccttat | 1440 |

| | |
|---|---|
| aaatcaaaag aatagaccga gatagggttg agtgttgttc cagtttggaa caagagtcca | 1500 |
| ctattaaaga acgtggactc caacgtcaaa gggcgaaaaa ccgtctatca gggcgatggc | 1560 |
| ccactacgtg aaccatcacc ctaatcaagt tttttggggt cgaggtgccg taaagcacta | 1620 |
| aatcggaacc ctaaagggag cccccgattt agagcttgac ggggaaagcc ggcgaacgtg | 1680 |
| gcgagaaagg aagggaagaa agcgaaagga gcgggcgcta gggcgctggc aagtgtagcg | 1740 |
| gtcacgctgc gcgtaaccac cacacccgcc gcgcttaatg cgccgctaca gggcgcgtcg | 1800 |
| cgccattcgc cattcaggct gcgcaactgt tgggaagggc gatcggtgcg ggcctcttcg | 1860 |
| ctattacgcc agctggcgaa ggggggatgt gctgcaaggc gattaagttg ggtaacgcca | 1920 |
| gggttttccc agtcacgacg ttgtaaaacg acggccagtg aattgtaata cgactcacta | 1980 |
| tagggcgaat tggagctcta gtacggatta aagccgccg agcgggcgac agccctccga | 2040 |
| cggaagactc tcctccgtgc gtcctcgtct tcaccggtcg cgttcctgaa acgcagatgt | 2100 |
| gcctcgcgcc gcactgctcc gaacaataaa gattctacaa tactagcttt tatggttatg | 2160 |
| aagaggaaaa attggcagta acctggcccc acaaaccttc aaattaacga atcaaattaa | 2220 |
| caaccatagg atgataatgc gattagtttt ttagccttat ttctggggta attaatcagc | 2280 |
| gaagcgatga tttttgatct attaacagat atataaatgg aaaagctgca taaccacttt | 2340 |
| aactaatact ttcaacattt tcagtttgta ttacttctta ttcaaatgtc ataaaagtat | 2400 |
| caacaaaaaa ttgttaatat acctctatac tttaacgtca aggagaaaaa accccggatt | 2460 |
| ctagaactag tggatccccc atcatggcta atcaaacaga acctccagaa tctaatacga | 2520 |
| aatatagtgt agttaccaaa atcctaagtt ttggccacac ttgttggaaa ttgcagagac | 2580 |
| cgtatacttt cattggagtg attagttgcg cctgtggatt gttcggtaga gagttattcc | 2640 |
| ataatactaa tttgctatca tggtctctga tgttgaaagc tttcagctca ttgatggtaa | 2700 |
| tactgtcagt gaatctatgt accaatatca taaaccagat cactgacctg gacatagaca | 2760 |
| gaatcaataa gccggacttg ccattggcga gcggggaaat gtccattgaa acagcatgga | 2820 |
| ttatgagtat tatagttgca ctaactggat tgatacttac gataaagctt aattgcggcc | 2880 |
| ctttgtttat atctctatat tgtgtcagca tactagtcgg ggcactatat tcagtaccgc | 2940 |
| cattcagatg gaagcaaaat cccaataccg cattctcaag ttattttatg ggactggtga | 3000 |
| tcgtcaattt tacctgctat tacgcaagca gggccgcctt tggactgcca ttcgagatgt | 3060 |
| cacccccgtt cacattcatt cttgcctttg tcaagtcaat gggtagcgca ctttttttgt | 3120 |
| gtaaagatgt ctctgacatt gaaggagatt ctaagcacgg tatatctacc cttgcgacga | 3180 |
| ggtatggagc aaaaaacatt actttccttt gctcaggaat cgtactgcta acctacgtaa | 3240 |
| gcgcgatatt ggctgcgatt atttggccac aagccttcaa gtccaacgtg atgctgttga | 3300 |
| gtcacgcaac cctggccttt tggcttatct ttcagactag agagttcgcg ttaactaatt | 3360 |
| acaatccaga ggcagggagg aagttttacg agttcatgtg gaagctgcac tacgctgaat | 3420 |
| acttagtcta tgtatttata taggatgggc tgcaggaatt cgatatcaag cttatcgata | 3480 |
| ccgtcgacct cgagtcatgt aattagttat gtcacgctta cattcacgcc ctcccccac | 3540 |
| atccgctcta accgaaaagg aaggagttag acaacctgaa gtctaggtcc ctatttattt | 3600 |
| ttttatagtt atgttagtat taagaacgtt atttatattt caaatttttc ttttttttct | 3660 |
| gtacagacgc gtgtacgcat gtaacattat actgaaaacc ttgcttgaga aggttttggg | 3720 |
| acgctcgaag gctttaattt gcggccggta cccagctttt gttcccttta gtgagggtta | 3780 |
| attccgagct tggcgtaatc atggtcatag ctgtttcctg tgtgaaattg ttatccgctc | 3840 |

```
acaattccac acaacatagg agccggaagc ataaagtgta aagcctgggg tgcctaatga   3900
gtgaggtaac tcacattaat tgcgttgcgc tcactgcccg ctttccagtc gggaaacctg   3960
tcgtgccagc tgcattaatg aatcggccaa cgcgcgggga gaggcggttt gcgtattggg   4020
cgctcttccg cttcctcgct cactgactcg ctgcgctcgg tcgttcggct gcggcgagcg   4080
gtatcagctc actcaaaggc ggtaatacgg ttatccacag aatcagggga taacgcagga   4140
aagaacatgt gagcaaaagg ccagcaaaag gccaggaacc gtaaaaaggc cgcgttgctg   4200
gcgtttttcc ataggctcgg ccccccctgac gagcatcaca aaaatcgacg ctcaagtcag   4260
aggtggcgaa acccgacagg actataaaga taccaggcgt ttccccctgg aagctccctc   4320
gtgcgctctc ctgttccgac cctgccgctt accggatacc tgtccgcctt tctcccttcg   4380
ggaagcgtgg cgctttctca atgctcacgc tgtaggtatc tcagttcggt gtaggtcgtt   4440
cgctccaagc tgggctgtgt gcacgaaccc cccgttcagc ccgaccgctg cgccttatcc   4500
ggtaactatc gtcttgagtc caacccggta agacacgact tatcgccact ggcagcagcc   4560
actggtaaca ggattagcag agcgaggtat gtaggcggtg ctacagagtt cttgaagtgg   4620
tggcctaact acggctacac tagaaggaca gtatttggta tctgcgctct gctgaagcca   4680
gttaccttcg gaaaaagagt tggtagctct tgatccggca acaaaccac cgctggtagc   4740
ggtggttttt ttgtttgcaa gcagcagatt acgcgcagaa aaaaaggatc tcaagaagat   4800
cctttgatct tttctacggg gtctgacgct cagtggaacg aaaactcacg ttaagggatt   4860
ttggtcatga gattatcaaa aaggatcttc acctagatcc ttttaaatta aaaatgaagt   4920
tttaaatcaa tctaaagtat atatgagtaa acttggtctg acagttacca atgcttaatc   4980
agtgaggcac ctatctcagc gatctgtcta tttcgttcat ccatagttgc ctgactgccc   5040
gtcgtgtaga taactacgat acgggagggc ttaccatctg gccccagtgc tgcaatgata   5100
ccgcgagacc cacgctcacc ggctccagat ttatcagcaa taaaccagcc agccggaagg   5160
gccgagcgca gaagtggtcc tgcaacttta tccgcctcca tccagtctat taattgttgc   5220
cgggaagcta gagtaagtag ttcgccagtt aatagtttgc gcaacgttgt tgccattgct   5280
acaggcatcg tggtgtcacg ctcgtcgttt ggtatggctt cattcagctc cggttcccaa   5340
cgatcaaggc gagttacatg atcccccatg ttgtgaaaaa aagcggttag ctccttcggt   5400
cctccgatcg ttgtcagaag taagttggcc gcagtgttat cactcatggt tatggcagca   5460
ctgcataatt ctcttactgt catgccatcc gtaagatgct tttctgtgac tggtgagtac   5520
tcaaccaagt cattctgaga atagtgtatg cggcgaccga gttgctcttg cccggcgtca   5580
atacgggata taccgcgcc acatagcaga actttaaaag tgctcatcat tggaaaacgt   5640
tcttcggggc gaaaactctc aaggatctta ccgctgttga tccagttc gatgtaaccc   5700
actcgtgcac ccaactgatc ttcagcatct tttactttca ccagcgtttc tgggtgagca   5760
aaaacaggaa ggcaaaatgc cgcaaaaaag ggaataaggg cgacacggaa atgttgaata   5820
ctcatactct tcctttttca atattattga agcatttatc agggttattg tctcatgagc   5880
ggatacatat ttgaatgtat ttagaaaaat aaacaaatag gggttccgcg cacatttccc   5940
cgaaaagtgc cacctgacgt ctaagaaacc attattatca tgacattaac ctataaaaat   6000
aggcgtatca cgaggccctt tcgtc                                        6025
```

```
<210> SEQ ID NO 34
<211> LENGTH: 6025
<212> TYPE: DNA
```

<213> ORGANISM: Artificial Sequence
<220> FEATURE:
<223> OTHER INFORMATION: Codon Optimized

<400> SEQUENCE: 34

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc ttttttttga tttcggtttc     240
tttgaaattt ttttgattcg gtaatctccg aacagaagga agaacgaagg aaggagcaca     300
gacttagatt ggtatatata cgcatatgta gtgttgaaga acatgaaat tgcccagtat     360
tcttaaccca actgcacaga acaaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aaatttgttt actaaaaaca catgtggata     600
tcttgactga tttttccatg gagggcacag ttaagccgct aaaggcatta tccgccaagt     660
acaatttttt actcttcgaa gacagaaaat ttgctgacat tggtaataca gtcaaattgc     720
agtactctgc gggtgtatac agaatagcag aatgggcaga cattacgaat gcacacggtg     780
tggtgggccc agtattgtt agcggtttga agcaggcggc agaagaagta acaaggaac     840
ctagaggcct tttgatgtta gcagaattgt catgcaaggg ctccctatct actggagaat     900
atactaaggg tactgttgac attgcgaaga gcgacaaaga ttttgttatc ggctttattg     960
ctcaaagaga catgggtgga agagatgaag gttacgattg gttgattatg cacccggtg    1020
tgggtttaga tgacaaggga gacgcattgg gtcaacagta tagaaccgtg gatgatgtgg    1080
tctctacagg atctgacatt attattgttg gaagaggact atttgcaaag ggaagggatg    1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta acgttaata ttttgttaaa attcgcgtta    1380
aatttttgtt aaatcagctc attttttaac cataggccg aaatcggcaa aatcccttat    1440
aaatcaaaag aatagaccga tagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttgggggt cgaggtgccg taaagcacta    1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
gggttttccc agtcacgacg ttgtaaaacg acggccagtg aattgtaata cgactcacta    1980
tagggcgaat tggagctcta gtacggatta aagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
```

```
caaccatagg atgataatgc gattagttttt ttagccttat ttctggggta attaatcagc    2280
gaagcgatga tttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatggcta atcaaacaga acctccagaa tctaatacga    2520
aatatagtgt agttaccaaa atcctaagtt ttggccacac ttgttggaaa ttgcagagac    2580
cgtatacttt cattggagtg attagttgcg cctgtggatt gttcggtaga gagttattcc    2640
ataatactaa tttgctatca tggtctctga tgttgaaagc tttcagctca ttgatggtaa    2700
tactgtcagt gaatctatgt accaatatca taaaccagat cactgacctg acatagaca     2760 gaatcaataa gccggacttg ccattggcga gcggggaaat gtccattgaa acagcatgga    2820
ttatgagtat tatagttgca ctaactggat tgatacttac gataaagctt aattgcggcc    2880 cttttgtttat atctctatat tgtgtcagca tactagtcgg ggcactatat tcagtaccgc    2940
cattcagatg gaagcaaaat cccaataccg cattctcaag ttatttttatg ggactggtga    3000 tcgtcaattt tacctgctat tacgcaagca gggccgcctt tggactgcca ttcgagatgt    3060
cacccccgtt cacattcatt cttgcctttg tcaagtcaat gggtagcgca cttttttgt     3120 gtaaagatgt ctctgacatt gaaggagatt ctaagcacgg tatatctacc cttgcgacga    3180
ggtatggagc aaaaaacatt actttccttt gctcaggaat cgtactgcta acctacgtaa    3240
gcgcgatatt ggctgcgatt atttggccac aagccttcaa gtccaacgtg atgctgttga    3300
gtcacgcaac cctggccttt tggcttatct ttcagactag agagttcgcg ttaactaatt    3360
acaatccaga ggcagggagg aagttttacg agttcatgtg gaagctgcac tacgctgaat    3420
acttagtcta tgtatttata taggatgggc tgcaggaatt cgatatcaag cttatcgata    3480
ccgtcgacct cgagtcatgt aattagttat gtcacgctta cattcacgcc ctccccccac    3540
atccgctcta accgaaaagg aaggagttag acaacctgaa gtctaggtcc ctatttattt    3600
ttttatagtt atgttagtat taagaacgtt atttatattt caaattttc ttttttttct     3660 gtacagacgc gtgtacgcat gtaacattat actgaaaacc ttgcttgaga aggttttggg    3720
acgctcgaag gctttaattt gcggccggta cccagctttt gttcccttta gtgagggtta    3780
attccgagct tggcgtaatc atggtcatag ctgtttcctg tgtgaaattg ttatccgctc    3840
acaattccac acaacatagg agccggaagc ataaagtgta aagcctgggg tgcctaatga    3900
gtgaggtaac tcacattaat tgcgttgcgc tcactgcccg ctttccagtc gggaaacctg    3960
tcgtgccagc tgcattaatg aatcggccaa cgcgcgggga gaggcggttt gcgtattggg    4020
cgctcttccg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200
gcgtttttcc ataggctcgg ccccctgac gagcatcaca aaaatcgacg ctcaagtcag     4260
aggtggcgaa acccgacagg actataaaga taccaggcgt tccccctgg aagctccctc     4320 gtgcgctctc ctgttccgac cctgccgctt accggatacc tgtccgcctt tctcccttcg    4380
ggaagcgtgg cgctttctca atgctcacgc tgtaggtatc tcagttcggt gtaggtcgtt    4440
cgctccaagc tgggctgtgt gcacgaaccc ccgttcagc ccgaccgctg cgccttatcc      4500
ggtaactatc gtcttgagtc caacccggta agacacgact tatcgccact ggcagcagcc    4560
```

```
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaagagt tggtagctct tgatccggca acaaaccac cgctggtagc     4740 ggtggttttt ttgtttgcaa gcagcagatt acgcgcagaa aaaaggatc tcaagaagat    4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactgccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgaaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga actttaaaag tgctcatcat tggaaaacgt    5640
tcttcggggc gaaaactctc aaggatctta ccgctgttga tccagttc gatgtaaccc     5700 actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct ccttttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgt ctaagaaacc attattatca tgacattaac ctataaaaat    6000
aggcgtatca cgaggccctt tcgtc                                         6025
```

<210> SEQ ID NO 35
<211> LENGTH: 6088
<212> TYPE: DNA
<213> ORGANISM: Artificial Sequence
<220> FEATURE:
<223> OTHER INFORMATION: Codon Optimized

<400> SEQUENCE: 35

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc ttttttttga tttcggtttc     240
tttgaaattt ttttgattcg gtaatctccg aacagaagga agaacgaagg aaggagcaca    300
gacttagatt ggtatatata cgcatatgta gtgttgaaga acatgaaat tgcccagtat     360 tcttaaccca actgcacaga acaaaaacct gcaggaaacg aagataaatc atgtcgaaag     420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
```

```
tcttgactga ttttccatg gagggcacag ttaagccgct aaaggcatta tccgccaagt     660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg cacccggtg   1020 tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta   1380
aatttttgtt aaatcagctc atttttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg gtaacgcca    1920 gggttttccc agtcacgacg ttgtaaaacg acggccagtg aattgtaata cgactcacta   1980
tagggcgaat tggagctcta gtacggatta aagccgccg agcgggcgac agccctccga    2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga ttttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatgagat tccatctat tttcactgct gttttgttcg    2520
ctgcttcttc tgctttggct gctccagttg ctaatcaaac agaacctcca gaatctaata   2580
cgaaatatag tgtagttacc aaaatcctaa gttttggcca cacttgttgg aaattgcaga   2640
gaccgtatac tttcattgga gtgattagtt gcgcctgtgg attgttcggt agagagttat   2700
tccataatac taatttgcta tcatggtctc tgatgttgaa agctttcagc tcattgatgg   2760
taatactgtc agtgaatcta tgtaccaata tcataaacca gatcactgac ctggacatag   2820
acagaatcaa taagccggac ttgccattgg cgagcgggga aatgtccatt gaaacagcat   2880
ggattatgag tattatagtt gcactaactg gattgatact tacgataaag cttaattgcg   2940
```

```
gcccttttgtt tatatctcta tattgtgtca gcatactagt cggggcacta tattcagtac    3000
cgccattcag atggaagcaa aatcccaata ccgcattctc aagttatttt atgggactgg    3060
tgatcgtcaa ttttacctgc tattacgcaa gcagggccgc ctttggactg ccattcgaga    3120
tgtcaccccc gttcacattc attcttgcct tgtcaagtc aatgggtagc gcacttttt    3180 tgtgtaaaga tgtctctgac attgaaggag attctaagca cggtatatct acccttgcga    3240
cgaggtatgg agcaaaaaac attactttcc tttgctcagg aatcgtactg ctaacctacg    3300
taagcgcgat attggctgcg attatttggc cacaagcctt caagtccaac gtgatgctgt    3360
tgagtcacgc aaccctggcc ttttggctta tctttcagac tagagagttc gcgttaacta    3420
attacaatcc agaggcaggg aggaagtttt acgagttcat gtggaagctg cactacgctg    3480
aatacttagt ctatgtattt ataggatg ggctgcagga attcgatatc aagcttatcg    3540
ataccgtcga cctcgagtca tgtaattagt tatgtcacgc ttacattcac gccctccccc    3600
cacatccgct ctaaccgaaa aggaaggagt tagacaacct gaagtctagg tccctattta    3660 ttttttata gttatgttag tattaagaac gttatttata tttcaaattt ttcttttttt    3720
tctgtacaga cgcgtgtacg catgtaacat tatactgaaa accttgcttg agaaggtttt    3780
gggacgctcg aaggctttaa tttgcggccg gtacccagct tttgttccct ttagtgaggg    3840
ttaattccga gcttggcgta atcatggtca tagctgtttc ctgtgtgaaa ttgttatccg    3900
ctcacaattc cacacaacat aggagccgga agcataaagt gtaaagctg gggtgcctaa    3960 tgagtgaggt aactcacatt aattgcgttg cgctcactgc ccgctttcca gtcgggaaac    4020
ctgtcgtgcc agctgcatta tgaatcggc caacgcgcgg ggagaggcgg tttgcgtatt    4080
gggcgctctt ccgcttcctc gctcactgac tcgctgcgct cggtcgttcg gctgcggcga    4140
gcggtatcag ctcactcaaa ggcggtaata cggttatcca cagaatcagg ggataacgca    4200
ggaaagaaca tgtgagcaaa aggccagcaa aaggccagga accgtaaaaa ggccgcgttg    4260
ctggcgtttt tccataggct cggcccccct gacgagcatc acaaaaatcg acgctcaagt    4320
cagaggtggc gaaacccgac aggactataa agataccagg cgttccccc tggaagctcc    4380 ctcgtgcgct ctcctgttcc gaccctgccg cttaccggat acctgtccgc ctttctccct    4440
tcgggaagcg tggcgctttc tcaatgctca cgctgtaggt atctcagttc ggtgtaggtc    4500
gttcgctcca agctgggctg tgtgcacgaa ccccccgttc agcccgaccg ctgcgcctta    4560
tccggtaact atcgtcttga gtccaacccg gtaagacacg acttatcgcc actggcagca    4620
gccactggta acaggattag cagagcgagg tatgtaggcg gtgctacaga gttcttgaag    4680
tggtggccta actacggcta cactagaagg acagtatttg gtatctgcgc tctgctgaag    4740
ccagttacct tcggaaaaag agttggtagc tcttgatccg gcaaacaaac caccgctggt    4800
agcggtggtt tttttgtttg caagcagcag attacgcgca gaaaaaaagg atctcaagaa    4860
gatcctttga tcttttctac ggggtctgac gctcagtgga acgaaaactc acgttaaggg    4920
attttggtca tgagattatc aaaaaggatc ttcacctaga tccttttaaa ttaaaaatga    4980
agttttaaat caatctaaag tatatatgag taaacttggt ctgacagtta ccaatgctta    5040
atcagtgagg cacctatctc agcgatctgt ctatttcgtt catccatagt tgcctgactg    5100
cccgtcgtgt agataactac gatacgggag ggcttaccat ctggccccag tgctgcaatg    5160
ataccgcgag acccacgctc accggctcca gatttatcag caataaacca gccagccgga    5220
agggccgagc gcagaagtgg tcctgcaact ttatccgcct ccatccagtc tattaattgt    5280
tgccgggaag ctagagtaag tagttcgcca gttaatagtt tgcgcaacgt tgttgccatt    5340
```

```
gctacaggca tcgtggtgtc acgctcgtcg tttggtatgg cttcattcag ctccggttcc    5400
caacgatcaa ggcgagttac atgatccccc atgttgtgaa aaaaagcggt tagctccttc    5460
ggtcctccga tcgttgtcag aagtaagttg gccgcagtgt tatcactcat ggttatggca    5520
gcactgcata attctcttac tgtcatgcca tccgtaagat gcttttctgt gactggtgag    5580
tactcaacca agtcattctg agaatagtgt atgcggcgac cgagttgctc ttgcccggcg    5640
tcaatacggg ataataccgc gccacatagc agaactttaa aagtgctcat cattggaaaa    5700
cgttcttcgg ggcgaaaact ctcaaggatc ttaccgctgt tgagatccag ttcgatgtaa    5760
cccactcgtg cacccaactg atcttcagca tcttttactt tcaccagcgt ttctgggtga    5820
gcaaaaacag gaaggcaaaa tgccgcaaaa aagggaataa gggcgacacg gaaatgttga    5880
atactcatac tcttccttt  tcaatattat tgaagcattt atcagggtta ttgtctcatg    5940
agcggataca tatttgaatg tatttagaaa aataaacaaa taggggttcc gcgcacattt    6000
ccccgaaaag tgccacctga cgtctaagaa accattatta tcatgacatt aacctataaa    6060
aataggcgta tcacgaggcc ctttcgtc                                       6088
```

<210> SEQ ID NO 36
<211> LENGTH: 1197
<212> TYPE: DNA
<213> ORGANISM: Artificial Sequence
<220> FEATURE:
<223> OTHER INFORMATION: Codon Optimized

<400> SEQUENCE: 36

```
atgggcctta gtctagtttg tacgttttct tttcagacga actaccacac gttgctgaat     60
ccgcacaata agaacccaaa aaactctcta ttgagctatc agcatcctaa gaccccgata    120
ataaagtctt cttacgataa cttccttcct aaatactgtt taacaaagaa cttcattta    180 ctggactga actctcataa ccgtataagt agccaatcca ggagcattcg tgcgggctca    240
gatcagattg aaggttcccc ccaccacgaa agtgacaact ccatagcgac caaaattctt    300
aattttgggc acacttgttg gaagttacaa agaccctacg tagtgaaagg tatgatatcc    360
atagcgtgtg gtctgtttgg ccgtgaattg tttaataaca gacacttatt cagttggggg    420
ttaatgtgga aggcttttt  tgctctagtt cccatcttga gttttaactt cttcgcggct    480
ataatgaacc aaatctacga cgtcgacatc gacaggatta taaaccgga tcttccactt    540 gtgtccggag aaatgtccat tgaaacggct tggatcctta gtattattgt tgcccttact    600
ggtcttattg tgaccattaa gctaaaatca gccccacttt tgtttttat  ctatatattt    660 ggcatctttg ccggattcgc gtattcagtt cccctatcc gttggaaaca tacccctttt    720
acgaacttcc ttataacaat ttcctcccat gttgggttgg ccttcacatc atactcagcg    780
acaacttcag cactaggatt gcccttcgtg tggaggcccg catttagctt tatcattgct    840
tttatgacgg ttatgggcat gacaatagca ttcgccaaag acattagtga tattgaaggt    900
gatgcaaaat acggtgtgtc aacggtcgcc actaagttag gagcaagaaa tatgacattc    960
gtggtgtcag gtgttttatt gcttaattat cttgtgtcca ttagcatcgg tataatctgg    1020
cctcaggttt tcaaatcaaa tatcatgatc ctatctcacg caattctagc tttctgcttg    1080
atctttcaga cgagagaatt ggctctagcc aactacgcat cagcacctag taggcagttc    1140
ttcgaattta tttggctatt gtattacgca gagtatttcg tgtatgtgtt catttaa      1197
```

<210> SEQ ID NO 37

<211> LENGTH: 969
<212> TYPE: DNA
<213> ORGANISM: Artificial Sequence
<220> FEATURE:
<223> OTHER INFORMATION: Codon Optimized

<400> SEQUENCE: 37

| | | | | | |
|---|---|---|---|---|---|
| atggcgggct | cagatcagat | tgaaggttcc | ccccaccacg | aaagtgacaa | ctccatagcg | 60 |
| accaaaattc | ttaattttgg | gcacacttgt | tggaagttac | aaagaccccta | cgtagtgaaa | 120 |
| ggtatgatat | ccatagcgtg | tggtctgttt | ggccgtgaat | tgtttaataa | cagacactta | 180 |
| ttcagttggg | ggttaatgtg | aaggcttttt | tttgctctag | ttcccatctt | gagttttaac | 240 |
| ttcttcgcgg | ctataatgaa | ccaaatctac | gacgtcgaca | tcgacaggat | taataaaccg | 300 |
| gatcttccac | ttgtgtccgg | agaaatgtcc | attgaaacgg | cttggatcct | tagtattatt | 360 |
| gttgcccta | ctggtcttat | tgtgaccatt | aagctaaaat | cagccccact | ttttgttttt | 420 |
| atctatatat | ttggcatctt | tgccggattc | gcgtattcag | ttcccctat | ccgttggaaa | 480 |
| caatacccct | ttacgaactt | ccttataaca | atttcctccc | atgttgggtt | ggccttcaca | 540 |
| tcatactcag | cgacaacttc | agcactagga | ttgcccttcg | tgtggaggcc | cgcatttagc | 600 |
| tttatcattg | cttttatgac | ggttatgggc | atgacaatag | cattcgccaa | agacattagt | 660 |
| gatattgaag | gtgatgcaaa | atacggtgtg | tcaacggtcg | ccactaagtt | aggagcaaga | 720 |
| aatatgacat | tcgtggtgtc | aggtgtttta | ttgcttaatt | atcttgtgtc | cattagcatc | 780 |
| ggtataatct | ggcctcaggt | tttcaaatca | aatatcatga | tcctatctca | cgcaattcta | 840 |
| gctttctgct | tgatctttca | gacgagagaa | ttggctctag | ccaactacgc | atcagcacct | 900 |
| agtaggcagt | tcttcgaatt | tatttggcta | ttgtattacg | cagagtattt | cgtgtatgtg | 960 |
| ttcatttaa | | | | | 969 |

<210> SEQ ID NO 38
<211> LENGTH: 1032
<212> TYPE: DNA
<213> ORGANISM: Artificial Sequence
<220> FEATURE:
<223> OTHER INFORMATION: Codon Optimized

<400> SEQUENCE: 38

| | | | | | |
|---|---|---|---|---|---|
| atgagattcc | catctatttt | cactgctgtt | ttgttcgctg | cttcttctgc | tttggctgct | 60 |
| ccagttgcgg | gctcagatca | gattgaaggt | tccccccacc | acgaaagtga | caactccata | 120 |
| gcgaccaaaa | ttcttaattt | tgggcacact | tgttggaagt | tacaaagacc | ctacgtagtg | 180 |
| aaaggtatga | tatccatagc | gtgtggtctg | tttggccgtg | aattgtttaa | taacagacac | 240 |
| ttattcagtt | gggggttaat | gtggaaggct | ttttttgctc | tagttcccat | cttgagtttt | 300 |
| aacttcttcg | cggctataat | gaaccaaatc | tacgacgtcg | acatcgacag | gattaataaa | 360 |
| ccggatcttc | cacttgtgtc | cggagaaatg | tccattgaaa | cggcttggat | ccttagtatt | 420 |
| attgttgccc | ttactggtct | tattgtgacc | attaagctaa | aatcagcccc | acttttttgtt | 480 |
| tttatctata | tatttggcat | ctttgccgga | ttcgcgtatt | cagttccccc | tatccgttgg | 540 |
| aaacaatacc | cctttacgaa | cttccttata | acaatttcct | cccatgttgg | gttggccttc | 600 |
| acatcatact | cagcgacaac | ttcagcacta | ggattgccct | tcgtgtggag | gcccgcattt | 660 |
| agctttatca | ttgcttttat | gacggttatg | ggcatgacaa | tagcattcgc | caaagacatt | 720 |
| agtgatattg | aaggtgatgc | aaaatacggt | gtgtcaacgg | tcgccactaa | gttaggagca | 780 |
| agaaatatga | cattcgtggt | gtcaggtgtt | ttattgctta | attatcttgt | gtccattagc | 840 |

```
atcggtataa tctggcctca ggttttcaaa tcaaatatca tgatcctatc tcacgcaatt    900
ctagctttct gcttgatctt tcagacgaga gaattggctc tagccaacta cgcatcagca    960
cctagtaggc agttcttcga atttatttgg ctattgtatt acgcagagta tttcgtgtat   1020
gtgttcattt aa                                                       1032
```

<210> SEQ ID NO 39
<211> LENGTH: 6262
<212> TYPE: DNA
<213> ORGANISM: Artificial Sequence
<220> FEATURE:
<223> OTHER INFORMATION: Codon Optimized

<400> SEQUENCE: 39

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accacgcttt tcaattcaat tcatcatttt tttttattc tttttttga tttcggtttc      240 tttgaaattt ttttgattcg gtaatctccg aacagaagga agaacgaagg aaggagcaca    300
gacttagatt ggtatatata cgcatatgta gtgttgaaga acatgaaat tgcccagtat    360 tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttttccatg gagggcacag ttaagccgct aaaggcatta tccgccaagt    660 acaattttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggttgaa gcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag gaagggatg    1140 ctaaggtaga gggtgaacgt tacagaaaag caggctggga agcatattg agaagatgcg   1200 gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta    1380
aatttttgtt aaatcagctc attttttaac caataggccg aaatcggcaa aatcccttat   1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga cgggcgcta gggcgctggc aagtgtagcg   1740
gtcacgctgc gcgtaaccac cacacccgcc gcgcttaatg cgccgctaca gggcgcgtcg   1800
```

```
cgccattcgc cattcaggct gcgcaactgt tgggaagggc gatcggtgcg ggcctcttcg      1860
ctattacgcc agctggcgaa gggggatgt gctgcaaggc gattaagttg ggtaacgcca       1920
gggttttccc agtcacgacg ttgtaaaacg acggccagtg aattgtaata cgactcacta     1980
tagggcgaat tggagctcta gtacggatta aagccgccg agcgggcgac agccctccga      2040
cggaagactc tcctccgtgc gtcctcgtct tcaccggtcg cgttcctgaa acgcagatgt     2100
gcctcgcgcc gcactgctcc gaacaataaa gattctacaa tactagcttt tatggttatg    2160
aagaggaaaa attggcagta acctggcccc acaaaccttc aaattaacga atcaaattaa     2220
caaccatagg atgataatgc gattagtttt ttagccttat ttctggggta attaatcagc    2280
gaagcgatga ttttgatct attaacagat atataaatgg aaaagctgca taaccacttt     2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatgggcc ttagtctagt ttgtacgttt tcttttcaga    2520
cgaactacca cacgttgctg aatccgcaca ataagaaccc aaaaaactct ctattgagct    2580
atcagcatcc taagacccg ataataaagt cttcttacga taactttcct tctaaatact    2640
gtttaacaaa gaactttcat ttactgggac tgaactctca taaccgtata agtagccaat    2700
ccaggagcat tcgtgcgggc tcagatcaga ttgaaggttc cccccaccac gaaagtgaca   2760
actccatagc gaccaaaatt cttaattttg ggcacacttg ttggaagtta caagaccct     2820 acgtagtgaa aggtatgata tccatagcgt gtggtctgtt tggccgtgaa ttgtttaata   2880
acagacactt attcagttgg ggttaatgt ggaaggcttt ttttgctcta gttcccatct    2940
tgagttttaa cttcttcgcg gctataatga accaaatcta cgacgtcgac atcgacagga   3000
ttaataaacc ggatcttcca cttgtgtccg gagaaatgtc cattgaaacg gcttggatcc   3060
ttagtattat tgttgcccct actggtctta ttgtgaccat taagctaaaa tcagccccac   3120
tttttgtttt tatctatata tttggcatct ttgccggatt cgcgtattca gttcccccta    3180
tccgttggaa acaatacccc tttacgaact tccttataac aatttcctcc catgttgggt   3240
tggccttcac atcatactca gcgacaactt cagcactagg attgcccttc gtgtggaggc   3300
ccgcatttag ctttatcatt gcttttatga cggttatggg catgacaata gcattcgcca   3360
aagacattag tgatattgaa ggtgatgcaa aatacggtgt gtcaacggtc gccactaagt   3420
taggagcaag aaatatgaca ttcgtggtgt caggtgtttt attgcttaat tatcttgtgt    3480
ccattagcat cggtataatc tggcctcagg ttttcaaatc aaatatcatg atcctatctc    3540
acgcaattct agctttctgc ttgatctttc agacgagaga attggctcta gccaactacg    3600
catcagcacc tagtaggcag ttcttcgaat ttatttggct attgtattac gcagagtatt    3660
tcgtgtatgt gttcatttaa gatgggctgc aggaattcga tatcaagctt atcgataccg   3720
tcgacctcga gtcatgtaat tagttatgtc acgcttacat tcacgccctc cccccacatc   3780
cgctctaacc gaaaaggaag gagttagaca acctgaagtc taggtcccta tttatttttt    3840
tatagttatg ttagtattaa gaacgttatt tatatttcaa attttctttt tttttctgta    3900
cagacgcgtg tacgcatgta acattatact gaaaaccttg cttgagaagg ttttgggacg    3960
ctcgaaggct ttaatttgcg gccggtaccc agcttttgtt ccctttagtg agggttaatt    4020
ccgagcttgg cgtaatcatg gtcatagctg tttcctgtgt gaaattgtta tccgctcaca    4080
attccacaca acatagggagc cggaagcata aagtgtaaag cctggggtgc ctaatgagtg   4140
aggtaactca cattaattgc gttgcgctca ctgcccgctt tccagtcggg aaacctgtcg    4200
```

```
tgccagctgc attaatgaat cggccaacgc gcggggagag gcggtttgcg tattgggcgc    4260
tcttccgctt cctcgctcac tgactcgctg cgctcggtcg ttcggctgcg gcgagcggta    4320
tcagctcact caaaggcggt aatacggtta tccacagaat caggggataa cgcaggaaag    4380
aacatgtgag caaaaggcca gcaaaaggcc aggaaccgta aaaaggccgc gttgctggcg    4440 ttttttccata ggctcggccc ccctgacgag catcacaaaa atcgacgctc aagtcagagg    4500
tggcgaaacc cgacaggact ataaagatac caggcgttcc ccctggaag ctccctcgtg    4560 cgctctcctg ttccgaccct gccgcttacc ggatacctgt ccgcctttct cccttcggga    4620
agcgtggcgc tttctcaatg ctcacgctgt aggtatctca gttcggtgta ggtcgttcgc    4680
tccaagctgg gctgtgtgca cgaacccccc gttcagcccg accgctgcgc cttatccggt    4740
aactatcgtc ttgagtccaa cccggtaaga cacgacttat cgccactggc agcagccact    4800
ggtaacagga ttagcagagc gaggtatgta ggcggtgcta cagagttctt gaagtggtgg    4860
cctaactacg gctacactag aaggacagta tttggtatct gcgctctgct gaagccagtt    4920
accttcggaa aaagagttgg tagctcttga tccggcaaac aaaccaccgc tggtagcggt    4980 ggttttttg tttgcaagca gcagattacg cgcagaaaaa aaggatctca agaagatcct    5040
ttgatctttt ctacggggtc tgacgctcag tggaacgaaa actcacgtta agggattttg    5100
gtcatgagat tatcaaaaag gatcttcacc tagatccttt taaattaaaa atgaagtttt    5160
aaatcaatct aaagtatata tgagtaaact tggtctgaca gttaccaatg cttaatcagt    5220
gaggcaccta tctcagcgat ctgtctattt cgttcatcca tagttgcctg actgcccgtc    5280
gtgtagataa ctacgatacg ggagggctta ccatctggcc ccagtgctgc aatgataccg    5340
cgagacccac gctcaccggc tccagattta tcagcaataa accagccagc cggaagggcc    5400
gagcgcagaa gtggtcctgc aactttatcc gcctccatcc agtctattaa ttgttgccgg    5460
gaagctagag taagtagttc gccagttaat agtttgcgca acgttgttgc cattgctaca    5520
ggcatcgtgg tgtcacgctc gtcgtttggt atggcttcat tcagctccgg ttcccaacga    5580
tcaaggcgag ttacatgatc ccccatgttg tgaaaaaaag cggttagctc cttcggtcct    5640
ccgatcgttg tcagaagtaa gttggccgca gtgttatcac tcatggttat ggcagcactg    5700
cataattctc ttactgtcat gccatccgta agatgctttt ctgtgactgg tgagtactca    5760
accaagtcat tctgagaata gtgtatgcgg cgaccgagtt gctcttgccc ggcgtcaata    5820
cgggataata ccgcgccaca tagcagaact ttaaaagtgc tcatcattgg aaaacgttct    5880
tcggggcgaa aactctcaag gatcttaccg ctgttgagat ccagttcgat gtaacccact    5940
cgtgcaccca actgatcttc agcatctttt actttcacca gcgtttctgg gtgagcaaaa    6000
acaggaaggc aaaatgccgc aaaaaaggga ataaggcga cacggaaatg ttgaatactc    6060
atactcttcc ttttttcaata ttattgaagc atttatcagg gttattgtct catgagcgga    6120
tacatatttg aatgtatttta gaaaaataaa caaatagggg ttccgcgcac atttccccga    6180
aaagtgccac ctgacgtcta agaaaccatt attatcatga cattaaccta taaaaatagg    6240
cgtatcacga ggccctttcg tc                                             6262
```

<210> SEQ ID NO 40
<211> LENGTH: 6034
<212> TYPE: DNA
<213> ORGANISM: Artificial Sequence
<220> FEATURE:
<223> OTHER INFORMATION: Codon Optimized

```
<400> SEQUENCE: 40
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc ttttttttga tttcggtttc     240
tttgaaattt ttttgattcg gtaatctccg aacagaagga agaacgaagg aaggagcaca     300
gacttagatt ggtatatata cgcatatgta gtgttgaaga acatgaaat tgcccagtat      360 tcttaaccca actgcacaga acaaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aaatttgttt actaaaaaca catgtggata     600
tcttgactga ttttccatg gagggcacag ttaagccgct aaaggcatta tccgccaagt      660
acaatttttt actcttcgaa gacagaaaat ttgctgacat tggtaataca gtcaaattgc     720
agtactctgc gggtgtatac agaatagcag aatgggcaga cattacgaat gcacacggtg     780
tggtgggccc aggtattgtt agcggtttga agcaggcggc agaagaagta acaaaggaac     840
ctagaggcct tttgatgtta gcagaattgt catgcaaggg ctccctatct actggagaat     900
atactaaggg tactgttgac attgcgaaga gcgacaaaga ttttgttatc ggctttattg     960
ctcaaagaga catgggtgga agagatgaag gttacgattg gttgattatg acacccggtg    1020
tgggtttaga tgacaaggga gacgcattgg gtcaacagta tagaaccgtg gatgatgtgg    1080
tctctacagg atctgacatt attattgttg gaagaggact atttgcaaag ggaagggatg    1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta acgttaata ttttgttaaa attcgcgtta     1380
aatttttgtt aaatcagctc attttttaac caataggccg aaatcggcaa aatcccttat    1440
aaatcaaaag aatagaccga gatagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt ttttggggt cgaggtgccg taaagcacta     1620
aatcggaacc ctaaagggag ccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa gggggatgt gctgcaaggc gattaagttg ggtaacgcca     1920
gggttttccc agtcacgacg ttgtaaaacg acggccagtg aattgtaata cgactcacta    1980
tagggcgaat tggagctcta gtacggatta gaagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga ttttttgatct attaacagat atataaatgg aaaagctgca taaccacttt    2340
```

```
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatggcgg gctcagatca gattgaaggt tcccccacc     2520 acgaaagtga caactccata gcgaccaaaa ttcttaattt tgggcacact tgttggaagt    2580
tacaaagacc ctacgtagtg aaaggtatga tatccatagc gtgtggtctg tttggccgtg    2640
aattgtttaa taacagacac ttattcagtt gggggttaat gtggaaggct tttttgctc     2700 tagttcccat cttgagtttt aacttcttcg cggctataat gaaccaaatc tacgacgtcg    2760
acatcgacag gattaataaa ccggatcttc cacttgtgtc cggagaaatg tccattgaaa    2820
cggcttggat ccttagtatt attgttgccc ttactggtct tattgtgacc attaagctaa    2880
aatcagcccc acttttttgtt tttatctata tatttggcat ctttgccgga ttcgcgtatt    2940
cagttccccc tatccgttgg aaacaataac cctttacgaa cttccttata acaatttcct    3000
cccatgttgg gttggccttc acatcatact cagcgacaac ttcagcacta ggattgccct    3060
tcgtgtggag gcccgcattt agctttatca ttgcttttat gacggttatg gcatgacaa     3120 tagcattcgc caaagacatt agtgatattg aaggtgatgc aaaatacggt gtgtcaacgg    3180
tcgccactaa gttaggagca agaaatatga cattcgtggt gtcaggtgtt ttattgctta    3240
attatcttgt gtccattagc atcggtataa tctggcctca ggttttcaaa tcaaatatca    3300
tgatcctatc tcacgcaatt ctagctttct gcttgatctt tcagacgaga gaattggctc    3360
tagccaacta cgcatcagca cctagtaggc agttcttcga atttatttgg ctattgtatt    3420
acgcagagta tttcgtgtat gtgttcattt aagatgggct gcaggaattc gatatcaagc    3480
ttatcgatac cgtcgacctc gagtcatgta attagttatg tcacgcttac attcacgccc    3540
tccccccaca tccgctctaa ccgaaaagga aggagttaga caacctgaag tctaggtccc    3600 tatttattt tttatagtta tgttagtatt aagaacgtta tttatatttc aaattttctt     3660 ttttttctg tacagacgcg tgtacgcatg taacattata ctgaaaacct tgcttgagaa     3720
ggttttggga cgctcgaagg ctttaatttg cggccggtac ccagcttttg ttcccttttag   3780 tgagggttaa ttccgagctt ggcgtaatca tggtcatagc tgtttcctgt gtgaaattgt    3840
tatccgctca caattccaca acatagga gccggaagca taaagtgtaa agcctggggt      3900
gcctaatgag tgaggtaact cacattaatt gcgttgcgct cactgcccgc tttccagtcg    3960
ggaaacctgt cgtgccagct gcattaatga atcggccaac gcgcgggag aggcggtttg     4020 cgtattgggc gctcttccgc ttcctcgctc actgactcgc tgcgctcggt cgttcggctg    4080
cggcgagcgg tatcagctca ctcaaaggcg gtaatacggt tatccacaga atcaggggat    4140
aacgcaggaa agaacatgtg agcaaaaggc cagcaaaagg ccaggaaccg taaaaaggcc    4200
gcgttgctgg cgttttttcca taggctcggc cccctgacg agcatcacaa aaatcgacgc    4260
tcaagtcaga ggtggcgaaa cccgacagga ctataaagat accaggcgtt cccccctgga    4320
agctccctcg tgcgctctcc tgttccgacc ctgccgctta ccggatacct gtccgccttt    4380
ctcccttcgg gaagcgtggc gctttctcaa tgctcacgct gtaggtatct cagttcggtg    4440
taggtcgttc gctccaagct gggctgtgtg cacgaacccc ccgttcagcc cgaccgctgc    4500
gccttatccg gtaactatcg tcttgagtcc aacccggtaa gacacgactt atcgccactg    4560
gcagcagcca ctggtaacag gattagcaga gcgaggtatg taggcggtgc tacagagttc    4620
ttgaagtggt ggcctaacta cggctacact agaaggacag tatttggtat ctgcgctctg    4680
```

```
ctgaagccag ttaccttcgg aaaaagagtt ggtagctctt gatccggcaa acaaaccacc    4740
gctggtagcg gtggttttt tgtttgcaag cagcagatta cgcgcagaaa aaaggatct     4800 caagaagatc ctttgatctt ttctacgggg tctgacgctc agtggaacga aaactcacgt    4860
taagggattt tggtcatgag attatcaaaa aggatcttca cctagatcct tttaaattaa    4920
aaatgaagtt ttaaatcaat ctaaagtata tatgagtaaa cttggtctga cagttaccaa    4980
tgcttaatca gtgaggcacc tatctcagcg atctgtctat ttcgttcatc catagttgcc    5040
tgactgcccg tcgtgtagat aactacgata cgggagggct taccatctgg ccccagtgct    5100
gcaatgatac cgcgagaccc acgctcaccg gctccagatt tatcagcaat aaaccagcca    5160
gccggaaggg ccgagcgcag aagtggtcct gcaactttat ccgcctccat ccagtctatt    5220
aattgttgcc gggaagctag agtaagtagt tcgccagtta atagtttgcg caacgttgtt    5280
gccattgcta caggcatcgt ggtgtcacgc tcgtcgtttg gtatggcttc attcagctcc    5340
ggttcccaac gatcaaggcg agttacatga tcccccatgt tgtgaaaaaa agcggttagc    5400
tccttcggtc ctccgatcgt tgtcagaagt aagttggccg cagtgttatc actcatggtt    5460
atggcagcac tgcataattc tcttactgtc atgccatccg taagatgctt ttctgtgact    5520
ggtgagtact caaccaagtc attctgagaa tagtgtatgc ggcgaccgag ttgctcttgc    5580
ccggcgtcaa tacggataa taccgcgcca catagcagaa ctttaaaagt gctcatcatt    5640
ggaaaacgtt cttcggggcg aaaactctca aggatcttac cgctgttgag atccagttcg    5700
atgtaaccca ctcgtgcacc caactgatct tcagcatctt ttactttcac cagcgtttct    5760
gggtgagcaa aaacaggaag gcaaaatgcc gcaaaaaagg gaataagggc gacacggaaa    5820
tgttgaatac tcatactctt ccttttttcaa tattattgaa gcatttatca gggttattgt    5880
ctcatgagcg gatacatatt tgaatgtatt tagaaaaata acaaataggg gttccgcgc    5940 acatttcccc gaaaagtgcc acctgacgtc taagaaacca ttattatcat gacattaacc    6000
tataaaaata ggcgtatcac gaggcccttt cgtc                                6034
```

<210> SEQ ID NO 41
<211> LENGTH: 6088
<212> TYPE: DNA
<213> ORGANISM: Artificial Sequence
<220> FEATURE:
<223> OTHER INFORMATION: Codon Optimized

<400> SEQUENCE: 41

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc ttttttttga tttcggtttc     240
tttgaaattt ttttgattcg gtaatctccg aacagaagga agaacgaagg aaggagcaca     300
gacttagatt ggtatatata cgcatatgta gtgttgaaga acatgaaat tgcccagtat     360 tcttaaccca actgcacaga acaaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aaatttgttt actaaaaaca catgtggata     600
tcttgactga ttttttccatg gagggcacag ttaagccgct aaaggcatta tccgccaagt     660
acaatttttt actcttcgaa gacagaaaat ttgctgacat tggtaataca gtcaaattgc     720
```

```
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg cacccggtg    1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta   1380
aatttttgtt aaatcagctc attttttaac caataggccg aaatcggcaa aatcccttat   1440
aaatcaaaag aatagaccga tagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt ttttgggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa gggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta aagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctgggta attaatcagc    2280
gaagcgatga ttttgatct attaacagat atataaatgg aaaagctgca taaccacttt   2340
aactaatact ttcaacattt tcagtttgta ttacttctta ttcaaatgtc ataaaagtat   2400
caacaaaaa ttgttaatat acctctatac tttaacgtca aggagaaaaa accccggatt   2460
ctagaactag tggatccccc atcatgagat tccatctat tttcactgct gttttgttcg   2520
ctgcttcttc tgctttggct gctccagttg ctaatcaaac agaacctcca gaatctaata   2580
cgaaatatag tgtagttacc aaaatcctaa gttttggcca cacttgttgg aaattgcaga   2640
gaccgtatac tttcattgga gtgattagtt gcgcctgtgg attgttcggt agagagttat   2700
tccataatac taatttgcta tcatggtctc tgatgttgaa agctttcagc tcattgatgg   2760
taatactgtc agtgaatcta tgtaccaata tcataaacca gatcactgac ctggacatag   2820
acagaatcaa taagccggac ttgccattgg cgagcgggga aatgtccatt gaaacagcat   2880
ggattatgag tattatagtt gcactaactg gattgatact tacgataaag cttaattgcg   2940
gccctttgtt tatatctcta tattgtgtca gcatactagt cggggcacta tattcagtac   3000
cgccattcag atggaagcaa aatcccaata ccgcattctc aagttatttt atgggactgg   3060
```

-continued

```
tgatcgtcaa ttttacctgc tattacgcaa gcagggccgc ctttggactg ccattcgaga      3120
tgtcaccccc gttcacattc attcttgcct ttgtcaagtc aatgggtagc gcactttttt      3180
tgtgtaaaga tgtctctgac attgaaggag attctaagca cggtatatct acccttgcga      3240
cgaggtatgg agcaaaaaac attactttcc tttgctcagg aatcgtactg ctaacctacg      3300
taagcgcgat attggctgcg attatttggc cacaagcctt caagtccaac gtgatgctgt      3360
tgagtcacgc aaccctggcc ttttggctta tctttcagac tagagagttc gcgttaacta      3420
attacaatcc agaggcaggg aggaagtttt acgagttcat gtggaagctg cactacgctg      3480
aatacttagt ctatgtattt atataggatg ggctgcagga attcgatatc aagcttatcg      3540
ataccgtcga cctcgagtca tgtaattagt tatgtcacgc ttacattcac gccctccccc      3600
cacatccgct ctaaccgaaa aggaaggagt tagacaacct gaagtctagg tccctattta      3660 ttttttttata gttatgttag tattaagaac gttatttata tttcaaattt ttcttttttt      3720
tctgtacaga cgcgtgtacg catgtaacat tatactgaaa accttgcttg agaaggtttt      3780
gggacgctcg aaggctttaa tttgcggccg gtacccagct tttgttccct ttagtgaggg      3840
ttaattccga gcttggcgta atcatggtca tagctgtttc ctgtgtgaaa ttgttatccg      3900
ctcacaattc cacacaacat aggagccgga agcataaagt gtaaagcctg gggtgcctaa      3960
tgagtgaggt aactcacatt aattgcgttg cgctcactgc ccgctttcca gtcgggaaac      4020
ctgtcgtgcc agctgcatta atgaatcggc caacgcgcgg ggagaggcgg tttgcgtatt      4080
gggcgctctt ccgcttcctc gctcactgac tcgctgcgct cggtcgttcg gctgcggcga      4140
gcggtatcag ctcactcaaa ggcggtaata cggttatcca cagaatcagg ggataacgca      4200
ggaaagaaca tgtgagcaaa aggccagcaa aaggccagga accgtaaaaa ggccgcgttg      4260
ctggcgtttt tccataggct cggccccccct gacgagcatc acaaaaatcg acgctcaagt      4320
cagaggtggc gaaacccgac aggactataa agataccagg cgttccccccc tggaagctcc      4380 ctcgtgcgct ctcctgttcc gaccctgccg cttaccggat acctgtccgc ctttctccct      4440
tcgggaagcg tggcgctttc tcaatgctca cgctgtaggt atctcagttc ggtgtaggtc      4500
gttcgctcca agctgggctg tgtgcacgaa ccccccgttc agcccgaccg ctgcgcctta      4560
tccggtaact atcgtcttga gtccaacccg gtaagacacg acttatcgcc actggcagca      4620
gccactggta acaggattag cagagcgagg tatgtaggcg gtgctacaga gttcttgaag      4680
tggtggccta actacggcta cactagaagg acagtatttg gtatctgcgc tctgctgaag      4740
ccagttacct tcggaaaaag agttggtagc tcttgatccg gcaaacaaac caccgctggt      4800
agcggtggtt ttttttgttg caagcagcag attacgcgca gaaaaaaagg atctcaagaa      4860
gatcctttga tcttttctac ggggtctgac gctcagtgga acgaaaactc acgttaaggg      4920
attttggtca tgagattatc aaaaaggatc ttcacctaga tccttttaaa ttaaaaatga      4980
agttttaaat caatctaaag tatatatgag taaacttggt ctgacagtta ccaatgctta      5040
atcagtgagg cacctatctc agcgatctgt ctatttcgtt catccatagt tgcctgactg      5100
cccgtcgtgt agataactac gatacgggag ggcttaccat ctggccccag tgctgcaatg      5160
ataccgcgag acccacgctc accggctcca gatttatcag caataaacca gccagccgga      5220
agggccgagc gcagaagtgg tcctgcaact ttatccgcct ccatccagtc tattaattgt      5280
tgccgggaag ctagagtaag tagttcgcca gttaatagtt tgcgcaacgt tgttgccatt      5340
gctacaggca tcgtggtgtc acgctcgtcg tttggtatgg cttcattcag ctccggttcc      5400
caacgatcaa ggcgagttac atgatccccc atgttgtgaa aaaagcggt tagctccttc       5460
```

```
ggtcctccga tcgttgtcag aagtaagttg ccgcagtgt tatcactcat ggttatggca    5520
gcactgcata attctcttac tgtcatgcca tccgtaagat gcttttctgt gactggtgag    5580
tactcaacca agtcattctg agaatagtgt atgcggcgac cgagttgctc ttgcccggcg    5640
tcaatacggg ataataccgc gccacatagc agaactttaa aagtgctcat cattggaaaa    5700
cgttcttcgg ggcgaaaact ctcaaggatc ttaccgctgt tgagatccag ttcgatgtaa    5760
cccactcgtg cacccaactg atcttcagca tcttttactt tcaccagcgt ttctgggtga    5820
gcaaaaacag gaaggcaaaa tgccgcaaaa agggaataa gggcgacacg gaaatgttga    5880
atactcatac tcttcctttt tcaatattat tgaagcattt atcagggtta ttgtctcatg    5940
agcggataca tatttgaatg tatttagaaa aataaacaaa taggggttcc gcgcacattt    6000
ccccgaaaag tgccacctga cgtctaagaa accattatta tcatgacatt aacctataaa    6060
aataggcgta tcacgaggcc ctttcgtc                                      6088

<210> SEQ ID NO 42
<211> LENGTH: 1203
<212> TYPE: DNA
<213> ORGANISM: Artificial Sequence
<220> FEATURE:
<223> OTHER INFORMATION: Codon Optimized

<400> SEQUENCE: 42
atggtatttt cctcagtgtg tagttttccg tcctctcttg gtacaaactt taagctggtg      60
cctagatcta attttaaggc ttcaagttca cattaccacg aaatcaacaa tttcattaac     120
aacaaaccca ttaaatttag ttatttctct tcaaggttgt attgcagtgc caagccaata     180
gtacacagag aaaacaagtt cacaaaatca ttctcactat cacacttaca acgtaaatct     240
tctatcaagg cccatggaga gatagaggct gatggaagta acgggacttc tgagttcaac     300
gtaatgaagt ccggaaatgc tatctggaga tttgtgaggc cgtatgccgc taaaggtgtc     360
ctgtttaact ccgcggcaat gttcgctaag gaacttgttg gaaatctgaa cttatttagc     420
tggccgttga tgttcaagat cctttcattt actcttgtca ttctgtgtat ctttgtatct     480
acatcaggca taaatcagat atatgatcta gacatcgata gactgaacaa accgaacttg     540
cccgtggcaa gcggggaaat tagcgtagaa ttggcatggt tacttactat agtatgtacg     600
attagtggac ttaccttaac cattataact aatagtggcc ccttttttcc gttcctttac     660
tcagcctcca tattctttgg tttcctatac tccgcccccc cgttccgttg aagaaaaac     720 ccctttaccg cctgcttttg caatgtgatg ttatacgtgg gaaccagtgt tggggtttat     780
tatgcctgca aagccagttt gggccttcct gccaattggt ctccagcatt ctgcctttta     840
ttttggttta ttagtctgct ttccatacct atcagcatag ctaaggattt atctgatatt     900
gaaggtgata ggaagtttgg aatcattact ttctctacta agttcggggc aaaaccgatc     960
gcgtacatat gtcacgggct tatgcttttg aattacgtga gtgttatggc cgcggccata    1020
atatggcctc aattcttcaa ctcctcagta atactgttat cacatgcctt catggcgatc    1080
tgggttttgt accaagcgtg gatactggag aaaagtaact atgcaacgga aacttgccag    1140
aaatattaca tcttcttatg gataatattc tcccttgagc acgcttttta cctattcatg    1200
tag                                                                 1203

<210> SEQ ID NO 43
<211> LENGTH: 1128
<212> TYPE: DNA
```

<213> ORGANISM: Artificial Sequence
<220> FEATURE:
<223> OTHER INFORMATION: Codon Optimized

<400> SEQUENCE: 43

```
atggcttcaa gttcacatta ccacgaaatc aacaatttca ttaacaacaa acccattaaa      60
tttagttatt tctcttcaag gttgtattgc agtgccaagc caatagtaca cagagaaaac     120
aagttcacaa atcattctc actatcacac ttacaacgta atcttctat caaggcccat       180
ggagagatag aggctgatgg aagtaacggg acttctgagt tcaacgtaat gaagtccgga    240
aatgctatct ggagatttgt gaggccgtat gccgctaaag gtgtcctgtt taactccgcg    300
gcaatgttcg ctaaggaact tgttggaaat ctgaacttat ttagctggcc gttgatgttc    360
aagatccttt catttactct tgtcattctg tgtatctttg tatctacatc aggcataaat    420
cagatatatg atctagacat cgatagactg aacaaaccga acttgcccgt ggcaagcggg    480
gaaattagcg tagaattggc atggttactt actatagtat gtacgattag tggacttacc    540
ttaaccatta taactaatag tggcccctttt tttccgttcc tttactcagc ctccatattc    600
tttggtttcc tatactccgc cccccgttc cgttggaaga aaacccctt taccgcctgc      660
ttttgcaatg tgatgttata cgtgggaacc agtgttgggg tttattatgc ctgcaaagcc    720
agtttgggcc ttcctgccaa ttggtctcca gcattctgcc ttttatttg gtttattagt    780
ctgctttcca tacctatcag catagctaag gatttatctg atattgaagg tgataggaag    840
tttggaatca ttactttctc tactaagttc ggggcaaaac cgatcgcgta catatgtcac    900
gggcttatgc ttttgaatta cgtgagtgtt atggccgcgg ccataatatg gcctcaattc    960
ttcaactcct cagtaatact gttatcacat gccttcatgg cgatctgggt tttgtaccaa  1020
gcgtggatac tggagaaaag taactatgca acggaaactt gccagaaata ttacatcttc  1080
ttatggataa tattctccct tgagcacgct ttttacctat tcatgtag                1128
```

<210> SEQ ID NO 44
<211> LENGTH: 1191
<212> TYPE: DNA
<213> ORGANISM: Artificial Sequence
<220> FEATURE:
<223> OTHER INFORMATION: Codon Optimized

<400> SEQUENCE: 44

```
atgagattcc catctatttt cactgctgtt ttgttcgctg cttcttctgc tttggctgct      60
ccagttgctt caagttcaca ttaccacgaa atcaacaatt tcattaacaa caaacccatt     120
aaatttagtt atttctcttc aaggttgtat tgcagtgcca agccaatagt acacagagaa    180
aacaagttca caaatcatt ctcactatca cacttacaac gtaaatcttc tatcaaggcc     240
catggagaga tagaggctga tggaagtaac gggacttctg agttcaacgt aatgaagtcc    300
ggaaatgcta tctggagatt tgtgaggccg tatgccgcta aaggtgtcct gtttaactcc    360
gcggcaatgt tcgctaagga acttgttgga aatctgaact tatttagctg gccgttgatg    420
ttcaagatcc tttcatttac tcttgtcatt ctgtgtatct ttgtatctac atcaggcata    480
aatcagatat atgatctaga catcgataga ctgaacaaac cgaacttgcc cgtggcaagc    540
ggggaaatta gcgtagaatt ggcatggtta cttactatag tatgtacgat tagtggactt    600
accttaacca ttataactaa tagtggcccc tttttttccgt tcctttactc agcctccata    660
ttctttggtt tcctatactc cgcccccccg ttccgttgga agaaaaaccc ctttaccgcc    720
tgctttttgca atgtgatgtt atacgtggga accagtgttg gggtttatta tgcctgcaaa    780
```

```
gccagtttgg gccttcctgc caattggtct ccagcattct gccttttatt ttggtttatt      840
agtctgcttt ccatacctat cagcatagct aaggatttat ctgatattga aggtgatagg      900
aagtttggaa tcattacttt ctctactaag ttcggggcaa aaccgatcgc gtacatatgt      960
cacgggctta tgcttttgaa ttcgtgagt gttatggccg cggccataat atggcctcaa     1020
ttcttcaact cctcagtaat actgttatca catgccttca tggcgatctg ggttttgtac     1080
caagcgtgga tactggagaa aagtaactat gcaacgaaaa cttgccagaa atattacatc     1140 ttccttatgga taatattctc ccttgagcac gcttttttacc tattcatgta g            1191
```

<210> SEQ ID NO 45
<211> LENGTH: 6268
<212> TYPE: DNA
<213> ORGANISM: Artificial Sequence
<220> FEATURE:
<223> OTHER INFORMATION: Codon Optimized

<400> SEQUENCE: 45

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc      180
accacgcttt tcaattcaat tcatcatttt ttttttattc ttttttttga tttcggtttc      240
tttgaaattt ttttgattcg gtaatctccg aacagaagga agaacgaagg aaggagcaca      300
gacttagatt ggtatatata cgcatatgta gtgttgaaga acatgaaat tgcccagtat      360 tcttaaccca actgcacaga acaaaaacct gcaggaaacg aagataaatc atgtcgaaag      420
ctacatataa ggaacgtgct gctactcatc ctagtcctgt tgctgccaag ctatttaata      480
tcatgcacga aaagcaaaca aacttgtgtg cttcattgga tgttcgtacc accaaggaat      540
tactggagtt agttgaagca ttaggtccca aaatttgttt actaaaaaca catgtggata      600
tcttgactga ttttttccatg gagggcacag ttaagccgct aaaggcatta tccgccaagt      660 acaattttttt actcttcgaa gacagaaaat ttgctgacat tggtaataca gtcaaattgc      720
agtactctgc gggtgtatac agaatagcag aatgggcaga cattacgaat gcacacggtg      780
tggtgggccc aggtattgtt agcggtttga agcaggcggc agaagaagta acaaaggaac      840
ctagaggcct ttgatgtta gcagaattgt catgcaaggg ctccctatct actggagaat      900
atactaaggg tactgttgac attgcgaaga gcgacaaaga ttttgttatc ggctttattg      960
ctcaaagaga catgggtgga agagatgaag gttacgattg ttgattatg acaccggtg     1020 tgggtttaga tgacaaggga gacgcattgg gtcaacagta tagaaccgtg gatgatgtgg     1080
tctctacagg atctgacatt attattgttg gaagaggact atttgcaaag gaagggatg      1140 ctaaggtaga gggtgaacgt tacagaaaag caggctggga agcatatttg agaagatgcg     1200
gccagcaaaa ctaaaaaact gtattataag taaatgcatg tatactaaac tcacaaatta     1260
gagcttcaat ttaattatat cagttattac cctgcggtgt gaaataccgc acagatgcgt     1320
aaggagaaaa taccgcatca ggaaattgta aacgttaata ttttgttaaa attcgcgtta     1380
aatttttgtt aaatcagctc attttttaac caataggccg aaatcggcaa atcccttat     1440 aaatcaaaag aatagaccga gatagggttg agtgttgttc cagtttggaa caagagtcca     1500
ctattaaaga acgtggactc caacgtcaaa gggcgaaaaa ccgtctatca gggcgatggc     1560
ccactacgtg aaccatcacc ctaatcaagt tttttgggtgt cgaggtgccg taaagcacta     1620
```

```
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
gggttttccc agtcacgacg ttgtaaaacg acggccagtg aattgtaata cgactcacta   1980
tagggcgaat tggagctcta gtacggatta gaagccgccg agcgggcgac agccctccga   2040
cggaagactc tcctccgtgc gtcctcgtct tcaccggtcg cgttcctgaa acgcagatgt   2100
gcctcgcgcc gcactgctcc gaacaataaa gattctacaa tactagcttt tatggttatg   2160
aagaggaaaa attggcagta acctggcccc acaaaccttc aaattaacga atcaaattaa   2220
caaccatagg atgataatgc gattagtttt ttagccttat ttctggggta attaatcagc   2280
gaagcgatga ttttttgatct attaacagat atataaatgg aaaagctgca taaccacttt   2340
aactaatact ttcaacattt tcagtttgta ttacttctta ttcaaatgtc ataaaagtat   2400
caacaaaaaa ttgttaatat acctctatac tttaacgtca aggagaaaaa accccggatt   2460
ctagaactag tggatccccc atcatggtat tttcctcagt gtgtagtttt ccgtcctctc   2520
ttggtacaaa ctttaagctg gtgcctagat ctaattttaa ggcttcaagt tcacattacc   2580
acgaaatcaa caatttcatt aacaacaaac ccattaaatt tagttatttc tcttcaaggt   2640
tgtattgcag tgccaagcca atagtacaca gagaaaacaa gttcacaaaa tcattctcac   2700
tatcacactt acaacgtaaa tcttctatca aggcccatgg agagatagag gctgatggaa   2760
gtaacgggac ttctgagttc aacgtaatga agtccggaaa tgctatctgg agatttgtga   2820
ggccgtatgc cgctaaaggt gtcctgttta actccgcggc aatgttcgct aaggaacttg   2880
ttggaaatct gaacttattt agctggccgt tgatgttcaa gatcctttca tttactcttg   2940
tcattctgtg tatctttgta tctacatcag gcataaatca gatatatgat ctagacatcg   3000
atagactgaa caaaccgaac ttgcccgtgg caagcgggga aattagcgta gaattggcat   3060
ggttacttac tatagtatgt acgattagtg gacttacctt aaccattata actaatagtg   3120
gccccttttt tccgttcctt tactcagcct ccatattctt tggtttccta tactccgccc   3180
ccccgttccg ttggaagaaa aacccctta ccgcctgctt ttgcaatgtg atgttatacg   3240
tgggaaccag tgttggggtt tattatgcct gcaaagccag tttgggcctt cctgccaatt   3300
ggtctccagc attctgcctt ttattttggt ttattagtct gctttccata cctatcagca   3360
tagctaagga tttatctgat attgaaggtg ataggaagtt tggaatcatt actttctcta   3420
ctaagttcgg ggcaaaaccg atcgcgtaca tatgtcacgg gcttatgctt ttgaattacg   3480
tgagtgttat ggccgcggcc ataatatggc ctcaattctt caactcctca gtaatactgt   3540
tatcacatgc cttcatggcg atctgggttt tgtaccaagc gtggatactg gagaaaagta   3600
actatgcaac ggaaacttgc cagaaatatt acatcttctt atggataata ttctcccttg   3660
agcacgcttt ttacctattc atgtaggatg ggctgcagga attcgatatc aagcttatcg   3720
ataccgtcga cctcgagtca tgtaattagt tatgtcacgc ttacattcac gccctccccc   3780
cacatccgct ctaaccgaaa aggaaggagt tagacaacct gaagtctagg tccctattta   3840 ttttttttata gttatgttag tattaagaac gttatttata tttcaaattt ttcttttttt   3900
tctgtacaga cgcgtgtacg catgtaacat tatactgaaa accttgcttg agaaggtttt   3960
gggacgctcg aaggctttaa tttgcggccg gtacccagct tttgttccct ttagtgaggg   4020
```

```
ttaattccga gcttggcgta atcatggtca tagctgtttc ctgtgtgaaa ttgttatccg    4080
ctcacaattc cacacaacat aggagccgga agcataaagt gtaaagcctg ggtgcctaa     4140 tgagtgaggt aactcacatt aattgcgttg cgctcactgc ccgctttcca gtcgggaaac    4200
ctgtcgtgcc agctgcatta atgaatcggc caacgcgcgg ggagaggcgg tttgcgtatt    4260
gggcgctctt ccgcttcctc gctcactgac tcgctgcgct cggtcgttcg gctgcggcga    4320
gcggtatcag ctcactcaaa ggcggtaata cggttatcca cagaatcagg ggataacgca    4380
ggaaagaaca tgtgagcaaa aggccagcaa aaggccagga accgtaaaaa ggccgcgttg    4440
ctggcgtttt tccataggct ccgcccccct gacgagcatc acaaaaatcg acgctcaagt    4500
cagaggtggc gaaacccgac aggactataa agataccagg cgttccccc tggaagctcc     4560 ctcgtgcgct ctcctgttcc gaccctgccg cttaccggat acctgtccgc ctttctccct    4620
tcgggaagcg tggcgctttc tcaatgctca cgctgtaggt atctcagttc ggtgtaggtc    4680
gttcgctcca agctgggctg tgtgcacgaa ccccccgttc agcccgaccg ctgcgcctta    4740
tccggtaact atcgtcttga gtccaacccg gtaagacacg acttatcgcc actggcagca    4800
gccactggta acaggattag cagagcgagg tatgtaggcg gtgctacaga gttcttgaag    4860
tggtggccta actacggcta cactagaagg acagtatttg gtatctgcgc tctgctgaag    4920
ccagttacct tcggaaaaag agttggtagc tcttgatccg gcaaacaaac caccgctggt    4980
agcggtggtt tttttgtttg caagcagcag attacgcgca gaaaaaaagg atctcaagaa    5040
gatcctttga tcttttctac ggggtctgac gctcagtgga acgaaaactc acgttaaggg    5100
attttggtca tgagattatc aaaaaggatc ttcacctaga tccttttaaa ttaaaaatga    5160
agttttaaat caatctaaag tatatatgag taaacttggt ctgacagtta ccaatgctta    5220
atcagtgagg cacctatctc agcgatctgt ctatttcgtt catccatagt tgcctgactg    5280
cccgtcgtgt agataactac gatacgggag ggcttaccat ctggccccag tgctgcaatg    5340
ataccgcgag acccacgctc accggctcca gatttatcag caataaacca gccagccgga    5400
agggccgagc gcagaagtgg tcctgcaact ttatccgcct ccatccagtc tattaattgt    5460
tgccgggaag ctagagtaag tagttcgcca gttaatagtt tgcgcaacgt tgttgccatt    5520
gctacaggca tcgtggtgtc acgctcgtcg tttggtatgg cttcattcag ctccggttcc    5580
caacgatcaa ggcgagttac atgatccccc atgttgtgaa aaaagcggt tagctccttc      5640 ggtcctccga tcgttgtcag aagtaagttg gccgcagtgt tatcactcat ggttatggca    5700
gcactgcata attctcttac tgtcatgcca tccgtaagat gcttttctgt gactggtgag    5760
tactcaacca agtcattctg agaatagtgt atgcggcgac cgagttgctc ttgcccggcg    5820
tcaatacggg ataataccgc gccacatagc agaactttaa aagtgctcat cattggaaaa    5880
cgttcttcgg ggcgaaaact ctcaaggatc ttaccgctgt tgagatccag ttcgatgtaa    5940
cccactcgtg cacccaactg atcttcagca tcttttactt tcaccagcgt ttctgggtga    6000
gcaaaaacag gaaggcaaaa tgccgcaaaa aagggaataa gggcgacacg gaaatgttga    6060
atactcatac tcttcctttt tcaatattat tgaagcattt atcagggtta ttgtctcatg    6120
agcggataca tatttgaatg tatttagaaa aataaacaaa taggggttcc gcgcacattt    6180
ccccgaaaag tgccacctga cgtctaagaa accattatta tcatgacatt aacctataaa    6240
aataggcgta tcacgaggcc ctttcgtc                                       6268
```

<210> SEQ ID NO 46

<211> LENGTH: 6268
<212> TYPE: DNA
<213> ORGANISM: Artificial Sequence
<220> FEATURE:
<223> OTHER INFORMATION: Codon Optimized

<400> SEQUENCE: 46

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accacgcttt | tcaattcaat | tcatcatttt | tttttattc | tttttttga | tttcggtttc | 240 |
| tttgaaattt | ttttgattcg | gtaatctccg | aacagaagga | agaacgaagg | aaggagcaca | 300 |
| gacttagatt | ggtatatata | cgcatatgta | gtgttgaaga | acatgaaat | tgcccagtat | 360 |
| tcttaaccca | actgcacaga | acaaaaacct | gcaggaaacg | aagataaatc | atgtcgaaag | 420 |
| ctacatataa | ggaacgtgct | gctactcatc | ctagtcctgt | tgctgccaag | ctatttaata | 480 |
| tcatgcacga | aaagcaaaca | aacttgtgtg | cttcattgga | tgttcgtacc | accaaggaat | 540 |
| tactggagtt | agttgaagca | ttaggtccca | aatttgtttt | actaaaaaca | catgtggata | 600 |
| tcttgactga | tttttccatg | gagggcacag | ttaagccgct | aaaggcatta | tccgccaagt | 660 |
| acaattttt | actcttcgaa | gacagaaaat | ttgctgacat | tggtaataca | gtcaaattgc | 720 |
| agtactctgc | gggtgtatac | agaatagcag | aatgggcaga | cattacgaat | gcacacggtg | 780 |
| tggtgggccc | aggtattgtt | agcggtttga | agcaggcggc | agaagaagta | acaaaggaac | 840 |
| ctagaggcct | tttgatgtta | gcagaattgt | catgcaaggg | ctccctatct | actggagaat | 900 |
| atactaaggg | tactgttgac | attgcgaaga | gcgacaaaga | ttttgttatc | ggctttattg | 960 |
| ctcaaagaga | catgggtgga | agagatgaag | gttacgattg | gttgattatg | acacccggtg | 1020 |
| tgggtttaga | tgacaaggga | gacgcattgg | gtcaacagta | tagaaccgtg | gatgatgtgg | 1080 |
| tctctacagg | atctgacatt | attattgttg | gaagaggact | atttgcaaag | gaagggatg | 1140 |
| ctaaggtaga | gggtgaacgt | tacagaaaag | caggctggga | agcatatttg | agaagatgcg | 1200 |
| gccagcaaaa | ctaaaaaact | gtattataag | taaatgcatg | tatactaaac | tcacaaatta | 1260 |
| gagcttcaat | ttaattatat | cagttattac | cctgcggtgt | gaaataccgc | acagatgcgt | 1320 |
| aaggagaaaa | taccgcatca | ggaaattgta | aacgttaata | ttttgttaaa | attcgcgtta | 1380 |
| aattttgtt | aaatcagctc | attttttaac | caataggccg | aaatcggcaa | aatcccttat | 1440 |
| aaatcaaaag | aatagaccga | gatagggttg | agtgttgttc | cagtttggaa | caagagtcca | 1500 |
| ctattaaaga | acgtggactc | caacgtcaaa | gggcgaaaaa | ccgtctatca | gggcgatggc | 1560 |
| ccactacgtg | aaccatcacc | ctaatcaagt | tttttgggt | cgaggtgccg | taaagcacta | 1620 |
| aatcggaacc | ctaaagggag | cccccgattt | agagcttgac | ggggaaagcc | ggcgaacgtg | 1680 |
| gcgagaaagg | aagggaagaa | agcgaaagga | gcgggcgcta | gggcgctggc | aagtgtagcg | 1740 |
| gtcacgctgc | gcgtaaccac | cacacccgcc | gcgcttaatg | cgccgctaca | gggcgcgtcg | 1800 |
| cgccattcgc | cattcaggct | gcgcaactgt | tgggaagggc | gatcggtgcg | ggcctcttcg | 1860 |
| ctattacgcc | agctggcgaa | gggggatgt | gctgcaaggc | gattaagttg | ggtaacgcca | 1920 |
| gggttttccc | agtcacgacg | ttgtaaaacg | acggccagtg | aattgtaata | cgactcacta | 1980 |
| tagggcgaat | tggagctcta | gtacggatta | gaagccgccg | agcgggcgac | agccctccga | 2040 |
| cggaagactc | tcctccgtgc | gtcctcgtct | tcaccggtcg | cgttcctgaa | acgcagatgt | 2100 |
| gcctcgcgcc | gcactgctcc | gaacaataaa | gattctacaa | tactagcttt | tatggttatg | 2160 |

```
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga ttttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatggtat tttcctcagt gtgtagtttt ccgtcctctc    2520
ttggtacaaa ctttaagctg gtgcctagat ctaatttttaa ggcttcaagt tcacattacc    2580
acgaaatcaa caatttcatt aacaacaaac ccattaaatt tagttatttc tcttcaaggt    2640
tgtattgcag tgccaagcca atagtacaca gagaaaacaa gttcacaaaa tcattctcac    2700
tatcacactt acaacgtaaa tcttctatca aggcccatgg agagatagag gctgatggaa    2760
gtaacgggac ttctgagttc aacgtaatga agtccggaaa tgctatctgg agatttgtga    2820
ggccgtatgc cgctaaaggt gtcctgttta actccgcggc aatgttcgct aaggaacttg    2880
ttggaaatct gaacttattt agctggccgt tgatgttcaa gatcctttca tttactcttg    2940
tcattctgtg tatctttgta tctacatcag gcataaatca gatatatgat ctagacatcg    3000
atagactgaa caaaccgaac ttgcccgtgg caagcgggga aattagcgta gaattggcat    3060
ggttacttac tatagtatgt acgattagtg gacttacctt aaccattata actaatagtg    3120
gccccttttt tccgttcctt tactcagcct ccatattctt tggtttccta tactccgccc    3180
ccccgttccg ttggaagaaa aacccccttta ccgcctgctt ttgcaatgtg atgttatacg    3240
tgggaaccag tgttggggtt tattatgcct gcaaagccag tttgggcctt cctgccaatt    3300
ggtctccagc attctgcctt ttattttggt ttattagtct gctttccata cctatcagca    3360
tagctaagga tttatctgat attgaaggtg ataggaagtt tggaatcatt actttctcta    3420
ctaagttcgg ggcaaaaccg atcgcgtaca tatgtcacgg gcttatgctt ttgaattacg    3480
tgagtgttat ggccgcggcc ataatatggc ctcaattctt caactcctca gtaatactgt    3540
tatcacatgc cttcatggcg atctgggttt tgtaccaagc gtggatactg agaaaaagta    3600
actatgcaac ggaaacttgc cagaaatatt acatcttctt atggataata ttctcccttg    3660
agcacgcttt ttacctattc atgtaggatg ggctgcagga attcgatatc aagcttatcg    3720
ataccgtcga cctcgagtca tgtaattagt tatgtcacgc ttacattcac gccctccccc    3780
cacatccgct ctaaccgaaa aggaaggagt tagacaacct gaagtctagg tccctattta    3840
ttttttata gttatgttag tattaagaac gttatttata tttcaaattt ttcttttttt    3900
tctgtacaga cgcgtgtacg catgtaacat tatactgaaa accttgcttg agaaggtttt    3960
gggacgctcg aaggctttaa tttgcggccg gtacccagct tttgttccct ttagtgaggg    4020
ttaattccga gcttggcgta atcatggtca tagctgtttc ctgtgtgaaa ttgttatccg    4080
ctcacaattc cacacaacat aggagccgga agcataaagt gtaaagcctg gggtgcctaa    4140
tgagtgaggt aactcacatt aattgcgttg cgctcactgc ccgctttcca gtcgggaaac    4200
ctgtcgtgcc agctgcatta atgaatcggc caacgcgcgg ggagaggcgg tttgcgtatt    4260
gggcgctctt ccgcttcctc gctcactgac tcgctgcgct cggtcgttcg gctgcggcga    4320
gcggtatcag ctcactcaaa ggcggtaata cggttatcca cagaatcagg ggataacgca    4380
ggaaagaaca tgtgagcaaa aggccagcaa aaggccagga accgtaaaaa ggccgcgttg    4440
ctggcgtttt tccataggct cggccccccct gacgagcatc acaaaaatcg acgctcaagt    4500
```

-continued

| | |
|---|---|
| cagaggtggc gaaacccgac aggactataa agataccagg cgttcccccc tggaagctcc | 4560 |
| ctcgtgcgct ctcctgttcc gaccctgccg cttaccggat acctgtccgc ctttctccct | 4620 |
| tcgggaagcg tggcgctttc tcaatgctca cgctgtaggt atctcagttc ggtgtaggtc | 4680 |
| gttcgctcca agctgggctg tgtgcacgaa ccccccgttc agcccgaccg ctgcgcctta | 4740 |
| tccggtaact atcgtcttga gtccaacccg gtaagacacg acttatcgcc actggcagca | 4800 |
| gccactggta acaggattag cagagcgagg tatgtaggcg gtgctacaga gttcttgaag | 4860 |
| tggtggccta actacggcta cactagaagg acagtatttg gtatctgcgc tctgctgaag | 4920 |
| ccagttacct tcggaaaaag agttggtagc tcttgatccg gcaaacaaac caccgctggt | 4980 |
| agcggtggtt ttttgtttg caagcagcag attacgcgca gaaaaaagg atctcaagaa | 5040 |
| gatcctttga tcttttctac ggggtctgac gctcagtgga acgaaaactc acgttaaggg | 5100 |
| attttggtca tgagattatc aaaaaggatc ttcacctaga tccttttaaa ttaaaaatga | 5160 |
| agttttaaat caatctaaag tatatatgag taaacttggt ctgacagtta ccaatgctta | 5220 |
| atcagtgagg cacctatctc agcgatctgt ctatttcgtt catccatagt tgcctgactg | 5280 |
| cccgtcgtgt agataactac gatacgggag ggcttaccat ctggccccag tgctgcaatg | 5340 |
| ataccgcgag acccacgctc accggctcca gatttatcag caataaacca gccagccgga | 5400 |
| agggccgagc gcagaagtgg tcctgcaact ttatccgcct ccatccagtc tattaattgt | 5460 |
| tgccgggaag ctagagtaag tagttcgcca gttaatagtt tgcgcaacgt tgttgccatt | 5520 |
| gctacaggca tcgtggtgtc acgctcgtcg tttggtatgg cttcattcag ctccggttcc | 5580 |
| caacgatcaa ggcgagttac atgatccccc atgttgtgaa aaaagcggt tagctccttc | 5640 |
| ggtcctccga tcgttgtcag aagtaagttg gccgcagtgt tatcactcat ggttatggca | 5700 |
| gcactgcata attctcttac tgtcatgcca tccgtaagat gcttttctgt gactggtgag | 5760 |
| tactcaacca agtcattctg agaatagtgt atgcggcgac cgagttgctc ttgcccggcg | 5820 |
| tcaatacggg ataataccgc gccacatagc agaactttaa aagtgctcat cattggaaaa | 5880 |
| cgttcttcgg ggcgaaaact ctcaaggatc ttaccgctgt tgagatccag ttcgatgtaa | 5940 |
| cccactcgtg cacccaactg atcttcagca tcttttactt tcaccagcgt ttctgggtga | 6000 |
| gcaaaaacag gaaggcaaaa tgccgcaaaa aagggaataa gggcgacacg gaaatgttga | 6060 |
| atactcatac tcttcctttt tcaatattat tgaagcattt atcagggtta ttgtctcatg | 6120 |
| agcggataca tatttgaatg tatttagaaa aataaacaaa taggggttcc gcgcacattt | 6180 |
| ccccgaaaag tgccacctga cgtctaagaa accattatta tcatgacatt aacctataaa | 6240 |
| aataggcgta tcacgaggcc ctttcgtc | 6268 |

<210> SEQ ID NO 47
<211> LENGTH: 6256
<212> TYPE: DNA
<213> ORGANISM: Artificial Sequence
<220> FEATURE:
<223> OTHER INFORMATION: Codon Optimized

<400> SEQUENCE: 47

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accacgcttt tcaattcaat tcatcatttt ttttttattc ttttttttga tttcggtttc | 240 |
| tttgaaattt ttttgattcg gtaatctccg aacagaagga agaacgaagg aaggagcaca | 300 |

```
gacttagatt ggtatatata cgcatatgta gtgttgaaga acatgaaatt tgcccagtat      360
tcttaaccca actgcacaga acaaaaacct gcaggaaacg aagataaatc atgtcgaaag      420
ctacatataa ggaacgtgct gctactcatc ctagtcctgt tgctgccaag ctatttaata      480
tcatgcacga aaagcaaaca aacttgtgtg cttcattgga tgttcgtacc accaaggaat      540
tactggagtt agttgaagca ttaggtccca aaatttgttt actaaaaaca catgtggata      600
tcttgactga ttttccatg gagggcacag ttaagccgct aaaggcatta tccgccaagt       660 acaattttt actcttcgaa gacagaaaat ttgctgacat tggtaataca gtcaaattgc       720
agtactctgc gggtgtatac agaatagcag aatgggcaga cattacgaat gcacacggtg      780
tggtgggccc aggtattgtt agcggtttga agcaggcggc agaagaagta acaaaggaac      840
ctagaggcct tttgatgtta gcagaattgt catgcaaggg ctccctatct actggagaat      900
atactaaggg tactgttgac attgcgaaga gcgacaaaga ttttgttatc ggctttattg      960
ctcaaagaga catgggtgga agagatgaag gttacgattg gttgattatg acacccggtg     1020
tgggtttaga tgacaaggga gacgcattgg gtcaacagta tagaaccgtg gatgatgtgg     1080
tctctacagg atctgacatt attattgttg aagaggact atttgcaaag ggaagggatg      1140
ctaaggtaga gggtgaacgt tacagaaaag caggctggga agcatatttg agaagatgcg     1200
gccagcaaaa ctaaaaaact gtattataag taaatgcatg tatactaaac tcacaaatta     1260
gagcttcaat ttaattatat cagttattac cctgcggtgt gaaataccgc acagatgcgt     1320
aaggagaaaa taccgcatca ggaaattgta acgttaata ttttgttaaa attcgcgtta      1380 aattttgtt aaatcagctc attttttaac caataggccg aaatcggcaa atcccttat      1440 aaatcaaaag aatagaccga gatagggttg agtgttgttc cagtttggaa caagagtcca     1500
ctattaaaga acgtggactc caacgtcaaa gggcgaaaaa ccgtctatca gggcgatggc     1560
ccactacgtg aaccatcacc ctaatcaagt ttttggggt cgaggtgccg taaagcacta      1620
aatcggaacc ctaaagggag ccccgattt agagcttgac ggggaaagcc ggcgaacgtg     1680
gcgagaaagg aagggaagaa agcgaaagga gcgggcgcta gggcgctggc aagtgtagcg     1740
gtcacgctgc gcgtaaccac cacacccgcc gcgcttaatg cgccgctaca gggcgcgtcg     1800
cgccattcgc cattcaggct gcgcaactgt tgggaagggc gatcggtgcg ggcctcttcg     1860
ctattacgcc agctggcgaa ggggggatgt gctgcaaggc gattaagttg ggtaacgcca     1920
gggttttccc agtcacgacg ttgtaaaacg acggccagtg aattgtaata cgactcacta     1980
tagggcgaat tggagctcta gtacggatta gaagccgccg agcgggcgac agccctccga     2040
cggaagactc tcctccgtgc gtcctcgtct tcaccggtcg cgttcctgaa acgcagatgt     2100
gcctcgcgcc gcactgctcc gaacaataaa gattctacaa tactagcttt tatggttatg     2160
aagaggaaaa attggcagta acctggcccc acaaaccttc aaattaacga atcaaattaa     2220
caaccatagg atgataatgc gattagtttt ttagccttat ttctgggta attaatcagc      2280 gaagcgatga ttttgatct attaacagat atataaatgg aaaagctgca taaccacttt      2340
aactaatact ttcaacattt tcagtttgta ttacttctta ttcaaatgtc ataaaagtat     2400
caacaaaaaa ttgttaatat acctctatac tttaacgtca aggagaaaaa accccggatt     2460
ctagaactag tggatccccc atcatgagat tcccatctat tttcactgct gttttgttcg     2520
ctgcttcttc tgctttggct gctccagttg cttcaagttc acattaccac gaaatcaaca     2580
atttcattaa caacaaaccc attaaattta gttatttctc ttcaaggttg tattgcagtg     2640
```

```
ccaagccaat agtacacaga gaaaacaagt tcacaaaatc attctcacta tcacacttac    2700
aacgtaaatc ttctatcaag gcccatggag agatagaggc tgatggaagt aacgggactt    2760
ctgagttcaa cgtaatgaag tccggaaatg ctatctggag atttgtgagg ccgtatgccg    2820
ctaaaggtgt cctgtttaac tccgcggcaa tgttcgctaa ggaacttgtt ggaaatctga    2880
acttatttag ctggccgttg atgttcaaga tcctttcatt tactcttgtc attctgtgta    2940
tctttgtatc tacatcaggc ataaatcaga tatatgatct agacatcgat agactgaaca    3000
aaccgaactt gcccgtggca agcggggaaa ttagcgtaga attggcatgg ttacttacta    3060
tagtatgtac gattagtgga cttaccttaa ccattataac taatagtggc ccctttttc     3120 cgttccttta ctcagcctcc atattctttg gtttcctata ctccgccccc ccgttccgtt    3180
ggaagaaaaa ccccttt acc gcctgctttt gcaatgtgat gttatacgtg gaaccagtg     3240 ttggggttta ttatgcctgc aaagccagtt tgggccttcc tgccaattgg tctccagcat    3300
tctgcctttt attttggttt attagtctgc tttccatacc tatcagcata gctaaggatt    3360
tatctgatat tgaaggtgat aggaagtttg gaatcattac tttctctact aagttcgggg    3420
caaaaccgat cgcgtacata tgtcacgggc ttatgctttt gaattacgtg agtgttatgg    3480
ccgcggccat aatatggcct caattcttca actcctcagt aatactgtta tcacatgcct    3540
tcatggcgat ctgggttttg taccaagcgt ggatactgga gaaaagtaac tatgcaacgg    3600
aaacttgcca gaaatattac atcttcttat ggataatatt ctcccttgag cacgcttttt   3660
acctattcat gtaggatggg ctgcaggaat tcgatatcaa gcttatcgat accgtcgacc    3720
tcgagtcatg taattagtta tgtcacgctt acattcacgc cctcccccca catccgctct    3780
aaccgaaaag gaaggagtta gacaacctga agtctaggtc cctatttatt tttttatagt    3840
tatgttagta ttaagaacgt tatttatatt tcaaattttt ctttttttc tgtacagacg     3900 cgtgtacgca tgtaacatta tactgaaaac cttgcttgag aaggttttgg gacgctcgaa    3960
ggctttaatt tgcggccggt acccagcttt tgttcccttt agtgagggtt aattccgagc    4020
ttggcgtaat catggtcata gctgtttcct gtgtgaaatt gttatccgct cacaattcca    4080
cacaacatag gagccggaag cataaagtgt aaagcctggg gtgcctaatg agtgaggtaa    4140
ctcacattaa ttgcgttgcg ctcactgccc gctttccagt cgggaaacct gtcgtgccag    4200
ctgcattaat gaatcggcca acgcgcgggg agaggcggtt tgcgtattgg gcgctcttcc    4260
gcttcctcgc tcactgactc gctgcgctcg tcgttcggc tgcggcgagc ggtatcagct      4320
cactcaaagg cggtaatacg gttatccaca gaatcagggg ataacgcagg aaagaacatg    4380
tgagcaaaag gccagcaaaa ggccaggaac cgtaaaaagg ccgcgttgct ggcgtttttc    4440
cataggctcg gcccccctga cgagcatcac aaaaatcgac gctcaagtca gaggtggcga    4500
aacccgacag gactataaag ataccaggcg ttccccctg gaagctccct cgtgcgctct     4560
cctgttccga ccctgccgct taccggatac ctgtccgcct ttctcccttc gggaagcgtg    4620
gcgctttctc aatgctcacg ctgtaggtat ctcagttcgg tgtaggtcgt tcgctccaag    4680
ctgggctgtg tgcacgaacc ccccgttcag cccgaccgct gcgccttatc cggtaactat    4740
cgtcttgagt ccaacccggt aagacacgac ttatcgccac tggcagcagc cactggtaac    4800
aggattagca gagcgaggta tgtaggcggt gctacagagt tcttgaagtg gtggcctaac    4860
tacggctaca ctagaaggac agtatttggt atctgcgctc tgctgaagcc agttaccttc    4920
ggaaaaagag ttggtagctc ttgatccggc aaacaaacca ccgctggtag cggtggtttt    4980
tttgtttgca agcagcagat tacgcgcaga aaaaaaggat ctcaagaaga tcctttgatc    5040
```

```
ttttctacgg ggtctgacgc tcagtggaac gaaaactcac gttaagggat tttggtcatg    5100
agattatcaa aaaggatctt cacctagatc cttttaaatt aaaaatgaag ttttaaatca    5160
atctaaagta tatatgagta aacttggtct gacagttacc aatgcttaat cagtgaggca    5220
cctatctcag cgatctgtct atttcgttca tccatagttg cctgactgcc cgtcgtgtag    5280
ataactacga tacgggaggg cttaccatct ggccccagtg ctgcaatgat accgcgagac    5340
ccacgctcac cggctccaga tttatcagca ataaaccagc cagccggaag ggccgagcgc    5400
agaagtggtc ctgcaacttt atccgcctcc atccagtcta ttaattgttg ccgggaagct    5460
agagtaagta gttcgccagt taatagtttg cgcaacgttg ttgccattgc tacaggcatc    5520
gtggtgtcac gctcgtcgtt tggtatggct tcattcagct ccggttccca acgatcaagg    5580
cgagttacat gatcccccat gttgtgaaaa aaagcggtta gctccttcgg tcctccgatc    5640
gttgtcagaa gtaagttggc cgcagtgtta tcactcatgg ttatggcagc actgcataat    5700
tctcttactg tcatgccatc cgtaagatgc ttttctgtga ctggtgagta ctcaaccaag    5760
tcattctgag aatagtgtat gcggcgaccg agttgctctt gcccggcgtc aatacgggat    5820
aataccgcgc cacatagcag aactttaaaa gtgctcatca ttggaaaacg ttcttcgggg    5880
cgaaaactct caaggatctt accgctgttg agatccagtt cgatgtaacc cactcgtgca    5940
cccaactgat cttcagcatc ttttactttc accagcgttt ctgggtgagc aaaaacagga    6000
aggcaaaatg ccgcaaaaaa gggaataagg gcgacacgga aatgttgaat actcatactc    6060
ttcctttttc aatattattg aagcatttat cagggttatt gtctcatgag cggatacata    6120
tttgaatgta tttagaaaaa taaacaaata ggggttccgc gcacatttcc ccgaaaagtg    6180
ccacctgacg tctaagaaac cattattatc atgacattaa cctataaaaa taggcgtatc    6240
acgaggccct ttcgtc                                                   6256
```

<210> SEQ ID NO 48
<211> LENGTH: 648
<212> TYPE: DNA
<213> ORGANISM: Artificial Sequence
<220> FEATURE:
<223> OTHER INFORMATION: Codon Optimized

<400> SEQUENCE: 48

```
atgagcatcg aaatggcctg ggtcctgacc atattctgtg ctatcagtgg gttaatactt     60
acaatcacta tgaacagcgg ccctctattt ccattcttgt actgtggatc tatatttgtt    120
gctggctttc tatatagtgc tccgcccttc agatttaaga ataaccactt cactgccctg    180
ctgtgtaatt acgtaatgtt tgtcagcaca acccttcaga tatactgcgc atacaaggcg    240
ggccttggcc ttccactgaa ttggagcccc gcgttctgcc tattagtgtg gttcttgtca    300
ttaatcgctg tcactatatg tattggcaaa gatttgtcag acattgaagg cgatagaaag    360 tcggcgtaa caaccttccc gacagaatac ggggcaaagc cctagcgct aatttgccac    420 ggcctgattc tattagacta cgtgggtctg atggcagccg ccataatctg gccgcagtta    480
ttcaactcta agctaatcct actgtctcat gcgtttatgg ccgtgtgggt cgtttatcag    540
gcttggattt tggaaaagag caattatacg accgaggcat gtcaaaagta ctatatgtac    600
ttatggacga tctattctgt cgagcacatc ttatatctgt tcatgtag                 648
```

<210> SEQ ID NO 49
<211> LENGTH: 423
<212> TYPE: DNA

<213> ORGANISM: Artificial Sequence
<220> FEATURE:
<223> OTHER INFORMATION: Codon Optimized

<400> SEQUENCE: 49

```
atggcataca aggcgggcct tggccttcca ctgaattgga gccccgcgtt ctgcctatta      60
gtgtggttct tgtcattaat cgctgtcact atatgtattg caaagatttt gtcagacatt     120
gaaggcgata gaaagttcgg cgtaacaacc ttcccgacag aatacggggc aaagcccata     180
gcgctaattt gccacggcct gattctatta gactacgtgg gtctgatggc agccgccata     240
atctggccgc agttattcaa ctctaagcta atcctactgt ctcatgcgtt tatggccgtg     300
tgggtcgttt atcaggcttg gattttggaa aagagcaatt atacgaccga ggcatgtcaa     360
aagtactata tgtacttatg gacgatctat tctgtcgagc acatcttata tctgttcatg     420
tag                                                                   423
```

<210> SEQ ID NO 50
<211> LENGTH: 485
<212> TYPE: DNA
<213> ORGANISM: Artificial Sequence
<220> FEATURE:
<223> OTHER INFORMATION: Codon Optimized

<400> SEQUENCE: 50

```
atgagattcc catctatttt cactgctgtt ttgttcgctg cttcttctgc tttggctgct      60
ccagttcata caaggcgggc cttggccttc cactgaattg gagccccgcg ttctgcctat     120
tagtgtggtt cttgtcatta atcgctgtca ctatatgtat tggcaaagat tgtcagaca     180
ttgaaggcga tagaaagttc ggcgtaacaa ccttcccgac agaatacggg caaagccca     240
tagcgctaat ttgccacggc ctgattctat tagactacgt gggtctgatg gcagccgcca     300
taatctggcc gcagttattc aactctaagc taatcctact gtctcatgcg tttatggccg     360
tgtgggtcgt ttatcaggct tggattttgg aaaagagcaa ttatacgacc gaggcatgtc     420
aaaagtacta tatgtactta tggacgatct attctgtcga gcacatctta tatctgttca     480
tgtag                                                                 485
```

<210> SEQ ID NO 51
<211> LENGTH: 5713
<212> TYPE: DNA
<213> ORGANISM: Artificial Sequence
<220> FEATURE:
<223> OTHER INFORMATION: Codon Optimized

<400> SEQUENCE: 51

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc tttttttttga tttcggtttc     240
tttgaaattt ttttgattcg gtaatctccg aacagaagga agaacgaagg aaggagcaca     300
gacttagatt ggtatatata cgcatatgta gtgttgaaga acatgaaatt gcccagtat     360
tcttaaccca actgcacaga acaaaaacct gcaggaaacg aagataaatc atgtcgaaag     420
ctacatataa ggaacgtgct gctactcatc ctagtcctgt tgctgccaag ctatttaata     480
tcatgcacga aaagcaaaca aacttgtgtg cttcattgga tgttcgtacc accaaggaat     540
tactggagtt agttgaagca ttaggtccca aaatttgttt actaaaaaca catgtggata     600
```

```
tcttgactga ttttccatg gagggcacag ttaagccgct aaaggcatta tccgccaagt    660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg cacccggtg    1020 tgggtttaga tgacaaggga gacgcattgg gtcaacagta tagaaccgtg gatgatgtgg    1080
tctctacagg atctgacatt attattgttg aagaggact atttgcaaag ggaagggatg    1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta aacgttaata ttttgttaaa attcgcgtta    1380 aattttttgtt aaatcagctc attttttaac caataggccg aaatcggcaa aatcccttat    1440
aaatcaaaag aatagaccga gatagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttggggt cgaggtgccg taaagcacta    1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa gggggatgt gctgcaaggc gattaagttg gtaacgccca    1920
gggttttccc agtcacgacg ttgtaaaacg acggccagtg aattgtaata cgactcacta    1980
tagggcgaat tggagctcta gtacggatta aagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga ttttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatgagca tcgaaatggc ctgggtcctg accatattct    2520
gtgctatcag tggttaata cttacaatca ctatgaacag cggccctcta tttccattct    2580
tgtactgtgg atctatattt gttgctggct ttctatatag tgctccgccc ttcagattta    2640
agaataacca cttcactgcc ctgctgtgta attacgtaat gtttgtcagc acaacccttc    2700
agatatactg cgcatacaag gcgggccttg gccttccact gaattggagc cccgcgttct    2760
gcctattagt gtggttcttg tcattaatcg ctgtcactat atgtattggc aaagatttgt    2820
cagacattga aggcgataga aagttcgcg taacaacctt cccgacagaa tacgggcaa    2880 agcccatagc gctaatttgc cacggcctga ttctattaga ctacgtgggt ctgatggcag    2940
```

```
ccgccataat ctggccgcag ttattcaact ctaagctaat cctactgtct catgcgttta    3000
tggccgtgtg ggtcgtttat caggcttgga ttttggaaaa gagcaattat acgaccgagg    3060
catgtcaaaa gtactatatg tacttatgga cgatctattc tgtcgagcac atcttatatc    3120
tgttcatgta ggatgggctg caggaattcg atatcaagct tatcgatacc gtcgacctcg    3180
agtcatgtaa ttagttatgt cacgcttaca ttcacgccct cccccacat ccgctctaac     3240 cgaaaaggaa ggagttagac aacctgaagt ctaggtccct atttattttt ttatagttat    3300
gttagtatta agaacgttat ttatatttca aattttctt tttttctgt acagacgcgt      3360 gtacgcatgt aacattatac tgaaaacctt gcttgagaag gttttgggac gctcgaaggc    3420
tttaatttgc ggccggtacc cagcttttgt tcccttagt gagggttaat tccgagcttg     3480
gcgtaatcat ggtcatagct gtttcctgtg tgaaattgtt atccgctcac aattccacac    3540
aacataggag ccggaagcat aaagtgtaaa gcctggggtg cctaatgagt gaggtaactc    3600
acattaattg cgttgcgctc actgcccgct ttccagtcgg gaaacctgtc gtgccagctg    3660
cattaatgaa tcggccaacg cgcggggaga ggcggtttgc gtattgggcg ctcttccgct    3720
tcctcgctca ctgactcgct gcgctcggtc gttcggctgc ggcgagcggt atcagctcac    3780
tcaaaggcgg taatacggtt atccacagaa tcagggata acgcaggaaa gaacatgtga     3840
gcaaaaggcc agcaaaaggc caggaaccgt aaaaaggccg cgttgctggc gtttttccat    3900
aggctcggcc cccctgacga gcatcacaaa aatcgacgct caagtcagag gtggcgaaac    3960
ccgacaggac tataaagata ccaggcgttc cccctggaa gctccctcgt gcgctctcct     4020
gttccgaccc tgccgcttac cggatacctg tccgcctttc tcccttcggg aagcgtggcg    4080
ctttctcaat gctcacgctg taggtatctc agttcggtgt aggtcgttcg ctccaagctg    4140
ggctgtgtgc acgaaccccc cgttcagccc gaccgctgcg ccttatccgg taactatcgt    4200
cttgagtcca acccggtaag acacgactta tcgccactgg cagcagccac tggtaacagg    4260
attagcagag cgaggtatgt aggcggtgct acagagttct tgaagtggtg gcctaactac    4320
ggctacacta aaggacagt atttggtatc tgcgctctgc tgaagccagt taccttcgga    4380
aaaagagttg gtagctcttg atccggcaaa caaaccaccg ctggtagcgg tggtttttt     4440 gtttgcaagc agcagattac gcgcagaaaa aaaggatctc aagaagatcc tttgatcttt    4500
tctacggggt ctgacgctca gtggaacgaa aactcacgtt aagggatttt ggtcatgaga    4560
ttatcaaaaa ggatcttcac ctagatcctt ttaaattaaa aatgaagttt taaatcaatc    4620
taaagtatat atgagtaaac ttggtctgac agttaccaat gcttaatcag tgaggcacct    4680
atctcagcga tctgtctatt tcgttcatcc atagttgcct gactgcccgt cgtgtagata    4740
actacgatac gggagggctt accatctggc cccagtgctg caatgatacc gcagaccca     4800 cgctcaccgg ctccagattt atcagcaata aaccagccag ccggaagggc cgagcgcaga    4860
agtggtcctg caactttatc cgcctccatc cagtctatta ttgttgccg ggaagctaga     4920 gtaagtagtt cgccagttaa tagtttgcgc aacgttgttg ccattgctac aggcatcgtg    4980
gtgtcacgct cgtcgtttgg tatggcttca ttcagctccg gttcccaacg atcaaggcga    5040
gttacatgat cccccatgtt gtgaaaaaaa gcggttagct ccttcggtcc tccgatcgtt    5100
gtcagaagta agttggccgc agtgttatca ctcatggtta tggcagcact gcataattct    5160
cttactgtca tgccatccgt aagatgcttt tctgtgactg gtgagtactc aaccaagtca    5220
ttctgagaat agtgtatgcg cgaccgagt tgctcttgcc cggcgtcaat acgggataat     5280
accgcgccac atagcagaac tttaaaagtg ctcatcattg gaaaacgttc ttcggggcga    5340
```

```
aaactctcaa ggatcttacc gctgttgaga tccagttcga tgtaacccac tcgtgcaccc       5400
aactgatctt cagcatcttt tactttcacc agcgtttctg ggtgagcaaa acaggaagg        5460 caaaatgccg caaaaaggg aataagggcg acacggaaat gttgaatact catactcttc        5520 cttttcaat attattgaag catttatcag ggttattgtc tcatgagcgg atacatattt        5580
gaatgtattt agaaaaataa acaaataggg gttccgcgca catttccccg aaaagtgcca       5640
cctgacgtct aagaaaccat tattatcatg acattaacct ataaaaatag gcgtatcacg       5700
aggccctttc gtc                                                         5713
```

<210> SEQ ID NO 52
<211> LENGTH: 5488
<212> TYPE: DNA
<213> ORGANISM: Artificial Sequence
<220> FEATURE:
<223> OTHER INFORMATION: Codon Optimized

<400> SEQUENCE: 52

```
tcgcgcgttt cggtgatgac ggtgaaaacc tctgacacat gcagctcccg gagacggtca         60
cagcttgtct gtaagcggat gccgggagca gacaagcccg tcaggcgcg tcagcgggtg        120 ttggcgggtg tcggggctgg cttaactatg cggcatcaga gcagattgta ctgagagtgc       180
accacgcttt tcaattcaat tcatcatttt ttttttattc ttttttttga tttcggtttc       240
tttgaaattt ttttgattcg gtaatctccg aacagaagga agaacgaagg aaggagcaca       300
gacttagatt ggtatatata cgcatatgta gtgttgaaga acatgaaat tgcccagtat       360 tcttaaccca actgcacaga acaaaaacct gcaggaaacg aagataaatc atgtcgaaag       420
ctacatataa ggaacgtgct gctactcatc ctagtcctgt tgctgccaag ctatttaata       480
tcatgcacga aaagcaaaca aacttgtgtg cttcattgga tgttcgtacc accaaggaat       540
tactggagtt agttgaagca ttaggtccca aaatttgttt actaaaaaca catgtggata       600
tcttgactga tttttccatg gagggcacag ttaagccgct aaaggcatta tccgccaagt       660 acaattttt actcttcgaa gacagaaaat ttgctgacat tggtaataca gtcaaattgc       720
agtactctgc gggtgtatac agaatagcag aatgggcaga cattacgaat gcacacggtg       780
tggtgggccc aggtattgtt agcggtttga agcaggcggc agaagaagta acaaaggaac       840
ctagaggcct tttgatgtta gcagaattgt catgcaaggg ctccctatct actggagaat       900
atactaaggg tactgttgac attgcgaaga gcgacaaaga ttttgttatc ggctttattg       960
ctcaaagaga catgggtgga agagatgaag gttacgattg gttgattatg acacccggtg      1020
tgggtttaga tgacaaggga gacgcattgg gtcaacagta tagaaccgtg gatgatgtgg      1080
tctctacagg atctgacatt attattgttg gaagaggact attttgcaaag gaagggatg      1140 ctaaggtaga gggtgaacgt tacagaaaag caggctggga agcatatttg agaagatgcg      1200
gccagcaaaa ctaaaaaact gtattataag taaatgcatg tatactaaac tcacaaatta      1260
gagcttcaat ttaattatat cagttattac cctgcggtgt gaaataccgc acagatgcgt      1320
aaggagaaaa taccgcatca ggaaattgta aacgttaata ttttgttaaa attcgcgtta      1380
aatttttgtt aaatcagctc attttttaac caataggccg aaatcggcaa aatcccttat      1440
aaatcaaaag aatagaccga gatagggttg agtgttgttc cagtttggaa caagagtcca      1500
ctattaaaga acgtggactc caacgtcaaa gggcgaaaaa ccgtctatca gggcgatggc      1560
ccactacgtg aaccatcacc ctaatcaagt tttttggggt cgaggtgccg taaagcacta      1620
```

```
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa gggggatgt gctgcaaggc gattaagttg ggtaacgcca     1920
gggttttccc agtcacgacg ttgtaaaacg acggccagtg aattgtaata cgactcacta    1980
tagggcgaat tggagctcta gtacggatta gaagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga ttttgatct attaacagat atataaatgg aaaagctgca taaccacttt     2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatggcat acaaggcggg ccttggcctt ccactgaatt    2520
ggagccccgc gttctgccta ttagtgtggt tcttgtcatt aatcgctgtc actatatgta    2580
ttggcaaaga tttgtcagac attgaaggcg atagaaagtt cggcgtaaca accttcccga    2640
cagaatacgg ggcaaagccc atagcgctaa tttgccacgg cctgattcta ttagactacg    2700
tgggtctgat ggcagccgcc ataatctggc cgcagttatt caactctaag ctaatcctac    2760
tgtctcatgc gtttatggcc gtgtgggtcg tttatcaggc ttggattttg gaaaagagca    2820
attatacgac cgaggcatgt caaaagtact atatgtactt atggacgatc tattctgtcg    2880
agcacatctt atatctgttc atgtaggatg ggctgcagga attcgatatc aagcttatcg    2940
ataccgtcga cctcgagtca tgtaattagt tatgtcacgc ttacattcac gccctccccc    3000
cacatccgct ctaaccgaaa aggaaggagt tagacaacct gaagtctagg tccctattta    3060 ttttttttata gttatgttag tattaagaac gttatttata tttcaaattt ttcttttttt    3120
tctgtacaga cgcgtgtacg catgtaacat tatactgaaa accttgcttg agaaggtttt    3180
gggacgctcg aaggctttaa tttgcggccg gtacccagct tttgttccct ttagtgaggg    3240
ttaattccga gcttggcgta atcatggtca tagctgtttc ctgtgtgaaa ttgttatccg    3300
ctcacaattc cacacaacat aggagccgga agcataaagt gtaaagcctg gggtgcctaa    3360
tgagtgaggt aactcacatt aattgcgttg cgctcactgc ccgctttcca gtcgggaaac    3420
ctgtcgtgcc agctgcatta tgaatcggc caacgcgcgg ggagaggcgg tttgcgtatt     3480
gggcgctctt ccgcttcctc gctcactgac tcgctgcgct cggtcgttcg gctgcggcga    3540
gcggtatcag ctcactcaaa ggcggtaata cggttatcca cagaatcagg gataacgca    3600 ggaaagaaca tgtgagcaaa aggccagcaa aaggccagga accgtaaaaa ggccgcgttg    3660
ctggcgtttt tccataggct cggcccccct gacgagcatc acaaaaatcg acgctcaagt    3720
cagaggtggc gaaacccgac aggactataa agataccagg cgttcccccc tggaagctcc    3780
ctcgtgcgct ctcctgttcc gaccctgccg cttaccggat acctgtccgc ctttctccct    3840
tcgggaagcg tggcgctttc tcaatgctca cgctgtaggt atctcagttc ggtgtaggtc    3900
gttcgctcca agctgggctg tgtgcacgaa ccccccgttc agcccgaccg ctgcgcctta    3960
tccggtaact atcgtcttga gtccaacccg gtaagacacg acttatcgcc actggcagca    4020
```

| | | |
|---|---|---|
| gccactggta acaggattag cagagcgagg tatgtaggcg gtgctacaga gttcttgaag | 4080 |
| tggtggccta actacggcta cactagaagg acagtatttg gtatctgcgc tctgctgaag | 4140 |
| ccagttacct tcggaaaaag agttggtagc tcttgatccg gcaaacaaac caccgctggt | 4200 |
| agcggtggtt ttttgtttg caagcagcag attacgcgca gaaaaaaagg atctcaagaa | 4260 |
| gatcctttga tcttttctac ggggtctgac gctcagtgga acgaaaactc acgttaaggg | 4320 |
| attttggtca tgagattatc aaaaaggatc ttcacctaga tccttttaaa ttaaaaatga | 4380 |
| agttttaaat caatctaaag tatatatgag taaacttggt ctgacagtta ccaatgctta | 4440 |
| atcagtgagg cacctatctc agcgatctgt ctatttcgtt catccatagt tgcctgactg | 4500 |
| cccgtcgtgt agataactac gatacgggag ggcttaccat ctggccccag tgctgcaatg | 4560 |
| ataccgcgag acccacgctc accggctcca gatttatcag caataaacca gccagccgga | 4620 |
| agggccgagc gcagaagtgg tcctgcaact ttatccgcct ccatccagtc tattaattgt | 4680 |
| tgccgggaag ctagagtaag tagttcgcca gttaatagtt tgcgcaacgt tgttgccatt | 4740 |
| gctacaggca tcgtggtgtc acgctcgtcg tttggtatgg cttcattcag ctccggttcc | 4800 |
| caacgatcaa ggcgagttac atgatccccc atgttgtgaa aaaagcggt tagctccttc | 4860 |
| ggtcctccga tcgttgtcag aagtaagttg gccgcagtgt tatcactcat ggttatggca | 4920 |
| gcactgcata attctcttac tgtcatgcca tccgtaagat gcttttctgt gactggtgag | 4980 |
| tactcaacca agtcattctg agaatagtgt atgcggcgac cgagttgctc ttgcccggcg | 5040 |
| tcaatacggg ataataccgc gccacatagc agaactttaa aagtgctcat cattggaaaa | 5100 |
| cgttcttcgg ggcgaaaact ctcaaggatc ttaccgctgt tgagatccag ttcgatgtaa | 5160 |
| cccactcgtg cacccaactg atcttcagca tcttttactt tcaccagcgt ttctgggtga | 5220 |
| gcaaaaacag gaaggcaaaa tgccgcaaaa aagggaataa gggcgacacg aaatgttga | 5280 |
| atactcatac tcttcctttt tcaatattat tgaagcattt atcagggtta ttgtctcatg | 5340 |
| agcggataca tatttgaatg tatttagaaa aataaacaaa taggggttcc gcgcacattt | 5400 |
| ccccgaaaag tgccacctga cgtctaagaa accattatta tcatgacatt aacctataaa | 5460 |
| aataggcgta tcacgaggcc ctttcgtc | 5488 |

<210> SEQ ID NO 53
<211> LENGTH: 5550
<212> TYPE: DNA
<213> ORGANISM: Artificial Sequence
<220> FEATURE:
<223> OTHER INFORMATION: Codon Optimized

<400> SEQUENCE: 53

| | | |
|---|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accacgcttt tcaattcaat tcatcatttt ttttttattc tttttttga tttcggtttc | 240 |
| tttgaaattt ttttgattcg gtaatctccg aacagaagga agaacgaagg aaggagcaca | 300 |
| gacttagatt ggtatatata cgcatatgta gtgttgaaga acatgaaat tgcccagtat | 360 |
| tcttaaccca actgcacaga acaaaaacct gcaggaaacg aagataaatc atgtcgaaag | 420 |
| ctacatataa ggaacgtgct gctactcatc ctagtcctgt tgctgccaag ctatttaata | 480 |
| tcatgcacga aaagcaaaca aacttgtgtg cttcattgga tgttcgtacc accaaggaat | 540 |

-continued

```
tactggagtt agttgaagca ttaggtccca aaatttgttt actaaaaaca catgtggata      600
tcttgactga ttttccatg gagggcacag ttaagccgct aaaggcatta tccgccaagt       660
acaatttttt actcttcgaa gacagaaaat tgctgacat tggtaataca gtcaaattgc       720
agtactctgc gggtgtatac agaatagcag aatgggcaga cattacgaat gcacacggtg     780
tggtgggccc aggtattgtt agcggtttga agcaggcggc agaagaagta acaaaggaac     840
ctagaggcct tttgatgtta gcagaattgt catgcaaggg ctccctatct actggagaat    900
atactaaggg tactgttgac attgcgaaga gcgacaaaga ttttgttatc ggctttattg     960
ctcaaagaga catgggtgga agagatgaag gttacgattg gttgattatg acacccggtg    1020
tgggtttaga tgacaaggga gacgcattgg gtcaacagta tagaaccgtg gatgatgtgg    1080
tctctacagg atctgacatt attattgttg gaagaggact atttgcaaag ggaagggatg    1140
ctaaggtaga gggtgaacgt tacagaaaag caggctggga agcatatttg agaagatgcg    1200
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta acgttaata ttttgttaaa attcgcgtta     1380 aattttgtt aaatcagctc attttttaac caataggccg aaatcggcaa aatcccttat     1440
aaatcaaaag aatagaccga datagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttgggt cgaggtgccg taaagcacta     1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
gggttttccc agtcacgacg ttgtaaaacg acggccagtg aattgtaata cgactcacta    1980
tagggcgaat tggagctcta gtacggatta gaagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga ttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcatgagat tccatctat tttcactgct gttttgttcg     2520
ctgcttcttc tgctttggct gctccagttc atacaaggcg ggccttggcc ttccactgaa    2580
ttggagcccc gcgttctgcc tattagtgtg gttcttgtca ttaatcgctg tcactatatg    2640
tattggcaaa gatttgtcag acattgaagg cgatagaaag ttcggcgtaa caaccttccc    2700
gacagaatac ggggcaaagc ccatagcgct aatttgccac ggcctgattc tattagacta    2760
cgtgggtctg atggcagccg ccataatctg gccgcagtta ttcaactcta agctaatcct    2820
actgtctcat gcgtttatgg ccgtgtgggt cgtttatcag gcttggattt tggaaaagag    2880
caattatacg accgaggcat gtcaaaagta ctatatgtac ttatggacga tctattctgt    2940
```

```
cgagcacatc ttatatctgt tcatgtagga tgggctgcag gaattcgata tcaagcttat    3000
cgataccgtc gacctcgagt catgtaatta gttatgtcac gcttacattc acgccctccc    3060
cccacatccg ctctaaccga aaaggaagga gttagacaac ctgaagtcta ggtccctatt    3120
tattttttta tagttatgtt agtattaaga acgttattta tatttcaaat ttttcttttt    3180
tttctgtaca gacgcgtgta cgcatgtaac attatactga aaaccttgct tgagaaggtt    3240
ttgggacgct cgaaggcttt aatttgcggc cggtacccag cttttgttcc ctttagtgag    3300
ggttaattcc gagcttggcg taatcatggt catagctgtt tcctgtgtga aattgttatc    3360
cgctcacaat tccacacaac ataggagccg gaagcataaa gtgtaaagcc tggggtgcct    3420
aatgagtgag gtaactcaca ttaattgcgt tgcgctcact gcccgctttc cagtcgggaa    3480
acctgtcgtg ccagctgcat taatgaatcg gccaacgcgc ggggagaggc ggtttgcgta    3540
ttgggcgctc ttccgcttcc tcgctcactg actcgctgcg ctcggtcgtt cggctgcggc    3600
gagcggtatc agctcactca aaggcggtaa tacggttatc cacagaatca ggggataacg    3660
caggaaagaa catgtgagca aaaggccagc aaaaggccag gaaccgtaaa aaggccgcgt    3720
tgctggcgtt tttccatagg ctcggccccc ctgacgagca tcacaaaaat cgacgctcaa    3780
gtcagaggtg gcgaaacccg acaggactat aaagatacca ggcgttcccc cctggaagct    3840
ccctcgtgcg ctctcctgtt ccgaccctgc cgcttaccgg atacctgtcc gcctttctcc    3900
cttcgggaag cgtggcgctt tctcaatgct cacgctgtag gtatctcagt tcggtgtagg    3960
tcgttcgctc caagctgggc tgtgtgcacg aaccccccgt tcagcccgac cgctgcgcct    4020
tatccggtaa ctatcgtctt gagtccaacc cggtaagaca cgacttatcg ccactggcag    4080
cagccactgg taacaggatt agcagagcga ggtatgtagg cggtgctaca gagttcttga    4140
agtggtggcc taactacggc tacactagaa ggacagtatt tggtatctgc gctctgctga    4200
agccagttac cttcggaaaa agagttggta gctcttgatc cggcaaacaa accaccgctg    4260
gtagcggtgg tttttttgtt tgcaagcagc agattacgcg cagaaaaaaa ggatctcaag    4320
aagatccttt gatcttttct acggggtctg acgctcagtg gaacgaaaac tcacgttaag    4380
ggattttggt catgagatta tcaaaaagga tcttcaccta gatcctttta aattaaaaat    4440
gaagttttaa atcaatctaa agtatatatg agtaaacttg gtctgacagt taccaatgct    4500
taatcagtga ggcacctatc tcagcgatct gtctatttcg ttcatccata gttgcctgac    4560
tgcccgtcgt gtagataact acgatacggg agggcttacc atctggcccc agtgctgcaa    4620
tgataccgcg agacccacgc tcaccggctc cagatttatc agcaataaac cagccagccg    4680
gaagggccga gcgcagaagt ggtcctgcaa ctttatccgc ctccatccag tctattaatt    4740
gttgccggga agctagagta agtagttcgc cagttaatag tttgcgcaac gttgttgcca    4800
ttgctacagg catcgtggtg tcacgctcgt cgtttggtat ggcttcattc agctccggtt    4860
cccaacgatc aaggcgagtt acatgatccc ccatgttgtg aaaaaaagcg gttagctcct    4920
tcggtcctcc gatcgttgtc agaagtaagt tggccgcagt gttatcactc atggttatgg    4980
cagcactgca taattctctt actgtcatgc catccgtaag atgcttttct gtgactggtg    5040
agtactcaac caagtcattc tgagaatagt gtatgcggcg accgagttgc tcttgcccgg    5100
cgtcaatacg ggataatacc gcgccacata gcagaacttt aaaagtgctc atcattggaa    5160
aacgttcttc gggtgcgaaaa ctctcaagga tcttaccgct gttgagatcc agttcgatgt    5220
aacccactcg tgcacccaac tgatcttcag catcttttac tttcaccagc gtttctgggt    5280
```

| | |
|---|---:|
| gagcaaaaac aggaaggcaa aatgccgcaa aaaagggaat aagggcgaca cggaaatgtt | 5340 |
| gaatactcat actcttcctt tttcaatatt attgaagcat ttatcagggt tattgtctca | 5400 |
| tgagcggata catatttgaa tgtatttaga aaaataaaca aatagggggtt ccgcgcacat | 5460 |
| ttccccgaaa agtgccacct gacgtctaag aaaccattat tatcatgaca ttaacctata | 5520 |
| aaaataggcg tatcacgagg ccctttcgtc | 5550 |

<210> SEQ ID NO 54
<211> LENGTH: 1155
<212> TYPE: DNA
<213> ORGANISM: Artificial Sequence
<220> FEATURE:
<223> OTHER INFORMATION: Codon Optimized

<400> SEQUENCE: 54

| | |
|---|---:|
| atggaattat cattatctct gggcgggccg acgatattcc ccagatatag agcaagctat | 60 |
| acttccacta aactgaccac tcatttctct aattttccgt ccaaattcag cacaaaaaat | 120 |
| ttccaccaga cgctatcttt ctacggacca acgagaggca gcaaatcatt gttgaatacc | 180 |
| catcagtgga ggaactccat aagagcctgc gccgaggcgg gggctgccgg gtcaaacccg | 240 |
| gtgctaaaca aggtctctga ctttagggac gcatgctggc gtttcttaag gccgcatact | 300 |
| ataaggggga ccaccctggg tagtatagcc ctagtagcaa gggcgcttat agaaaatccc | 360 |
| aacttaatca agtggagtct tttactgaag gctttctctg cttactagcc ttaatttgc | 420 |
| gggaacggct acattgtagg aatcaaccaa atctatgaca taggtattga taggtcaac | 480 |
| aaaccgtacc ttcccatagc cgcgggtgat tgtcagtcc agagtgcttg gtaccttgta | 540 |
| atattgtttg ccgttgcggg tctactaact gttggcttca atttggggcc gttcattacg | 600 |
| tctctatact gcttaggact tgttctgggg acaatatata gcgttccacc ctttaggatg | 660 |
| aaaagatttc cggttgcagc attcttaatc attgcgaccg tgaggggttt tctattaaac | 720 |
| tttggtgtat actacgccac aagagctgca ttgggcttaa cctttgaatg gagtagtgcg | 780 |
| gttgcgttca ttacgacctt cgttacatta ttcgctttgg tgatagctat aacgaaagat | 840 |
| ctgccagacg tggagggaga ccgtaaattt cagatcagca cattcgcaac aaagcttggt | 900 |
| gtgagaaaca tcgcgtatct tggatctgga ctattattat taaactacat tggggcaatt | 960 |
| gcggcggcca tttatatgcc tcaggctttt aagagaaatt taatgcttcc tatccacacc | 1020 |
| atcttggcgt tgagccttgt cttccaggcc tgggtcttgg aacaagcgaa ttacaccaag | 1080 |
| gaggctattg ctgggttcta tagattcatt tggaatttgt tctatgtaga atacattata | 1140 |
| ttccccttta tatag | 1155 |

<210> SEQ ID NO 55
<211> LENGTH: 933
<212> TYPE: DNA
<213> ORGANISM: Artificial Sequence
<220> FEATURE:
<223> OTHER INFORMATION: Codon Optimized

<400> SEQUENCE: 55

| | |
|---|---:|
| atggccgggt caaacccggt gctaaacaag gtctctgact ttagggacgc atgctggcgt | 60 |
| ttcttaaggc cgcatactat aagggggacc accctgggta gtatagccct agtagcaagg | 120 |
| gcgcttatag aaaatcccaa cttaatcaag tggagtcttt tactgaaggc tttctctggc | 180 |
| ttactagcct taatttgcgg gaacggctac attgtaggaa tcaaccaaat ctatgacata | 240 |
| ggtattgata aggtcaacaa accgtacctt cccatagccg cgggtgattt gtcagtccag | 300 |

```
agtgcttggt accttgtaat attgtttgcc gttgcgggtc tactaactgt tggcttcaat    360
tttgggccgt tcattacgtc tctatactgc ttaggacttg ttctggggac aatatatagc    420
gttccaccct ttaggatgaa aagatttccg gttgcagcat tcttaatcat tgcgaccgtg    480
aggggttttc tattaaactt tggtgtatac tacgccacaa gagctgcatt gggcttaacc    540
tttgaatgga gtagtgcggt tgcgttcatt acgaccttcg ttacattatt cgctttggtg    600
atagctataa cgaaagatct gccagacgtg gagggagacc gtaaatttca gatcagcaca    660
ttcgcaacaa agcttggtgt gagaaacatc gcgtatcttg atctggact attattatta    720 aactacattg gggcaattgc ggcggccatt tatatgcctc aggcttttaa gagaaattta    780
atgcttccta tccacaccat cttggcgttg agccttgtct tccaggcctg gtcttggaa    840 caagcgaatt acaccaagga ggctattgct gggttctata gattcatttg gaatttgttc    900
tatgtagaat acattatatt cccctttata tag    933
```

```
<210> SEQ ID NO 56
<211> LENGTH: 996
<212> TYPE: DNA
<213> ORGANISM: Artificial Sequence
<220> FEATURE:
<223> OTHER INFORMATION: Codon Optimized

<400> SEQUENCE: 56
atgagattcc catctatttt cactgctgtt ttgttcgctg cttcttctgc tttggctgct     60
ccagttgccg ggtcaaaccc ggtgctaaac aaggtctctg actttaggga cgcatgctgg    120
cgtttcttaa ggccgcatac tataagggg accaccctgg gtagtatagc cctagtagca    180
agggcgctta tagaaaatcc caacttaatc aagtggagtc ttttactgaa ggctttctct    240
ggcttactag ccttaatttg cgggaacggc tacattgtag gaatcaacca aatctatgac    300
ataggtattg ataaggtcaa caaaccgtac cttcccatag ccgcgggtga tttgtcagtc    360
cagagtgctt ggtaccttgt aatattgttt gccgttgcgg gtctactaac tgttggcttc    420
aattttgggc cgttcattac gtctctatac tgcttaggac ttgttctggg gacaatatat    480
agcgttccac cctttaggat gaaaagattt ccggttgcag cattcttaat cattgcgacc    540
gtgaggggtt ttctattaaa ctttggtgta tactacgcca caagagctgc attgggctta    600
acctttgaat ggagtagtgc ggttgcgttc attacgacct tcgttacatt attcgctttg    660
gtgatagcta taacgaaaga tctgccagac gtggagggag accgtaaatt tcagatcagc    720
acattcgcaa caaagcttgg tgtgagaaac atcgcgtatc ttggatctgg actattatta    780
ttaaactaca ttggggcaat tgcggcggcc atttatatgc ctcaggcttt taagagaaat    840
ttaatgcttc ctatccacac catcttggcg ttgagccttg tcttccaggc ctgggtcttg    900
gaacaagcga attacaccaa ggaggctatt gctgggttct atagattcat ttggaatttg    960
ttctatgtag aatacattat attccccttt atatag    996
```

```
<210> SEQ ID NO 57
<211> LENGTH: 6220
<212> TYPE: DNA
<213> ORGANISM: Artificial Sequence
<220> FEATURE:
<223> OTHER INFORMATION: Codon Optimized

<400> SEQUENCE: 57
tcgcgcgttt cggtgatgac ggtgaaaacc tctgacacat gcagctcccg gagacggtca     60
```

-continued

| | |
|---|---|
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accacgcttt tcaattcaat tcatcatttt ttttttattc ttttttttga tttcggtttc | 240 |
| tttgaaatttt ttttgattcg gtaatctccg aacagaagga agaacgaagg aaggagcaca | 300 |
| gacttagatt ggtatatata cgcatatgta gtgttgaaga acatgaaat tgcccagtat | 360 |
| tcttaaccca actgcacaga acaaaaacct gcaggaaacg aagataaatc atgtcgaaag | 420 |
| ctacatataa ggaacgtgct gctactcatc ctagtcctgt tgctgccaag ctatttaata | 480 |
| tcatgcacga aaagcaaaca aacttgtgtg cttcattgga tgttcgtacc accaaggaat | 540 |
| tactggagtt agttgaagca ttaggtccca aaatttgttt actaaaaaca catgtggata | 600 |
| tcttgactga ttttttccatg gagggcacag ttaagccgct aaaggcatta tccgccaagt | 660 |
| acaatttttt actcttcgaa gacagaaaat ttgctgacat tggtaataca gtcaaattgc | 720 |
| agtactctgc gggtgtatac agaatagcag aatgggcaga cattacgaat gcacacggtg | 780 |
| tggtgggccc aggtattgtt agcggtttga agcaggcggc agaagaagta acaaaggaac | 840 |
| ctagaggcct tttgatgtta gcagaattgt catgcaaggg ctccctatct actggagaat | 900 |
| atactaaggg tactgttgac attgcgaaga gcgacaaaga ttttgttatc ggctttattg | 960 |
| ctcaaagaga catgggtgga agagatgaag gttacgattg gttgattatg acacccggtg | 1020 |
| tgggtttaga tgacaaggga gacgcattgg gtcaacagta tagaaccgtg gatgatgtgg | 1080 |
| tctctacagg atctgacatt attattgttg gaagaggact atttgcaaag ggaagggatg | 1140 |
| ctaaggtaga gggtgaacgt tacagaaaag caggctggga agcatatttg agaagatgcg | 1200 |
| gccagcaaaa ctaaaaaact gtattataag taaatgcatg tatactaaac tcacaaatta | 1260 |
| gagcttcaat ttaattatat cagttattac cctgcggtgt gaaataccgc acagatgcgt | 1320 |
| aaggagaaaa taccgcatca ggaaattgta aacgttaata ttttgttaaa attcgcgtta | 1380 |
| aatttttgtt aaatcagctc attttttaac caataggccg aaatcggcaa aatcccttat | 1440 |
| aaatcaaaag aatagaccga gatagggttg agtgttgttc cagtttggaa caagagtcca | 1500 |
| ctattaaaga acgtggactc caacgtcaaa gggcgaaaaa ccgtctatca gggcgatggc | 1560 |
| ccactacgtg aaccatcacc ctaatcaagt tttttgggt cgaggtgccg taaagcacta | 1620 |
| aatcggaacc ctaaagggag cccccgattt agagcttgac ggggaaagcc ggcgaacgtg | 1680 |
| gcgagaaagg aagggaagaa agcgaaagga gcgggcgcta gggcgctggc aagtgtagcg | 1740 |
| gtcacgctgc gcgtaaccac cacacccgcc gcgcttaatg cgccgctaca gggcgcgtcg | 1800 |
| cgccattcgc cattcaggct gcgcaactgt tgggaagggc gatcggtgcg ggcctcttcg | 1860 |
| ctattacgcc agctggcgaa gggggatgt gctgcaaggc gattaagttg ggtaacgcca | 1920 |
| gggttttccc agtcacgacg ttgtaaaacg acggccagtg aattgtaata cgactcacta | 1980 |
| tagggcgaat tggagctcta gtacggatta aagccgccg agcgggcgac agccctccga | 2040 |
| cggaagactc tcctccgtgc gtcctcgtct tcaccggtcg cgttcctgaa acgcagatgt | 2100 |
| gcctcgcgcc gcactgctcc gaacaataaa gattctacaa tactagcttt tatggttatg | 2160 |
| aagaggaaaa attggcagta acctggcccc acaaaccttc aaattaacga atcaaattaa | 2220 |
| caaccatagg atgataatgc gattagtttt ttagccttat ttctgggta attaatcagc | 2280 |
| gaagcgatga tttttgatct attaacagat atataaatgg aaaagctgca taaccacttt | 2340 |
| aactaatact ttcaacattt tcagtttgta ttacttctta ttcaaatgtc ataaaagtat | 2400 |
| caacaaaaaa ttgttaatat acctctatac tttaacgtca aggagaaaaa accccggatt | 2460 |

```
ctagaactag tggatccccc atcatggaat tatcattatc tctgggcggg ccgacgatat    2520
tccccagata tagagcaagc tatacttcca ctaaactgac cactcatttc tctaattttc    2580
cgtccaaatt cagcacaaaa aatttccacc agacgctatc tttctacgga ccaacgagag    2640
gcagcaaatc attgttgaat acccatcagt ggaggaactc cataagagcc tgcgccgagg    2700
cgggggctgc cgggtcaaac ccggtgctaa acaaggtctc tgactttagg gacgcatgct    2760
ggcgtttctt aaggccgcat actataaggg ggaccaccct gggtagtata gccctagtag    2820
caagggcgct tatagaaaat cccaacttaa tcaagtggag tcttttactg aaggctttct    2880
ctggcttact agccttaatt tgcgggaacg gctacattgt aggaatcaac caaatctatg    2940
acataggtat tgataaggtc aacaaaccgt accttcccat agccgcgggt gatttgtcag    3000
tccagagtgc ttggtacctt gtaatattgt ttgccgttgc gggtctacta actgttggct    3060
tcaattttgg gccgttcatt acgtctctat actgcttagg acttgttctg gggacaatat    3120
atagcgttcc acccctttagg atgaaaagat ttccggttgc agcattctta atcattgcga    3180
ccgtgagggg ttttctatta aactttggtg tatactacgc cacaagagct gcattgggct    3240
taacctttga atggagtagt gcggttgcgt tcattacgac cttcgttaca ttattcgctt    3300
tggtgatagc tataacgaaa gatctgccag acgtggaggg agaccgtaaa tttcagatca    3360
gcacattcgc aacaaagctt ggtgtgagaa acatcgcgta tcttggatct ggactattat    3420
tattaaacta cattggggca attgcggcgg ccatttatat gcctcaggct tttaagagaa    3480
atttaatgct tcctatccac accatcttgg cgttgagcct tgtcttccag gcctgggtct    3540
tggaacaagc gaattacacc aaggaggcta ttgctgggtt ctatagattc atttggaatt    3600
tgttctatgt agaatacatt atattcccct ttatatagga tgggctgcag gaattcgata    3660
tcaagcttat cgataccgtc gacctcgagt catgtaatta gttatgtcac gcttacattc    3720
acgccctccc cccacatccg ctctaaccga aaggaagga gttagacaac ctgaagtcta    3780
ggtccctatt tatttttta tagttatgtt agtattaaga acgttattta tatttcaaat    3840 tttcttttt tttctgtaca gacgcgtgta cgcatgtaac attatactga aaaccttgct    3900
tgagaaggtt ttgggacgct cgaaggcttt aatttgcggc cggtacccag cttttgttcc    3960
ctttagtgag ggttaattcc gagcttggcg taatcatggt catagctgtt tcctgtgtga    4020
aattgttatc cgctcacaat tccacacaac ataggagccg gaagcataaa gtgtaaagcc    4080
tggggtgcct aatgagtgag gtaactcaca ttaattgcgt tgcgctcact gcccgctttc    4140
cagtcgggaa acctgtcgtg ccagctgcat taatgaatcg ccaacgcgc ggggagaggc    4200 ggtttgcgta ttgggcgctc ttccgcttcc tcgctcactg actcgctgcg ctcggtcgtt    4260
cggctgcggc gagcggtatc agctcactca aaggcggtaa tacggttatc cacagaatca    4320
ggggataacg caggaaagaa catgtgagca aaaggccagc aaaaggccag gaaccgtaaa    4380
aaggccgcgt tgctggcgtt tttccatagg ctccgccccc ctgacgagca tcacaaaaat    4440
cgacgctcaa gtcagaggtg gcgaaacccg acaggactat aaagatacca ggcgttcccc    4500
cctggaagct ccctcgtgcg ctctcctgtt ccgaccctgc cgcttaccgg atacctgtcc    4560
gcctttctcc cttcgggaag cgtggcgctt tctcaatgct cacgctgtag gtatctcagt    4620
tcggtgtagg tcgttcgctc caagctgggc tgtgtgcacg aaccccccgt tcagcccgac    4680
cgctgcgcct tatccggtaa ctatcgtctt gagtccaacc cggtaagaca cgacttatcg    4740
ccactggcag cagccactgg taacaggatt agcagagcga ggtatgtagg cggtgctaca    4800
```

-continued

```
gagttcttga agtggtggcc taactacggc tacactagaa ggacagtatt tggtatctgc    4860
gctctgctga agccagttac cttcggaaaa agagttggta gctcttgatc cggcaaacaa    4920
accaccgctg gtagcggtgg ttttttttgtt tgcaagcagc agattacgcg cagaaaaaaa    4980
ggatctcaag aagatccttt gatcttttct acggggtctg acgctcagtg gaacgaaaac    5040
tcacgttaag ggattttggt catgagatta tcaaaaagga tcttcaccta gatccttttta    5100
aattaaaaat gaagttttaa atcaatctaa agtatatatg agtaaacttg gtctgacagt    5160
taccaatgct taatcagtga ggcacctatc tcagcgatct gtctatttcg ttcatccata    5220
gttgcctgac tgcccgtcgt gtagataact acgatacggg agggcttacc atctggcccc    5280
agtgctgcaa tgataccgcg agacccacgc tcaccggctc cagatttatc agcaataaac    5340
cagccagccg gaagggccga gcgcagaagt ggtcctgcaa ctttatccgc ctccatccag    5400
tctattaatt gttgccggga agctagagta agtagttcgc cagttaatag tttgcgcaac    5460
gttgttgcca ttgctacagg catcgtggtg tcacgctcgt cgtttggtat ggcttcattc    5520
agctccggtt cccaacgatc aaggcgagtt acatgatccc ccatgttgtg aaaaaaagcg    5580
gttagctcct tcggtcctcc gatcgttgtc agaagtaagt tggccgcagt gttatcactc    5640
atggttatgg cagcactgca taattctctt actgtcatgc catccgtaag atgcttttct    5700
gtgactggtg agtactcaac caagtcattc tgagaatagt gtatgcggcg accgagttgc    5760
tcttgcccgg cgtcaatacg ggataatacc gcgccacata gcagaacttt aaaagtgctc    5820
atcattggaa aacgttcttc ggggcgaaaa ctctcaagga tcttaccgct gttgagatcc    5880
agttcgatgt aacccactcg tgcacccaac tgatcttcag catctttttac tttcaccagc    5940
gtttctgggt gagcaaaaac aggaaggcaa aatgccgcaa aaaagggaat aagggcgaca    6000
cggaaatgtt gaatactcat actcttcctt tttcaatatt attgaagcat ttatcagggt    6060
tattgtctca tgagcggata catatttgaa tgtatttaga aaaataaaca ataggggtt    6120
ccgcgcacat ttccccgaaa agtgccacct gacgtcaag aaaccattat tatcatgaca    6180
ttaacctata aaaataggcg tatcacgagg cccttttcgtc                        6220
```

<210> SEQ ID NO 58
<211> LENGTH: 6220
<212> TYPE: DNA
<213> ORGANISM: Artificial Sequence
<220> FEATURE:
<223> OTHER INFORMATION: Codon Optimized

<400> SEQUENCE: 58

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accacgcttt tcaattcaat tcatcatttt tttttttattc ttttttttga tttcggtttc    240
tttgaaattt ttttgattcg gtaatctccg aacagaagga agaacgaagg aaggagcaca    300
gacttagatt ggtatatata cgcatatgta gtgttgaaga acatgaaat tgcccagtat    360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga tttttccatg gagggcacag ttaagccgct aaaggcatta tccgccaagt    660
```

| | |
|---|---|
| acaatttttt actcttcgaa gacagaaaat ttgctgacat tggtaataca gtcaaattgc | 720 |
| agtactctgc gggtgtatac agaatagcag aatgggcaga cattacgaat gcacacggtg | 780 |
| tggtgggccc aggtattgtt agcggtttga agcaggcggc agaagaagta acaaaggaac | 840 |
| ctagaggcct tttgatgtta gcagaattgt catgcaaggg ctccctatct actggagaat | 900 |
| atactaaggg tactgttgac attgcgaaga gcgacaaaga ttttgttatc ggctttattg | 960 |
| ctcaaagaga catgggtgga agagatgaag gttacgattg gttgattatg cacccggtg | 1020 |
| tgggtttaga tgacaaggga gacgcattgg gtcaacagta tagaaccgtg gatgatgtgg | 1080 |
| tctctacagg atctgacatt attattgttg gaagaggact atttgcaaag ggaagggatg | 1140 |
| ctaaggtaga gggtgaacgt tacagaaaag caggctggga agcatatttg agaagatgcg | 1200 |
| gccagcaaaa ctaaaaaact gtattataag taaatgcatg tatactaaac tcacaaatta | 1260 |
| gagcttcaat ttaattatat cagttattac cctgcggtgt gaaataccgc acagatgcgt | 1320 |
| aaggagaaaa taccgcatca ggaaattgta aacgttaata ttttgttaaa attcgcgtta | 1380 |
| aattttttgtt aaatcagctc atttttaac caataggccg aaatcggcaa atcccttat | 1440 |
| aaatcaaaag aatagaccga gatagggttg agtgttgttc cagtttggaa caagagtcca | 1500 |
| ctattaaaga acgtggactc caacgtcaaa gggcgaaaaa ccgtctatca gggcgatggc | 1560 |
| ccactacgtg aaccatcacc ctaatcaagt tttttgggt cgaggtgccg taaagcacta | 1620 |
| aatcggaacc ctaaagggag cccccgattt agagcttgac ggggaaagcc ggcgaacgtg | 1680 |
| gcgagaaagg aagggaagaa agcgaaagga gcgggcgcta gggcgctggc aagtgtagcg | 1740 |
| gtcacgctgc gcgtaaccac cacacccgcc gcgcttaatg cgccgctaca gggcgcgtcg | 1800 |
| cgccattcgc cattcaggct gcgcaactgt tgggaagggc gatcggtgcg ggcctcttcg | 1860 |
| ctattacgcc agctggcgaa ggggggatgt gctgcaaggc gattaagttg ggtaacgcca | 1920 |
| gggtttttccc agtcacgacg ttgtaaaacg acggccagtg aattgtaata cgactcacta | 1980 |
| tagggcgaat tggagctcta gtacggatta gaagccgccg agcgggcgac agccctccga | 2040 |
| cggaagactc tcctccgtgc gtcctcgtct tcaccggtcg cgttcctgaa acgcagatgt | 2100 |
| gcctcgcgcc gcactgctcc gaacaataaa gattctacaa tactagcttt tatggttatg | 2160 |
| aagaggaaaa attggcagta acctggcccc acaaaccttc aaattaacga atcaaattaa | 2220 |
| caaccatagg atgataatgc gattagtttt ttagccttat ttctggggta attaatcagc | 2280 |
| gaagcgatga ttttttgatct attaacagat atataaatgg aaaagctgca taaccacttt | 2340 |
| aactaatact ttcaacattt tcagtttgta ttacttctta ttcaaatgtc ataaaagtat | 2400 |
| caacaaaaaa ttgttaatat acctctatac tttaacgtca aggagaaaaa accccggatt | 2460 |
| ctagaactag tggatccccc atcatggaat tatcattatc tctgggcggg ccgacgatat | 2520 |
| tcccccagata tagagcaagc tatacttcca ctaaactgac cactcatttc tctaatttc | 2580 |
| cgtccaaatt cagcacaaaa aatttccacc agacgctatc tttctacgga ccaacgagag | 2640 |
| gcagcaaatc attgttgaat acccatcagt ggaggaactc cataagagcc tgcgccgagg | 2700 |
| cgggggctgc cgggtcaaac ccggtgctaa acaaggtctc tgactttagg gacgcatgct | 2760 |
| ggcgtttctt aaggccgcat actataaggg ggaccaccct gggtagtata gccctagtag | 2820 |
| caagggcgct tatagaaaat cccaacttaa tcaagtggag tcttttactg aaggctttct | 2880 |
| ctggcttact agccttaatt tgcgggaacg gctacattgt aggaatcaac caaatctatg | 2940 |
| acataggtat tgataaggtc aacaaaccgt accttcccat agccgcgggt gatttgtcag | 3000 |

```
tccagagtgc ttggtacctt gtaatattgt ttgccgttgc gggtctacta actgttggct    3060
tcaattttgg gccgttcatt acgtctctat actgcttagg acttgttctg gggacaatat    3120
atagcgttcc acccttttagg atgaaaagat ttccggttgc agcattctta atcattgcga   3180
ccgtgagggg ttttctatta aactttggtg tatactacgc cacaagagct gcattgggct    3240
taacctttga atggagtagt gcggttgcgt tcattacgac cttcgttaca ttattcgctt    3300
tggtgatagc tataacgaaa gatctgccag acgtggaggg agaccgtaaa tttcagatca    3360
gcacattcgc aacaaagctt ggtgtgagaa acatcgcgta tcttggatct ggactattat    3420
tattaaacta cattggggca attgcggcgg ccatttatat gcctcaggct tttaagagaa    3480
atttaatgct tcctatccac accatcttgg cgttgagcct tgtcttccag gcctgggtct    3540
tggaacaagc gaattacacc aaggaggcta ttgctgggtt ctatagattc atttggaatt    3600
tgttctatgt agaatacatt atattcccct ttatatagga tgggctgcag gaattcgata    3660
tcaagcttat cgataccgtc gacctcgagt catgtaatta gttatgtcac gcttacattc    3720
acgccctccc cccacatccg ctctaaccga aaaggaagga gttagacaac ctgaagtcta    3780
ggtccctatt tatttttttta tagttatgtt agtattaaga acgttattta tatttcaaat    3840
ttttcttttt tttctgtaca gacgcgtgta cgcatgtaac attatactga aaaccttgct    3900
tgagaaggtt ttgggacgct cgaaggcttt aatttgcggc cggtacccag cttttgttcc    3960
ctttagtgag ggttaattcc gagcttggcg taatcatggt catagctgtt tcctgtgtga    4020
aattgttatc cgctcacaat tccacacaac ataggagccg aagcataaa gtgtaaagcc    4080
tggggtgcct aatgagtgag gtaactcaca ttaattgcgt tgcgctcact gcccgctttc    4140
cagtcgggaa acctgtcgtg ccagctgcat taatgaatcg gccaacgcgc ggggagaggc    4200
ggtttgcgta ttgggcgctc ttccgcttcc tcgctcactg actcgctgcg ctcggtcgtt    4260
cggctgcggc gagcggtatc agctcactca aaggcggtaa tacggttatc cacagaatca    4320
ggggataacg caggaaagaa catgtgagca aaaggccagc aaaaggccag gaaccgtaaa    4380
aaggccgcgt tgctggcgtt tttccatagg ctcggccccc ctgacgagca tcacaaaaat    4440
cgacgctcaa gtcagaggtg gcgaaacccg acaggactat aaagatacca ggcgttcccc    4500
cctggaagct ccctcgtgcg ctctcctgtt ccgaccctgc cgcttaccgg atacctgtcc    4560
gcctttctcc cttcgggaag cgtggcgctt tctcaatgct cacgctgtag gtatctcagt    4620
tcggtgtagg tcgttcgctc caagctgggc tgtgtgcacg aaccccccgt tcagcccgac    4680
cgctgcgcct tatccggtaa ctatcgtctt gagtccaacc cggtaagaca cgacttatcg    4740
ccactggcag cagccactgg taacaggatt agcagagcga ggtatgtagg cggtgctaca    4800
gagttcttga agtggtggcc taactacggc tacactagaa ggacagtatt tggtatctgc    4860
gctctgctga agccagttac cttcggaaaa agagttggta gctcttgatc cggcaaacaa    4920
accaccgctg gtagcggtgg ttttttttgtt tgcaagcagc agattacgcg cagaaaaaaa    4980
ggatctcaag aagatccttt gatctttttct acggggtctg acgctcagtg gaacgaaaac    5040
tcacgttaag ggattttggt catgagatta tcaaaaagga tcttcaccta gatccttta    5100
aattaaaaat gaagttttaa atcaatctaa agtatatatg agtaaacttg gtctgacagt    5160
taccaatgct taatcagtga ggcacctatc tcagcgatct gtctatttcg ttcatccata    5220
gttgcctgac tgcccgtcgt gtagataact acgatacggg agggcttacc atctggcccc    5280
agtgctgcaa tgataccgcg agacccacgc tcaccggctc cagatttatc agcaataaac    5340
cagccagccg gaagggccga gcgcagaagt ggtcctgcaa ctttatccgc ctccatccag    5400
```

```
tctattaatt gttgccggga agctagagta agtagttcgc cagttaatag tttgcgcaac    5460
gttgttgcca ttgctacagg catcgtggtg tcacgctcgt cgtttggtat ggcttcattc    5520
agctccggtt cccaacgatc aaggcgagtt acatgatccc ccatgttgtg aaaaaaagcg    5580
gttagctcct tcggtcctcc gatcgttgtc agaagtaagt tggccgcagt gttatcactc    5640
atggttatgg cagcactgca taattctctt actgtcatgc catccgtaag atgcttttct    5700
gtgactggtg agtactcaac caagtcattc tgagaatagt gtatgcggcg accgagttgc    5760
tcttgcccgg cgtcaatacg ggataatacc gcgccacata gcagaacttt aaaagtgctc    5820
atcattggaa aacgttcttc ggggcgaaaa ctctcaagga tcttaccgct gttgagatcc    5880
agttcgatgt aacccactcg tgcacccaac tgatcttcag catcttttac tttcaccagc    5940
gtttctgggt gagcaaaaac aggaaggcaa aatgccgcaa aaaagggaat aagggcgaca    6000
cggaaatgtt gaatactcat actcttcctt tttcaatatt attgaagcat ttatcagggt    6060
tattgtctca tgagcggata catatttgaa tgtatttaga aaaataaaca aataggggtt    6120
ccgcgcacat ttccccgaaa agtgccacct gacgtctaag aaaccattat tatcatgaca    6180
ttaacctata aaataggcg tatcacgagg ccctttcgtc                          6220
```

<210> SEQ ID NO 59
<211> LENGTH: 6061
<212> TYPE: DNA
<213> ORGANISM: Artificial Sequence
<220> FEATURE:
<223> OTHER INFORMATION: Codon Optimized

<400> SEQUENCE: 59

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc    180
accacgcttt tcaattcaat tcatcatttt ttttttattc tttttttttga tttcggtttc    240 tttgaaattt ttttgattcg gtaatctccg aacagaagga agaacgaagg aaggagcaca    300
gacttagatt ggtatatata cgcatatgta gtgttgaaga acatgaaat tgcccagtat     360 tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttttccatg gagggcacag ttaagccgct aaaggcatta tccgccaagt    660 acaattttt actcttcgaa gacagaaaat ttgctgacat tggtaataca gtcaaattgc     720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta taggaaccgtg gatgatgtgg   1080 tctctacagg atctgacatt attattgttg gaagaggact atttgcaaag ggaagggatg   1140
ctaaggtaga gggtgaacgt tacagaaaag caggctggga agcatatttg agaagatgcg   1200
```

```
gccagcaaaa ctaaaaaact gtattataag taaatgcatg tatactaaac tcacaaatta    1260
gagcttcaat ttaattatat cagttattac cctgcggtgt gaaataccgc acagatgcgt    1320
aaggagaaaa taccgcatca ggaaattgta aacgttaata ttttgttaaa attcgcgtta    1380 aattttttgtt aaatcagctc atttttttaac caataggccg aaatcggcaa aatcccttat   1440
aaatcaaaag aatagaccga gatagggttg agtgttgttc cagtttggaa caagagtcca    1500
ctattaaaga acgtggactc caacgtcaaa gggcgaaaaa ccgtctatca gggcgatggc    1560
ccactacgtg aaccatcacc ctaatcaagt tttttgggt cgaggtgccg taaagcacta    1620
aatcggaacc ctaaagggag cccccgattt agagcttgac ggggaaagcc ggcgaacgtg    1680
gcgagaaagg aagggaagaa agcgaaagga gcgggcgcta gggcgctggc aagtgtagcg    1740
gtcacgctgc gcgtaaccac cacacccgcc gcgcttaatg cgccgctaca gggcgcgtcg    1800
cgccattcgc cattcaggct gcgcaactgt tgggaagggc gatcggtgcg ggcctcttcg    1860
ctattacgcc agctggcgaa ggggggatgt gctgcaaggc gattaagttg ggtaacgcca    1920
gggttttccc agtcacgacg ttgtaaaacg acggccagtg aattgtaata cgactcacta    1980
tagggcgaat tggagctcta gtacggatta gaagccgccg agcgggcgac agccctccga    2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga ttttgatct attaacagat atataaatgg aaaagctgca taaccacttt    2340
aactaatact ttcaacattt tcagtttgta ttacttctta ttcaaatgtc ataaagtat    2400 caacaaaaaa ttgttaatat acctctatac tttaacgtca aggagaaaaa accccggatt    2460
ctagaactag tggatccccc atcatgagat tccatctat tttcactgct gttttgttcg    2520
ctgcttcttc tgctttggct gctccagttg ccgggtcaaa cccggtgcta acaaggtct    2580 ctgactttag ggacgcatgc tggcgttttct taaggccgca tactataagg gggaccaccc    2640
tgggtagtat agccctagta gcaagggcgc ttatagaaaa tcccaactta atcaagtgga    2700
gtcttttact gaaggctttc tctggcttac tagccttaat ttgcgggaac ggctacattg    2760
taggaatcaa ccaaatctat gacataggta ttgataaggt caacaaaccg taccttccca    2820
tagccgcggg tgatttgtca gtccagagtg cttggtacct tgtaatattg tttgccgttg    2880
cgggtctact aactgttggc ttcaattttg ggccgttcat tacgtctcta tactgcttag    2940
gacttgttct ggggacaata tatagcgttc cacccttag gatgaaaaga tttccggttg    3000
cagcattctt aatcattgcg accgtgaggg gttttctatt aaactttggt gtatactacg    3060
ccacaagagc tgcattgggc ttaacctttg aatggagtag tgcggttgcg ttcattacga    3120
ccttcgttac attattcgct ttggtgatag ctataacgaa agatctgcca gacgtggagg    3180
gagaccgtaa atttcagatc agcacattcg caacaaagct tggtgtgaga acatcgcgt    3240 atcttggatc tggactatta ttattaaact acattgggc aattgcggcg gccatttata    3300
tgcctcaggc ttttaagaga aatttaatgc ttcctatcca caccatcttg gcgttgagcc    3360
ttgtcttcca ggcctgggtc ttggaacaag cgaattacac caaggaggct attgctgggt    3420
tctatagatt catttggaat ttgttctatg tagaatacat tatattcccc tttatatagg    3480
atgggctgca ggaattcgat atcaagctta tcgataccgt cgacctcgag tcatgtaatt    3540
agttatgtca cgcttacatt cacgccctcc ccccacatcc gctctaaccg aaaaggaagg    3600
```

```
agttagacaa cctgaagtct aggtccctat ttatttttt atagttatgt tagtattaag    3660
aacgttattt atatttcaaa tttttctttt ttttctgtac agacgcgtgt acgcatgtaa    3720
cattatactg aaaaccttgc ttgagaaggt tttgggacgc tcgaaggctt taatttgcgg    3780
ccggtaccca gcttttgttc cctttagtga gggttaattc cgagcttggc gtaatcatgg    3840
tcatagctgt ttcctgtgtg aaattgttat ccgctcacaa ttccacacaa cataggagcc    3900
ggaagcataa agtgtaaagc ctggggtgcc taatgagtga gtaactcac attaattgcg    3960 ttgcgctcac tgcccgcttt ccagtcggga aacctgtcgt gccagctgca ttaatgaatc    4020
ggccaacgcg cggggagagg cggtttgcgt attgggcgct cttccgcttc ctcgctcact    4080
gactcgctgc gctcggtcgt tcggctgcgg cgagcggtat cagctcactc aaaggcggta    4140
atacggttat ccacagaatc aggggataac gcaggaaaga acatgtgagc aaaaggccag    4200
caaaaggcca ggaaccgtaa aaaggccgcg ttgctggcgt ttttccatag gctcggcccc    4260
cctgacgagc atcacaaaaa tcgacgctca agtcagaggt ggcgaaaccc gacaggacta    4320
taaagatacc aggcgttccc ccctggaagc tccctcgtgc gctctcctgt tccgaccctg    4380
ccgcttaccg gatacctgtc cgcctttctc ccttcgggaa gcgtggcgct ttctcaatgc    4440
tcacgctgta ggtatctcag ttcggtgtag tcgttcgct ccaagctggg ctgtgtgcac    4500
gaaccccccg ttcagcccga ccgctgcgcc ttatccggta actatcgtct tgagtccaac    4560
ccggtaagac acgacttatc gccactggca gcagccactg gtaacaggat tagcagagcg    4620
aggtatgtag gcggtgctac agagttcttg aagtggtggc ctaactacgg ctacactaga    4680
aggacagtat ttggtatctg cgctctgctg aagccagtta ccttcggaaa aagagttggt    4740
agctcttgat ccggcaaaca aaccaccgct ggtagcggtg gtttttttgt ttgcaagcag    4800
cagattacgc gcagaaaaaa aggatctcaa gaagatcctt tgatctttc tacgggtct    4860 gacgctcagt ggaacgaaaa ctcacgttaa gggattttgg tcatgagatt atcaaaaagg    4920
atcttcacct agatcctttt aaattaaaaa tgaagtttta atcaatcta agtatatat    4980 gagtaaactt ggtctgacag ttaccaatgc ttaatcagtg aggcacctat ctcagcgatc    5040
tgtctatttc gttcatccat agttgcctga ctgcccgtcg tgtagataac tacgatacgg    5100
gagggcttac catctggccc cagtgctgca atgataccgc gagacccacg ctcaccggct    5160
ccagatttat cagcaataaa ccagccagcc ggaagggccg agcgcagaag tggtcctgca    5220
actttatccg cctccatcca gtctattaat tgttgccggg aagctagagt aagtagttcg    5280
ccagttaata gtttgcgcaa cgttgttgcc attgctacag gcatcgtggt gtcacgctcg    5340
tcgtttggta tggcttcatt cagctccggt tcccaacgat caaggcgagt tacatgatcc    5400
cccatgttgt gaaaaaaagc ggttagctcc ttcggtcctc cgatcgttgt cagaagtaag    5460
ttggccgcag tgttatcact catggttatg gcagcactgc ataattctct tactgtcatg    5520
ccatccgtaa gatgcttttc tgtgactggt gagtactcaa ccaagtcatt ctgagaatag    5580
tgtatgcggc gaccgagttg ctcttgcccg gcgtcaatac gggataatac cgcgccacat    5640
agcagaactt taaaagtgct catcattgga aaacgttctt cggggcgaaa actctcaagg    5700
atcttaccgc tgttgagatc cagttcgatg taacccactc gtgcacccaa ctgatcttca    5760
gcatctttta ctttcaccag cgtttctggg tgagcaaaaa caggaaggca aaatgccgca    5820
aaaaagggaa taagggcgac acggaaatgt tgaatactca tactcttcct ttttcaatat    5880
tattgaagca tttatcaggg ttattgtctc atgagcggat acatatttga atgtatttag    5940
```

| | |
|---|---|
| aaaaataaac aaatagggt tccgcgcaca tttccccgaa aagtgccacc tgacgtctaa | 6000 |
| gaaaccatta ttatcatgac attaacctat aaaaataggc gtatcacgag gcccttcgt | 6060 |
| c | 6061 |

<210> SEQ ID NO 60
<211> LENGTH: 1161
<212> TYPE: DNA
<213> ORGANISM: Artificial Sequence
<220> FEATURE:
<223> OTHER INFORMATION: Codon Optimized

<400> SEQUENCE: 60

| | |
|---|---|
| atgaatcatt tgagagctga aggtccagct tctgttttgg ctattggtac tgctaatcca | 60 |
| gaaaatattt tgattcaaga tgaatttcca gattattatt ttagagttac taaatctgaa | 120 |
| catatgactc aattgaaaga aaaatttaga aaaatttgtg ataaatctat gattagaaaa | 180 |
| agaaattgtt ttttgaatga agaacatttg aaacaaaatc caagattggt tgaacatgaa | 240 |
| atgcaaactt tggatgctag acaagatatg ttggttgttg aagttccaaa attgggtaaa | 300 |
| gatgcttgtg ctaaagctat taagaatgg ggtcaaccaa aatctaaaat tactcatttg | 360 |
| attttactt ctgcttctac tactgatatg ccaggtgctg attatcattg tgctaaattg | 420 |
| ttgggtttgt ctccatctgt taaaagagtt atgatgtatc aattgggttg ttatggtggt | 480 |
| ggtactgttt tgagaattgc taaagatatt gctgaaaata taaaggtgc tagagttttg | 540 |
| gctgtttgtt gtgatattat ggcttgtttg tttagaggtc catctgattc tgatttggaa | 600 |
| gcttctttgt tggttggtca agctatttt ggtgatggtc tgctgctgt tattgttggt | 660 |
| gctgaaccag atgaatctgt tggtgaaaga ccaattttg aattggttc tactggtcaa | 720 |
| actatttgc caaattctga aggtactatt ggtggtcata ttagagaagc tggttttgatt | 780 |
| tttgatttgc ataaagatgt tccaatgttg atttctaata atattgaaaa atgtttgatt | 840 |
| gaagctttta ctccaattgg tatttctgat tggaattcta tttttttgat tactcatcca | 900 |
| ggtggtaaag ctatttgga taaagttgaa gaaaaattgg atttgaaaaa agaaaaattt | 960 |
| gttgattcta gacatgtttt gtctgaacat ggtaatatgt cttcttctac tgttttgttt | 1020 |
| gttatggatg aattgagaaa aagatctttg gaagaaggta atctactac tggtgatggt | 1080 |
| tttgaatggg gtgttttgtt tggttttggt ccaggtttga ctgttgaaag agttgttgtt | 1140 |
| agatctgttc aattaaaata t | 1161 |

<210> SEQ ID NO 61
<211> LENGTH: 1155
<212> TYPE: DNA
<213> ORGANISM: Artificial Sequence
<220> FEATURE:
<223> OTHER INFORMATION: Codon Optimized

<400> SEQUENCE: 61

| | |
|---|---|
| atgaatcatt tgagagctga aggtccagct tctgttttgg ctattggtac tgctaatcca | 60 |
| gaaaatattt tgattcaaga tgaatttcca gattattatt ttagagttac taaatctgaa | 120 |
| catatgactc aattgaaaga aaaatttaga aaaatttgtg ataaatctat gattagaaaa | 180 |
| agaaattgtt ttttgaatga agaacatttg aaacaaaatc caagattggt tgaacatgaa | 240 |
| atgcaaactt tggatgctag acaagatatg ttggttgttg aagttccaaa attgggtaaa | 300 |
| gatgcttgtg ctaaagctat taagaatgg ggtcaaccaa aatctaaaat tactcatttg | 360 |
| attttactt ctgcttctac tactgatatg ccaggtgctg attatcattg tgctaaattg | 420 |

```
ttgggtttgt ctccatctgt taaaagagtt atgatgtatc aattgggttg ttatggtggt    480
ggtactgttt tgagaattgc taaagatatt gctgaaaata ataaaggtgc tagagttttg    540
gctgtttgtt gtgatattat ggcttgtttg tttagaggtc catctgattc tgatttggaa    600
ttgttggttg gtcaagctat ttttggtgat ggtgctgctg ctgttattgt tggtgctgaa    660
ccagatgaat ctgttggtga agaccaatt tttgaattgg tttctactgg tcaaactatt     720
ttgccaaatt ctgaaggtac tattggtggt catattagag aagctggttt gattttgat    780 ttgcataaag atgttccaat gttgatttct aataatattg aaaaatgttt gattgaagct    840
tttactccaa ttggtatttc tgattggaat tctattttt ggattactca tccaggtggt    900
aaagctattt tggataaagt tgaagaaaaa ttgcatttga atctgataa atttgttgat     960 tctagacatg ttttgtctga acatggtaat atgtcttctt ctactgtttt gtttgttatg   1020
gatgaattga gaaaaagatc tttggaagaa ggtaaatcta ctactggtga tggttttgaa   1080
tggggtgttt tgtttggttt tggtccaggt ttgactgttg aaagagttgt tgttagatct   1140
gttccaatta aatat                                                    1155

<210> SEQ ID NO 62
<211> LENGTH: 1155
<212> TYPE: DNA
<213> ORGANISM: Artificial Sequence
<220> FEATURE:
<223> OTHER INFORMATION: Codon Optimized

<400> SEQUENCE: 62
atgaatcatt tgagagctga aggtccagct tctgttttgg ctattggtac tgctaatcca     60
gaaaatattt tgattcaaga tgaatttcca gattattatt ttagagttac taaatctgaa    120
catatgactc aattgaaaga aaatttaga aaaatttgtg ataaatctat gattagaaaa    180
agaaattgtt ttttgaatga agaacatttg aaacaaaatc caagattggt tgaacatgaa    240
atgcaaactt ggatgctag acaagatatg ttggttgttg aagttccaaa attgggtaaa    300
gatgcttgtg ctaaagctat taagaatgg ggtcaaccaa atctaaaat tactcatttg    360 attttactt ctgcttctac tactgatatg ccaggtgctg attatcattg tgctaaattg    420
ttgggtttgt ctccatctgt taaaagagtt atgatgtatc aattgggttg ttatggtggt    480
ggtactgttt tgagaattgc taaagatatt gctgaaaata ataaaggtgc tagagttttg    540
gctgtttgtt gtgatattat ggcttgtttg tttagaggtc catctgattc tgatttggaa    600
ttgttggttg gtcaagctat ttttggtgat ggtgctgctg ctgttattgt tggtgctgaa    660
ccagatgaat ctgttggtga agaccaatt tttgaattgg tttctactgg tcaaactatt     720
ttgccaaatt ctgaaggtac tattggtggt catattagag aagctggttt gattttgat    780 ttgcataaag atgttccaat gttgatttct aataatattg aaaaatgttt gattgaagct    840
tttactccaa ttggtatttc tgattggaat tctattttt ggattactca tccaggtggt    900
aaagctattt tggataaagt tgaagaaaaa ttgcatttga aaaagaaaa atttgttgat     960 tctagacatg ttttgtctga acatggtaat atgtcttctt ctactgtttt gtttgttatg   1020
gatgaattga gaaaaagatc tttggaagaa ggtaaatcta ctactggtga tggttttgaa   1080
tggggtgttt tgtttggttt tggtccaggt ttgactgttg aaactgttgt tttgagatct   1140
gttccaatta attat                                                    1155

<210> SEQ ID NO 63
```

```
<211> LENGTH: 1155
<212> TYPE: DNA
<213> ORGANISM: Artificial Sequence
<220> FEATURE:
<223> OTHER INFORMATION: Codon Optimized

<400> SEQUENCE: 63
atgaatcatt tgagagctga aggtccagct tctgttttgg ctattggtac tgctaatcca      60
gaaaatattt tgttgcaaga tgaatttcca gattattatt ttagagttac taaatctgaa     120
catatgactc aattgaaaga aaaatttaga aaaatttgtg ataaatctat gattagaaaa     180
agaaattgtt ttttgaatga agaacatttg aaacaaaatc caagattggt tgaacatgaa     240
atgcaaactt tggatgctag acaagatatg ttggttgttg aagttccaaa attgggtaaa     300
gatgcttgtg ctaaagctat taagaatgg ggtcaaccaa atctaaaat tactcatttg      360
attttactt ctgcttctac tactgatatg ccaggtgctg attatcattg tgctaaattg     420
ttgggtttgt ctccatctgt taaaagagtt atgatgtatc aattgggttg ttatggtggt     480
ggtactgttt tgagaattgc taaagatatt gctgaaaata taaaggtgc tagagttttg      540
gctgtttgtt gtgatattat ggcttgtttg tttagaggtc catctgaatc tgatttggaa     600
ttgttggttg gtcaagctat ttttggtgat ggtgctgctg ctgttattgt tggtgctgaa     660
ccagatgaat ctgttggtga agaccaatt tttgaattgg tttctactgg tcaaactatt      720
ttgccaaatt ctgaaggtac tattggtggt catattagag aagctggttt gatttttgat     780
ttgcataaag atgttccaat gttgatttct aataatattg aaaaatgttt gattgaagct     840
tttactccaa ttggtatttc tgattggaat tctatttttt ggattactca tccaggtggt     900
aaagctattt tggataaagt tgaagaaaaa ttgcatttga atctgataa atttgttgat      960
tctagacatg ttttgtctga acatggtaat atgtcttctt ctactgtttt gtttgttatg    1020
gatgaattga gaaaagatc tttggaagaa ggtaaatcta ctactggtga tggttttgaa     1080
tggggtgttt gtttggttt tggtccaggt ttgactgttg aaagagttgt tgttagatct    1140
gttccaatta aatat                                                     1155

<210> SEQ ID NO 64
<211> LENGTH: 1155
<212> TYPE: DNA
<213> ORGANISM: Artificial Sequence
<220> FEATURE:
<223> OTHER INFORMATION: Codon Optimized

<400> SEQUENCE: 64
atgaatcatt tgagagctga aggtccagct tctgttttgg ctattggtac tgctaatcca      60
gaaaatattt tgattcaaga tgaatttcca gattattatt ttagagttac taaatctgaa     120
catatgactc aattgaaaga aaaatttaga aaaatttgtg ataaatctat gattagaaaa     180
agaaatattt ttttgaatga agaacatttg aaacaaaatc caaaattggt tgaacatgat     240
gttcaaactt tggatgctag acaagatatg ttggttgttg aagttccaaa attgggtaaa     300
gatgcttgtg ctaaagctat taagaatgg ggtcaaccaa atctaaaat tactcatttg      360
attttactt ctgcttctac tactgatatg ccaggtgctg attatcattg tgctaaattg     420
ttgggtttgt ctccatctgt taaaagagtt atgatgtatc aattgggttg ttatggtggt     480
ggtactgttt tgagaattgc taaagatatt gctgaaaata taaaggtgc tagagttttg      540
gctgtttgtt gtgatattat ggcttgtttg tttagaggtc catctgattc tgatttggaa     600
ttgttggttg gtcaagctat ttttggtgat ggtgctgctg ctgttattgt tggtgctgaa     660
```

```
ccagatgaat ctgttggtga aagaccaatt tttgaattgg tttctactgg tcaaactatt      720
ttgccaaatt ctgaaggtac tattggtggt catattagaa agctggtttt gattttgat       780 ttgcataaag atgttccaat gttgatttct aataatattg aaaaatgttt gattgaagct      840
tttactccaa ttggtatttc tgattggaat tctattttt ggattactca tccaggtggt       900
aaagctattt tggataaagt tgaagaaaaa ttgcatttga atctgataa atttgttgat       960 tctagacatg ttttgtctga acatggtaat atgtcttctt ctactgtttt gtttgttatg     1020
gatgaattga aaaaagatc tttggaagaa ggtaaatcta ctactggtga tggttttgaa      1080
tggggtgttt tgtttggttt tggtccaggt ttgactgttg aaagagttgt tgttagatct     1140
gttccaatta aatat                                                     1155
```

<210> SEQ ID NO 65
<211> LENGTH: 1155
<212> TYPE: DNA
<213> ORGANISM: Artificial Sequence
<220> FEATURE:
<223> OTHER INFORMATION: Codon Optimized

<400> SEQUENCE: 65

```
atgaatcatt tgagagctga aggtccagct tctgttttgg ctattggtac tgctaatcca       60
gaaaatattt tgattcaaga tgaatttcca gattatatt ttagagttac taaatctgaa       120
catatgactc aattgaaaga aaaatttaga aaaatttgtg ataaatctat gattagaaaa      180
agaaattgtt ttttgaatga agaacatttg aaacaaaatc caagattggt tgaacatgaa      240
atgcaaactt tggatgctag acaagatatg ttggttgttg aagttccaaa attgggtaaa      300
gatgcttgtg ctaaagctat taagaatggg ggtcaaccaa atctaaaat tactcatttg      360 attttactt ctgcttctac tactgatatg ccaggtgctg attatcattg tgctaaattg       420
ttgggtttgt ctccatctgt taaaagagtt atgatgtatc aattgggttg ttatggtggt      480
ggtactgttt tgagaattgc taaagatatt gctgaaaata taaaggtgc tagagttttg      540 gctgtttgtt gtgatatgac tgcttgtttg tttagaggtc catctgattc taatttggaa      600
ttgttggttg gtcaagctat tttggtgat ggtgctgctg ctgttattgt tggtgctgaa       660
ccagatgaat ctgttggtga aagaccaatt tttgaattgg tttctactgg tcaaactttt      720
ttgccaaatt ctgaaggtac tattggtggt catattagag agctggtttt gatgtttgat     780
ttgcataaag atgttccaat gttgatttct aataatattg aaaaatgttt gattgaagct      840
tttactccaa ttggtatttc tgattggaat tctattttt ggattactca tccaggtggt       900
aaagctattt tggataaagt tgaagaaaaa ttgcatttga atctgataa atttgttgat       960 tctagacatg ttttgtctga acatggtaat atgtcttctt ctactgtttt gtttgttatg     1020
gatgaattga aaaaagatc tttggaagaa ggtaaatcta ctactggtga tggttttgaa      1080
tggggtgttt tgtttggttt tggtccaggt ttgactgttg aaagagttgt tttgagatct     1140
gttccaatta attat                                                     1155
```

<210> SEQ ID NO 66
<211> LENGTH: 1173
<212> TYPE: DNA
<213> ORGANISM: Artificial Sequence
<220> FEATURE:
<223> OTHER INFORMATION: Codon Optimized

<400> SEQUENCE: 66

| | |
|---|---|
| atggaagaaa ttaaaggtgt tttgaaagct aaagatgttg gttgtgttgc tactattttg | 60 |
| gctattggta ctgctaatcc attgaattgt gttaatcaag atgaattttt gcattcttat | 120 |
| tttaaattga ctaataatca taataatact tcttttaaag aattgtttac tagaatttgt | 180 |
| aataattcta tgattaaaaa tagatatatg catttgactg aagatatttt gaaagaaaat | 240 |
| ccaaatttgt gtgattatgc tgctcaatct ttgaatacta gacaagatat taaaattaaa | 300 |
| gaaattccaa aattggctga agagctgct atggttgcta ttaaagaatg ggtaaaacca | 360 |
| atttctaatt tgactcatat tatttttcat tcttctactg gtgctgctga tatgccaggt | 420 |
| gctgattatc aattggttaa atctttgggt ttgaatagat ctattaaaag aattatgttg | 480 |
| tataatttgg gttgttttgc tggtggtact gttttgagag ttgctaaaga tttggttgaa | 540 |
| aataatttgg gtgcttctgt tttggctgtt tgtgctgaaa ttacttctgc tgatgctact | 600 |
| tttggtagat tgtctgaaga tgataaaggt agattggttg gtcatgctat ttttggtgat | 660 |
| ggtgctgctg cttttggttat tggtaatgct gatgatccag aaaataaagg tttgtttcaa | 720 |
| attgtttcta cttctcaaac tatttttgcca aattctgaag gttgtattga aggtcatatt | 780 |
| agagaagatg gtgttacttt tactttgtct ccaagagttc aaaaattgat tggtgataat | 840 |
| attgaaactt gttgatggaa agcttttact ccatttaaaa tttctgattg gaattctttg | 900 |
| ttttgggttg ttcatccagg tggtgctgct attttgagag aagttgaatc tagagttggt | 960 |
| ttggaacaag aaaaattgag agcttcttgg catgttttga gagaatatgg taatatttct | 1020 |
| tctgcttctg ttttgtttat tttggatgaa atgagaaata atctttggaa agaaggtaga | 1080 |
| aaaactactg gtgaaggtaa aaattggggt gttttgtttg gttttggtcc aggtttgact | 1140 |
| gttgaaactg ttgttttgca ttctattcca att | 1173 |

<210> SEQ ID NO 67
<211> LENGTH: 1155
<212> TYPE: DNA
<213> ORGANISM: Artificial Sequence
<220> FEATURE:
<223> OTHER INFORMATION: Codon Optimized

<400> SEQUENCE: 67

| | |
|---|---|
| atgaatcatt tgagagctga aggtccagct tctgttttgg ctattggtac tgctaatcca | 60 |
| gaaaatattt tgattcaaga tgaatttcca gattattatt ttagagttac taaatctgaa | 120 |
| catatgactc aattgaaaga aaaatttaga aaaatttgtg ataaatctat gattagaaaa | 180 |
| agaaattgtt ttttgaatga agaacatttg aaacaaaatc caagattggt tgaacatgaa | 240 |
| atgcaaactt ggatgctag acaagatatg ttggttgttg aagttccaaa attgggtaaa | 300 |
| gatgcttgtg ctaaagctat taagaatggg ggtcaaccaa atctaaaat tactcatttg | 360 |
| atttttactt ctgcttctac tactgatatg ccaggtgctg attatcattg tgctaaattg | 420 |
| ttgggttttgt ctccatctgt taaaagagtt atgatgtatc aattgggttg ttatggtggt | 480 |
| ggtactgttt tgagaattgc taaagatatt gctgaaaata taaaggtgc tagagttttg | 540 |
| gctgtttgtt gtgatattat ggcttgtttg tttagaggtc catctgattc tgatttggaa | 600 |
| ttgttggttg gtcaagctat ttttggtgat ggtgctgctg ctgttattgt tggtgctgaa | 660 |
| ccagatgaat ctgttggtga agaccaattt ttgaattgg tttctactgg tcaaactatt | 720 |
| tgccaaattt ctgaaggtac tattggtggt catattagag aagctggttt gattttttgat | 780 |
| ttgcataaag atgttccaat gttgatttct aataatattg aaaaatgttt gattgaagct | 840 |
| tttactccaa ttggtatttc tgattggaat tctatttttt ggattactca tccaggtggt | 900 |

```
aaagctattt tggataaagt tgaagaaaaa ttgcatttga atctgataa atttgttgat    960 tctagacatg ttttgtctga acatggtaat atgtcttctt ctactgtttt gtttgttatg   1020
gatgaattga gaaaaagatc tttggaagaa ggtaaatcta ctactggtga tggttttgaa   1080
tggggtgttt tgtttggttt tggtccaggt ttgactgttg aaagagttgt tgttagatct   1140
gttccaatta aatat                                                    1155
```

<210> SEQ ID NO 68
<211> LENGTH: 1200
<212> TYPE: DNA
<213> ORGANISM: Artificial Sequence
<220> FEATURE:
<223> OTHER INFORMATION: Codon Optimized

<400> SEQUENCE: 68

```
atgaatcatt tgagagctga aggtccagct tctgttttgg ctattggtac tgctaatcca     60
gaaaatattt tgattcaaga tgaatttcca gattattatt ttagagttac taaatctgaa    120
catatgactc aattgaaaga aaaatttaga aaaattgtg ataaatctat gattagaaaa    180
agaaattgtt ttttgaatga gaacatttg aaacaaaatc caagattggt tgaacatgaa    240
atgcaaactt ggatgctag acaagatatg ttggttgttg aagttccaaa attgggtaaa    300
gatgcttgtg ctaaagctat taagaatgg ggtcaaccaa atctaaaat tactcatttg    360 attttactt ctgcttctac tactgatatg ccaggtgctg attatcattg tgctaaattg    420 ttgggttgt ctccatctgt taaagagtt atgatgtatc aattgggttg ttatggtggt    480
ggtactgttt tgagaattgc taaagatatt gctgaaaata taaaggtgc tagagttttg    540 gctgtttgtt gtgatattat ggcttgtttg tttagaggtc catctgattc tgatttggaa    600
ttgttggttg gtcaagctat tttggtgat ggtgctgctg ctgttattgt tggtgctgaa    660
ccagatgaat ctgttggtga agaccaatt tttgaattgg tttctactgg tcaaactatt    720
ttgccaaatt ctgaaggtac tattggtggt catattagag aagctggttt gatttttgat    780
ttgcataaag atgttccaat gttgatttct aataatattg aaaatgttt gattgaagct    840 tttactccaa ttggtatttc tgattggaat tctatttttt ggattactca tccaggtggt    900
aaagctattt tggataaagt tgaagaaaaa ttgcatttga atctgataa atttgttgat    960 tctagacatg ttttgtctga acatggtaat atgtcttctt ctactgtttt gtttgttatg   1020
gatgaattga gaaaaagatc tttggaagaa ggtaaatcta ctactggtga tggttttgaa   1080
tggggtgttt tgtttggttt tggtccaggt ttgactgttg aaagaggtag atggagaaaa   1140
ggtaatttgc cattggaaat ggatttgtct ggtgtttttt ttttgggttt ggatcaagtt   1200
```

<210> SEQ ID NO 69
<211> LENGTH: 1167
<212> TYPE: DNA
<213> ORGANISM: Artificial Sequence
<220> FEATURE:
<223> OTHER INFORMATION: Codon Optimized

<400> SEQUENCE: 69

```
atggttactg ttgaagaatt tagaaaagct caaagagctg aaggtccagc tactattatg     60
gctattggta ctgctactcc agctaattgt gttttgcaat ctgaatatcc agattattat    120
tttagaatta ctaattctga acataaaact gaattgaaag aaaaatttaa agaatgtgt    180 gataaatcta tgattagaaa aagatatatg catttgactg aagaattttt gaaagaaaat    240
```

```
ccaaatttgt gtgcttatga agctccatct ttggatgcta gacaagatat ggttgttgtt    300
gaagttccaa aattgggtaa agaagctgct actaaagcta ttaaagaatg gggtcaacca    360
aaatctaaaa ttactcattt ggttttttgt actacttctg tgttgatat gccaggtgct     420 gattatcaat tgactaaatt gttgggtttg agaccatctg ttaaaagatt gatgatgtat    480
caacaaggtt gttttgctgg tggtactgtt ttgagattgg ctaaagattt ggctgaaaat    540
aataaaggtg ctagagtttt ggttgttttgt tctgaaatta ctgctgttac ttttagaggt    600
ccaaatgata ctcatttgga ttctttggtt ggtcaagctt gtttggtga tggttctgct     660 gctttgattg ttggttctga tccaattcca gaagttgaaa aaccaatttt tgaattggtt    720
tctgctgctc aaactatttt gccagattct gatggtgcta ttgatggtca tttgagagaa    780 gttggttga cttttcattt gttgaaagat gttccaggtt tgatttctaa aaatattgaa     840
aaatctttga atgaagcttt taaaccattg ggtatttctg attggaattc tttgttttgg    900
attgctcatc caggtggtcc agctatttg gatcaagttg aatctaaatt ggctttgaaa    960
actgaaaaat tgagagctac tagacatgtt ttgtctgaat atggtaatat gtcttctgct   1020
tgtgttttgt ttatttttga tgaaatgaga agaaaatgtg ttgaagatgg tttgaatact   1080
actggtgaag gtttggaatg gggtgttttg tttggttttg gtccaggttt gactgttgaa   1140
actgttgttt tgcattctgt tgctatt                                       1167
```

<210> SEQ ID NO 70
<211> LENGTH: 573
<212> TYPE: DNA
<213> ORGANISM: Artificial Sequence
<220> FEATURE:
<223> OTHER INFORMATION: Codon Optimized

<400> SEQUENCE: 70

```
atgaatcatt tgagagctga aggtccagct tctgttttgg ctattggtac tgctaatcca    60
gaaaatattt tgattcaaga tgaatttcca gattattatt ttagagttac taaatctgaa   120
catatgactc aattgaaaga aaatttaga aaaatttgtg ataaatctat gattagaaaa    180
agaaattgtt ttttgaatga agaacatttg aaacaaaatc caagattggc tgaacatgaa   240
atgcaaactt tggatgctag acaagatatg ttggttgttg aagttccaaa attgggtaaa   300
gatgcttgtg ctaaagctat taagaatggg ggtcaaccaa atctaaaat tactcatttg    360 atttttactt ctgcttctac tactgatatg ccaggtgctg attatcattg tgctaaattg    420 ttgggttttgt ctccatctgt taaaagagtt atgatgtatc aattgggttg ttatggtggt    480
ggtactgttt tgagaattgc taaagatatt gctgaaaata taaaggtgc tagagttttg    540 gctgtttgtt gtgatattat ggcttttttt ttt                                573
```

<210> SEQ ID NO 71
<211> LENGTH: 597
<212> TYPE: DNA
<213> ORGANISM: Artificial Sequence
<220> FEATURE:
<223> OTHER INFORMATION: Codon Optimized

<400> SEQUENCE: 71

```
atggcttgtt tgtttagagg tccatctgaa tctgatttgg aattgttggt tggtcaagct    60
atttttggtg atggtgctgc tgctgttatt gttggtgctg aaccagatga atctgttggt   120
gaaagaccaa ttttgaatt ggtttctact ggtcaaacta ttttgccaaa ttctgaaggt    180
actattggtg gtcatattag agaagctggt ttgattttg atttgcataa agatgttcca    240
```

```
atgttgattt ctaataatat tgaaaaatgt tgattgaag ctttactcc aattggtatt      300 tctgattgga attctatttt ttggattact catccaggtg gtaaagctat tttggataaa    360
gttgaagaaa aattgcattt gaaatctgat aaatttgttg attctagaca tgttttgtct    420
gaacatggta atatgtcttc ttctactgtt ttgtttgtta tggatgaatt gagaaaaaga    480
tctttggaag aaggtaaatc tactactggt gatggttttg aatggggtgt tttgtttggt    540
tttggtccag gtttgactgt tgaaagagtt gttgttagat ctgttccaat taaatat       597
```

<210> SEQ ID NO 72
<211> LENGTH: 936
<212> TYPE: DNA
<213> ORGANISM: Artificial Sequence
<220> FEATURE:
<223> OTHER INFORMATION: Codon Optimized

<400> SEQUENCE: 72

```
atgaatttgg aaatattga taaagttaat tctccaggta ctgaagataa agatttgat     60 tctagagctt ctggttctaa aactaatggt tgtgaatctt ctgataatga agttgaatct    120
tctattaatg ctaatccaaa ttctatttct ggttcttctt ctggttttgg taatggtaaa    180
agagaaggtg ttaaaagagc tgctccaggt gatattgctc aacttctag acattataga    240 tctttgtcta tggattctta tatgggttct ttgcaatttg atgatgaatc tttgaaattg    300
ttgccattgg gtactggtgt tggtttgcaa tctccaaatt ctttggctga tggtaattct    360
actaaatttg gtatggaatt tccaaatggt gaatttaatg ctgttgaatt gaaaaaaatt    420
atggaatctg aaaaattgac tgaaattgct ttgtctgatc aaaaagagc taaaagaatt    480 ttggctaata dacaatctgc tgctagatct aaagaaagaa gatctagata tatttctgaa    540
ttggaacata aagttcaaac tttgcaaact gaagctacta cttgtctgc tcaagttact     600 aaattgcaaa gagattctgt tggttttgact tctcaaaatt ctgaattgaa atttagagtt    660
caagctatgg aacaacaagc tcaattgaaa gatgctttga tgatgctttg agagctgaa     720 gttcaaagat tgaaattgac tgctgctgaa ttgtctggtg aagctcatttt gtctaattgt    780 atggctcaac aattgtctat taatcaacaa atgtatcaaa tgcaacatag acaaactgtt    840
caattgaatt tgtatcaaat gcaacaacaa caacaacata tgaaatgtc ttctcaaacca    900 tgttctggtg aagttactga acatgaatct tctaaa                            936
```

<210> SEQ ID NO 73
<211> LENGTH: 10349
<212> TYPE: DNA
<213> ORGANISM: Artificial Sequence
<220> FEATURE:
<223> OTHER INFORMATION: Codon Optimized

<400> SEQUENCE: 73

```
attcagctcc ggttcccaac gatcaaggcg agttacatga tcccccatgt tgtgaaaaaa    60
agcggttagc tccttcggtc ctccgatcgt tgtcagaagt aagttggccg cagtgttatc    120
actcatggtt atggcagcac tgcataattc tcttactgtc atgccatccg taagatgctt    180
ttctgtgact ggtgagtact caaccaagtc attctgagaa tagtgtatgc ggcgaccgag    240
ttgctcttgc ccggcgtcaa tacgggataa taccgcgcca catagcagaa ctttaaaagt    300
gctcatcatt ggaaaacgtt cttcggggcg aaaactctca aggatcttac cgctgttgag    360
atccagttcg atgtaaccca ctcgtgcacc caactgatct tcagcatctt ttactttcac    420
```

```
cagcgtttct gggtgagcaa aaacaggaag gcaaaatgcc gcaaaaaagg gaataagggc      480
gacacggaaa tgttgaatac tcatactctt ccttttcaa tattattgaa gcatttatca       540
gggttattgt ctcatgagcg gatacatatt tgaatgtatt tagaaaaata aacaaatagg      600
ggttccgcgc acatttcccc gaaaagtgcc acctgacgtc taagaaacca ttattatcat     660
gacattaacc tataaaaata ggcgtatcac gaggcccttt cgtctcgcgc gtttcggtga     720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt     900
cgtaaggccg tttctgacag agtaaaattc ttgagggaac tttcaccatt atgggaaatg      960
gttcaagaag gtattgactt aaactccatc aaatggtcag gtcattgagt gtttttatt       1020 tgttgtatt tttttttttt agagaaaatc ctccaatatc aaattaggaa tcgtagtttc       1080
atgattttct gttcaccta acttttgtg tggtgccctc ctccttgtca atattaatgt       1140
taaagtgcaa ttctttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt    1320
catttataaa gtttatgtac aaatatcata aaaaagaga atcttttaa gcaaggattt     1380 tcttaacttc ttcggcgaca gcatcaccga cttcggtggt actgttggaa ccacctaaat    1440
caccagttct gataccgtca tccaaaacct tttaactgc atcttcaatg gccttacctt      1500
cttcaggcaa gttcaatgac aatttcaaca tcattgcagc agacaagata gtggcgatag    1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca aataggcaat ggtggctcat    1920
gttgtagggc catgaaagcg gccattcttg tgattctttg cacttctgga acggtgtatt    1980
gttcactatc ccaagcgaca ccatcaccat cgtcttcctt tctcttacca agtaaaatac    2040
ctcccactaa ttctctgaca caacgaagt cagtaccttt agcaaattgt ggcttgattg      2100
gagataagtc taaagagag tcggatgcaa agttacatgg tcttaagttg gcgtacaatt     2160
gaagttcttt acggattttt agtaaacctt gttcaggtct aacactaccg gtaccccatt    2220
taggaccacc cacagcacct aacaaaacgg catcaaccrt cttggaggct tccagcgcct    2280
catctggaag tgggacacct gtagcatcga tagcagcacc accaattaaa tgattttcga    2340
aatcgaactt gacattggaa cgaacatcag aaatagcttt aagaaccta atggcttcgg    2400 ctgtgatttc ttgaccaacg tggtcacctg gcaaaacgac gatcttctta ggggcagaca    2460
taggggcaga cattagaatg gtatatcctt gaaatatata tatatattgc tgaaatgtaa    2520
aaggtaagaa aagttagaaa gtaagacgat tgctaaccac ctattggaaa aaacaatagg    2580
tccttaaata atattgtcaa cttcaagtat tgtgatgcaa gcatttagtc atgaacgctt    2640
ctctattcta tatgaaaagc cggttccggc ctctcacctt tccttttct cccaatttt     2700 cagttgaaaa aggtatatgc gtcaggcgac ctctgaaatt aacaaaaaat ttccagtcat    2760
cgaatttgat tctgtgcgat agcgcccctg tgtgttctcg ttatgttgag gaaaaaata    2820
```

-continued

```
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac     3000
aaggaagtac aggacaattg attttgaaga gaatgtggat tttgatgtaa ttgttgggat    3060
tccatttta ataaggcaat aatattaggt atgtggatat actagaagtt ctcctcgagg     3120
gtcgatatgc ggtgtgaaat accgcacaga tgcgtaagga gaaaataccg catcaggaaa   3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaccgtc tatcagggcg atggcccact acgtgaacca tcacccctaat   3420
caagtttttt ggggtcgagg tgccgtaaag cactaaatcg aaccctaaa gggagccccc     3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacaggcg cgtcgcgcca ttcgccattc aggctgcgca     3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggag ggcgtgaatg taagcgtgac ataactaatt     4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcataccct tgaaatagac atcgtgatga ttaccgtta acaatgtttt     4560
tgaggcacca aacataacag gacctaatgc caattcaccg atacctggct tatttttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gaccttttgca tcttgaacaa atttagcgaa accagagact aaaggactac cgttgtacaa    4980
ggcaatagat gcaccattta acaaactagc ataaaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
```

```
accactggag aataagatgt tagtataagc atcaacaggt tgttctctgg cagtaaactc    5220
gcagttttta aactccttgg ctcttcctaa aaagtaatcc caagatatgt caccatctct    5280
caattctgca ccaatgttag aaccactaca agggataact attgccattg gggatttagc    5340
ttcaactact cttgaataca atggtattct cttttacct ctgatgatgt gatcttgtgt     5400
gaaaattgcc ttagctttgg ataatctcaa tctagttgag atttcagggg cggaaaatga    5460
atctgctata gagacaacta cgtaaccagc caatactatg ccaaatata taacaacagc     5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt   5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg actttttcag ggtctggaat   6000
ccaagcaggt ggggctggac cgaaatcctt gtagcaacca taaacaaca tttggtgtaa    6060
ggagaaaggc aaatctggtg acaagatatg gttagcgatg ttgatccaag tttgaggggt   6120
tgcagcacca taattacaaa cgatttctgc caatctacca tgtaatgttt ctgctacttc    6180
tgaggtgata cccaatgcga tgaaatctga ggcaacgact gaatccaagg acttatagtt   6240
tttacccatt cttttaatcg tggatccttc aaaaattctt acttttttt tggatggacg     6300
caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacgattag aagccgccga gcgggtgaca gccctccgaa ggaagactct cctccgtgcg     6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt ctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata   6900
cctctatact ttaacgtcaa ggagaaaaaa ccccggatcc gtaatacgac tcactataat   6960
gaatcatttg agagctgaag gtccagcttc tgttttggct attggtactg ctaatccaga   7020
aaatatttg attcaagatg aatttccaga ttattatttt agagttacta aatctgaaca     7080
tatgactcaa ttgaaagaaa aatttagaaa aatttgtgat aaatctatga ttagaaaaag   7140
aaattgtttt ttgaatgaag aacatttgaa acaaatcca agattggttg aacatgaaat     7200
gcaaactttg gatgctagac aagatatgtt ggttgttgaa gttccaaaat tgggtaaaga    7260
tgcttgtgct aaagctatta agaatgggg tcaaccaaaa tctaaaatta ctcatttgat     7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta agatattgc tgaaaataat aaaggtgcta gagttttggc    7500
tgtttgttgt gatattatgg cttgtttgtt tagaggtcca tctgattctg atttggaatt   7560
```

```
gttggttggt caagctattt ttggtgatgg tgctgctgct gttattgttg gtgctgaacc   7620
agatgaatct gttggtgaaa gaccaatttt tgaattggtt tctactggtc aaactatttt   7680
gccaaattct gaaggtacta ttggtggtca tattagagaa gctggtttga ttttgatttt   7740
gcataaagat gttccaatgt tgatttctaa taatattgaa aaatgtttga ttgaagcttt   7800
tactccaatt ggtatttctg attggaattc tatttttttgg attactcatc caggtggtaa   7860
agctatttttg gataaagttg aagaaaaatt gcatttgaaa tctgataaat ttgttgattc   7920
tagacatgtt ttgtctgaac atggtaatat gtcttcttct actgttttgt tgttatgga   7980
tgaattgaga aaaagatctt tggaagaagg taaatctact actggtgatg gttttgaatg   8040
gggtgttttg tttggttttg gtccaggttt gactgttgaa agagttgttg ttagatctgt   8100
tccaattaaa tatgaaggta gaggttcctt gttaacttgt ggtgacgttg aagaaaaccc   8160
aggtcctatg gccgtcaagc atttgatagt attgaagttt aaagatgaaa tcacagaagc   8220
tcaaaaggaa gaatttttca agacctacgt taatttggtc aacattatac ctgctatgaa   8280
agatgtatac tggggtaaag acgttacaca aaagaaagaa gaaggttata cacacattgt   8340
cgaagtaacc ttcgaatcag ttgaaactat ccaagattac atcattcatc cagctcacgt   8400
tggttttggt gacgtttaca gatccttctg ggaaaaattg ttgatcttcg attacacccc   8460
aagaaagtga tgatgggctg caggaattcg atatcaagct tatcgatacc gtcgacctcg   8520
agtcatgtaa ttagttatgt cacgcttaca ttcacgccct ccccccacat ccgctctaac   8580
cgaaaaggaa ggagttagac aacctgaagt ctaggtccct atttatttt ttatagttat   8640
gttagtatta agaacgttat ttatatttca aattttctt ttttttctgt acagacgcgt   8700
gtacgcatgt aacattatac tgaaaaccctt gcttgagaag gttttgggac gctcgaaggc   8760
tttaatttgc ggccggtacc cagcttttgt tccctttagt gagggttaat tccgagcttg   8820
gcgtaatcat ggtcatagct gtttcctgtg tgaaattgtt atccgctcac aattccacac   8880
aacataggag ccggaagcat aaagtgtaaa gcctggggtg cctaatgagt gaggtaactc   8940
acattaattg cgttgcgctc actgcccgct ttccagtcgg gaaacctgtc gtgccagctg   9000
cattaatgaa tcggccaacg cgcggggaga ggcggtttgc gtattgggcg ctcttccgct   9060
tcctcgctca ctgactcgct gcgctcggtc gttcggctgc ggcgagcggt atcagctcac   9120
tcaaaggcgg taatacggtt atccacagaa tcaggggata acgcaggaaa gaacatgtga   9180
gcaaaaggcc agcaaaaggc caggaaccgt aaaaaggccg cgttgctggc gttttttccat   9240
aggctcggcc cccctgacga gcatcacaaa aatcgacgct caagtcagag gtggcgaaac   9300
ccgacaggac tataaagata ccaggcgttc cccctggaa gctccctcgt gcgctctcct   9360
gttccgaccc tgccgcttac cggatacctg tccgcctttc tcccttcggg aagcgtggcg   9420
ctttctcaat gctcacgctg taggtatctc agttcggtgt aggtcgttcg ctccaagctg   9480
ggctgtgtgc acgaaccccc cgttcagccc gaccgctgcg ccttatccgg taactatcgt   9540
cttgagtcca acccggtaag acacgactta tcgccactgg cagcagccac tggtaacagg   9600
attagcagag cgaggtatgt aggcggtgct acagagttct tgaagtggtg gcctaactac   9660
ggctacacta gaaggacagt atttggtatc tgcgctctgc tgaagccagt taccttcgga   9720
aaaagagttg gtagctcttg atccggcaaa caaaccaccg ctggtagcgg tggttttttt   9780
gtttgcaagc agcagattac gcgcagaaaa aaaggatctc aagaagatcc tttgatcttt   9840
tctacggggt ctgacgctca gtggaacgaa aactcacgtt aagggatttt ggtcatgaga   9900
```

```
ttatcaaaaa ggatcttcac ctagatcctt ttaaattaaa aatgaagttt taaatcaatc    9960
taaagtatat atgagtaaac ttggtctgac agttaccaat gcttaatcag tgaggcacct   10020
atctcagcga tctgtctatt tcgttcatcc atagttgcct gactgccgt cgtgtagata    10080 actacgatac gggagggctt accatctggc cccagtgctg caatgatacc gcgagaccca   10140
cgctcaccgg ctccagattt atcagcaata aaccagccag ccggaagggc cgagcgcaga   10200
agtggtcctg caactttatc cgcctccatc cagtctatta attgttgccg ggaagctaga   10260
gtaagtagtt cgccagttaa tagtttgcgc aacgttgttg ccattgctac aggcatcgtg   10320
gtgtcacgct cgtcgtttgg tatggcttc                                    10349
```

<210> SEQ ID NO 74
<211> LENGTH: 10349
<212> TYPE: DNA
<213> ORGANISM: Artificial Sequence
<220> FEATURE:
<223> OTHER INFORMATION: Codon Optimized

<400> SEQUENCE: 74

```
attcagctcc ggttcccaac gatcaaggcg agttacatga tcccccatgt tgtgaaaaaa      60
agcggttagc tccttcggtc ctccgatcgt tgtcagaagt aagttggccg cagtgttatc     120
actcatggtt atggcagcac tgcataattc tcttactgtc atgccatccg taagatgctt     180
ttctgtgact ggtgagtact caaccaagtc attctgagaa tagtgtatgc ggcgaccgag     240
ttgctcttgc ccggcgtcaa tacgggataa taccgcgcca catagcagaa ctttaaaagt     300
gctcatcatt ggaaaacgtt cttcggggcg aaaactctca aggatcttac cgctgttgag     360
atccagttcg atgtaaccca ctcgtgcacc caactgatct tcagcatctt ttactttcac     420
cagcgtttct gggtgagcaa aaacaggaag gcaaaatgcc gcaaaaaagg gaataagggc     480
gacacggaaa tgttgaatac tcatactctt cctttttcaa tattattgaa gcatttatca     540
gggttattgt ctcatgagcg gatacatatt tgaatgtatt tagaaaaata aacaaatagg     600
ggttccgcgc acatttcccc gaaaagtgcc acctgacgtc taagaaacca ttattatcat     660
gacattaacc tataaaaata ggcgtatcac gaggcccttt cgtctcgcgc gtttcggtga     720
tgacggtgaa aacctctgac acatgcagct cccggagacg gtcacagctt gtctgtaagc     780
ggatgccggg agcagacaag cccgtcaggg cgcgtcagcg ggtgttggcg ggtgtcgggg     840
ctggcttaac tatgcggcat cagagcagat tgtactgaga gtgcaccata tcgactacgt     900
cgtaaggccg tttctgacag agtaaaattc ttgagggaac tttcaccatt atgggaaatg     960
gttcaagaag gtattgactt aaactccatc aaatggtcag gtcattgagt gttttttatt    1020
tgttgtattt tttttttttt agagaaaatc ctccaatatc aaattaggaa tcgtagtttc    1080
atgattttct gttacaccta acttttgtg tggtgccctc ctccttgtca atattaatgt    1140
taaagtgcaa ttcttttccc ttatcacgtt gagccattag tatcaatttg cttacctgta    1200
ttcctttact atcctccttt ttctccttct tgataaatgt atgtagattg cgtatatagt    1260
ttcgtctacc ctatgaacat attccatttt gtaatttcgt gtcgtttcta ttatgaattt    1320
catttataaa gttatgtac aaatatcata aaaaagaga tcttttaa gcaaggattt      1380 tcttaacttc ttcggcgaca gcatcaccga cttcggtggt actgttggaa ccacctaaat    1440
caccagttct gatacctgca tccaaaacct ttttaactgc atcttcaatg gccttacctt    1500
cttcaggcaa gttcaatgac aatttcaaca tcattgcagc agacaagata gtggcgatag    1560
ggtcaacctt attctttggc aaatctggag cagaaccgtg gcatggttcg tacaaaccaa    1620
```

```
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca caacgaagt cagtaccttt agcaaattgt ggcttgattg   2100
gagataagtc taaaagagag tcggatgcaa agttacatgg tcttaagttg cgtacaatt   2160
gaagttcttt acggattttt agtaaacctt gttcaggtct aacactaccg gtacccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaaccta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tccttttct cccaattttt   2700
cagttgaaaa aggtatatgc gtcaggcgac tctgaaatt aacaaaaaat ttccagtcat   2760
cgaatttgat tctgtgcgat agcgcccctg tgtgttctcg ttatgttgag gaaaaaata   2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gttttgaac acacatgaac   3000
aaggaagtac aggacaattg attttgaaga gaatgtggat tttgatgtaa ttgttgggat   3060
tccattttta ataaggcaat aatattaggt atgtggatat actagaagtt ctcctcgagg   3120
gtcgatatgc ggtgtgaaat accgcacaga tgcgtaagga gaaataccg catcaggaaa   3180
ttgtaaacgt taatatttg ttaaaattcg cgttaaattt ttgttaaatc agctcatttt   3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaccgtc tatcagggcg atggcccact acgtgaacca tcaccctaat   3420
caagtttttt ggggtcgagg tgccgtaaag cactaaatcg gaaccctaaa gggagccccc   3480
gatttagagc ttgacgggga agccggcga acgtggcgag aaaggaaggg aagaaagcga   3540
aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct cttcgctatt acgccagctg gcgaaggggg   3720
gatgtgctgc aaggcgatta agttgggtaa cgccaggggtt ttcccagtca cgacgttgta   3780
aaacgacggc cagtgaattg taatacgact cactataggg cgaattggag ctctagtcgc   3840
aaattaaagc cttcgagcgt cccaaaacct tctcaagcaa ggttttcagt ataatgttac   3900
atgcgtacac gcgtctgtac agaaaaaaaa gaaaaatttg aaatataaat aacgttctta   3960
```

```
atactaacat aactataaaa aaataaatag ggacctagac ttcaggttgt ctaactcctt    4020
ccttttcggt tagagcggat gtgggggag  ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacccc tgaaatagac atcgtgatga ttaccgttta acaatgtttt    4560
tgaggcacca aacataacag gacctaatgc caattcaccg atacctggct tattttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaccaac  caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctctttctaa aaagtaatcc caagatatgt caccatctct    5280
caattctgca ccaatgttag aaccactaca agggataact attgccattg gggatttagc    5340
ttcaactact cttgaataca atggtattct cttttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttttcag ggtctggaat    6000
ccaagcaggt ggggctggac cgaaatcctt gtagcaacca taaacaaca  tttggtgtaa    6060
ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt acttttttt  tggatggacg    6300
caaagaagtt taataatcat attacatggc attaccacca tatacatatc catatacata    6360
```

```
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020 aaatatttg attcaagatg aatttccaga ttattatttt agagttacta aatctgaaca    7080
tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta agatattgc tgaaaataat aaaggtgcta gagttttggc    7500
tgtttgttgt gatattatgg cttgtttgtt tagaggtcca tctgattctg atttggaatt    7560
gttggttggt caagctattt ttggtgatgg tgctgctgct gttattgttg gtgctgaacc    7620
agatgaatct gttggtgaaa gaccaatttt tgaattggtt tctactgg tc aaactatttt    7680 gccaaattct gaaggtacta ttggtggtca tattagagaa gctggtttga ttttgatt    7740 gcataaagat gttccaatgt tgatttctaa taatattgaa aaatgtttga ttgaagcttt    7800
tactccaatt ggtatttctg attggaattc tattttttgg attactcatc caggtggtaa    7860 agctatttg gataaagttg aagaaaaatt gcatttgaaa aaagaaaaat tgttgattc    7920 tagacatgtt ttgtctgaac atggtaatat gtcttcttct actgtttgt ttgttatgga    7980 tgaattgaga aaaagatctt tggaagaagg taaatctact actggtgatg gttttgaatg    8040
gggtgttttg tttggttttg gtccaggttt gactgttgaa actgttgttt tgagatctgt    8100
tccaattaat tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaatttttca agacctacgt taatttggtc aacattatac ctgctatgaa    8280
agatgtatac tggggtaaag acgttacaca aagaaagaa gaaggttata cacacattgt    8340
cgaagtaacc ttcgaatcag ttgaaactat ccaagattac atcattcatc cagctcacgt    8400
tggttttggt gacgtttaca gatccttctg ggaaaaattg ttgatcttcg attcaccccc    8460
aagaaagtga tgatgggctg caggaattcg atatcaagct tatcgatacc gtcgacctcg    8520
agtcatgtaa ttagttatgt cacgcttaca ttcacgccct ccccccacat ccgctctaac    8580
cgaaaaggaa ggagttagac aacctgaagt ctaggtcccct atttatttt ttatagttat    8640 gttagtatta agaacgttat ttatatttca aatttttctt ttttttctgt acagacgcgt    8700
```

| | |
|---|---|
| gtacgcatgt aacattatac tgaaaaccttt gcttgagaag gttttgggac gctcgaaggc | 8760 |
| tttaatttgc ggccggtacc cagcttttgt tccctttagt gagggttaat tccgagcttg | 8820 |
| gcgtaatcat ggtcatagct gtttcctgtg tgaaattgtt atccgctcac aattccacac | 8880 |
| aacataggag ccggaagcat aaagtgtaaa gcctggggtg cctaatgagt gaggtaactc | 8940 |
| acattaattg cgttgcgctc actgcccgct ttccagtcgg gaaacctgtc gtgccagctg | 9000 |
| cattaatgaa tcggccaacg cgcggggaga ggcggtttgc gtattgggcg ctcttccgct | 9060 |
| tcctcgctca ctgactcgct gcgctcggtc gttcggctgc ggcgagcggt atcagctcac | 9120 |
| tcaaaggcgg taatacggtt atccacagaa tcaggggata acgcaggaaa gaacatgtga | 9180 |
| gcaaaaggcc agcaaaaggc caggaaccgt aaaaaggccg cgttgctggc gtttttccat | 9240 |
| aggctcggcc cccctgacga gcatcacaaa aatcgacgct caagtcagag gtggcgaaac | 9300 |
| ccgacaggac tataaagata ccaggcgttc ccccctggaa gctccctcgt gcgctctcct | 9360 |
| gttccgaccc tgccgcttac cggatacctg tccgcctttc tcccttcggg aagcgtggcg | 9420 |
| ctttctcaat gctcacgctg taggtatctc agttcggtgt aggtcgttcg ctccaagctg | 9480 |
| ggctgtgtgc acgaaccccc cgttcagccc gaccgctgcg ccttatccgg taactatcgt | 9540 |
| cttgagtcca acccggtaag acacgactta tcgccactgg cagcagccac tggtaacagg | 9600 |
| attagcagag cgaggtatgt aggcggtgct acagagttct tgaagtggtg gcctaactac | 9660 |
| ggctacacta gaaggacagt atttggtatc tgcgctctgc tgaagccagt taccttcgga | 9720 |
| aaaagagttg gtagctcttg atccggcaaa caaaccaccg ctggtagcgg tggttttttt | 9780 |
| gtttgcaagc agcagattac gcgcagaaaa aaaggatctc aagaagatcc tttgatcttt | 9840 |
| tctacggggt ctgacgctca gtggaacgaa aactcacgtt aagggatttt ggtcatgaga | 9900 |
| ttatcaaaaa ggatcttcac ctagatcctt ttaaattaaa aatgaagttt taaatcaatc | 9960 |
| taaagtatat atgagtaaac ttggtctgac agttaccaat gcttaatcag tgaggcacct | 10020 |
| atctcagcga tctgtctatt tcgttcatcc atagttgcct gactgcccgt cgtgtagata | 10080 |
| actacgatac gggagggctt accatctggc cccagtgctg caatgatacc gcgagaccca | 10140 |
| cgctcaccgg ctccagattt atcagcaata aaccagccag ccggaagggc cgagcgcaga | 10200 |
| agtggtcctg caactttatc cgcctccatc cagtctatta attgttgccg ggaagctaga | 10260 |
| gtaagtagtt cgccagttaa tagtttgcgc aacgttgttg ccattgctac aggcatcgtg | 10320 |
| gtgtcacgct cgtcgtttgg tatggcttc | 10349 |

<210> SEQ ID NO 75
<211> LENGTH: 10349
<212> TYPE: DNA
<213> ORGANISM: Artificial Sequence
<220> FEATURE:
<223> OTHER INFORMATION: Codon Optimized

<400> SEQUENCE: 75

| | |
|---|---|
| attcagctcc ggttcccaac gatcaaggcg agttacatga tccccatgt tgtgaaaaaa | 60 |
| agcggttagc tccttcggtc ctccgatcgt tgtcagaagt aagttggccg cagtgttatc | 120 |
| actcatggtt atgcagcac tgcataattc tcttactgtc atgccatccg taagatgctt | 180 |
| ttctgtgact ggtgagtact caaccaagtc attctgagaa tagtgtatgc ggcgaccgag | 240 |
| ttgctcttgc ccggcgtcaa tacgggataa taccgcgcca catagcagaa ctttaaaagt | 300 |
| gctcatcatt ggaaaacgtt cttcgggcg aaaactctca aggatcttac cgctgttgag | 360 |
| atccagttcg atgtaaccca ctcgtgcacc caactgatct tcagcatctt ttactttcac | 420 |

-continued

```
cagcgtttct gggtgagcaa aaacaggaag gcaaaatgcc gcaaaaaagg gaataagggc      480
gacacggaaa tgttgaatac tcatactctt cctttttcaa tattattgaa gcatttatca      540
gggttattgt ctcatgagcg gatacatatt tgaatgtatt tagaaaaata aacaaatagg      600
ggttccgcgc acatttcccc gaaaagtgcc acctgacgtc taagaaacca ttattatcat      660
gacattaacc tataaaaata ggcgtatcac gaggcccttt cgtctcgcgc gtttcggtga      720
tgacggtgaa aacctctgac acatgcagct cccggagacg gtcacagctt gtctgtaagc      780
ggatgccggg agcagacaag cccgtcaggg cgcgtcagcg ggtgttggcg ggtgtcgggg      840
ctggcttaac tatgcggcat cagagcagat tgtactgaga gtgcaccata tcgactacgt      900
cgtaaggccg tttctgacag agtaaaattc ttgagggaac tttcaccatt atgggaaatg      960
gttcaagaag gtattgactt aaactccatc aaatggtcag gtcattgagt gttttttatt     1020
tgttgtattt ttttttttt agagaaaatc ctccaatatc aaattaggaa tcgtagtttc      1080 atgatttttct gttacaccta acttttttgtg tggtgccctc ctccttgtca atattaatgt     1140
taaagtgcaa ttcttttttcc ttatcacgtt gagccattag tatcaatttg cttacctgta     1200
ttcctttact atcctccttt ttctccttct tgataaatgt atgtagattg cgtatatagt     1260
ttcgtctacc ctatgaacat attccatttt gtaatttcgt gtcgtttcta ttatgaattt     1320
catttataaa gttatgtac aaatatcata aaaaagaga atctttttaa gcaaggattt       1380
tcttaacttc ttcggcgaca gcatcaccga cttcggtggt actgttggaa ccacctaaat     1440
caccagttct gatacctgca tccaaaacct ttttaactgc atcttcaatg gccttacctt     1500
cttcaggcaa gttcaatgac aatttcaaca tcattgcagc agacaagata gtggcgatag     1560
ggtcaacctt attctttggc aaatctggag cagaaccgtg gcatggttcg tacaaaccaa     1620
atgcggtgtt cttgtctggc aaagaggcca aggacgcaga tggcaacaaa cccaaggaac     1680
ctgggataac ggaggcttca tcggagatga tatcaccaaa catgttgctg gtgattataa     1740
taccatttag gtgggttggg ttcttaacta ggatcatggc ggcagaatca atcaattgat     1800
gttgaacctt caatgtaggg aattcgttct tgatggtttc ctccacagtt tttctccata     1860
atcttgaaga ggccaaaaca ttagctttat ccaaggacca aataggcaat ggtggctcat     1920
gttgtagggc catgaaagcg gccattcttg tgattctttg cacttctgga acggtgtatt     1980
gttcactatc ccaagcgaca ccatcaccat cgtcttcctt tctcttacca agtaaaatac     2040
ctcccactaa ttctctgaca acaacgaagt cagtaccttt agcaaattgt ggcttgattg     2100
gagataagtc taaaagagag tcggatgcaa agttacatgg tcttaagttg gcgtacaatt     2160
gaagttcttt acggattttt agtaaacctt gttcaggtct aacactaccg gtaccccatt     2220
taggaccacc cacagcacct aacaaaacgg catcaacctt cttggaggct tccagcgcct     2280
catctggaag tgggacacct gtagcatcga tagcagcacc accaattaaa tgattttcga     2340
aatcgaactt gacattggaa cgaacatcag aaatagcttt aagaaccta atggcttcgg      2400 ctgtgatttc ttgaccaacg tggtcacctg gcaaaacgac gatcttctta ggggcagaca     2460
tagggcagag cattgaatg gtatatcctt gaaatatata tatatattgc tgaaatgtaa      2520
aaggtaagaa aagttagaaa gtaagacgat tgctaaccac ctattggaaa aaacaatagg     2580
tccttaaata atattgtcaa cttcaagtat tgtgatgcaa gcatttagtc atgaacgctt     2640
ctctattcta tatgaaaagc cggttccggc ctctcacctt tccttttttct cccaatttttt    2700 cagttgaaaa aggtatatgc gtcaggcgac ctctgaaatt aacaaaaaat ttccagtcat     2760
```

-continued

```
cgaatttgat tctgtgcgat agcgcccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac     3000
aaggaagtac aggacaattg atttgaaga gaatgtggat tttgatgtaa ttgttgggat     3060
tccattttta ataaggcaat aatattaggt atgtggatat actagaagtt ctcctcgagg    3120
gtcgatatgc ggtgtgaaat accgcacaga tgcgtaagga gaaaataccg catcaggaaa    3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaccgtc tatcagggcg atggcccact acgtgaacca tcaccctaat     3420
caagtttttt ggggtcgagg tgccgtaaag cactaaatcg gaaccctaaa gggagccccc    3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aataaaatag ggacctagac ttcaggttgt ctaactcctt    4020
ccttttcggt tagagcggat gtgggggagg ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacccct tgaaatagac atcgtgatga ttaccgttta acaatgtttt    4560
tgaggcacca acataacag gacctaatgc caattcaccg atacctggct tatttttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccatttta acaaactagc ataaaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
```

```
accactggag aataagatgt tagtataagc atcaacaggt tgttctctgg cagtaaactc    5220
gcagttttta aactccttgg ctctttctaa aaagtaatcc aagatatgt caccatctct    5280 caattctgca ccaatgttag aaccactaca agggataact attgccattg gggatttagc    5340
ttcaactact cttgaataca atggtattct cttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattagga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag ggtctggaat    6000 ccaagcaggt ggggctggac cgaaatcctt gtagcaacca taaaacaaca tttggtgtaa    6060
ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt acttttttt tggatggacg    6300 caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa cttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagcccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020
aaatattttg ttgcaagatg aatttccaga ttattatttt agagttacta atctgaaca     7080 tatgactcaa ttgaaagaaa aattagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta agatattgc tgaaaataat aaaggtgcta gagttttggc    7500
```

```
tgtttgttgt gatattatgg cttgtttgtt tagaggtcca tctgaatctg atttggaatt    7560
gttggttggt caagctattt ttggtgatgg tgctgctgct gttattgttg gtgctgaacc    7620
agatgaatct gttggtgaaa gaccaatttt tgaattggtt tctactggtc aaactatttt    7680
gccaaattct gaaggtacta ttggtggtca tattagagaa gctggtttga tttttgattt    7740
gcataaagat gttccaatgt tgatttctaa taatattgaa aaatgtttga ttgaagcttt    7800
tactccaatt ggtatttctg attggaattc tattttttgg attactcatc caggtggtaa    7860
agctattttg gataaagttg aagaaaaatt gcatttgaaa tctgataaat tgttgattc     7920 tagacatgtt ttgtctgaac atggtaatat gtcttcttct actgttttgt ttgttatgga    7980
tgaattgaga aaaagatctt tggaagaagg taaatctact actggtgatg ttttgaatg     8040 gggtgttttg tttggttttg gtccaggttt gactgttgaa agagttgttg ttagatctgt    8100
tccaattaaa tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaattttca agacctacgt taatttggtc aacattatac ctgctatgaa    8280
agatgtatac tggggtaaag acgttacaca aaagaaagaa gaaggttata cacacattgt    8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct ccccccacat ccgctctaac    8580
cgaaaaggaa ggagttagac aacctgaagt ctaggtccct atttattttt ttatagttat    8640
gttagtatta agaacgttat ttatatttca aatttttctt tttttctgt acagacgcgt     8700 gtacgcatgt aacattatac tgaaaacctt gcttgagaag gttttgggac gctcgaaggc    8760
tttaatttgc ggccggtacc cagcttttgt tccctttagt gagggttaat tccgagcttg    8820
gcgtaatcat ggtcatagct gtttcctgtg tgaaattgtt atccgctcac aattccacac    8880
aacataggag ccggaagcat aaagtgtaaa gcctggggtg cctaatgagt gaggtaactc    8940
acattaattg cgttgcgctc actgcccgct ttccagtcgg gaaacctgtc gtgccagctg    9000
cattaatgaa tcggccaacg cgcggggaga ggcggtttgc gtattgggcg ctcttccgct    9060
tcctcgctca ctgactcgct gcgctcggtc gttcggctgc ggcgagcggt atcagctcac    9120
tcaaaggcgg taatacggtt atccacagaa tcaggggata acgcaggaaa gaacatgtga    9180
gcaaaaggcc agcaaaaggc caggaaccgt aaaaaggccg cgttgctggc gtttttccat    9240
aggctcggcc cccctgacga gcatcacaaa aatcgacgct caagtcagag gtggcgaaac    9300
ccgacaggac tataaagata ccaggcgttc ccccctggaa gctccctcgt gcgctctcct    9360
gttccgaccc tgccgcttac cggatacctg tccgcctttc tcccttcggg aagcgtggcg    9420
ctttctcaat gctcacgctg taggtatctc agttcggtgt aggtcgttcg ctccaagctg    9480
ggctgtgtgc acgaaccccc cgttcagccc gaccgctgcg ccttatccgg taactatcgt    9540
cttgagtcca acccggtaag acacgactta tcgccactgg cagcagccac tggtaacagg    9600
attagcagag cgaggtatgt aggcggtgct acagagttct tgaagtggtg cctaactac     9660 ggctacacta gaaggacagt atttggtatc tgcgctctgc tgaagccagt taccttcgga    9720
aaaagagttg gtagctcttg atccggcaaa caaaccaccg ctggtagcgg tggtttttt     9780 gtttgcaagc agcagattac gcgcagaaaa aaggatctc aagaagatcc tttgatcttt    9840
tctacggggt ctgacgctca gtggaacgaa aactcacgtt aagggatttt ggtcatgaga    9900
```

| | | | |
|---|---|---|---|
| ttatcaaaaa | ggatcttcac | ctagatcctt | ttaaattaaa  aatgaagttt  taaatcaatc | 9960 |
| taaagtatat | atgagtaaac | ttggtctgac | agttaccaat  gcttaatcag  tgaggcacct | 10020 |
| atctcagcga | tctgtctatt | tcgttcatcc | atagttgcct  gactgcccgt  cgtgtagata | 10080 |
| actacgatac | gggagggctt | accatctggc | cccagtgctg  caatgatacc  gcgagaccca | 10140 |
| cgctcaccgg | ctccagattt | atcagcaata | aaccagccag  ccggaagggc  cgagcgcaga | 10200 |
| agtggtcctg | caactttatc | cgcctccatc | cagtctatta  attgttgccg  ggaagctaga | 10260 |
| gtaagtagtt | cgccagttaa | tagtttgcgc | aacgttgttg  ccattgctac  aggcatcgtg | 10320 |
| gtgtcacgct | cgtcgtttgg | tatggcttc  |  | 10349 |

<210> SEQ ID NO 76
<211> LENGTH: 10349
<212> TYPE: DNA
<213> ORGANISM: Artificial Sequence
<220> FEATURE:
<223> OTHER INFORMATION: Codon Optimized

<400> SEQUENCE: 76

| | | | |
|---|---|---|---|
| attcagctcc | ggttcccaac | gatcaaggcg | agttacatga  tcccccatgt  tgtgaaaaaa | 60 |
| agcggttagc | tccttcggtc | ctccgatcgt | tgtcagaagt  aagttggccg  cagtgttatc | 120 |
| actcatggtt | atggcagcac | tgcataattc | tcttactgtc  atgccatccg  taagatgctt | 180 |
| ttctgtgact | ggtgagtact | caaccaagtc | attctgagaa  tagtgtatgc  ggcgaccgag | 240 |
| ttgctcttgc | ccggcgtcaa | tacgggataa | taccgcgcca  catagcagaa  ctttaaaagt | 300 |
| gctcatcatt | ggaaaacgtt | cttcggggcg | aaaactctca  aggatcttac  cgctgttgag | 360 |
| atccagttcg | atgtaaccca | ctcgtgcacc | caactgatct  tcagcatctt  ttactttcac | 420 |
| cagcgtttct | gggtgagcaa | aaacaggaag | gcaaaatgcc  gcaaaaaagg  gaataagggc | 480 |
| gacacggaaa | tgttgaatac | tcatactctt | cctttttcaa  tattattgaa  gcatttatca | 540 |
| gggttattgt | ctcatgagcg | gatacatatt | tgaatgtatt  tagaaaaata  aacaaatagg | 600 |
| ggttccgcgc | acatttcccc | gaaaagtgcc | acctgacgtc  taagaaacca  ttattatcat | 660 |
| gacattaacc | tataaaaata | ggcgtatcac | gaggcccttt  cgtctcgcgc  gtttcggtga | 720 |
| tgacggtgaa | aacctctgac | acatgcagct | cccggagacg  gtcacagctt  gtctgtaagc | 780 |
| ggatgccggg | agcagacaag | cccgtcaggg | cgcgtcagcg  ggtgttggcg  ggtgtcgggg | 840 |
| ctggcttaac | tatgcggcat | cagagcagat | tgtactgaga  gtgcaccata  tcgactacgt | 900 |
| cgtaaggccg | tttctgacag | agtaaaattc | ttgagggaac  tttcaccatt  atgggaaatg | 960 |
| gttcaagaag | gtattgactt | aaactccatc | aaatggtcag  gtcattgagt  gttttttatt | 1020 |
| tgttgtattt | ttttttttt | agagaaaatc | ctccaatatc  aaattaggaa  tcgtagtttc | 1080 |
| atgattttct | gttacaccta | acttttgtg | tggtgccctc  ctccttgtca  atattaatgt | 1140 |
| taaagtgcaa | ttcttttcc | ttatcacgtt | gagccattag  tatcaatttg  cttacctgta | 1200 |
| ttcctttact | atcctccttt | ttctccttct | tgataaatgt  atgtagattg  cgtatatagt | 1260 |
| ttcgtctacc | ctatgaacat | attccatttt | gtaatttcgt  gtcgtttcta  ttatgaattt | 1320 |
| catttataaa | gtttatgtac | aaatatcata | aaaaaagaga  atctttttaa  gcaaggattt | 1380 |
| tcttaacttc | ttcggcgaca | gcatcaccga | cttcggtggt  actgttggaa  ccacctaaat | 1440 |
| caccagttct | gatacctgca | tccaaaacct | ttttaactgc  atcttcaatg  gccttacctt | 1500 |
| cttcaggcaa | gttcaatgac | aatttcaaca | tcattgcagc  agacaagata  gtggcgatag | 1560 |

```
ggtcaacctt attctttggc aaatctggag cagaaccgtg gcatggttcg tacaaaccaa    1620
atgcggtgtt cttgtctggc aaagaggcca aggacgcaga tggcaacaaa cccaaggaac    1680
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca aataggcaat ggtggctcat    1920
gttgtagggc catgaaagcg gccattcttg tgattctttg cacttctgga acggtgtatt    1980
gttcactatc ccaagcgaca ccatcaccat cgtcttcctt tctcttacca agtaaaatac    2040
ctcccactaa ttctctgaca acaacgaagt cagtaccttt agcaaattgt ggcttgattg    2100
gagataagtc taaagagag tcggatgcaa agttacatgg tcttaagttg gcgtacaatt    2160
gaagttcttt acggattttt agtaaacctt gttcaggtct aacactaccg gtaccccatt    2220
taggaccacc cacagcacct aacaaaacgg catcaacctt cttggaggct tccagcgcct    2280
catctggaag tgggacacct gtagcatcga tagcagcacc accaattaaa tgattttcga    2340
aatcgaactt gacattggaa cgaacatcag aaatagcttt aagaaccta atggcttcgg    2400 ctgtgatttc ttgaccaacg tggtcacctg gcaaaacgac gatcttctta ggggcagaca    2460
taggggcaga cattagaatg gtatatcctt gaatatata tatatattgc tgaaatgtaa    2520
aaggtaagaa aagttagaaa gtaagacgat tgctaaccac ctattggaaa aaacaatagg    2580
tccttaaata atattgtcaa cttcaagtat tgtgatgcaa gcatttagtc atgaacgctt    2640
ctctattcta tatgaaaagc cggttccggc ctctcacctt tccttttcct cccaattttt    2700
cagttgaaaa aggtatatgc gtcaggcgac ctctgaaatt aacaaaaaat ttccagtcat    2760
cgaatttgat tctgtgcgat agcgccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac    3000 aaggaagtac aggacaattg attttgaaga gaatgtggat tttgatgtaa ttgttgggat    3060 tccatttta ataaggcaat aatattaggt atgtggatat actagaagtt ctcctcgagg    3120
gtcgatatgc ggtgtgaaat accgcacaga tgcgtaagga gaaaataccg catcaggaaa    3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420
caagtttttt ggggtcgagg tgccgtaaag cactaaatcg aaccctaaa gggagccccc    3480 gatttagagc ttgacgggga agccggcga acgtggcgag aaaggaaggg aagaagcga    3540 aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct ttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
```

```
atactaacat aactataaaa aaataaatag ggacctagac ttcaggttgt ctaactcctt    4020
ccttttcggt tagagcggat gtgggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacct tgaaatagac atcgtgatga ttaccgttta acaatgtttt    4560
tgaggcacca acataacag gacctaatgc caattcaccg atacctggct tattttagg    4620 cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220 gcagtttta aactccttgg ctcttttctaa aaagtaatcc caagatatgt caccatctct    5280
caattctgca ccaatgttag aaccactaca agggataact attgccattg gggatttagc    5340
ttcaactact cttgaataca atggtattct cttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag ggtctggaat    6000 ccaagcaggt ggggctggac cgaaatcctt gtagcaacca taaacaaca tttggtgtaa    6060 ggagaaaggc aaatctggtg acaagatatg gttagcgatg ttgatccaag tttgagggt    6120 tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt actttttttt tggatggacg    6300
```

```
caaagaagtt taataatcat attacatggc attaccacca tatacatatc catatacata      6360
tccatatcta atcttactta tatgttgtgg aaatgtaaag agccccatta tcttagccta      6420
aaaaaacctt ctctttggaa ctttcagtaa tacgcttaac tgctcattgc tatattgaag      6480
tacggattag aagccgccga gcgggtgaca gccctccgaa ggaagactct cctccgtgcg      6540
tcctcgtctt caccggtcgc gttcctgaaa cgcagatgtg cctcgcgccg cactgctccg      6600
aacaataaag attctacaat actagctttt atggttatga agaggaaaaa ttggcagtaa      6660
cctggcccca caaaccttca aatgaacgaa tcaaattaac aaccatagga tgataatgcg      6720
attagttttt tagccttatt ctggggtaa ttaatcagcg aagcgatgat ttttgatcta       6780
ttaacagata tataaatgca aaaactgcat aaccacttta actaatactt tcaacatttt      6840
cggtttgtat tacttcttat tcaaatgtaa taaaagtatc aacaaaaaat tgttaatata      6900
cctctatact ttaacgtcaa ggagaaaaaa ccccggatcc gtaatacgac tcactataat      6960
gaatcatttg agagctgaag gtccagcttc tgttttggct attggtactg ctaatccaga      7020
aaatattttg attcaagatg aatttccaga ttattatttt agagttacta aatctgaaca      7080
tatgactcaa ttgaaagaaa aatttagaaa aatttgtgat aaatctatga ttagaaaaag      7140
aaatatttt ttgaatgaag aacatttgaa acaaaatcca aaattggttg aacatgatgt       7200
tcaaactttg gatgctagac aagatatgtt ggttgttgaa gttccaaaat tgggtaaaga      7260
tgcttgtgct aaagctatta agaatggggg tcaaccaaaa tctaaaatta ctcatttgat      7320
ttttacttct gcttctacta ctgatatgcc aggtgctgat tatcattgtg ctaaattgtt      7380
gggtttgtct ccatctgtta aaagagttat gatgtatcaa ttgggttgtt atggtggtgg      7440
tactgttttg agaattgcta agatattgc tgaaaataat aaaggtgcta gagttttggc       7500
tgtttgttgt gatattatgg cttgtttgtt tagaggtcca tctgattctg atttggaatt      7560
gttggttggt caagctattt ttggtgatgg tgctgctgct gttattgttg gtgctgaacc      7620
agatgaatct gttggtgaaa gaccaatttt tgaattggtt tctactggtc aaactatttt      7680
gccaaattct gaaggtacta ttggtggtca tattagagaa gctggtttga ttttgatttt      7740
gcataaagat gttccaatgt tgatttctaa taatattgaa aaatgtttga ttgaagcttt      7800
tactccaatt ggtatttctg attggaattc tatttttttgg attactcatc caggtggtaa      7860
agctattttg gataaagttg aagaaaaatt gcatttgaaa tctgataaat ttgttgattc      7920
tagacatgtt ttgtctgaac atggtaatat gtcttcttct actgttttgt tgttatggga      7980
tgaattgaga aaaagatctt tggaagaagg taaatctact actggtgatg gttttgaatg      8040
gggtgttttg tttggttttg gtccaggttt gactgttgaa agagttgttg ttagatctgt      8100
tccaattaaa tatgaaggta gaggttcctt gttaacttgt ggtgacgttg aagaaaaccc      8160
aggtcctatg gccgtcaagc atttgatagt attgaagttt aaagatgaaa tcacagaagc      8220
tcaaaaggaa gaatttttca agacctacgt taatttggtc aacattatac ctgctatgaa      8280
agatgtatac tggggtaaag acgttacaca aaagaaagaa gaaggttata cacacattgt      8340
cgaagtaacc ttcgaatcag ttgaaactat ccaagattac atcattcatc cagctcacgt      8400
tggttttggt gacgtttaca gatccttctg ggaaaaattg ttgatcttcg attacacccc      8460
aagaaagtga tgatgggctg caggaattcg atatcaagct tatcgatacc gtcgacctcg      8520
agtcatgtaa ttagttatgt cacgcttaca ttcacgccct ccccccacat ccgctctaac      8580
cgaaaaggaa ggagttagac aacctgaagt ctaggtccct atttattttt ttatagttat      8640
gttagtatta agaacgttat ttatatttca aattttcttt ttttttctgt acagacgcgt      8700
```

```
gtacgcatgt aacattatac tgaaaacctt gcttgagaag gttttgggac gctcgaaggc    8760
tttaatttgc ggccggtacc cagcttttgt tccctttagt gagggttaat tccgagcttg    8820
gcgtaatcat ggtcatagct gtttcctgtg tgaaattgtt atccgctcac aattccacac    8880
aacataggag ccggaagcat aaagtgtaaa gcctggggtg cctaatgagt gaggtaactc    8940
acattaattg cgttgcgctc actgcccgct ttccagtcgg gaaacctgtc gtgccagctg    9000
cattaatgaa tcggccaacg cgcggggaga ggcggtttgc gtattgggcg ctcttccgct    9060
tcctcgctca ctgactcgct gcgctcggtc gttcggctgc ggcgagcggt atcagctcac    9120
tcaaaggcgg taatacggtt atccacagaa tcaggggata acgcaggaaa gaacatgtga    9180
gcaaaaggcc agcaaaaggc caggaaccgt aaaaaggccg cgttgctggc gtttttccat    9240
aggctcggcc cccctgacga gcatcacaaa aatcgacgct caagtcagag gtggcgaaac    9300
ccgacaggac tataaagata ccaggcgttc ccccctggaa gctccctcgt gcgctctcct    9360
gttccgaccc tgccgcttac cggatacctg tccgcctttc tcccttcggg aagcgtggcg    9420
ctttctcaat gctcacgctg taggtatctc agttcggtgt aggtcgttcg ctccaagctg    9480
ggctgtgtgc acgaaccccc cgttcagccc gaccgctgcg ccttatccgg taactatcgt    9540
cttgagtcca acccggtaag acacgactta tcgccactgg cagcagccac tggtaacagg    9600
attagcagag cgaggtatgt aggcggtgct acagagttct tgaagtggtg cctaactac     9660 ggctacacta aaggacagt atttggtatc tgcgctctgc tgaagccagt taccttcgga    9720
aaaagagttg gtagctcttg atccggcaaa caaaccaccg ctggtagcgg tggttttttt    9780
gtttgcaagc agcagattac gcgcagaaaa aaaggatctc aagaagatcc tttgatcttt    9840
tctacggggt ctgacgctca gtggaacgaa aactcacgtt aagggatttt ggtcatgaga    9900
ttatcaaaaa ggatcttcac ctagatcctt ttaaattaaa aatgaagttt taaatcaatc    9960
taaagtatat atgagtaaac ttggtctgac agttaccaat gcttaatcag tgaggcacct   10020
atctcagcga tctgtctatt tcgttcatcc atagttgcct gactgcccgt cgtgtagata   10080
actacgatac gggagggctt accatctggc cccagtgctg caatgatacc gcgagaccca   10140
cgctcaccgg ctccagattt atcagcaata aaccagccag ccggaagggc cgagcgcaga   10200
agtggtcctg caactttatc cgcctccatc cagtctatta attgttgccg gaagctaga    10260 gtaagtagtt cgccagttaa tagtttgcgc aacgttgttg ccattgctac aggcatcgtg   10320
gtgtcacgct cgtcgtttgg tatggcttc                                    10349
```

<210> SEQ ID NO 77
<211> LENGTH: 10349
<212> TYPE: DNA
<213> ORGANISM: Artificial Sequence
<220> FEATURE:
<223> OTHER INFORMATION: Codon Optimized

<400> SEQUENCE: 77

```
attcagctcc ggttcccaac gatcaaggcg agttacatga tccccatgt tgtgaaaaaa       60 agcggttagc tccttcggtc ctccgatcgt tgtcagaagt aagttggccg cagtgttatc     120
actcatggtt atggcagcac tgcataattc tcttactgtc atgccatccg taagatgctt     180
ttctgtgact ggtgagtact caaccaagtc attctgagaa tagtgtatgc ggcgaccgag     240
ttgctcttgc ccggcgtcaa tacgggataa taccgcgcca catagcagaa ctttaaaagt     300
gctcatcatt ggaaaacgtt cttcggggcg aaaactctca aggatcttac cgctgttgag     360
```

```
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt ccttttttcaa tattattgaa gcatttatca   540
gggttattgt ctcatgagcg atacatatt tgaatgtatt tagaaaaata aacaaatagg    600
ggttccgcgc acatttcccc gaaaagtgcc acctgacgtc taagaaacca ttattatcat   660
gacattaacc tataaaaata ggcgtatcac gaggcccttt cgtctcgcgc gtttcggtga   720
tgacggtgaa aacctctgac acatgcagct cccggagacg gtcacagctt gtctgtaagc   780
ggatgccggg agcagacaag cccgtcaggg cgcgtcagcg ggtgttggcg ggtgtcgggg   840
ctggcttaac tatgcggcat cagagcagat tgtactgaga gtgcaccata tcgactacgt   900
cgtaaggccg tttctgacag agtaaaaattc ttgagggaac tttcaccatt atgggaaatg   960
gttcaagaag gtattgactt aaactccatc aaatggtcag gtcattgagt gttttttatt   1020
tgttgtattt tttttttttt agagaaaatc ctccaatatc aaattaggaa tcgtagtttc   1080 atgatttct gttacaccta acttttttgtg tggtgccctc ctccttgtca atattaatgt   1140
taaagtgcaa ttcttttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaagaga atcttttaa gcaaggattt    1380 tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca aagtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt tccttttctt cccaattttt   2700
cagttgaaaa aggtatatgc gtcaggcgac ctctgaaatt aacaaaaaat ttccagtcat   2760
```

```
cgaatttgat tctgtgcgat agcgccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttttgaac acacatgaac    3000 aaggaagtac aggacaattg attttgaaga gaatgtggat tttgatgtaa ttgttgggat    3060
tccattttta ataaggcaat aatattaggt atgtggatat actagaagtt ctcctcgagg    3120
gtcgatatgc ggtgtgaaat accgcacaga tgcgtaagga gaaaataccg catcaggaaa    3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420
caagtttttt ggggtcgagg tgccgtaaag cactaaatcg gaaccctaaa gggagccccc    3480
gatttagagc ttgacgggga agccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacccct tgaaatagac atcgtgatga ttaccgttta acaatgtttt    4560
tgaggcacca aacataacag gacctaatgc caattcaccg ataccggct tatttttagg    4620 cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct acaatagat ggtacgacac ccaacattgt    4920
gacctttgca tcttgaacaa atttagcgaa accagagact aaaggactac cgttgtacaa    4980
ggcaatagat gcaccattta acaaactagc ataaccaaac caaggaccca tcatccaacc    5040
caaattagtt ggccatacta taacgtcacc ttttctaata tccaaatgag accaaccatc    5100
```

```
agcagcagcc ttcaatgggg tggcttgtgt ccaaggaatt gcttttggtt cacctgtagt     5160
accactggag aataagatgt tagtataagc atcaacaggt tgttctctgg cagtaaactc     5220
gcagttttta aactccttgg ctctttctaa aaagtaatcc aagatatgt caccatctct      5280 caattctgca ccaatgttag aaccactaca agggataact attgccattg gggatttagc     5340
ttcaactact cttgaataca atggtattct cttttacct ctgatgatgt gatcttgtgt      5400
gaaaattgcc ttagctttgg ataatctcaa tctagttgag atttcagggg cggaaaatga     5460
atctgctata gagacaacta cgtaaccagc caatactatg gccaaatata taacaacagc    5520
atcaacatgc attggcatat cgatggctat tgcacaacct ttttctaaac ccatttcttc     5580
caatgcataa ccaaccaacc aaactctctt tctcaattga tctaatgtca acttattcaa     5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag ggtctggaat     6000 ccaagcaggt ggggctggac cgaaatcctt gtagcaacca taaacaaca tttggtgtaa     6060 ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt actttttttt tggatggacg    6300
caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaccttca aatgaacgaa tcaaattaac aaccatagga tgataatgcg     6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020
aaatattttg attcaagatg aatttccaga ttattatttt agagttacta aatctgaaca    7080
tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat gggtaaaga     7260 tgcttgtgct aaagctatta agaatggggg tcaaccaaaa tctaaaatta ctcatttgat    7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta agatattgc tgaaaataat aaaggtgcta gagttttggc     7500
```

```
tgtttgttgt gatatgactg cttgtttgtt tagaggtcca tctgattcta atttggaatt    7560
gttggttggt caagctattt ttggtgatgg tgctgctgct gttattgttg gtgctgaacc    7620
agatgaatct gttggtgaaa gaccaatttt tgaattggtt tctactggtc aaactttttt    7680
gccaaattct gaaggtacta ttggtggtca tattagagaa gctggtttga tgtttgattt    7740
gcataaagat gttccaatgt tgatttctaa taatattgaa aaatgtttga ttgaagcttt    7800
tactccaatt ggtatttctg attggaattc tattttttgg attactcatc caggtggtaa    7860
agctattttg gataaagttg aagaaaaatt gcatttgaaa tctgataaat ttgttgattc    7920
tagacatgtt ttgtctgaac atggtaatat gtcttcttct actgttttgt ttgttatgga    7980
tgaattgaga aaaagatctt tggaagaagg taaatctact actggtgatg gttttgaatg    8040
gggtgttttg tttggttttg gtccaggttt gactgttgaa agagttgttt tgagatctgt    8100
tccaattaat tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaattttttca agacctacgt taatttggtc aacattatac ctgctatgaa    8280
agatgtatac tggggtaaag acgttacaca aagaaagaa gaaggttata cacacattgt    8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct ccccccacat ccgctctaac    8580
cgaaaaggaa ggagttagac aacctgaagt ctaggtccct atttattttt ttatagttat    8640
gttagtatta agaacgttat ttatatttca aattttctt ttttttctgt acagacgcgt    8700
gtacgcatgt aacattatac tgaaaacctt gcttgagaag gttttgggac gctcgaaggc    8760
tttaatttgc ggccggtacc cagcttttgt tccctttagt gagggttaat tccgagcttg    8820
gcgtaatcat ggtcatagct gtttcctgtg tgaaattgtt atccgctcac aattccacac    8880
aacataggag ccggaagcat aaagtgtaaa gcctggggtg cctaatgagt gaggtaactc    8940
acattaattg cgttgcgctc actgcccgct ttccagtcgg gaaacctgtc gtgccagctg    9000
cattaatgaa tcggccaacg cgcggggaga ggcggtttgc gtattgggcg ctcttccgct    9060
tcctcgctca ctgactcgct gcgctcggtc gttcggctgc ggcgagcggt atcagctcac    9120
tcaaaggcgg taatacggtt atccacagaa tcaggggata acgcaggaaa gaacatgtga    9180
gcaaaaggcc agcaaaaggc caggaaccgt aaaaaggccg cgttgctggc gttttttccat    9240
aggctcggcc cccctgacga gcatcacaaa aatcgacgct caagtcagag gtggcgaaac    9300
ccgacaggac tataaagata ccaggcgttc cccctggaa gctccctcgt gcgctctcct    9360
gttccgaccc tgccgcttac cggatacctg tccgccttc tcccttcggg aagcgtggcg    9420
ctttctcaat gctcacgctg taggtatctc agttcggtgt aggtcgttcg ctccaagctg    9480
ggctgtgtgc acgaaccccc cgttcagccc gaccgctgcg ccttatccgg taactatcgt    9540
cttgagtcca acccggtaag acacgactta tcgccactgg cagcagccac tggtaacagg    9600
attagcagag cgaggtatgt aggcggtgct acagagttct tgaagtggtg gcctaactac    9660
ggctacacta gaaggacagt atttggtatc tgcgctctgc tgaagccagt taccttcgga    9720
aaaagagttg gtagctcttg atccggcaaa caaaccaccg ctggtagcgg tggtttttt    9780
gtttgcaagc agcagattac gcgcagaaaa aaaggatctc aagaagatcc tttgatcttt    9840
```

| | |
|---|---|
| tctacggggt ctgacgctca gtggaacgaa aactcacgtt aagggatttt ggtcatgaga | 9900 |
| ttatcaaaaa ggatcttcac ctagatcctt ttaaattaaa aatgaagttt taaatcaatc | 9960 |
| taaagtatat atgagtaaac ttggtctgac agttaccaat gcttaatcag tgaggcacct | 10020 |
| atctcagcga tctgtctatt tcgttcatcc atagttgcct gactgcccgt cgtgtagata | 10080 |
| actacgatac gggagggctt accatctggc cccagtgctg caatgatacc gcgagaccca | 10140 |
| cgctcaccgg ctccagattt atcagcaata accagccag ccggaagggc cgagcgcaga | 10200 |
| agtggtcctg caactttatc cgcctccatc cagtctatta attgttgccg ggaagctaga | 10260 |
| gtaagtagtt cgccagttaa tagtttgcgc aacgttgttg ccattgctac aggcatcgtg | 10320 |
| gtgtcacgct cgtcgtttgg tatggcttc | 10349 |

<210> SEQ ID NO 78
<211> LENGTH: 10367
<212> TYPE: DNA
<213> ORGANISM: Artificial Sequence
<220> FEATURE:
<223> OTHER INFORMATION: Codon Optimized

<400> SEQUENCE: 78

| | |
|---|---|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |
| ttctgtgact ggtgagtact caaccaagtc attctgagaa tagtgtatgc ggcgaccgag | 240 |
| ttgctcttgc ccggcgtcaa tacgggataa taccgcgcca catagcagaa ctttaaaagt | 300 |
| gctcatcatt ggaaaacgtt cttcgggcg aaaactctca aggatcttac cgctgttgag | 360 |
| atccagttcg atgtaaccca ctcgtgcacc caactgatct tcagcatctt ttactttcac | 420 |
| cagcgtttct gggtgagcaa aacaggaag gcaaaatgcc gcaaaaaagg gaataagggc | 480 |
| gacacggaaa tgttgaatac tcatactctt ccttttcaa tattattgaa gcatttatca | 540 |
| gggttattgt ctcatgagcg gatacatatt tgaatgtatt tagaaaaata aacaaatagg | 600 |
| ggttccgcgc acatttcccc gaaaagtgcc acctgacgtc taagaaacca ttattatcat | 660 |
| gacattaacc tataaaaata ggcgtatcac gaggcccttt cgtctcgcgc gtttcggtga | 720 |
| tgacggtgaa aacctctgac acatgcagct cccggagacg gtcacagctt gtctgtaagc | 780 |
| ggatgccggg agcagacaag cccgtcaggg cgcgtcagcg ggtgttggcg ggtgtcgggg | 840 |
| ctggcttaac tatgcggcat cagagcagat tgtactgaga gtgcaccata tcgactacgt | 900 |
| cgtaaggccg tttctgacag agtaaaattc ttgagggaac tttcaccatt atgggaaatg | 960 |
| gttcaagaag gtattgactt aaactccatc aaatggtcag gtcattgagt ttttttatt | 1020 |
| tgttgtattt tttttttttt agagaaaatc ctccaatatc aaattaggaa tcgtagtttc | 1080 |
| atgattttct gttacaccta acttttgtg tggtgccctc ctccttgtca atattaatgt | 1140 |
| taaagtgcaa ttcttttcc ttatcacgtt gagccattag tatcaatttg cttacctgta | 1200 |
| ttcctttact atcctccttt ttctccttct tgataaatgt atgtagattg cgtatatagt | 1260 |
| ttcgtctacc ctatgaacat attccatttt gtaattcgt gtcgtttcta ttatgaatt | 1320 |
| catttataaa gtttatgtac aaatatcata aaaaagaga atctttttaa gcaaggattt | 1380 |
| tcttaacttc ttcggcgaca gcatcaccga cttcggtggt actgttggaa ccacctaaat | 1440 |
| caccagttct gatacctgca tccaaaacct ttttaactgc atcttcaatg gccttacctt | 1500 |
| cttcaggcaa gttcaatgac aatttcaaca tcattgcagc agacaagata gtggcgatag | 1560 |

```
ggtcaacctt attctttggc aaatctggag cagaaccgtg gcatggttcg tacaaaccaa    1620
atgcggtgtt cttgtctggc aaagaggcca aggacgcaga tggcaacaaa cccaaggaac    1680
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca ataggcaat ggtggctcat     1920 gttgtagggc catgaaagcg gccattcttg tgattctttg cacttctgga acggtgtatt    1980
gttcactatc ccaagcgaca ccatcaccat cgtcttcctt tctcttacca aagtaaatac    2040
ctcccactaa ttctctgaca acaacgaagt cagtaccttt agcaaattgt ggcttgattg    2100
gagataagtc taaagagag tcggatgcaa agttacatgg tcttaagttg gcgtacaatt     2160
gaagttcttt acggattttt agtaaacctt gttcaggtct aacactaccg gtacccatt     2220 taggaccacc cacagcacct aacaaaacgg catcaacctt cttggaggct tccagcgcct    2280
catctggaag tgggacacct gtagcatcga tagcagcacc accaattaaa tgattttcga    2340
aatcgaactt gacattggaa cgaacatcag aaatagcttt aagaaccta atggcttcgg     2400 ctgtgatttc ttgaccaacg tggtcacctg gcaaaacgac gatcttctta ggggcagaca    2460 tagggcaga cattgaatg gtatatcctt gaaatatata tatatattgc tgaaatgtaa       2520
aaggtaagaa aagttagaaa gtaagacgat tgctaaccac ctattggaaa aaacaatagg    2580
tccttaaata atattgtcaa cttcaagtat tgtgatgcaa gcatttagtc atgaacgctt    2640
ctctattcta tatgaaaagc cggttccggc ctctcacctt tcctttttct cccaattttt    2700
cagttgaaaa aggtatatgc gtcaggcgac tctgaaatt aacaaaaaat ttccagtcat     2760
cgaatttgat tctgtgcgat agcgccctg tgtgttctcg ttatgttgag gaaaaaata     2820 atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac      3000 aaggaagtac aggacaattg attttgaaga gaatgtggat tttgatgtaa ttgttgggat    3060 tccatttta ataaggcaat aatattaggt atgtggatat actagaagtt ctcctcgagg     3120
gtcgatatgc ggtgtgaaat accgcacaga tgcgtaagga gaaataccg catcaggaaa     3180 ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaccgtc tatcagggcg atggcccact acgtgaacca tcaccctaat     3420
caagtttttt ggggtcgagg tgccgtaaag cactaaatcg gaaccctaaa gggagccccc    3480
gatttagagc ttgacgggga agccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct ttcgctatt acgccagctg gcgaaggggg     3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
```

-continued

```
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggggag ggcgtgaatg taagcgtgac ataactaatt   4080
acatgatcat tcgaaatgac tgaattgttg tctcaaaact cttctcatga tcttgtttgt    4140
tgcagttcta ggtaaggatg acaatgggac aactctagta actttgaata atgggttcaa   4200
tttcttttgc aaacccaagt taaaggataa tctcaattgg ttcaaatcaa tggttgtgtc   4260
gtttgaatcc ttcaatacga aaaatatgac caattgttct ggaccaccac ccaaaggtgg   4320
aacaccaata gcagtggttt caaaaactct gtcatctact tcattacaga ctctttcgat   4380
ttcgatagaa ctaattttga taccaccgat gttcatagtg tcatcggctc taccgtgtgc   4440
atggtagtaa ccgttagagg tcaattcgaa aatgtcacca tgtcttctca atacttcacc   4500
attcaaggtt ggcatacccct tgaaatagac atcgtgatga ttaccgttta acaatgtttt   4560
tgaggcacca acataacag gacctaatgc caattcaccg ataccctggct tattttttagg   4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt   4740
accaccacac atttctataa ctggcttgta gttagctcta cccattaacc acaaatattc   4800
gtctacatta gaggcttcac cggatgaaga aaagcatctt atggtggacc aatcgtaacc   4860
tgaaacacaa tttgtggatt tccatgatct tacaatagat ggtacgacac ccaacattgt   4920
gaccttttgca tcttgaacaa atttagcgaa accagagact aaaggactac cgttgtacaa   4980
ggcaatagat gcaccattta acaaactagc ataaccaac caaggaccca tcatccaacc    5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctcttttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
ggagtttacg ttcaagcaat ttttagctga gttcaagtaa ccaccaggta accattcaga   5760
accacctggg ttgttgatgt catctcttct caagatacat tctgggtcct tagagaaact   5820
aattttcatt tcatccatca atactgttct ccaatagact tcagggtttc taacagaaaa   5880
ttcttggaag tgagaaaaag aagaaattgg atctttgtac tttacaccca aaaattcttt   5940
acctctcttt tccaacaaag cacccaaatt agttgacttg acttttttcag ggtctggaat   6000
ccaagcaggt ggggctggac cgaaatcctt gtagcaacca taaacaaca tttggtgtaa   6060
ggagaaaggc aaatctggtg acaagatatg gttagcgatg ttgatccaag tttgagggt    6120
tgcagcacca taattacaaa cgatttctgc caatctacca tgtaatgttt ctgctacttc   6180
tgaggtgata cccaatgcga tgaaatctga ggcaacgact gaatccaagg acttatagtt   6240
tttacccatt cttttaatcg tggatccttc aaaaaattctt acttttttttt tggatggacg   6300
```

```
caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt ctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
ggaagaaatt aaaggtgttt tgaaagctaa agatgttggt tgtgttgcta ctattttggc    7020
tattggtact gctaatccat tgaattgtgt taatcaagat gaattttttgc attcttattt    7080 taaattgact aataatcata ataatacttc ttttaaagaa ttgtttacta gaatttgtaa    7140
taattctatg attaaaaata gatatatgca tttgactgaa gatattttga aagaaaatcc    7200
aaatttgtgt gattatgctg ctcaatcttt gaatactaga caagatatta aaattaaaga    7260
aattccaaaa ttggctgaaa gagctgctat ggttgctatt aaagaatggg gtaaaccaat    7320
ttctaatttg actcatatta ttttttcattc ttctactggt gctgctgata tgccaggtgc    7380
tgattatcaa ttggttaaat ctttgggttt gaatagatct attaaaagaa ttatgttgta    7440
taatttgggt tgttttgctg gtggtactgt tttgagagtt gctaaagatt tggttgaaaa    7500
taatttgggt gcttctgttt tggctgtttg tgctgaaatt acttctgctg atgctacttt    7560
tggtagattg tctgaagatg ataaaggtag attggttggt catgctatttt ttggtgatgg    7620 tgctgctgct ttggttattg gtaatgctga tgatccagaa aataaaggtt tgtttcaaat    7680
tgtttctact tctcaaacta ttttgccaaa ttctgaaggt tgtattgaag gtcatattag    7740
agaagatggt gttacttta ctttgtctcc aagagttcca aaattgattg gtgataatat    7800
tgaaacttgt ttgatggaag cttttactcc atttaaaatt tctgattgga attctttgtt    7860
ttgggttgtt catccaggtg gtgctgctat tttgagagaa gttgaatcta gagttggttt    7920
ggaacaagaa aaattgagag cttcttggca tgttttgaga gaatatggta atatttcttc    7980
tgcttctgtt ttgtttatttt tggatgaaat gagaaataaa tctttggaag aaggtagaaa    8040
aactactggt gaaggtaaaa attggggtgt tttgtttggt tttggtccag gtttgactgt    8100
tgaaacttgt gttttgcatt ctattccaat tgaaggtaga ggttccttgt aacttgtgg    8160 tgacgttgaa gaaacccag gtcctatggc cgtcaagcat ttgatagtat tgaagtttaa    8220
agatgaaatc acagaagctc aaaaggaaga attttttcaag acctacgtta atttggtcaa    8280
cattatacct gctatgaaag atgtatactg gggtaaagac gttacacaaa agaaagaaga    8340
aggttataca cacattgtcg aagtaacctt cgaatcagtt gaaactatcc aagattacat    8400
cattcatcca gctcacgttg gttttggtga cgttacaga tccttctggg aaaaattgtt    8460
gatcttcgat tacaccccaa gaaagtgatg atgggctgca ggaattcgat atcaagctta    8520
tcgataccgt cgacctcgag tcatgtaatt agttatgtca cgcttacatt cacgccctcc    8580
ccccacatcc gctctaaccg aaaaggaagg agttagacaa cctgaagtct aggtccctat    8640
```

```
ttatttttt  atagttatgt  tagtattaag  aacgttattt  atatttcaaa  ttttctttt    8700 ttttctgtac  agacgcgtgt  acgcatgtaa  cattatactg  aaaaccttgc  ttgagaaggt   8760
tttgggacgc  tcgaaggctt  taatttgcgg  ccggtaccca  gcttttgttc  cctttagtga   8820
gggttaattc  cgagcttggc  gtaatcatgg  tcatagctgt  ttcctgtgtg  aaattgttat   8880
ccgctcacaa  ttccacacaa  cataggagcc  ggaagcataa  agtgtaaagc  ctggggtgcc   8940
taatgagtga  ggtaactcac  attaattgcg  ttgcgctcac  tgcccgcttt  ccagtcggga   9000
aacctgtcgt  gccagctgca  ttaatgaatc  ggccaacgcg  cggggagagg  cggtttgcgt   9060
attgggcgct  cttccgcttc  ctcgctcact  gactcgctgc  gctcggtcgt  tcggctgcgg   9120
cgagcggtat  cagctcactc  aaaggcggta  atacggttat  ccacagaatc  aggggataac   9180
gcaggaaaga  acatgtgagc  aaaaggccag  caaaaggcca  ggaaccgtaa  aaaggccgcg   9240
ttgctggcgt  ttttccatag  gctcggcccc  cctgacgagc  atcacaaaaa  tcgacgctca   9300
agtcagaggt  ggcgaaaccc  gacaggacta  taaagatacc  aggcgttccc  cctggaagc   9360 tccctcgtgc  gctctcctgt  tccgaccctg  ccgcttaccg  gatacctgtc  gcctttctc   9420 ccttcgggaa  gcgtggcgct  ttctcaatgc  tcacgctgta  ggtatctcag  ttcggtgtag   9480
gtcgttcgct  ccaagctggg  ctgtgtgcac  gaaccccccg  ttcagcccga  ccgctgcgcc   9540
ttatccggta  actatcgtct  tgagtccaac  ccggtaagac  acgacttatc  gccactggca   9600
gcagccactg  gtaacaggat  tagcagagcg  aggtatgtag  cggtgctac  agagttcttg   9660 aagtggtggc  ctaactacgg  ctacactaga  aggacagtat  ttggtatctg  cgctctgctg   9720
aagccagtta  ccttcggaaa  aagagttggt  agctcttgat  ccggcaaaca  aaccaccgct   9780
ggtagcggtg  gttttttgt  ttgcaagcag  cagattacgc  gcagaaaaaa  aggatctcaa   9840
gaagatcctt  tgatctttc  tacggggtct  gacgctcagt  ggaacgaaaa  ctcacgttaa   9900
gggattttgg  tcatgagatt  atcaaaaagg  atcttcacct  agatcctttt  aaattaaaaa   9960
tgaagtttta  aatcaatcta  agtatatat  gagtaaactt  ggtctgacag  ttaccaatgc  10020
ttaatcagtg  aggcacctat  ctcagcgatc  tgtctatttc  gttcatccat  agttgcctga  10080
ctgcccgtcg  tgtagataac  tacgatacgg  gagggcttac  catctggccc  cagtgctgca  10140
atgataccgc  gagacccacg  ctcaccggct  ccagatttat  cagcaataaa  ccagccagcc  10200
ggaagggccg  agcgcagaag  tggtcctgca  actttatccg  cctccatcca  gtctattaat  10260
tgttgccggg  aagctagagt  aagtagttcg  ccagttaata  gtttgcgcaa  cgttgttgcc  10320
attgctacag  gcatcgtggt  gtcacgctcg  tcgtttggta  tggcttc              10367
```

<210> SEQ ID NO 79  
<211> LENGTH: 10349  
<212> TYPE: DNA  
<213> ORGANISM: Artificial Sequence  
<220> FEATURE:  
<223> OTHER INFORMATION: Codon Optimized

<400> SEQUENCE: 79

```
attcagctcc  ggttcccaac  gatcaaggcg  agttacatga  tcccccatgt  tgtgaaaaaa    60
agcggttagc  tccttcggtc  ctccgatcgt  tgtcagaagt  aagttggccg  cagtgttatc   120
actcatggtt  atggcagcac  tgcataattc  tcttactgtc  atgccatccg  taagatgctt   180
ttctgtgact  ggtgagtact  caaccaagtc  attctgagaa  tagtgtatgc  ggcgaccgag   240
ttgctcttgc  ccggcgtcaa  tacgggataa  taccgcgcca  catagcagaa  ctttaaaagt   300
gctcatcatt  ggaaaacgtt  cttcggggcg  aaaactctca  aggatcttac  cgctgttgag   360
```

```
atccagttcg atgtaaccca ctcgtgcacc caactgatct tcagcatctt ttactttcac      420
cagcgtttct gggtgagcaa aaacaggaag gcaaaatgcc gcaaaaagg gaataagggc       480 gacacggaaa tgttgaatac tcatactctt ccttttcaa tattattgaa gcatttatca      540
gggttattgt ctcatgagcg gatacatatt tgaatgtatt tagaaaaata aacaaatagg      600
ggttccgcgc acatttcccc gaaaagtgcc acctgacgtc taagaaacca ttattatcat      660
gacattaacc tataaaaata ggcgtatcac gaggcccttt cgtctcgcgc gtttcggtga      720
tgacggtgaa aacctctgac acatgcagct cccggagacg gtcacagctt gtctgtaagc      780
ggatgccggg agcagacaag cccgtcaggg cgcgtcagcg ggtgttggcg ggtgtcgggg      840
ctggcttaac tatgcggcat cagagcagat tgtactgaga gtgcaccata tcgactacgt      900
cgtaaggccg tttctgacag agtaaaattc ttgagggaac tttcaccatt atgggaaatg      960
gttcaagaag gtattgactt aaactccatc aaatggtcag gtcattgagt gttttttatt     1020
tgttgtattt tttttttttt agagaaaatc ctccaatatc aaattaggaa tcgtagtttc     1080
atgattttct gttcaccta acttttgtg tggtgccctc ctccttgtca atattaatgt       1140
taaagtgcaa ttcttttcc ttatcacgtt gagccattag tatcaatttg cttacctgta      1200
ttcctttact atcctccttt ttctccttct tgataaatgt atgtagattg cgtatatagt     1260
ttcgtctacc ctatgaacat attccatttt gtaatttcgt gtcgtttcta ttatgaattt     1320
catttataaa gtttatgtac aaatatcata aaaaaagaga atcttttaa gcaaggattt      1380 tcttaacttc ttcggcgaca gcatcaccga cttcggtggt actgtggaa ccacctaaat      1440 caccagttct gatacctgca tccaaaacct ttttaactgc atcttcaatg gccttacctt     1500
cttcaggcaa gttcaatgac aatttcaaca tcattgcagc agacaagata gtggcgatag     1560
ggtcaacctt attctttggc aaatctggag cagaaccgtg gcatggttcg tacaaaccaa     1620
atgcggtgtt cttgtctggc aaagaggcca aggacgcaga tggcaacaaa cccaaggaac     1680
ctgggataac ggaggcttca tcggagatga tatcaccaaa catgttgctg gtgattataa     1740
taccatttag gtgggttggg ttcttaacta ggatcatggc ggcagaatca atcaattgat     1800
gttgaacctt caatgtaggg aattcgttct tgatggtttc ctccacagtt tttctccata     1860
atcttgaaga ggccaaaaca ttagctttat ccaaggacca aataggcaat ggtggctcat     1920
gttgtagggc catgaaagcg gccattcttg tgattctttg cacttctgga acggtgtatt     1980
gttcactatc ccaagcgaca ccatcaccat cgtcttcctt tctcttacca aagtaaatac     2040
ctcccactaa ttctctgaca acaacgaagt cagtaccttt agcaaattgt ggcttgattg     2100
gagataagtc taaaagagag tcggatgcaa agttacatgg tcttaagttg cgtacaatt      2160 gaagttcttt acggatttt agtaaacctt gttcaggtct aacactaccg gtacccatt       2220 taggaccacc cacagcacct aacaaaacgg catcaacctt cttggaggct tccagcgcct     2280
catctggaag tgggacacct gtagcatcga tagcagcacc accaattaaa tgattttcga     2340
aatcgaactt gacattggaa cgaacatcag aaatagcttt aagaacctta atggcttcgg     2400
ctgtgatttc ttgaccaacg tggtcacctg gcaaaacgac gatcttctta ggggcagaca     2460
taggggcaga cattagaatg gtatatcctt gaaatatata tatatattgc tgaaatgtaa     2520
aaggtaagaa aagttagaaa gtaagacgat tgctaaccac ctattggaaa aaacaatagg     2580
tccttaaata atattgtcaa cttcaagtat tgtgatgcaa gcatttagtc atgaacgctt     2640
ctctattcta tatgaaaagc cggttccggc ctctcacctt tcctttttct cccaattttt     2700
```

```
cagttgaaaa aggtatatgc gtcaggcgac ctctgaaatt aacaaaaaat ttccagtcat    2760
cgaatttgat tctgtgcgat agcgcccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttttgaac acacatgaac    3000 aaggaagtac aggacaattg attttgaaga gaatgtggat tttgatgtaa ttgttgggat    3060
tccattttta ataaggcaat aatattaggt atgtggatat actagaagtt ctcctcgagg    3120
gtcgatatgc ggtgtgaaat accgcacaga tgcgtaagga gaaataccg catcaggaaa    3180 ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420 caagttttttt ggggtcgagg tgccgtaaag cactaaatcg gaaccctaaa gggagccccc    3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaggataa tctcaattgg ttcaaatcaa tggttgtgtc    4260
gtttgaatcc ttcaatacga aaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcataccct tgaaatagac atcgtgatga ttaccgttta acaatgtttt    4560
tgaggcacca aacataacag gacctaatgc caattcaccg ataccctggcт tattttttagg    4620 cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaccaaac caaggaccca tcatccaacc    5040
caaattagtt ggccatacta taacgtcacc ttttctaata tccaaatgag accaaccatc    5100
```

| | |
|---|---|
| agcagcagcc ttcaatgggg tggcttgtgt ccaaggaatt gcttttggtt cacctgtagt | 5160 |
| accactggag aataagatgt tagtataagc atcaacaggt tgttctctgg cagtaaactc | 5220 |
| gcagttttta aactccttgg ctctttctaa aaagtaatcc caagatatgt caccatctct | 5280 |
| caattctgca ccaatgttag aaccactaca agggataact attgccattg gggatttagc | 5340 |
| ttcaactact cttgaataca atggtattct cttttacct ctgatgatgt gatcttgtgt | 5400 |
| gaaaattgcc ttagctttgg ataatctcaa tctagttgag atttcagggg cggaaaatga | 5460 |
| atctgctata gagacaacta cgtaaccagc caatactatg ccaaatata taacaacagc | 5520 |
| atcaacatgc attggcatat cgatggctat tgcacaacct ttttctaaac ccatttcttc | 5580 |
| caatgcataa ccaaccaacc aaactctctt tctcaattga tctaatgtca acttattcaa | 5640 |
| aggcaagtca tcgttaccct cgtctctcca aacgatcata gtatcgttca atttcttatt | 5700 |
| ggagtttacg ttcaagcaat ttttagctga gttcaagtaa ccaccaggta accattcaga | 5760 |
| accacctggg ttgttgatgt catctcttct caagatacat tctgggtcct tagagaaact | 5820 |
| aattttcatt tcatccatca atactgttct ccaatagact tcagggtttc taacagaaaa | 5880 |
| ttcttggaag tgagaaaaag aagaaattgg atctttgtac tttacaccca aaaattcttt | 5940 |
| acctctcttt tccaacaaag cacccaaatt agttgacttg acttttcag ggtctggaat | 6000 |
| ccaagcaggt ggggctggac cgaaatcctt gtagcaacca taaacaaca tttggtgtaa | 6060 |
| ggagaaaggc aaatctggtg acaagatatg gttagcgatg ttgatccaag tttgaggggt | 6120 |
| tgcagcacca taattacaaa cgatttctgc caatctacca tgtaatgttt ctgctacttc | 6180 |
| tgaggtgata cccaatgcga tgaaatctga ggcaacgact gaatccaagg acttatagtt | 6240 |
| tttacccatt cttttaatcg tggatccttc aaaaattctt acttttttt tggatggacg | 6300 |
| caaagaagtt taataatcat attacatggc attaccacca tatacatatc catatacata | 6360 |
| tccatatcta atcttactta tatgttgtgg aaatgtaaag agccccatta tcttagccta | 6420 |
| aaaaaacctt ctctttggaa ctttcagtaa tacgcttaac tgctcattgc tatattgaag | 6480 |
| tacggattag aagccgccga gcgggtgaca gccctccgaa ggaagactct cctccgtgcg | 6540 |
| tcctcgtctt caccggtcgc gttcctgaaa cgcagatgtg cctcgcgccg cactgctccg | 6600 |
| aacaataaag attctacaat actagctttt atggttatga agaggaaaaa ttggcagtaa | 6660 |
| cctggcccca caaaccttca aatgaacgaa tcaaattaac aaccatagga tgataatgcg | 6720 |
| attagttttt tagccttatt tctggggtaa ttaatcagcg aagcgatgat ttttgatcta | 6780 |
| ttaacagata tataaatgca aaaactgcat aaccactta actaatactt tcaacatttt | 6840 |
| cggtttgtat tacttcttat tcaaatgtaa taaaagtatc aacaaaaaat tgttaatata | 6900 |
| cctctatact ttaacgtcaa ggagaaaaaa ccccggatcc gtaatacgac tcactataat | 6960 |
| gaatcatttg agagctgaag gtccagcttc tgttttggct attggtactg ctaatccaga | 7020 |
| aaatatttg attcaagatg aatttccaga ttattatttt agagttacta aatctgaaca | 7080 |
| tatgactcaa ttgaaagaaa aatttagaaa aatttgtgat aaatctatga ttagaaaaag | 7140 |
| aaattgtttt ttgaatgaag aacatttgaa acaaaatcca agattggttg aacatgaaat | 7200 |
| gcaaactttg gatgctagac aagatatgtt ggttgttgaa gttccaaaat tgggtaaaga | 7260 |
| tgcttgtgct aaagctatta agaatgggg tcaaccaaaa tctaaaatta ctcatttgat | 7320 |
| ttttacttct gcttctacta ctgatatgcc aggtgctgat tatcattgtg ctaaattgtt | 7380 |
| gggtttgtct ccatctgtta aaagagttat gatgtatcaa ttgggttgtt atggtggtgg | 7440 |

```
tactgttttg agaattgcta aagatattgc tgaaaataat aaaggtgcta gagttttggc    7500
tgtttgttgt gatattatgg cttgtttgtt tagaggtcca tctgattctg atttggaatt    7560
gttggttggt caagctattt ttggtgatgg tgctgctgct gttattgttg gtgctgaacc    7620
agatgaatct gttggtgaaa gaccaatttt tgaattggtt tctactggtc aaactatttt    7680
gccaaattct gaaggtacta ttggtggtca tattagagaa gctggtttga ttttttgattt   7740
gcataaagat gttccaatgt tgatttctaa taatattgaa aaatgtttga ttgaagcttt    7800
tactccaatt ggtatttctg attggaattc tattttttgg attactcatc caggtggtaa    7860
agctattttg gataaagttg aagaaaaatt gcatttgaaa tctgataaat ttgttgattc    7920
tagacatgtt ttgtctgaac atggtaatat gtcttcttct actgttttgt ttgttatgga    7980
tgaattgaga aaaagatctt tggaagaagg taaatctact actggtgatg gttttgaatg    8040
gggtgttttg tttggttttg gtccaggttt gactgttgaa agagttgttg ttagatctgt    8100
tccaattaaa tatgaaggta gaggttcctt gttaacttgt ggtgacgttg aagaaaaccc    8160
aggtcctatg gccgtcaagc atttgatagt attgaagttt aaagatgaaa tcacagaagc    8220
tcaaaaggaa gaattttttca agacctacgt taatttggtc aacattatac ctgctatgaa    8280
agatgtatac tggggtaaag acgttacaca aagaaagaa gaaggttata cacacattgt     8340
cgaagtaacc ttcgaatcag ttgaaactat ccaagattac atcattcatc cagctcacgt    8400
tggttttggt gacgtttaca gatccttctg ggaaaaattg ttgatcttcg attacacccc    8460
aagaaagtga tgatgggctg caggaattcg atatcaagct tatcgatacc gtcgacctcg    8520
agtcatgtaa ttagttatgt cacgcttaca ttcacgccct cccccacat ccgctctaac     8580
cgaaaaggaa ggagttagac aacctgaagt ctaggtccct atttatttt ttatagttat     8640
gttagtatta agaacgttat ttatatttca aatttttctt ttttttctgt acagacgcgt    8700
gtacgcatgt aacattatac tgaaaaccctt gcttgagaag gttttgggac gctcgaaggc   8760
tttaattttgc ggccggtacc cagcttttgt tccctttagt gagggttaat tccgagcttg    8820
gcgtaatcat ggtcatagct gtttcctgtg tgaaattgtt atccgctcac aattccacac    8880
aacataggag ccggaagcat aaagtgtaaa gcctggggtg cctaatgagt gaggtaactc    8940
acattaattg cgttgcgctc actgcccgct ttccagtcgg gaaacctgtc gtgccagctg    9000
cattaatgaa tcggccaacg cgcggggaga ggcggtttgc gtattgggcg ctcttccgct    9060
tcctcgctca ctgactcgct gcgctcggtc gttcggctgc ggcgagcggt atcagctcac   9120
tcaaaggcgg taatacggtt atccacagaa tcagggggata acgcaggaaa gaacatgtga   9180
gcaaaaggcc agcaaaaggc caggaaccgt aaaaaggccg cgttgctggc gttttttccat  9240
aggctcggcc cccctgacga gcatcacaaa aatcgacgct caagtcagag gtggcgaaac    9300
ccgacaggac tataaagata ccaggcgttc ccccctggaa gctccctcgt gcgctctcct    9360
gttccgaccc tgccgcttac cggatacctg tccgcctttc tcccttcggg aagcgtggcg    9420
ctttctcaat gctcacgctg taggtatctc agttcggtgt aggtcgttcg ctccaagctg    9480
ggctgtgtgc acgaaccccc cgttcagccc gaccgctgcg ccttatccgg taactatcgt    9540
cttgagtcca acccggtaag acacgactta tcgccactgg cagcagccac tggtaacagg    9600
attagcagag cgaggtatgt aggcggtgct acagagttct tgaagtggtg gcctaactac    9660
ggctacacta aaggacagt atttggtatc tgcgctctgc tgaagccagt taccttcgga     9720
aaaagagttg gtagctcttg atccggcaaa caaaccaccg ctggtagcgg tggtttttttt   9780
gtttgcaagc agcagattac gcgcagaaaa aaaggatctc aagaagatcc tttgatcttt    9840
```

```
tctacggggt ctgacgctca gtggaacgaa aactcacgtt aagggatttt ggtcatgaga    9900
ttatcaaaaa ggatcttcac ctagatcctt ttaaattaaa aatgaagttt taaatcaatc    9960
taaagtatat atgagtaaac ttggtctgac agttaccaat gcttaatcag tgaggcacct   10020
atctcagcga tctgtctatt tcgttcatcc atagttgcct gactgcccgt cgtgtagata   10080
actacgatac gggagggctt accatctggc cccagtgctg caatgatacc gcgagaccca   10140
cgctcaccgg ctccagattt atcagcaata accagccag ccggaagggc cgagcgcaga    10200
agtggtcctg caactttatc cgcctccatc cagtctatta attgttgccg gaagctaga    10260 gtaagtagtt cgccagttaa tagtttgcgc aacgttgttg ccattgctac aggcatcgtg   10320
gtgtcacgct cgtcgtttgg tatggcttc                                     10349
```

<210> SEQ ID NO 80
<211> LENGTH: 10394
<212> TYPE: DNA
<213> ORGANISM: Artificial Sequence
<220> FEATURE:
<223> OTHER INFORMATION: Codon Optimized

<400> SEQUENCE: 80

```
attcagctcc ggttcccaac gatcaaggcg agttacatga tcccccatgt tgtgaaaaaa      60
agcggttagc tccttcggtc ctccgatcgt tgtcagaagt aagttggccg cagtgttatc     120
actcatggtt atggcagcac tgcataattc tcttactgtc atgccatccg taagatgctt     180
ttctgtgact ggtgagtact caaccaagtc attctgagaa tagtgtatgc ggcgaccgag     240
ttgctcttgc ccggcgtcaa tacgggataa taccgcgcca catagcagaa ctttaaaagt     300
gctcatcatt ggaaaacgtt cttcggggcg aaaactctca aggatcttac cgctgttgag     360
atccagttcg atgtaaccca ctcgtgcacc caactgatct tcagcatctt ttactttcac     420
cagcgtttct gggtgagcaa aaacaggaag gcaaaatgcc gcaaaaaagg gaataagggc     480
gacacggaaa tgttgaatac tcatactctt ccttttcaa tattattgaa gcatttatca      540
gggttattgt ctcatgagcg gatacatatt tgaatgtatt tagaaaaata acaaataggg     600
ggttccgcgc acatttcccc gaaaagtgcc acctgacgtc taagaaacca ttattatcat     660
gacattaacc tataaaaata ggcgtatcac gaggcccttt cgtctcgcgc gtttcggtga     720
tgacggtgaa aacctctgac acatgcagct cccggagacg gtcacagctt gtctgtaagc     780
ggatgccggg agcagacaag cccgtcaggg cgcgtcagcg ggtgttggcg ggtgtcgggg     840
ctggcttaac tatgcggcat cagagcagat tgtactgaga gtgcaccata tcgactacgt     900
cgtaaggccg tttctgacag agtaaaattc ttgagggaac tttcaccatt atgggaaatg     960
gttcaagaag gtattgactt aaactccatc aaatggtcag gtcattgagt gtttttatt    1020 tgttgtattt tttttttttt agagaaaatc ctccaatatc aaattaggaa tcgtagtttc    1080 atgatttct gttacaccta acttttgtg tggtgccctc ctccttgtca atattaatgt      1140
taaagtgcaa ttcttttttcc ttatcacgtt gagccattag tatcaatttg cttacctgta    1200
ttcctttact atcctccttt ttctccttct tgataaatgt atgtagattg cgtatatagt    1260
ttcgtctacc ctatgaacat attccatttt gtaatttcgt gtcgtttcta ttatgaattt    1320
catttataaa gtttatgtac aaatatcata aaaaagaga atcttttaa gcaaggattt      1380 tcttaacttc ttcggcgaca gcatcaccga cttcggtggt actgtggaa ccacctaaat     1440 caccagttct gatacctgca tccaaaacct ttttaactgc atcttcaatg gccttacctt    1500
```

-continued

```
cttcaggcaa gttcaatgac aatttcaaca tcattgcagc agacaagata gtggcgatag    1560
ggtcaacctt attctttggc aaatctggag cagaaccgtg gcatggttcg tacaaaccaa    1620
atgcggtgtt cttgtctggc aaagaggcca aggacgcaga tggcaacaaa cccaaggaac    1680
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca aataggcaat ggtggctcat    1920
gttgtagggc catgaaagcg gccattcttg tgattctttg cacttctgga acggtgtatt    1980
gttcactatc ccaagcgaca ccatcaccat cgtcttcctt tctcttacca aagtaaatac    2040
ctcccactaa ttctctgaca acaacgaagt cagtaccttt agcaaattgt ggcttgattg    2100
gagataagtc taaaagagag tcggatgcaa agttacatgg tcttaagttg gcgtacaatt    2160
gaagttcttt acggattttt agtaaacctt gttcaggtct aacactaccg gtaccccatt    2220
taggaccacc cacagcacct aacaaaacgg catcaacctt cttggaggct tccagcgcct    2280
catctggaag tgggacacct gtagcatcga tagcagcacc accaattaaa tgattttcga    2340
aatcgaactt gacattggaa cgaacatcag aaatagcttt aagaacctta atggcttcgg    2400
ctgtgatttc ttgaccaacg tggtcacctg gcaaaacgac gatcttctta ggggcagaca    2460
taggggcaga cattagaatg gtatatcctt gaaatatata tatatattgc tgaaatgtaa    2520
aaggtaagaa aagttagaaa gtaagacgat tgctaaccac ctattggaaa aaacaatagg    2580
tccttaaata atattgtcaa cttcaagtat tgtgatgcaa gcatttagtc atgaacgctt    2640
ctctattcta tatgaaaagc cggttccggc ctctcacctt tcctttttct cccaattttt    2700
cagttgaaaa aggtatatgc gtcaggcgac tctgaaatt aacaaaaaat ttccagtcat    2760
cgaatttgat tctgtgcgat agcgcccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttttgaac acacatgaac    3000 aaggaagtac aggacaattg attttgaaga gaatgtggat tttgatgtaa ttgttgggat    3060 tccatttta ataaggcaat aatattaggt atgtggatat actagaagtt ctcctcgagg    3120
gtcgatatgc ggtgtgaaat accgcacaga tgcgtaagga gaaataccg catcaggaaa    3180 ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaccgtc tatcagggcg atggcccact acgtgaacca tcaccctaat    3420
caagtttttt ggggtcgagg tgccgtaaag cactaaatcg gaaccctaaa gggagccccc    3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacaggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
```

```
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
cctttcggt  tagagcggat gtgggggag  ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaggataa  tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctcttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcatacct  tgaaatagac atcgtgatga ttaccgttta acaatgtttt    4560
tgaggcacca acataacag  gacctaatgc caattcaccg atacctggct tatttttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagag ggtacgacac ccaacattgt    4920
gacctttgca tcttgaacaa atttagcgaa accagagact aaaggactac cgttgtacaa    4980
ggcaatagat gcaccattta acaaactagc ataaccaac  caaggaccca tcatccaacc    5040
caaattagtt ggccatacta acgtcacc   ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctcttttctaa aaagtaatcc caagatatgt caccatctct    5280
caattctgca ccaatgttag aaccactaca agggataact attgccattg gggatttagc    5340
ttcaactact cttgaataca atggtattct cttttacct  ctgatgatgt gatcttgtgt    5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttaccct cgtctctcca acgatcata  gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aatttttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag  ggtctggaat    6000
ccaagcaggt ggggctggac cgaaatcctt gtagcaacca taaacaaca  tttggtgtaa    6060
ggagaaaggc aaatctggtg acaagatatg gttagcgatg ttgatccaag tttgaggggt    6120
tgcagccaca taattacaaa cgatttctgc caatctacca tgtaatgttt ctgctacttc    6180
tgaggtgata cccaatgcga tgaaatctga ggcaacgact gaatccaagg acttatagtt    6240
```

```
tttacccatt cttttaatcg tggatccttc aaaaattctt acttttttt tggatggacg     6300 caaagaagtt taataatcat attacatggc attaccacca tatacatatc catatacata    6360
tccatatcta atcttactta tatgttgtgg aaatgtaaag agccccatta tcttagccta    6420
aaaaaacctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
gaatcatttg agagctgaag gtccagcttc tgttttggct attggtactg ctaatccaga    7020
aaatattttg attcaagatg aatttccaga ttattatttt agagttacta aatctgaaca    7080
tatgactcaa ttgaaagaaa aatttagaaa aatttgtgat aaatctatga ttagaaaaag    7140
aaattgtttt ttgaatgaag aacatttgaa acaaaatcca agattggttg aacatgaaat    7200
gcaaactttg gatgctagac aagatatgtt ggttgttgaa gttccaaaat tgggtaaaga    7260
tgcttgtgct aaagctatta agaatgggg tcaaccaaaa tctaaaatta ctcatttgat     7320
ttttacttct gcttctacta ctgatatgcc aggtgctgat tatcattgtg ctaaattgtt    7380
gggtttgtct ccatctgtta aaagagttat gatgtatcaa ttgggttgtt atggtggtgg    7440
tactgttttg agaattgcta aagatattgc tgaaaataat aaaggtgcta gagttttggc    7500
tgtttgttgt gatattatgg cttgtttgtt tagaggtcca tctgattctg atttggaatt    7560
gttggttggt caagctattt ttggtgatgg tgctgctgct gttattgttg gtgctgaacc    7620
agatgaatct gttggtgaaa gaccaatttt tgaattggtt tctactggtc aaactatttt    7680
gccaaattct gaaggtacta ttggtggtca tattagagaa gctggttttga ttttgatttt    7740 gcataaagat gttccaatgt tgatttctaa taatattgaa aaatgtttga ttgaagcttt    7800
tactccaatt ggtatttctg attggaattc tatttttgg attactcatc caggtggtaa    7860
agctattttg gataaagttg aagaaaaatt gcatttgaaa tctgataaat ttgttgattc    7920
tagacatgtt ttgtctgaac atggtaatat gtcttcttct actgttttgt ttgttatgga    7980
tgaattgaga aaaagatctt tggaagaagg taaatctact actggtgatg gtttttgaatg   8040 gggtgttttg tttggtttg tccaggtttt gactgttgaa agaggtagat ggagaaaagg     8100
taatttgcca ttggaaatgg atttgtctgg tgttttttt ttgggtttgg atcaagttga     8160
aggtagaggt tccttgttaa cttgtggtga cgttgaagaa aacccaggtc ctatggccgt    8220
caagcatttg atagtattga agtttaaaga tgaaatcaca gaagctcaaa aggaagaatt    8280
tttcaagacc tacgttaatt tggtcaacat tatacctgct atgaaagatg tatactgggg    8340
taaagacgtt acacaaaaga aagaagaagg ttatacacac attgtcgaag taaccttcga    8400
atcagttgaa actatccaag attacatcat tcatccagct cacgttggtt ttggtgacgt    8460
ttacagatcc ttctgggaaa aattgttgat cttcgattac accccaagaa agtgatgatg    8520
ggctgcagga attcgatatc aagcttatcg ataccgtcga cctcgagtca tgtaattagt    8580
tatgtcacgc ttacattcac gccctccccc cacatccgct ctaaccgaaa aggaaggagt    8640
```

-continued

| | | |
|---|---|---|
| tagacaacct gaagtctagg tccctattta ttttttttata gttatgttag tattaagaac | 8700 |
| gttatttata tttcaaattt ttctttttttt tctgtacaga cgcgtgtacg catgtaacat | 8760 |
| tatactgaaa accttgcttg agaaggtttt gggacgctcg aaggctttaa tttgcggccg | 8820 |
| gtacccagct tttgttccct ttagtgaggg ttaattccga gcttggcgta atcatggtca | 8880 |
| tagctgtttc ctgtgtgaaa ttgttatccg ctcacaattc cacacaacat aggagccgga | 8940 |
| agcataaagt gtaaagcctg gggtgcctaa tgagtgaggt aactcacatt aattgcgttg | 9000 |
| cgctcactgc ccgctttcca gtcgggaaac ctgtcgtgcc agctgcatta atgaatcggc | 9060 |
| caacgcgcgg ggagaggcgg tttgcgtatt gggcgctctt ccgcttcctc gctcactgac | 9120 |
| tcgctgcgct cggtcgttcg gctgcggcga gcggtatcag ctcactcaaa ggcggtaata | 9180 |
| cggttatcca cagaatcagg ggataacgca ggaaagaaca tgtgagcaaa aggccagcaa | 9240 |
| aaggccagga accgtaaaaa ggccgcgttg ctggcgtttt tccataggct cggcccccct | 9300 |
| gacgagcatc acaaaaatcg acgctcaagt caggaggtggc gaaacccgac aggactataa | 9360 |
| agataccagg cgttcccccc tggaagctcc ctcgtgcgct ctcctgttcc gaccctgccg | 9420 |
| cttaccggat acctgtccgc ctttctccct cgggaagcg tggcgctttc tcaatgctca | 9480 |
| cgctgtaggt atctcagttc ggtgtaggtc gttcgctcca agctgggctg tgtgcacgaa | 9540 |
| ccccccgttc agcccgaccg ctgcgcctta tccggtaact atcgtcttga gtccaacccg | 9600 |
| gtaagacacg acttatcgcc actggcagca gccactggta acaggattag cagagcgagg | 9660 |
| tatgtaggcg gtgctacaga gttcttgaag tggtggccta actacggcta cactagaagg | 9720 |
| acagtatttg gtatctgcgc tctgctgaag ccagttacct tcggaaaaag agttggtagc | 9780 |
| tcttgatccg gcaaacaaac caccgctggt agcggtggtt ttttttgtttg caagcagcag | 9840 |
| attacgcgca gaaaaaaagg atctcaagaa gatcctttga tcttttctac ggggtctgac | 9900 |
| gctcagtgga acgaaaactc acgttaaggg attttggtca tgagattatc aaaaaggatc | 9960 |
| ttcacctaga tccttttaaa ttaaaaatga agttttaaat caatctaaag tatatatgag | 10020 |
| taaacttggt ctgacagtta ccaatgctta atcagtgagg cacctatctc agcgatctgt | 10080 |
| ctatttcgtt catccatagt tgcctgactg cccgtcgtgt agataactac gatacgggag | 10140 |
| ggcttaccat ctggccccag tgctgcaatg ataccgcgag acccacgctc accggctcca | 10200 |
| gatttatcag caataaacca gccagccgga agggccgagc gcagaagtgg tcctgcaact | 10260 |
| ttatccgcct ccatccagtc tattaattgt tgccgggaag ctagagtaag tagttcgcca | 10320 |
| gttaatagtt tgcgcaacgt tgttgccatt gctacaggca tcgtggtgtc acgctcgtcg | 10380 |
| tttggtatgg cttc | 10394 |

<210> SEQ ID NO 81
<211> LENGTH: 10361
<212> TYPE: DNA
<213> ORGANISM: Artificial Sequence
<220> FEATURE:
<223> OTHER INFORMATION: Codon Optimized

<400> SEQUENCE: 81

| | | |
|---|---|---|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |
| ttctgtgact ggtgagtact caaccaagtc attctgagaa tagtgtatgc ggcgaccgag | 240 |

-continued

```
ttgctcttgc ccggcgtcaa tacgggataa taccgcgcca catagcagaa ctttaaaagt    300
gctcatcatt ggaaaacgtt cttcggggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt cctttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggccctt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gtttttatt   1020
tgttgtattt tttttttt agagaaaatc ctccaatatc aaattaggaa tcgtagtttc   1080
atgattttct gttacaccta acttttgtg tggtgccctc ctccttgtca atattaatgt   1140
taaagtgcaa ttcttttcc ttatcacgtt gagccattag tatcaatttg cttacctgta   1200
ttccttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gtttatgtac aaatatcata aaaaagaga atcttttaa gcaaggattt   1380
tcttaacttc ttcggcgaca gcatcaccga cttcggtggt actgttggaa ccacctaaat   1440
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaaccct caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca agtaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
```

```
ctctattcta tatgaaaagc cggttccggc ctctcacctt tccttttttct cccaattttt    2700
cagttgaaaa aggtatatgc gtcaggcgac ctctgaaatt aacaaaaaat ttccagtcat    2760
cgaatttgat tctgtgcgat agcgcccctg tgtgttctcg ttatgttgag gaaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttttgaac acacatgaac    3000
aaggaagtac aggacaattg attttgaaga gaatgtggat tttgatgtaa ttgttgggat    3060
tccatttttta ataaggcaat aatattaggt atgtggatat actagaagtt ctcctcgagg    3120
gtcgatatgc ggtgtgaaat accgcacaga tgcgtaagga gaaaataccg catcaggaaa    3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420
caagtttttt ggggtcgagg tgccgtaaag cactaaatcg gaaccctaaa gggagccccc    3480
gatttagagc ttgacgggga agccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcgt tagagcggat gtgggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcataccct tgaaatagac atcgtgatga ttaccgttta acaatgtttt    4560
tgaggcacca aacataacag gacctaatgc caattcaccg atacctggct tatttttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
```

-continued

| | | | | | |
|---|---|---|---|---|---|
| ggcaatagat | gcaccattta | acaaactagc | ataaaccaac | caaggaccca | tcatccaacc | 5040 |
| caaattagtt | ggccatacta | taacgtcacc | ttttctaata | tccaaatgag | accaaccatc | 5100 |
| agcagcagcc | ttcaatgggg | tggcttgtgt | ccaaggaatt | gcttttggtt | cacctgtagt | 5160 |
| accactggag | aataagatgt | tagtataagc | atcaacaggt | tgttctctgg | cagtaaactc | 5220 |
| gcagtttta | aactccttgg | ctctttctaa | aaagtaatcc | caagatatgt | caccatctct | 5280 |
| caattctgca | ccaatgttag | aaccactaca | agggataact | attgccattg | gggatttagc | 5340 |
| ttcaactact | cttgaataca | atggtattct | ctttttacct | ctgatgatgt | gatcttgtgt | 5400 |
| gaaaattgcc | ttagctttgg | ataatctcaa | tctagttgag | atttcagggg | cggaaaatga | 5460 |
| atctgctata | gagacaacta | cgtaaccagc | caatactatg | gccaaatata | taacaacagc | 5520 |
| atcaacatgc | attggcatat | cgatggctat | tgcacaacct | ttttctaaac | ccatttcttc | 5580 |
| caatgcataa | ccaaccaacc | aaactctctt | tctcaattga | tctaatgtca | acttattcaa | 5640 |
| aggcaagtca | tcgttaccct | cgtctctcca | aacgatcata | gtatcgttca | atttcttatt | 5700 |
| ggagtttacg | ttcaagcaat | ttttagctga | gttcaagtaa | ccaccaggta | accattcaga | 5760 |
| accacctggg | ttgttgatgt | catctcttct | caagatacat | tctgggtcct | tagagaaact | 5820 |
| aattttcatt | tcatccatca | atactgttct | ccaatagact | tcagggtttc | taacagaaaa | 5880 |
| ttcttggaag | tgagaaaaag | aagaaattgg | atctttgtac | tttacaccca | aaaattcttt | 5940 |
| acctctcttt | tccaacaaag | cacccaaatt | agttgacttg | actttttcag | ggtctggaat | 6000 |
| ccaagcaggt | ggggctggac | cgaaatcctt | gtagcaacca | taaacaaca | tttggtgtaa | 6060 |
| ggagaaaggc | aaatctggtg | acaagatatg | gttagcgatg | ttgatccaag | tttgaggggt | 6120 |
| tgcagcacca | taattacaaa | cgatttctgc | caatctacca | tgtaatgttt | ctgctacttc | 6180 |
| tgaggtgata | cccaatgcga | tgaaatctga | ggcaacgact | gaatccaagg | acttatagtt | 6240 |
| tttacccatt | cttttaatcg | tggatccttc | aaaaattctt | actttttttt | tggatggacg | 6300 |
| caaagaagtt | taataatcat | attacatggc | attaccacca | tatacatatc | catatacata | 6360 |
| tccatatcta | atcttactta | tatgttgtgg | aaatgtaaag | agccccatta | tcttagccta | 6420 |
| aaaaaacctt | ctctttggaa | ctttcagtaa | tacgcttaac | tgctcattgc | tatattgaag | 6480 |
| tacggattag | aagccgccga | gcgggtgaca | gccctccgaa | ggaagactct | cctccgtgcg | 6540 |
| tcctcgtctt | caccggtcgc | gttcctgaaa | cgcagatgtg | cctcgcgccg | cactgctccg | 6600 |
| aacaataaag | attctacaat | actagctttt | atggttatga | agaggaaaaa | ttggcagtaa | 6660 |
| cctggcccca | caaaccttca | aatgaacgaa | tcaaattaac | aaccatagga | tgataatgcg | 6720 |
| attagttttt | tagccttatt | tctggggtaa | ttaatcagcg | aagcgatgat | ttttgatcta | 6780 |
| ttaacagata | tataaatgca | aaaactgcat | aaccactta | actaatactt | tcaacatttt | 6840 |
| cggtttgtat | tacttcttat | tcaaatgtaa | taaagtatc | aacaaaaaat | tgttaatata | 6900 |
| cctctatact | ttaacgtcaa | ggagaaaaaa | ccccggatcc | gtaatacgac | tcactataat | 6960 |
| ggttactgtt | gaagaattta | gaaaagctca | agagctgaa | ggtccagcta | ctattatggc | 7020 |
| tattggtact | gctactccag | ctaattgtgt | tttgcaatct | gaatatccag | attattattt | 7080 |
| tagaattact | aattctgaac | ataaaactga | attgaaagaa | aaatttaaaa | gaatgtgtga | 7140 |
| taaatctatg | attagaaaaa | gatatatgca | tttgactgaa | gaaattttga | agaaaatcc | 7200 |
| aaatttgtgt | gcttatgaag | ctccatcttt | ggatgctaga | caagatatgg | ttgttgttga | 7260 |
| agttccaaaa | ttgggtaaag | aagctgctac | taaagctatt | aaagaatggg | gtcaaccaaa | 7320 |
| atctaaaatt | actcatttgg | tttttgtac | tacttctggt | gttgatatgc | caggtgctga | 7380 |

```
ttatcaattg actaaattgt tgggtttgag accatctgtt aaaagattga tgatgtatca   7440
acaaggttgt tttgctggtg gtactgtttt gagattggct aaagatttgg ctgaaaataa   7500
taaaggtgct agagttttgg ttgtttgttc tgaaattact gctgttactt ttagaggtcc   7560
aaatgatact catttggatt cttggttgg tcaagctttg tttggtgatg gttctgctgc    7620
tttgattgtt ggttctgatc caattccaga agttgaaaaa ccaattttg aattggtttc    7680
tgctgctcaa actattttgc cagattctga tggtgctatt gatggtcatt tgagagaagt   7740
tggtttgact tttcatttgt tgaaagatgt tccaggtttg atttctaaaa atattgaaaa   7800
atctttgaat gaagcttta aaccattggg tatttctgat tggaattctt tgttttggat   7860
tgctcatcca ggtggtccag ctattttgga tcaagttgaa tctaaattgg ctttgaaaac   7920
tgaaaaattg agagctacta gacatgtttt gtctgaatat ggtaatatgt cttctgcttg   7980
tgttttgttt attttggatg aaatgagaag aaaatgtgtt gaagatggtt tgaatactac   8040
tggtgaaggt ttggaatggg gtgttttgtt tggttttggt ccaggtttga ctgttgaaac   8100
tgttgttttg cattctgttg ctattgaagg tagaggttcc ttgttaactt gtggtgacgt   8160
tgaagaaaac ccaggtccta tggccgtcaa gcatttgata gtattgaagt ttaaagatga   8220
aatcacagaa gctcaaaagg aagaattttt caagacctac gttaatttgg tcaacattat   8280
acctgctatg aaagatgtat actggggtaa agacgttaca caaagaaag aagaaggtta    8340
tacacacatt gtcgaagtaa ccttcgaatc agttgaaact atccaagatt acatcattca   8400
tccagctcac gttggttttg gtgacgttta cagatccttc tgggaaaaat tgttgatctt   8460
cgattacacc ccaagaaagt gatgatgggc tgcaggaatt cgatatcaag cttatcgata   8520
ccgtcgacct cgagtcatgt aattagttat gtcacgctta cattcacgcc ctccccccac   8580
atccgctcta accgaaaagg aaggagttag acaacctgaa gtctaggtcc ctatttattt   8640
ttttatagtt atgttagtat taagaacgtt atttatattt caaattttc ttttttttct    8700
gtacagacgc gtgtacgcat gtaacattat actgaaaacc ttgcttgaga aggttttggg   8760
acgctcgaag gctttaattt gcggccggta cccagctttt gttcccttta gtgagggtta   8820
attccgagct tggcgtaatc atggtcatag ctgtttcctg tgtgaaattg ttatccgctc   8880
acaattccac acaacatagg agccggaagc ataaagtgta aagcctgggg tgcctaatga   8940
gtgaggtaac tcacattaat tgcgttgcgc tcactgcccg ctttccagtc gggaaacctg   9000
tcgtgccagc tgcattaatg aatcggccaa cgcgcgggga gaggcggttt gcgtattggg   9060
cgctcttccg cttcctcgct cactgactcg ctgcgctcgg tcgttcggct gcggcgagcg   9120
gtatcagctc actcaaaggc ggtaatacgg ttatccacag aatcagggga taacgcagga   9180
aagaacatgt gagcaaaagg ccagcaaaag gccaggaacc gtaaaaaggc cgcgttgctg   9240
gcgttttcc ataggctcgg ccccctgac gagcatcaca aaaatcgacg ctcaagtcag    9300
aggtggcgaa acccgacagg actataaaga taccaggcgt tccccctgg aagctccctc    9360
gtgcgctctc ctgttccgac cctgccgctt accggatacc tgtccgcctt tctcccttcg   9420
ggaagcgtgg cgctttctca atgctcacgc tgtaggtatc tcagttcggt gtaggtcgtt   9480
cgctccaagc tgggctgtgt gcacgaaccc ccgttcagc cgaccgctg cgccttatcc      9540
ggtaactatc gtcttgagtc aacccggta agacacgact tatcgccact ggcagcagcc    9600
actggtaaca ggattagcag agcgaggtat gtaggcggtg ctacagagtt cttgaagtgg   9660
tggcctaact acggctacac tagaaggaca gtatttggta tctgcgctct gctgaagcca   9720
```

| | | |
|---|---|---|
| gttaccttcg gaaaaagagt tggtagctct tgatccggca acaaaccac cgctggtagc | 9780 | |
| ggtggttttt ttgtttgcaa gcagcagatt acgcgcagaa aaaaaggatc tcaagaagat | 9840 | |
| cctttgatct tttctacggg gtctgacgct cagtggaacg aaaactcacg ttaagggatt | 9900 | |
| ttggtcatga gattatcaaa aaggatcttc acctagatcc ttttaaatta aaaatgaagt | 9960 | |
| tttaaatcaa tctaaagtat atatgagtaa acttggtctg acagttacca atgcttaatc | 10020 | |
| agtgaggcac ctatctcagc gatctgtcta tttcgttcat ccatagttgc ctgactgccc | 10080 | |
| gtcgtgtaga taactacgat acgggagggc ttaccatctg gccccagtgc tgcaatgata | 10140 | |
| ccgcgagacc cacgctcacc ggctccagat ttatcagcaa taaaccagcc agccggaagg | 10200 | |
| gccgagcgca gaagtggtcc tgcaacttta tccgcctcca tccagtctat taattgttgc | 10260 | |
| cgggaagcta gagtaagtag ttcgccagtt aatagtttgc gcaacgttgt tgccattgct | 10320 | |
| acaggcatcg tggtgtcacg ctcgtcgttt ggtatggctt c | 10361 | |

<210> SEQ ID NO 82
<211> LENGTH: 9767
<212> TYPE: DNA
<213> ORGANISM: Artificial Sequence
<220> FEATURE:
<223> OTHER INFORMATION: Codon Optimized

<400> SEQUENCE: 82

| | | |
|---|---|---|
| attcagctcc ggttcccaac gatcaaggcg agttacatga tcccccatgt tgtgaaaaaa | 60 | |
| agcggttagc tccttcggtc ctccgatcgt tgtcagaagt aagttggccg cagtgttatc | 120 | |
| actcatggtt atgcagcac tgcataattc tcttactgtc atgccatccg taagatgctt | 180 | |
| ttctgtgact ggtgagtact caaccaagtc attctgagaa tagtgtatgc ggcgaccgag | 240 | |
| ttgctcttgc ccggcgtcaa tacgggataa taccgcgcca catagcagaa ctttaaaagt | 300 | |
| gctcatcatt ggaaaacgtt cttcggggcg aaaactctca aggatcttac cgctgttgag | 360 | |
| atccagttcg atgtaaccca ctcgtgcacc caactgatct tcagcatctt ttactttcac | 420 | |
| cagcgtttct gggtgagcaa aaacaggaag gcaaaatgcc gcaaaaaagg gaataagggc | 480 | |
| gacacggaaa tgttgaatac tcatactctt cctttttcaa tattattgaa gcatttatca | 540 | |
| gggttattgt ctcatgagcg gatacatatt tgaatgtatt tagaaaaata aacaaatagg | 600 | |
| ggttccgcgc acatttcccc gaaaagtgcc acctgacgtc taagaaacca ttattatcat | 660 | |
| gacattaacc tataaaaata ggcgtatcac gaggcccttt cgtctcgcgc gtttcggtga | 720 | |
| tgacggtgaa aacctctgac acatgcagct cccggagacg gtcacagctt gtctgtaagc | 780 | |
| ggatgccggg agcagacaag cccgtcaggg cgcgtcagcg ggtgttggcg ggtgtcgggg | 840 | |
| ctggcttaac tatgcggcat cagagcagat tgtactgaga gtgcaccata tcgactacgt | 900 | |
| cgtaaggccg tttctgacag agtaaaattc ttgagggaac tttcaccatt atgggaaatg | 960 | |
| gttcaagaag gtattgactt aaactccatc aaatggtcag gtcattgagt gttttttatt | 1020 | |
| tgttgtattt tttttttttt agagaaaatc ctccaatatc aaattaggaa tcgtagtttc | 1080 | |
| atgattttct gttacaccta acttttgtg tggtgccctc ctccttgtca atattaatgt | 1140 | |
| taaagtgcaa ttcttttcc ttatcacgtt gagccattag tatcaatttg cttacctgta | 1200 | |
| ttcctttact atcctccttt ttctccttct tgataaatgt atgtagattg cgtatatagt | 1260 | |
| ttcgtctacc ctatgaacat attccatttt gtaattcgt gtcgtttcta ttatgaattt | 1320 | |
| catttataaa gtttatgtac aaatatcata aaaaagaga atcttttaa gcaaggattt | 1380 | |
| tcttaacttc ttcggcgaca gcatcaccga cttcggtggt actgttggaa ccacctaaat | 1440 | |

```
caccagttct gatacctgca tccaaaacct ttttaactgc atcttcaatg gccttacctt   1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca ataggcaat ggtggctcat    1920 gttgtagggc catgaaagcg gccattcttg tgattctttg cacttctgga acggtgtatt   1980
gttcactatc ccaagcgaca ccatcaccat cgtcttcctt tctcttacca agtaaatac    2040 ctcccactaa ttctctgaca caacgaagt cagtaccttt agcaaattgt ggcttgattg     2100
gagataagtc taaagagag tcggatgcaa agttacatgg tcttaagttg gcgtacaatt     2160
gaagttcttt acggattttt agtaaacctt gttcaggtct aacactaccg gtaccccatt   2220
taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaacctta atggcttcgg   2400
ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580
tccttaaata atattgtcaa cttcaagtat tgtgatgcaa gcatttagtc atgaacgctt   2640
ctctattcta tatgaaaagc cggttccggc ctctcacctt cctttttct cccaattttt     2700 cagttgaaaa aggtatatgc gtcaggcgac tctgaaatt aacaaaaaat ttccagtcat    2760
cgaatttgat tctgtgcgat agcgccctg tgtgttctcg ttatgttgag gaaaaaaata    2820
atggttgcta agagattcga actcttgcat cttacgatac ctgagtattc ccacagttaa   2880
ctgcggtcaa gatatttctt gaatcaggcg ccttagaccg ctcggccaaa caaccaatta   2940
cttgttgaga aatagagtat aattatccta taaatataac gttttgaac acacatgaac     3000 aaggaagtac aggacaattg attttgaaga gaatgtggat tttgatgtaa ttgttgggat   3060 tccatttta ataaggcaat aatattaggt atgtggatat actagaagtt ctcctcgagg     3120
gtcgatatgc ggtgtgaaat accgcacaga tgcgtaagga gaaataccg catcaggaaa   3180 ttgtaaacgt taatatttg ttaaaattcg cgttaaattt ttgttaaatc agctcatttt      3240
ttaaccaata ggccgaaatc ggcaaaatcc cttataaatc aaaagaatag accgagatag   3300
ggttgagtgt tgttccagtt tggaacaaga gtccactatt aaagaacgtg gactccaacg   3360
tcaaagggcg aaaaccgtc tatcagggcg atggcccact cgtgaaccat cacccctaat    3420
caagtttttt ggggtcgagg tgccgtaaag cactaaatcg aaccctaaa gggagccccc    3480 gatttagagc ttgacgggga agccggcga acgtggcgag aaggaaggg aagaaagcga    3540 aaggagcggg cgctagggcg ctggcaagtg tagcggtcac gctgcgcgta accaccacac   3600
ccgccgcgct taatgcgccg ctacagggcg cgtcgcgcca ttcgccattc aggctgcgca   3660
actgttggga agggcgatcg gtgcgggcct ttcgctatt acgccagctg gcgaagggg     3720 gatgtgctgc aaggcgatta agttgggtaa cgccagggtt ttcccagtca cgacgttgta   3780
```

-continued

```
aaacgacggc cagtgaattg taatacgact cactatagggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
ccttttcggt tagagcggat gtgggggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcataccct tgaaatagac atcgtgatga ttaccgtttta acaatgtttt    4560
tgaggcacca acataacag gacctaatgc caattcaccg atacctggct tattttttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gacctttgca tcttgaacaa atttagcgaa accagagact aaaggactac cgttgtacaa    4980
ggcaatagat gcaccattta acaaactagc ataaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagttttta aactccttgg ctcttttctaa aaagtaatcc caagatatgt caccatctct    5280
caattctgca ccaatgttag aaccactaca agggataact attgccattg gggatttagc    5340
ttcaactact cttgaataca atggtattct ctttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg gccaaatata taacaacagc    5520
atcaacatgc attggcatat cgatggctat tgcacaacct ttttctaaac ccatttcttc    5580
caatgcataa ccaaccaacc aaactctctt tctcaattga tctaatgtca acttattcaa    5640
aggcaagtca tcgttacccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttttcag ggtctggaat    6000
ccaagcaggt ggggctggac cgaaatcctt gtagcaacca taaaacaaca tttggtgtaa    6060
ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
```

```
tgaggtgata cccaatgcga tgaaatctga ggcaacgact gaatccaagg acttatagtt   6240
tttacccatt cttttaatcg tggatccttc aaaaattctt actttttttt tggatggacg   6300
caaagaagtt taataatcat attacatggc attaccacca tatacatatc catatacata   6360
tccatatcta atcttactta tatgttgtgg aaatgtaaag agccccatta tcttagccta   6420
aaaaaacctt ctctttggaa ctttcagtaa tacgcttaac tgctcattgc tatattgaag   6480
tacggattag aagccgccga gcgggtgaca gccctccgaa ggaagactct cctccgtgcg   6540
tcctcgtctt caccggtcgc gttcctgaaa cgcagatgtg cctcgcgccg cactgctccg   6600
aacaataaag attctacaat actagctttt atggttatga agaggaaaaa ttggcagtaa   6660
cctggcccca caaccttca atgaacgaa tcaaattaac aaccatagga tgataatgcg    6720
attagttttt tagccttatt tctggggtaa ttaatcagcg aagcgatgat ttttgatcta   6780
ttaacagata tataaatgca aaaactgcat aaccacttta actaatactt tcaacatttt   6840
cggtttgtat tacttcttat tcaaatgtaa taaaagtatc aacaaaaaat tgttaatata   6900
cctctatact ttaacgtcaa ggagaaaaaa ccccggatcc gtaatacgac tcactataat   6960
gaatcatttg agagctgaag gtccagcttc tgttttggct attggtactg ctaatccaga   7020
aaatattttg attcaagatg aatttccaga ttattatttt agagttacta aatctgaaca   7080
tatgactcaa ttgaaagaaa aatttagaaa aatttgtgat aaatctatga ttagaaaaag   7140
aaattgtttt ttgaatgaag aacatttgaa acaaaatcca agattggctg aacatgaaat   7200
gcaaactttg gatgctagac aagatatgtt ggttgttgaa gttccaaaat tgggtaaaga   7260
tgcttgtgct aaagctatta agaatggggg tcaaccaaaa tctaaaatta ctcatttgat   7320
ttttacttct gcttctacta ctgatatgcc aggtgctgat tatcattgtg ctaaattgtt   7380
gggtttgtct ccatctgtta aaagagttat gatgtatcaa ttgggttgtt atggtggtgg   7440
tactgttttg agaattgcta aagatattgc tgaaaataat aaaggtgcta gagttttggc   7500
tgtttgttgt gatattatgg cttttttttt tgaaggtaga ggttccttgt taacttgtgg   7560
tgacgttgaa gaaacccag gtcctatggc cgtcaagcat ttgatagtat tgaagtttaa    7620
agatgaaatc acagaagctc aaaaggaaga atttttcaag acctacgtta atttggtcaa   7680
cattatacct gctatgaaag atgtatactg gggtaaagac gttacacaaa agaaagaaga   7740
aggttataca cacattgtcg aagtaacctt cgaatcagtt gaaactatcc aagattacat   7800
cattcatcca gctcacgttg gttttggtga cgtttacaga tccttctggg aaaaattgtt   7860
gatcttcgat tacaccccaa gaaagtgatg atgggctgca ggaattcgat atcaagctta   7920
tcgataccgt cgacctcgag tcatgtaatt agttatgtca cgcttacatt cacgccctcc   7980
ccccacatcc gctctaaccg aaaaggaagg agttagacaa cctgaagtct aggtccctat   8040 ttatttttt atagttatgt tagtattaag aacgttattt atatttcaaa ttttttcttt     8100
ttttctgtac agacgcgtgt acgcatgtaa cattatactg aaaaccttgc ttgagaaggt   8160
tttgggacgc tcgaaggctt taatttgcgg ccggtaccca gcttttgttc cctttagtga   8220
gggttaattc cgagcttggc gtaatcatgg tcatagctgt ttcctgtgtg aaattgttat   8280
ccgctcacaa ttccacacaa cataggagcc ggaagcataa agtgtaaagc ctggggtgcc   8340
taatgagtga ggtaactcac attaattgcg ttgcgctcac tgcccgcttt ccagtcggga   8400
aacctgtcgt gccagctgca ttaatgaatc ggccaacgcg cggggagagg cggtttgcgt   8460
attgggcgct cttccgcttc ctcgctcact gactcgctgc gctcggtcgt tcggctgcgg   8520
```

| | |
|---|---:|
| cgagcggtat cagctcactc aaaggcggta atacggttat ccacagaatc aggggataac | 8580 |
| gcaggaaaga acatgtgagc aaaaggccag caaaaggcca ggaaccgtaa aaaggccgcg | 8640 |
| ttgctggcgt ttttccatag gctcggcccc cctgacgagc atcacaaaaa tcgacgctca | 8700 |
| agtcagaggt ggcgaaaccc gacaggacta taaagatacc aggcgttccc ccctggaagc | 8760 |
| tccctcgtgc gctctcctgt tccgaccctg ccgcttaccg gatacctgtc cgcctttctc | 8820 |
| ccttcgggaa gcgtggcgct ttctcaatgc tcacgctgta ggtatctcag ttcggtgtag | 8880 |
| gtcgttcgct ccaagctggg ctgtgtgcac gaaccccccg ttcagcccga ccgctgcgcc | 8940 |
| ttatccggta actatcgtct tgagtccaac ccggtaagac acgacttatc gccactggca | 9000 |
| gcagccactg gtaacaggat tagcagagcg aggtatgtag gcggtgctac agagttcttg | 9060 |
| aagtggtggc ctaactacgg ctacactaga aggacagtat ttggtatctg cgctctgctg | 9120 |
| aagccagtta ccttcggaaa aagagttggt agctcttgat ccggcaaaca aaccaccgct | 9180 |
| ggtagcggtg gtttttttgt ttgcaagcag cagattacgc gcagaaaaaa aggatctcaa | 9240 |
| gaagatcctt tgatcttttc tacggggtct gacgctcagt ggaacgaaaa ctcacgttaa | 9300 |
| gggattttgg tcatgagatt atcaaaaagg atcttcacct agatcctttt aaattaaaaa | 9360 |
| tgaagtttta aatcaatcta agtatatat gagtaaactt ggtctgacag ttaccaatgc | 9420 |
| ttaatcagtg aggcacctat ctcagcgatc tgtctatttc gttcatccat agttgcctga | 9480 |
| ctgcccgtcg tgtagataac tacgatacgg gagggcttac catctggccc cagtgctgca | 9540 |
| atgataccgc gagacccacg ctcaccggct ccagatttat cagcaataaa ccagccagcc | 9600 |
| ggaagggccg agcgcagaag tggtcctgca actttatccg cctccatcca gtctattaat | 9660 |
| tgttgccggg aagctagagt aagtagttcg ccagttaata gtttgcgcaa cgttgttgcc | 9720 |
| attgctacag gcatcgtggt gtcacgctcg tcgtttggta tggcttc | 9767 |

<210> SEQ ID NO 83
<211> LENGTH: 9791
<212> TYPE: DNA
<213> ORGANISM: Artificial Sequence
<220> FEATURE:
<223> OTHER INFORMATION: Codon Optimized

<400> SEQUENCE: 83

| | |
|---|---:|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |
| ttctgtgact ggtgagtact caaccaagtc attctgagaa tagtgtatgc ggcgaccgag | 240 |
| ttgctcttgc ccggcgtcaa tacgggataa taccgcgcca catagcagaa ctttaaaagt | 300 |
| gctcatcatt ggaaaacgtt cttcggggcg aaaactctca aggatcttac cgctgttgag | 360 |
| atccagttcg atgtaaccca ctcgtgcacc caactgatct tcagcatctt ttactttcac | 420 |
| cagcgtttct gggtgagcaa aaacaggaag gcaaaatgcc gcaaaaaagg gaataagggc | 480 |
| gacacggaaa tgttgaatac tcatactctt cctttttcaa tattattgaa gcatttatca | 540 |
| gggttattgt ctcatgagcg gatacatatt tgaatgtatt tagaaaaata aacaaatagg | 600 |
| ggttccgcgc acatttcccc gaaaagtgcc acctgacgtc taagaaacca ttattatcat | 660 |
| gacattaacc tataaaaata ggcgtatcac gaggcccttt cgtctcgcgc gtttcggtga | 720 |
| tgacggtgaa aacctctgac acatgcagct cccggagacg gtcacagctt gtctgtaagc | 780 |
| ggatgccggg agcagacaag cccgtcaggg cgcgtcagcg ggtgttggcg ggtgtcgggg | 840 |

```
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gttttttatt   1020
tgttgtattt ttttttttttt agagaaaatc ctccaatatc aaattaggaa tcgtagtttc   1080
atgattttct gttacaccta acttttgtg tggtgccctc ctccttgtca atattaatgt    1140
taaagtgcaa ttcttttttcc ttatcacgtt gagccattag tatcaatttg cttacctgta   1200
ttcctttact atcctccttt ttctccttct tgataaatgt atgtagattg cgtatatagt   1260
ttcgtctacc ctatgaacat attccatttt gtaatttcgt gtcgtttcta ttatgaattt   1320
catttataaa gttatgtac aaatatcata aaaaagaga atcttttttaa gcaaggattt    1380 tcttaacttc ttcggcgaca gcatcaccga cttcggtggt actgttggaa ccacctaaat   1440
caccagttct gatacctgca tccaaaacct tttaactgc atcttcaatg gccttacctt    1500
cttcaggcaa gttcaatgac aatttcaaca tcattgcagc agacaagata gtggcgatag   1560
ggtcaacctt attctttggc aaatctggag cagaaccgtg gcatggttcg tacaaaccaa   1620
atgcggtgtt cttgtctggc aaagaggcca aggacgcaga tggcaacaaa cccaaggaac   1680
ctgggataac ggaggcttca tcggagatga tatcaccaaa catgttgctg gtgattataa   1740
taccatttag gtgggttggg ttcttaacta ggatcatggc ggcagaatca atcaattgat   1800
gttgaacctt caatgtaggg aattcgttct tgatggtttc ctccacagtt tttctccata   1860
atcttgaaga ggccaaaaca ttagctttat ccaaggacca aataggcaat ggtggctcat   1920
gttgtagggc catgaaagcg gccattcttg tgattctttg cacttctgga acggtgtatt   1980
gttcactatc ccaagcgaca ccatcaccat cgtcttcctt tctcttacca agtaaaatac   2040
ctcccactaa ttctctgaca acaacgaagt cagtaccttt agcaaattgt ggcttgattg   2100
gagataagtc taaaagagag tcggatgcaa agttacatgg tcttaagttg gcgtacaatt   2160
gaagttcttt acggattttt agtaaaacctt gttcaggtct aacactaccg gtacccatt    2220 taggaccacc cacagcacct aacaaaacgg catcaacctt cttggaggct tccagcgcct   2280
catctggaag tgggacacct gtagcatcga tagcagcacc accaattaaa tgattttcga   2340
aatcgaactt gacattggaa cgaacatcag aaatagcttt aagaaccta atggcttcgg   2400 ctgtgatttc ttgaccaacg tggtcacctg gcaaaacgac gatcttctta ggggcagaca   2460
taggggcaga cattagaatg gtatatcctt gaaatatata tatatattgc tgaaatgtaa   2520
aaggtaagaa aagttagaaa gtaagacgat tgctaaccac ctattggaaa aaacaatagg   2580 tccttaaaata atattgtcaa cttcaagtat tgtgatgcaa gcatttagtc atgaacgctt   2640
ctctattcta tatgaaaagc cggttccggc ctctcacctt tccttttctct cccaattttt    2700 cagttgaaaa aggtatatgc gtcaggcgac ctctgaaatt aacaaaaaat ttccagtcat   2760
cgaatttgat tctgtgcgat agcgcccctg tgtgttctcg ttatgttgag gaaaaaata    2820 atggttgcta agagattcga actcttgcat cttacgatac ctgagtattc ccacagttaa   2880
ctgcggtcaa gatatttctt gaatcaggcg cctttagaccg ctcggccaaa caaccaatta    2940
cttgttgaga aatagagtat aattatccta taaatataac gttttgaac acacatgaac   3000 aaggaagtac aggacaattg attttgaaga gaatgtggat tttgatgtaa ttgttgggat   3060
tccattttta ataaggcaat aatattaggt atgtggatat actagaagtt ctcctcgagg   3120
gtcgatatgc ggtgtgaaat accgcacaga tgcgtaagga gaaaataccg catcaggaaa   3180
```

```
ttgtaaacgt taatatttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420
caagtttttt ggggtcgagg tgccgtaaag cactaaatcg gaaccctaaa gggagccccc    3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacaggcgc gtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag gacctagac ttcaggttgt ctaactcctt    4020
cctttcggt tagagcggat gtgggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaggataa tctcaattgg ttcaaatcaa tggttgtgtc    4260
gtttgaatcc ttcaatacga aaatatgac caattgttct ggaccaccac ccaaaggtgg    4320
aacaccaata gcagtggttt caaaaactct gtcatctact tcattacaga ctctttcgat    4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcataccct tgaaatagac atcgtgatga ttaccgttta acaatgttt    4560
tgaggcacca acataacag gacctaatgc caattcaccg ataccctggct tattttagg    4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
gaccttgca tcttgaacaa atttagcgaa accagagact aaaggactac cgttgtacaa    4980
ggcaatagat gcaccattta acaaactagc ataaaccaac caaggaccca tcatccaacc    5040
caaattagtt ggccatacta taacgtcacc ttttctaata tccaaatgag accaaccatc    5100
agcagcagcc ttcaatgggg tggcttgtgt ccaaggaatt gcttttggtt cacctgtagt    5160
accactggag aataagatgt tagtataagc atcaacaggt tgttctctgg cagtaaactc    5220
gcagtttta aactccttgg ctctttctaa aaagtaatcc caagatatgt caccatctct    5280
caattctgca ccaatgttag aaccactaca agggataact attgccattg gggatttagc    5340
ttcaactact cttgaataca atggtattct cttttacct ctgatgatgt gatcttgtgt    5400
gaaaattgcc ttagctttgg ataatctcaa tctagttgag atttcagggg cggaaaatga    5460
atctgctata gagacaacta cgtaaccagc caatactatg ccaaatata taacaacagc    5520
atcaacatgc attggcatat cgatggctat tgcacaacct ttttctaaac ccatttcttc    5580
```

```
caatgcataa ccaaccaacc aaactctctt tctcaattga tctaatgtca acttattcaa    5640
aggcaagtca tcgttaccct cgtctctcca aacgatcata gtatcgttca atttcttatt    5700
ggagtttacg ttcaagcaat ttttagctga gttcaagtaa ccaccaggta accattcaga    5760
accacctggg ttgttgatgt catctcttct caagatacat tctgggtcct tagagaaact    5820
aattttcatt tcatccatca atactgttct ccaatagact tcagggtttc taacagaaaa    5880
ttcttggaag tgagaaaaag aagaaattgg atctttgtac tttacaccca aaaattcttt    5940
acctctcttt tccaacaaag cacccaaatt agttgacttg acttttcag gtctggaat     6000 ccaagcaggt ggggctggac cgaaatcctt gtagcaacca taaacaaca tttggtgtaa     6060 ggagaaaggc aaatctggtg acaagatatg gttagcgatg ttgatccaag tttgaggggt    6120
tgcagcacca taattacaaa cgatttctgc caatctacca tgtaatgttt ctgctacttc    6180
tgaggtgata cccaatgcga tgaaatctga ggcaacgact gaatccaagg acttatagtt    6240
tttacccatt cttttaatcg tggatccttc aaaaattctt actttttttt tggatggacg    6300
caaagaagtt taataatcat attacatggc attaccacca tatacatatc catatacata    6360
tccatatcta atcttactta tatgttgtgg aaatgtaaag agccccatta tcttagccta    6420
aaaaaccctt ctctttggaa ctttcagtaa tacgcttaac tgctcattgc tatattgaag    6480
tacggattag aagccgccga gcgggtgaca gccctccgaa ggaagactct cctccgtgcg    6540
tcctcgtctt caccggtcgc gttcctgaaa cgcagatgtg cctcgcgccg cactgctccg    6600
aacaataaag attctacaat actagctttt atggttatga agaggaaaaa ttggcagtaa    6660
cctggcccca caaaccttca aatgaacgaa tcaaattaac aaccatagga tgataatgcg    6720
attagttttt tagccttatt tctggggtaa ttaatcagcg aagcgatgat ttttgatcta    6780
ttaacagata tataaatgca aaaactgcat aaccacttta actaatactt tcaacatttt    6840
cggtttgtat tacttcttat tcaaatgtaa taaaagtatc aacaaaaaat tgttaatata    6900
cctctatact ttaacgtcaa ggagaaaaaa ccccggatcc gtaatacgac tcactataat    6960
ggcttgtttg tttagaggtc catctgaatc tgatttggaa ttgttggttg gtcaagctat    7020
ttttggtgat ggtgctgctg ctgttattgt tggtgctgaa ccagatgaat ctgttggtga    7080
aagaccaatt tttgaattgg tttctactgg tcaaactatt ttgccaaatt ctgaaggtac    7140
tattggtggt catattagag aagctggttt gattttttgat ttgcataaag atgttccaat    7200
gttgatttct aataatattg aaaaatgttt gattgaagct tttactccaa ttggtatttc    7260
tgattggaat tctatttttt ggattactca tccaggtggt aaagctattt tggataaagt    7320
tgaagaaaaa ttgcatttga atctgataa atttgttgat tctagacatg ttttgtctga    7380
acatggtaat atgtcttctt ctactgtttt gtttgttatg gatgaattga gaaaaagatc    7440
tttggaagaa ggtaaatcta ctactggtga tggttttgaa tggggtgttt tgtttggttt    7500
tggtccaggt ttgactgttg aaagagttgt tgttagatct gttccaatta aatatgaagg    7560
tagaggttcc ttgttaactt gtggtgacgt tgaagaaaac ccaggtccta tggccgtcaa    7620
gcatttgata gtattgaagt ttaaagatga aatcacagaa gctcaaaagg aagaattttt    7680
caagacctac gttaatttgg tcaacattat acctgctatg aaagatgtat actggggtaa    7740
agacgttaca caaagaaag aagaaggtta tacacacatt gtcgaagtaa ccttcgaatc    7800
agttgaaact atccaagatt acatcattca tccagctcac gttggttttg gtgacgttta    7860
cagatccttc tgggaaaaat tgttgatctt cgattacacc ccaagaaagt gatgatgggc    7920
```

| | |
|---|---|
| tgcaggaatt cgatatcaag cttatcgata ccgtcgacct cgagtcatgt aattagttat | 7980 |
| gtcacgctta cattcacgcc ctccccccac atccgctcta accgaaaagg aaggagttag | 8040 |
| acaacctgaa gtctaggtcc ctatttattt ttttatagtt atgttagtat taagaacgtt | 8100 |
| atttatattt caaattttc ttttttttct gtacagacgc gtgtacgcat gtaacattat | 8160 |
| actgaaaacc ttgcttgaga aggttttggg acgctcgaag gctttaattt gcggccggta | 8220 |
| cccagctttt gttcccttta gtgagggtta attccgagct tggcgtaatc atggtcatag | 8280 |
| ctgtttcctg tgtgaaattg ttatccgctc acaattccac acaacatagg agccggaagc | 8340 |
| ataaagtgta aagcctgggg tgcctaatga gtgaggtaac tcacattaat tgcgttgcgc | 8400 |
| tcactgcccg ctttccagtc gggaaacctg tcgtgccagc tgcattaatg aatcggccaa | 8460 |
| cgcgcggga gaggcggttt gcgtattggg cgctcttccg cttcctcgct cactgactcg | 8520 |
| ctgcgctcgg tcgttcggct gcggcgagcg gtatcagctc actcaaaggc ggtaatacgg | 8580 |
| ttatccacag aatcagggga taacgcagga aagaacatgt gagcaaaagg ccagcaaaag | 8640 |
| gccaggaacc gtaaaaaggc cgcgttgctg gcgttttcc ataggctcgg ccccctgac | 8700 |
| gagcatcaca aaaatcgacg ctcaagtcag aggtggcgaa acccgacagg actataaaga | 8760 |
| taccaggcgt tcccccctgg aagctccctc gtgcgctctc ctgttccgac cctgccgctt | 8820 |
| accggatacc tgtccgcctt tctcccttcg ggaagcgtgg cgctttctca atgctcacgc | 8880 |
| tgtaggtatc tcagttcggt gtaggtcgtt cgctccaagc tgggctgtgt gcacgaaccc | 8940 |
| cccgttcagc ccgaccgctg cgccttatcc ggtaactatc gtcttgagtc aacccggta | 9000 |
| agacacgact tatcgccact ggcagcagcc actggtaaca ggattagcag agcgaggtat | 9060 |
| gtaggcggtg ctacagagtt cttgaagtgg tggcctaact acggctacac tagaaggaca | 9120 |
| gtatttggta tctgcgctct gctgaagcca gttaccttcg gaaaaagagt tggtagctct | 9180 |
| tgatccggca aacaaaccac cgctggtagc ggtggttttt ttgtttgcaa gcagcagatt | 9240 |
| acgcgcagaa aaaaggatc tcaagaagat cctttgatct tttctacggg gtctgacgct | 9300 |
| cagtggaacg aaaactcacg ttaagggatt ttggtcatga gattatcaaa aaggatcttc | 9360 |
| acctagatcc ttttaaatta aaaatgaagt tttaaatcaa tctaaagtat atatgagtaa | 9420 |
| acttggtctg acagttacca atgcttaatc agtgaggcac ctatctcagc gatctgtcta | 9480 |
| tttcgttcat ccatagttgc ctgactgccc gtcgtgtaga taactacgat acgggagggc | 9540 |
| ttaccatctg gccccagtgc tgcaatgata ccgcgagacc cacgctcacc ggctccagat | 9600 |
| ttatcagcaa taaaccagcc agccggaagg gccgagcgca gaagtggtcc tgcaacttta | 9660 |
| tccgcctcca tccagtctat taattgttgc cgggaagcta gagtaagtag ttcgccagtt | 9720 |
| aatagtttgc gcaacgttgt tgccattgct acaggcatcg tggtgtcacg ctcgtcgttt | 9780 |
| ggtatggctt c | 9791 |

<210> SEQ ID NO 84
<211> LENGTH: 10130
<212> TYPE: DNA
<213> ORGANISM: Artificial Sequence
<220> FEATURE:
<223> OTHER INFORMATION: Codon Optimized

<400> SEQUENCE: 84

| | |
|---|---|
| attcagctcc ggttcccaac gatcaaggcg agttacatga tcccccatgt tgtgaaaaaa | 60 |
| agcggttagc tccttcggtc ctccgatcgt tgtcagaagt aagttggccg cagtgttatc | 120 |
| actcatggtt atggcagcac tgcataattc tcttactgtc atgccatccg taagatgctt | 180 |

```
ttctgtgact ggtgagtact caaccaagtc attctgagaa tagtgtatgc ggcgaccgag    240
ttgctcttgc ccggcgtcaa tacgggataa taccgcgcca catagcagaa ctttaaaagt    300
gctcatcatt ggaaaacgtt cttcggggcg aaaactctca aggatcttac cgctgttgag    360
atccagttcg atgtaaccca ctcgtgcacc caactgatct tcagcatctt ttactttcac    420
cagcgtttct gggtgagcaa aaacaggaag gcaaaatgcc gcaaaaaagg gaataagggc    480
gacacggaaa tgttgaatac tcatactctt ccttttcaa tattattgaa gcatttatca    540
gggttattgt ctcatgagcg gatacatatt tgaatgtatt tagaaaaata aacaaatagg    600
ggttccgcgc acatttcccc gaaaagtgcc acctgacgtc taagaaacca ttattatcat    660
gacattaacc tataaaaata ggcgtatcac gaggcccttt cgtctcgcgc gtttcggtga    720
tgacggtgaa aacctctgac acatgcagct cccggagacg gtcacagctt gtctgtaagc    780
ggatgccggg agcagacaag cccgtcaggg cgcgtcagcg ggtgttggcg ggtgtcgggg    840
ctggcttaac tatgcggcat cagagcagat tgtactgaga gtgcaccata tcgactacgt    900
cgtaaggccg tttctgacag agtaaaattc ttgagggaac tttcaccatt atgggaaatg    960
gttcaagaag gtattgactt aaactccatc aaatggtcag gtcattgagt gtttttatt    1020 tgttgtattt ttttttttt agagaaaatc ctccaatatc aaattaggaa tcgtagtttc    1080
atgattttct gttacaccta acttttttgtg tggtgccctc ctccttgtca atattaatgt    1140
taaagtgcaa ttcttttttcc ttatcacgtt gagccattag tatcaatttg cttacctgta    1200
ttcctttact atcctccttt ttctccttct tgataaatgt atgtagattg cgtatatagt    1260
ttcgtctacc ctatgaacat attccatttt gtaatttcgt gtcgtttcta ttatgaattt    1320
catttataaa gttatgtac aaatatcata aaaaagaga atcttttttaa gcaaggattt    1380 tcttaacttc ttcggcgaca gcatcaccga cttcggtggt actgttggaa ccacctaaat    1440
caccagttct gatacctgca tccaaaacct ttttaactgc atcttcaatg gccttacctt    1500
cttcaggcaa gttcaatgac aatttcaaca tcattgcagc agacaagata gtggcgatag    1560
ggtcaaccct tattctttggc aaatctggag cagaaccgtg gcatggttcg tacaaaccaa    1620
atgcggtgtt cttgtctggc aaagaggcca aggacgcaga tggcaacaaa cccaaggaac    1680
ctgggataac ggaggcttca tcggagatga tatcaccaaa catgttgctg gtgattataa    1740
taccatttag gtgggttggg ttcttaacta ggatcatggc ggcagaatca atcaattgat    1800
gttgaacctt caatgtaggg aattcgttct tgatggtttc ctccacagtt tttctccata    1860
atcttgaaga ggccaaaaca ttagctttat ccaaggacca aataggcaat ggtggctcat    1920
gttgtagggc catgaaagcg gccattcttg tgattctttg cacttctgga acggtgtatt    1980
gttcactatc ccaagcgaca ccatcaccat cgtcttcctt tctcttacca agtaaaatac    2040
ctcccactaa ttctctgaca caacgaagt cagtaccttt agcaaattgt ggcttgattg    2100
gagataagtc taaagagag tcggatgcaa agttacatgg tcttaagttg gcgtacaatt    2160
gaagttcttt acggattttt agtaaaccct gttcaggtct aacactaccg gtaccccatt    2220
taggaccacc cacagcacct aacaaaacgg catcaaccct cttggaggct tccagcgcct    2280
catctggaag tgggacacct gtagcatcga tagcagcacc accaattaaa tgattttcga    2340
aatcgaactt gacattggaa cgaacatcag aaatagcttt aagaaccttta atggcttcgg    2400 ctgtgatttc ttgaccaacg tggtcacctg gcaaaacgac gatcttctta ggggcagaca    2460
taggggcaga cattagaatg gtatatcctt gaaatatata tatatattgc tgaaatgtaa    2520
```

```
aaggtaagaa aagttagaaa gtaagacgat tgctaaccac ctattggaaa aaacaatagg    2580
tccttaaata atattgtcaa cttcaagtat tgtgatgcaa gcatttagtc atgaacgctt    2640
ctctattcta tatgaaaagc cggttccggc ctctcacctt tccttttct cccaattttt    2700
cagttgaaaa aggtatatgc gtcaggcgac ctctgaaatt aacaaaaaat ttccagtcat    2760
cgaatttgat tctgtgcgat agcgcccctg tgtgttctcg ttatgttgag aaaaaaata    2820
atggttgcta agagattcga actcttgcat cttacgatac ctgagtattc ccacagttaa    2880
ctgcggtcaa gatatttctt gaatcaggcg ccttagaccg ctcggccaaa caaccaatta    2940
cttgttgaga aatagagtat aattatccta taaatataac gttttgaac acacatgaac     3000
aaggaagtac aggacaattg attttgaaga gaatgtggat tttgatgtaa ttgttgggat    3060
tccatttta ataaggcaat aatattaggt atgtggatat actagaagtt ctcctcgagg     3120
gtcgatatgc ggtgtgaaat accgcacaga tgcgtaagga gaaataccg catcaggaaa     3180
ttgtaaacgt taatattttg ttaaaattcg cgttaaattt ttgttaaatc agctcatttt    3240
ttaaccaata ggccgaaatc ggcaaaatcc cttataaatc aaaagaatag accgagatag    3300
ggttgagtgt tgttccagtt tggaacaaga gtccactatt aaagaacgtg gactccaacg    3360
tcaaagggcg aaaaaccgtc tatcagggcg atggcccact acgtgaacca tcaccctaat    3420
caagttttt ggggtcgagg tgccgtaaag cactaaatcg gaaccctaaa gggagccccc     3480
gatttagagc ttgacgggga aagccggcga acgtggcgag aaaggaaggg aagaaagcga    3540
aaggagcggg cgctagggcg ctggcaagtg tagcggtcac gctgcgcgta accaccacac    3600
ccgccgcgct taatgcgccg ctacagggcg cgtcgcgcca ttcgccattc aggctgcgca    3660
actgttggga agggcgatcg gtgcgggcct cttcgctatt acgccagctg gcgaaggggg    3720
gatgtgctgc aaggcgatta agttgggtaa cgccagggtt ttcccagtca cgacgttgta    3780
aaacgacggc cagtgaattg taatacgact cactataggg cgaattggag ctctagtcgc    3840
aaattaaagc cttcgagcgt cccaaaacct tctcaagcaa ggttttcagt ataatgttac    3900
atgcgtacac gcgtctgtac agaaaaaaaa gaaaaatttg aaatataaat aacgttctta    3960
atactaacat aactataaaa aaataaatag ggacctagac ttcaggttgt ctaactcctt    4020
cctttttcggt tagagcggat gtgggggag ggcgtgaatg taagcgtgac ataactaatt    4080
acatgatcat tcgaaatgac tgaattgttg tctcaaaact cttctcatga tcttgtttgt    4140
tgcagttcta ggtaaggatg acaatgggac aactctagta actttgaata atgggttcaa    4200
tttcttttgc aaacccaagt taaaggataa tctcaattgg ttcaaatcaa tggttgtgtc    4260
gtttgaatcc ttcaatacga aaaatatgac caattgttct ggaccaccac ccaaaggtgg    4320
aacaccaata gcagtggttt caaaaactct gtcatctact tcattacaga ctcttttcgat   4380
ttcgatagaa ctaattttga taccaccgat gttcatagtg tcatcggctc taccgtgtgc    4440
atggtagtaa ccgttagagg tcaattcgaa aatgtcacca tgtcttctca atacttcacc    4500
attcaaggtt ggcataccct tgaaatagac atcgtgatga ttaccgttta acaatgtttt    4560
tgaggcacca acataacag gacctaatgc caattcaccg atacctggct tattttagg     4620
cattgggtaa ccgttcttat ctaatatgta caaggtgcaa cccatacatt gggatgaaaa    4680
agaacttaaa gattgagctt gcaaaaatga accagcagaa aaagcaccac cgatttctgt    4740
accaccacac atttctataa ctggcttgta gttagctcta cccattaacc acaaatattc    4800
gtctacatta gaggcttcac cggatgaaga aaagcatctt atggtggacc aatcgtaacc    4860
tgaaacacaa tttgtggatt tccatgatct tacaatagat ggtacgacac ccaacattgt    4920
```

```
gacctttgca tcttgaacaa atttagcgaa accagagact aaaggactac cgttgtacaa   4980
ggcaatagat gcaccattta acaaactagc ataaaccaac caaggaccca tcatccaacc   5040
caaattagtt ggccatacta taacgtcacc ttttctaata tccaaatgag accaaccatc   5100
agcagcagcc ttcaatgggg tggcttgtgt ccaaggaatt gcttttggtt cacctgtagt   5160
accactggag aataagatgt tagtataagc atcaacaggt tgttctctgg cagtaaactc   5220
gcagttttta aactccttgg ctctttctaa aaagtaatcc caagatatgt caccatctct   5280
caattctgca ccaatgttag aaccactaca agggataact attgccattg gggatttagc   5340
ttcaactact cttgaataca atggtattct ctttttacct ctgatgatgt gatcttgtgt   5400
gaaaattgcc ttagctttgg ataatctcaa tctagttgag atttcagggg cggaaaatga   5460
atctgctata gagacaacta cgtaaccagc caatactatg gccaaatata taacaacagc   5520
atcaacatgc attggcatat cgatggctat tgcacaacct ttttctaaac ccatttcttc   5580
caatgcataa ccaaccaacc aaactctctt tctcaattga tctaatgtca acttattcaa   5640
aggcaagtca tcgttaccct cgtctctcca aacgatcata gtatcgttca atttcttatt   5700
ggagtttacg ttcaagcaat ttttagctga gttcaagtaa ccaccaggta accattcaga   5760
accacctggg ttgttgatgt catctcttct caagatacat tctgggtcct tagagaaact   5820
aattttcatt tcatccatca atactgttct ccaatagact tcagggtttc taacagaaaa   5880
ttcttggaag tgagaaaaag aagaaattgg atctttgtac tttacaccca aaaattcttt   5940
acctctcttt tccaacaaag cacccaaatt agttgacttg acttttcag ggtctggaat   6000 ccaagcaggt ggggctggac cgaaatcctt gtagcaacca taaaacaaca tttggtgtaa   6060
ggagaaaggc aaatctggtg acaagatatg gttagcgatg ttgatccaag tttgaggggt   6120
tgcagcacca taattacaaa cgatttctgc caatctacca tgtaatgttt ctgctacttc   6180
tgaggtgata cccaatgcga tgaaatctga ggcaacgact gaatccaagg acttatagtt   6240
tttacccatt cttttaatcg tggatccttc aaaaattctt actttttttt tggatggacg   6300
caaagaagtt taataatcat attacatggc attaccacca tatacatatc catatacata   6360
tccatatcta atcttactta tatgttgtgg aaatgtaaag agccccatta tcttagccta   6420
aaaaaacctt ctctttggaa ctttcagtaa tacgcttaac tgctcattgc tatattgaag   6480
tacggattag aagccgccga gcgggtgaca gccctccgaa ggaagactct cctccgtgcg   6540
tcctcgtctt caccggtcgc gttcctgaaa cgcagatgtg cctcgcgccg cactgctccg   6600
aacaataaag attctacaat actagctttt atggttatga agaggaaaaa ttggcagtaa   6660
cctggcccca caaaccttca aatgaacgaa tcaaattaac aaccatagga tgataatgcg   6720
attagttttt tagccttatt tctggggtaa ttaatcagcg aagcgatgat ttttgatcta   6780
ttaacagata tataaatgca aaaactgcat aaccacttta actaatactt tcaacatttt   6840
cggtttgtat tacttcttat tcaaatgtaa taaaagtatc aacaaaaaat tgttaatata   6900
cctctatact ttaacgtcaa ggagaaaaaa ccccggatcc gtaatacgac tcactataat   6960
gaatttggaa atatattgata aagttaattc tccaggtact gaagataaag attttgattc   7020
tagagcttct ggttctaaaa ctaatggttg tgaatcttct gataatgaag ttgaatcttc   7080
tattaatgct aatccaaatt ctatttctgg ttcttcttct ggttttggta atggtaaaag   7140
agaaggtgtt aaaagagctg ctccaggtga tattgctcca acttctagac attatagatc   7200
tttgtctatg gattcttata tgggttcttt gcaatttgat gatgaatctt tgaaattgtt   7260
```

```
gccattgggt actggtgttg gtttgcaatc tccaaattct ttggctgatg gtaattctac    7320
taaatttggt atggaatttc caaatggtga atttaatgct gttgaattga aaaaaattat    7380
ggaatctgaa aaattgactg aaattgcttt gtctgatcca aaaagagcta aaagaatttt    7440
ggctaatgaa caatctgctg ctagatctaa agaaagaaga tctagatata tttctgaatt    7500
ggaacataaa gttcaaactt tgcaaactga agctactact ttgtctgctc aagttactaa    7560
attgcaaaga gattctgttg gtttgacttc tcaaaattct gaattgaaat ttagagttca    7620
agctatggaa caacaagctc aattgaaaga tgctttgaat gatgctttga gagctgaagt    7680
tcaaagattg aaattgactg ctgctgaatt gtctggtgaa gctcatttgt ctaattgtat    7740
ggctcaacaa ttgtctatta atcaacaaat gtatcaaatg caacatagac aaactgttca    7800
attgaatttg tatcaaatgc aacaacaaca acaacataat gaaatgtctt ctcaaccatg    7860
ttctggtgaa gttactgaac atgaatcttc taaagaaggt agaggttcct tgttaacttg    7920
tggtgacgtt gaagaaaacc caggtcctat ggccgtcaag catttgatag tattgaagtt    7980
taaagatgaa atcacagaag ctcaaaagga agaattttc aagacctacg ttaatttggt    8040
caacattata cctgctatga agatgtata ctggggtaaa gacgttacac aaaagaaaga    8100
agaaggttat acacacattg tcgaagtaac cttcgaatca gttgaaacta ccaagattaa    8160
catcattcat ccagctcacg ttggttttgg tgacgtttac agatccttct gggaaaaatt    8220
gttgatcttc gattacaccc caagaaagtg atgatgggct gcaggaattc gatatcaagc    8280
ttatcgatac cgtcgacctc gagtcatgta attagttatg tcacgcttac attcacgccc    8340
tccccccaca tccgctctaa ccgaaaagga aggagttaga caacctgaag tctaggtccc    8400
tatttatttt tttatagtta tgttagtatt aagaacgtta tttatatttc aaattttct    8460 ttttttctg tacagacgcg tgtacgcatg taacattata ctgaaaacct tgcttgagaa    8520
ggttttggga cgctcgaagg ctttaatttg cggccggtac ccagcttttg ttccctttag    8580
tgagggttaa ttccgagctt ggcgtaatca tggtcatagc tgtttcctgt gtgaaattgt    8640
tatccgctca caattccaca acatagga gccggaagca taaagtgtaa agcctggggt    8700
gcctaatgag tgaggtaact cacattaatt gcgttgcgct cactgcccgc tttccagtcg    8760
ggaaacctgt cgtgccagct gcattaatga atcggccaac gcgcggggag aggcggtttg    8820
cgtattgggc gctcttccgc ttcctcgctc actgactcgc tgcgctcggt cgttcggctg    8880
cggcgagcgg tatcagctca ctcaaaggcg gtaatacggt tatccacaga atcaggggat    8940
aacgcaggaa agaacatgtg agcaaaaggc cagcaaaagg ccaggaaccg taaaaaggcc    9000
gcgttgctgg cgtttttcca taggctcggc ccccctgacg agcatcacaa aaatcgacgc    9060
tcaagtcaga ggtggcgaaa cccgacagga ctataaagat accaggcgtt cccccctgga    9120
agctccctcg tgcgctctcc tgttccgacc ctgccgctta ccggatacct gtccgccttt    9180
ctcccttcgg gaagcgtggc gctttctcaa tgctcacgct gtaggtatct cagttcggtg    9240
taggtcgttc gctccaagct gggctgtgtg cacgaacccc ccgttcagcc cgaccgctgc    9300
gccttatccg gtaactatcg tcttgagtcc aacccggtaa gacacgactt atcgccactg    9360
gcagcagcca ctggtaacag gattagcaga gcgaggtatg taggcggtgc tacagagttc    9420
ttgaagtggt ggcctaacta cggctacact agaaggacag tatttggtat ctgcgctctg    9480
ctgaagccag ttaccttcgg aaaaagagtt ggtagctctt gatccggcaa acaaaccacc    9540
gctggtagcg gtggtttttt tgtttgcaag cagcagatta cgcgcagaaa aaaggatct    9600 caagaagatc ctttgatctt ttctacgggg tctgacgctc agtggaacga aaactcacgt    9660
```

```
taagggattt tggtcatgag attatcaaaa aggatcttca cctagatcct tttaaattaa    9720
aaatgaagtt ttaaatcaat ctaaagtata tatgagtaaa cttggtctga cagttaccaa    9780
tgcttaatca gtgaggcacc tatctcagcg atctgtctat ttcgttcatc catagttgcc    9840
tgactgcccg tcgtgtagat aactacgata cgggagggct taccatctgg ccccagtgct    9900
gcaatgatac cgcgagaccc acgctcaccg gctccagatt tatcagcaat aaaccagcca    9960
gccggaaggg ccgagcgcag aagtggtcct gcaactttat ccgcctccat ccagtctatt   10020
aattgttgcc gggaagctag agtaagtagt tcgccagtta atagtttgcg caacgttgtt   10080
gccattgcta caggcatcgt ggtgtcacgc tcgtcgtttg gtatggcttc              10130
```

```
<210> SEQ ID NO 85
<211> LENGTH: 2274
<212> TYPE: DNA
<213> ORGANISM: Artificial Sequence
<220> FEATURE:
<223> OTHER INFORMATION: Codon Optimized

<400> SEQUENCE: 85
```

```
atgtatatgt atcaagaagt ttatttggtt ccaactttgt cttatttgta tttggttgtt      60
gttttgttgc catctatttt tttttctttt agaagaatgg cttttaaatc tttggattct     120
gttacttctt ctgatattgc tgctttgggt attgaaccac aattggctca ttctttgcat     180
ggtagattgg ctgaaattgt ttctaatcat ggttctgcta ctccacatac ttggagatgt     240
atttcttctc atttgttgtc tccagatttg ccattttctt tgcatcaaat gttgtattat     300
ggttgttata agattttggg tccagatcca ccagcttgga ttccagatgc tgaaaatgct     360
atttctacta atgttggtaa attgttggaa aaaagaggta agaattttt gggtgttaaa     420 tataaagatc caatttctaa ttttttctgat tttcaagaat tttctgttac taatccagaa     480
gtttattgga gaactatttt ggatgaaatg aatatttctt tttctaaacc accagaatgt     540
attttgagag aaaaattttc tagagatggt caaattttga atccaggtgg tgaatggttg     600
ccaggtgctt ttattaatcc agctaaaaat tgtttggatt tgaattgtaa atctttggat     660
gatactatga ttttgtggag agatgaaggt aaagatgatt tgccagttaa taaaatgact     720
ttgaaagaat tgagatctga gtttggttg gttgcttatg ctttgaaaga attggaattg     780
gaaggtggtt ctgctattgc tattgatatg ccaatgaatg ttcattctgt tgttatttat     840
ttggctattg ttttggctgg ttatgttgtt gtttctattg ctgattcttt tgctgctcca     900
gaaatttcta ctagattgaa aatttctaaa gctaaagcta tttttactca agatttgatt     960
gttagaggtg aaaaactat tccattgtat tctagaattg ttgaagctca atctccattg    1020
gctattgtta ttccatctaa aggtttttct gtttctgctc aattgagaca tggtgatgtt    1080
tcttggcatg attttttgaa tagagctaat aaatttaaaa attatgaatt gctgctgtt    1140 gaacaaccaa ttgatgctta tactaatatt ttgttttctt ctggtactac tggtgaacca    1200
aaagctattc catggactca agctactcca tttaaagctg ctgctgatgc ttggtgtcat    1260
atggatattc aaaaggtga tgttgttgct tggccaacta atttggttg gatgatgggt    1320 ccatggttgg tttatgcttc ttttgttaat ggtgcttcta ttgctttgta taatggttct    1380 ccattggggtt ctggttttgc taaatttgtt caagatgcta agttactat gttgggtgtt    1440 attccatcta ttgttagaac ttggaaatct actaattgtg ttgctggtta tgattggtct    1500
actattagat gttttctc tactggtgaa gcttctaata ttgatgaata tttgtggttg    1560
```

```
atgggtagag cttattataa accagttatt gaatattgtg gtggtactga aattggtggt    1620
ggttttgtta ctggttcttt gttgcaagct caatctttgg ctgctttttc tactccagct    1680
atgggttgtt ctttgtttat tttgggttct gatggttatc caattccaaa acataaacca    1740
ggtattggtg aattggcttt gggtccattg atgtttggtg cttctaaaac tttgttgaat    1800
gctgatcatt atgatgttta ttttaaaaga atgccatctt gaatggtaa agttttgaga     1860 agacatggtg atatgtttga attgacttct aaaggttatt atcatgctca tggtagagct    1920
gatgatacta tgaatttggg tggtattaaa gtttcttctg ttgaaattga aagaatttgt    1980
aatgaagctg atgaaaaagt tttggaaact gctgctattg gtgttccacc attggctggt    2040
ggtccagaac aattggttat tgctgttgtt ttgaaaaatt ctgatagaac tactgttgat    2100
ttgaatcaat tgagattgtc ttttaattct gctgttcaaa aaaaattgaa tccattgttt    2160
agagtttcta gagttgttcc attgtcttct tgccaagaa ctgctactaa taaagttatg     2220
agaagaattt tgagacaaca atttactcaa ttggataaat cttctaaaat ttaa          2274
```

<210> SEQ ID NO 86
<211> LENGTH: 2331
<212> TYPE: DNA
<213> ORGANISM: Artificial Sequence
<220> FEATURE:
<223> OTHER INFORMATION: Codon Optimized

<400> SEQUENCE: 86

```
atggctttgg aattgccaca tttgttgcca tataaattgg ttaaaggtca aactttggtt     60
gctcaagctg ctagagctga attggcttct tcttcttctt cttctgttat tttgaaatct    120
aattttatta ataataatta tattaattat tgtaataata ataataataa tgaaagaaga    180
ttggttgtta aagagattg ggaaactatg gcttcttctc catctcattc tagaaataat     240
aatgatatta gaactattaa tcatttgaga catgttgatt ctatggctac tatgccatct    300
ggtgctggta aaattccaag attgaatgct gttattttgg gtgaagcttt ggctactgaa    360
gaaaatgatt tggttttttcc aactgatgaa ttttctcaac aagctcatgt tccatctcca    420
caaaaatatt tggaaatgta taaaagatct attgaagatc cagctggttt tggtctgaa    480 attgcttctc aattttattg gaaacaaaaa tgggatgatt ctgtttattc tgaaaatttg    540
gatgttctca aggtagagt taatattgaa tggtttaaag gtggtattac taatatttgt    600
tataattgtt tggataaaaa tgttgaagct ggtttgggtg ataaaattgc tttgtattgg    660
gaaggtaatg atactggttt tgatgattct ttgacttatt ctcaattgtt gcataaagtt    720
tgtcaattgg ctaattattt gaaagatatg ggtgttcaaa aaggtgatgc tgttgttatt    780
tatttgccaa tgttgttgga attgccaatt actatgttgg cttgtgctag aattggtgct    840
gttcattctg ttgttttgc tggttttttct gctgaatctt tgtctcaaag aattattgat    900
tgtaaaccaa aagttgttat tacttgtaat gctgttaaaa gaggtccaaa aattattcat    960
ttgaaagata ttgttgatgc tgctttggtt gaatctgcta aaactggtgt tccaattgat    1020
acttgtttgg tttatgaaaa tcaattggct atgaaagag atattactaa atggcaagat    1080
ggtagagata tttggtggca agatgttatt ccaaaatatc caactgaatg tgctgttgaa    1140
tgggttgatg ctgaagatcc attgtttttg ttgtatactt ctggttctac tggtaaacca    1200
aaaggtgttt tgcatactac tggtggttat atgtttata ctgctactac ttttaaatat    1260
gcttttgatt ataaaccatc tgatgtttat tggtgtactg ctgattgtgg ttggattact    1320
ggtcattctt atgttactta tggtccattg ttgaatggtg cttcttgtat tgttttgaa    1380
```

-continued

```
ggtgctccaa attatccaga ttctggtaga tgttgggata ttgttgataa atataaagtt    1440 actattttt  atactgctcc aactttggtt agatctttga tgagagatgg tgatgaatat    1500
gttactagat attctagaaa atctttgaga attttgggtt ctgttggtga accaattaat    1560
ccatctgctt ggagatggtt ttataatgtt gttggtgatt ctagatgtcc aatttctgat    1620
acttggtggc aaactgaaac tggtggtttt atgattactc cattgccagg tgcttggcca    1680
caaaaaccag gttctgctac ttttccattt tttggtgtta aaccagttat tgttgatgaa    1740
aaaggtgttg aaattgaagg tgaatgttct ggttatttgt gtgttaaagg ttcttggcca    1800
ggtgctttta gaactttgta tggtgattat gaaagatatg aaactactta ttttaaacca    1860
tttactggtt attatttttac tggtgatggt tgttctagag ataaagatgg ttatcattgg    1920
ttgactggta gagttgatga tgttattaat gtttctggtc atagaattgg tactgctgaa    1980
gttgaatctg ctttggtttc tcatccaaaa tgtgctgaag ctgctgttgt tggtattgaa    2040
catgaagtta aaggtcaagc tatttatgct tttgttactt tggttgaagg tgaaccatat    2100
tctgaagaat tgagaaaatc tttgattttg tctgttagaa aacaaattgg tgcttttgct    2160
gctccagaaa gaattcattg ggctccaggt ttgccaaaaa ctagatctgg taaaattatg    2220
agaagaattt tgagaaaaat tgcttctggt caattggatg aattgggtga tacttctact    2280
ttggctgatc caaatgttgt tgaacaattg atttctttgt ctaattgtta g              2331
```

<210> SEQ ID NO 87
<211> LENGTH: 1662
<212> TYPE: DNA
<213> ORGANISM: Artificial Sequence
<220> FEATURE:
<223> OTHER INFORMATION: Codon Optimized

<400> SEQUENCE: 87

```
atggaaaaaa aacaagataa tcataataat aataataata atggtgatga acaagaagaa      60 tttatttttta gatctaaatt gccagatatt tatattccaa atcatccacc attgcattct    120
tattgttttg aaaatatttc tcaatttaaa gatagaccat gtttgattaa tggtgctact    180
ggtgaaacta ttacttatgc tgatgttgat ttgacttcta gaaaagttgc tgctggtttg    240
gataaaattg gtattaaaca aggtgatgtt attatgttgt tgttgagaaa ttgtccagaa    300
tttgtttatt cttttttggc tgcttctcat attggtgctg ttgttactac tgctaatcca    360
ttttatactg ctgctgaagt tgctaaacaa gctgctgctt ctaatactaa attggttatt    420
actttgtctg gttttattga taaagttaga gattttactg gtgatggtat taaagttgtt    480
tgtgttgatg ctccaccaga tgaatctgaa tatttgcatt tttctgtttt gactcaagct    540
gatgaatctg aaattccaga tgttgaaatt aaaccagatg atgttgttgc tttgccatat    600
tcttctggta ctactggttt gccaaaaggt gttatgttga ctcatagagt tatggttact    660
ggtgttgctc aacaagttga tgtgataat ccaaattggc attttcatca aaatgatgtt    720
attttgtgtg ttttgccagt ttttcatatt tattgtttga atgctatttt gttgtgtggt    780
ttgagagttg gtgcttctat tttgattatg gaaaaatttg aaatgaaaaa aatggttgaa    840
ttgattgaaa aatttaaagt tactattgct ccagttgttc caccaattgt tttgtctgtt    900
gttaaatttc cagatttgca tagatatgat ttgtcttcta ttagaactat tatgtctggt    960
ggtgctccaa tgggtaaaga tttggaagaa gctgttaaag aaaaatttcc acatgttact    1020
ttgggtcaag gttatggtat gactgaagct gaatgtttgt ctttgtgttt gggttttgct    1080
```

```
aaagaaccat tttccaactaa atttggtact tgtggtactg ttgttagaaa tgctgaaatg   1140
aaaattgttg atccaaatac tggtgcttct ttgccaagaa atcaatctgg tgaaatttgt   1200
attagaggta acaaattat gaaaggttat attaatgatt ttgaagctac taaaggtact    1260
attgatgaag ctggttggtt gcatactggt gatattggtt ttgttgatga tgatgatgaa   1320
ttgtttattg ttgatagatt gaaagaattg attaaatata aaggttttca agttgctcca   1380
gctgaattgg aatctttgtt gattgctcat ccaaatattt ctgatgctgc tgttgttcca   1440
atgaaagatg aagctgctgg tgaagttcca gttgcttttg ttgttagatc taatggttct   1500
aaaatttctg aagaagatat taaacaatat atttctaaac aagttgtttt ttataaaaga   1560
attgctaaag ttttttttat tgaagaaatt ccaaaatctc cagctggtaa aattttgaga   1620
aaatctttga gagctagatt ggttactgaa caagctattt aa                      1662
```

<210> SEQ ID NO 88
<211> LENGTH: 1719
<212> TYPE: DNA
<213> ORGANISM: Artificial Sequence
<220> FEATURE:
<223> OTHER INFORMATION: Codon Optimized

<400> SEQUENCE: 88

```
atgatttcta ttgctccacc attgaaaact caaataaac aagaaatttc tactattgat    60
cataatgatc ataatcaaga acatattttt aaatctaaat tgccagaaat tccaatttct   120
aataatattc cattgcattc ttatattttt caaaatttgc agaaaaatc taatagacca    180 tgtttgatta ctggtactac tactcaaact acttattctt attctcaaac tcatcatatt   240
gctaaaaaaa ttgctaaagg tttgtctaaa ttgaatatta ataaaaatga tgttattatg   300
attttgttgc caaattgtcc agaatttatt tttttctttt ttggtgcttc tatgattggt   360
gctgctatta ctactgctaa tccatttttat acttctccag aaattttttaa acaattgcaa   420 atttctaaag ctaaattggt tattactcaa actcaatttg tttctaaatt gattgatttt   480
ccagaaaaag ttattggtag agattttact gttgttactg ttgatggtga tgaaaatcca   540
tctccagaaa attgtttgcc attttctatt ttgactggtg aagatgaaac tgaagaaatt   600
tctattgatc caaatgatcc aattgctatt ccatttttctt ctggtactac tggtttgcca   660
aaaggtgttt ttttgactca taaaaatttg attacttctg ttgctcaaca agttgatggt   720
gataatccaa atatgtattt gagatctgat gatgttgttt tgtgtgtttt gccattgttt   780
catatttatt ctttgaattc tgttttgttg tgtgctttga gagttggtgc ttctgttttg   840
ttggttccaa aatttgaaat tggtactttg ttggaattga ttcaaaaaca tagagttact   900
gttgctccag ttgttccacc attggttttg ggtttggcta aaatccagt tgtttctgaa    960 tttgatttgt cttctattag aatggttttg tctggtgctg ctccattggg tatggaattg   1020
gaagatgctt tgagaagaag agttccacaa gctgttattg tcaaggtta tggtatgact   1080 gaagctggtc agttttgtc tatgtgtttg gcttttgcta acaaccatt tccaactaaa    1140 tctggttctt gtggtactgt tgttagaaat gctcaattga agttattga tccagaaact   1200 ggtgcttctt gtcttataa tcaaccaggt gaaatttgta ttagaggtca tcaaattatg   1260
aaaggttatt tggataattc tgatgctact gctaatacta ttgatgttga tggttggttg   1320
catactggtg atattggtta tgttgatgat gatgatgaaa ttttttattgt tgatagagtt   1380 aaagaaatta ttaaatttaa aggttttcaa gttccaccag ctgaattgga agcttttgttg   1440 atttctcatc catctattgc tgatgctgct gttgttccac aaaaagatga agttgctggt   1500
```

```
gaagttccag ttgctttgt tgttaaatct aataataaag attttgattt gtctgaagat    1560
gctgttaaag aatttattgc taaacaagtt gttttttata aaaaattgca taaagtttat    1620
tttgttcatt ctattccaaa atctccatct ggtaaaattt tgagaaaaga tttggttgct    1680
aaattggctt tggcttctac tttgattatt tcttcttaa                          1719
```

<210> SEQ ID NO 89  
<211> LENGTH: 2184  
<212> TYPE: DNA  
<213> ORGANISM: Artificial Sequence  
<220> FEATURE:  
<223> OTHER INFORMATION: Condon Optimized

<400> SEQUENCE: 89

```
atgggtagaa aatctatttc tgaagttggt gttgaagatt tggttcaagc tggtttgact      60
actgaagaag ctactggttt tcaaagagtt ttgaaagatt ctttgtcttg tactaaaggt     120
tctgatccat ctgaagtttg agacatttg gttgctagaa gagttttgaa accatggcat      180
ccacatggtt tgcatcaatt ggtttattat tctgtttatg ctcattggga tgtttcttct     240
aaaggtccac caccatattg gtttccatct ttgtatgaat ctaaacatac taatatgggt     300
ggtattatgg aaaaacatgg ttcttctttg ttgggtccat tgtataaaga tccaattact     360
tcttattctt tgtttcaaaa attttctgct caacatccag aagcttattg gtctattgtt     420
ttgaaagaat gtctgtttc ttttcaagaa gaaccaaaat gtattttgga tagatctgat      480
ttgaaatcta acatggtgg ttcttggttg ccaggttctg ttttgaatat tgctgaatgt      540
tgtttgttgc caactgctta tccaagaaaa gatgatgatt ctttggctat tgtttggaga     600
gatgaaggtt gtgatgattc tggtattaat attattactt tgaaacaatt gagagaacaa     660
gttatttctg ttgctaaagc tttggatgct atgttttcta aaggtgatgc tattgctatt     720
gatatgccaa tgactgctaa tgctgttatt atttatttgg ctattatttt gtctggtttg     780
gttgttgttt ctattgctga ttcttttgct ccaaaagaaa tttctattag attgagagtt     840
tctcaagcta aagctatttt tactcaagat tttattttga ggttctag aaaatttcca       900 ttgtattcta gagttgttga agctgctcca gataaagtta ttgttttgcc agctattggt     960
tctaatgttg gtattcaatt gagagaacaa gatatgtctt ggggtgattt tttgtcttct    1020
gttggtacta gatctagaaa ttattctcca tgttatcaac cagttgatac tttgattaat    1080
attttgtttt cttctggtac tactggtgaa ccaaaagcta ttccatggac tcaattgtct    1140
ccaattagat gtgctgctga atcttgggct catatggata tgcaagttgg tgatgttttt    1200
tgttggccaa ctaatttggg ttgggttatg ggtccaattt tgatttttc ttcttttttg     1260 tctggtgcta ctttggcttt gtatcatggt tctccattgg ttatggttt tggtaaattt     1320 gttcaagatg ctggtgttac taaattgggt actgttccat ctttggttaa agcttggaaa    1380
aatactcaat gtatgaatgg tttggattgg actaaaatta atgttttgc ttctactggt      1440 gaaacttcta atgttgatga tgatttgtgg ttgtcttcta gagcttatta taaaccagtt    1500
attgaatgtt gtggtggtac tgaattgtct tcttcttata ttcaaggttc tttgttgcaa    1560
ccacaagctt ttggtgcttt ttctactact tctatgacta cttctttggt tattttggat    1620
gaacatggta atccatttcc agatgatcaa gcttgtattg gtgaagttgg tttgtttcca    1680
ttgtatttgg gtgctactga tagattgttg aatgctgatc atgaagaagt ttatttttaaa    1740 ggtatgccat tgtataaagg tatgagattg agaagacatg gtgatattat taaaagaact    1800
```

```
gttggtggtt attttattgt tcaaggtaga gctgatgata ctatgaattt gggtggtatt      1860
aaaacttctt ctgttgaaat tgaaagagtt tgtgatagag ctgatgaatc tattgttgaa      1920
actgctgctg tttctgtttc tccagttgat ggtggtccag aacaattggt tatgtttgtt      1980
gttttgaaaa atggttataa ttctgaagct gaaaatttga aactaaaatt ttctaaagct      2040
attcaatcta atttgaatcc attgtttaaa gttagatttg ttaaaattgt tccagaattt      2100
ccaagaactg cttctaataa attgttgaga agagttttga gagatcaaat taaacatgaa      2160
ttgtctgctc attctagaat ttaa                                             2184
```

<210> SEQ ID NO 90
<211> LENGTH: 2172
<212> TYPE: DNA
<213> ORGANISM: Artificial Sequence
<220> FEATURE:
<223> OTHER INFORMATION: Codon Optimized

<400> SEQUENCE: 90

```
atgtctattt ctgaagttgg tgttgaagat ttggttcaag ctggtttgac tactgaagaa        60
gctactggtt tcaaagagt tttgaaagat tctttgtctt gtactaaagg ttctgatcca       120
tctgaagttt ggagacattt ggttgctaga agagctttga aaccatggca tccacatggt       180
ttgcatcaat ggtttattta ttctgtttat gctcattggg atgtttcttc taaaggtcca       240
ccaccatatt ggtttccatc tttgtatgaa tctaaacata ctaatatggg tggtattatg       300
gaaaaacatg gttcttcttt gttgggtcca ttgtataaag atccaattac ttcttattct       360
ttgtttcaaa aattttctgc tcaacatcca gaagcttatt ggtctattgt tttgaaagaa       420
ttgtctgttt cttttcaaga gaaccaaaa tgtattttgg atagatctga tttgaaatct       480
aaacatggtg gttcttggtt gccaggttct gttttgaatg ttgctgaatg ttgtttgttg       540
ccaactgctt atccaagaaa agatgatgat tctttggcta ttgtttggag atgtgaaggt       600
tgtgatgatt ctggtattaa tattattact ttgaaacaat tgagagaaca agttatttct       660
gttgctaaag ctttggatgc tatgtttcct aaaggtgatg ctattgctat tgatatgcca       720
atgactgcta atgctgttat tatttatttg gctattattt tgtctggttt ggttgttgtt       780
tctattgctg attcttttgc tccaaaagaa atttctatta gattgagagt ttctcaagct       840
aaagctattt ttactcaaga ttttattttg agaggttcta gaaaatttcc attgtattct       900
agagttgttg aagctgctcc agataaagtt attgttttgc cagctattgg ttctaatgtt       960
ggtattcaat tgagagaaca agatatgtct tggggtgatt ttttgtcttc tgttggtact      1020
agatctagaa attattctcc atgttatcaa ccagttgata ctttgattaa tattttgttt      1080
tcttctggta ctactggtga accaaaagct attccatgga ctcaattgtc tccaattaga      1140
tgtgctgctg aatcttgggc tcatatggat atgcaagttg gtgatgtttt tgttggcca      1200 actaatttgg gttgggttat gggtccaatt ttgatttttt cttctttttt gtctggtgct      1260
actttggctt tgtatcatgg ttctccattg ggttatggtt ttggtaaatt tgttcaagat      1320
gctggtgtta ctaaattggg tactgttcca tctttggtta agcttggaaa aatactcaa       1380 tgtatgaatg gttggattg gactaaaatt aaatgttttg cttctactgg tgaaacttct      1440
aatgttgatg atgatttgtg ttgtcttct agagcttatt ataaaccagt tattgaatgt      1500
tgtggtggta ctgaattgtc ttcttcttat attcaaggtt ctttgttgca accacaagct      1560
tttggtgctt ttctactac ttctatgact acttctttgg ttattttgga tgaacatggt      1620
aatccatttc cagatgatca agcttgtatt ggtgaagttg gtttgttcc attgtatttg      1680
```

```
ggtgctactg atagattgtt gaatgctgat catgaagaag tttattttaa agaatgtcat    1740
tatactaaag aatgtgcttc tgaaacttgg agatattatc aaagaactgt tggtggttat    1800
tttattgttc aaggtagagc tgatgatact atgaatttgg gtggtattaa aacttcttct    1860
gttgaaattg aaagagtttg tgatagagct gatgaatcta ttgttgaaac tgctgctgtt    1920
tctgtttctc cagttgatgg tggtccagaa caattggtta tgtttgttgt tttgaaaaat    1980
ggttataatt ctgaagctga aaatttgaga actaaatttt ctaaagctat tcaatctaat    2040
ttgaatccat tgtttaaagt tagatttgtt aaaattgttc cagaatttcc aagaactgct    2100
tctaataaat tgttgagaag agttttgaga gatcaaatta acatgaatt gtctgctcat    2160 tctagaattt aa                                                        2172
```

<210> SEQ ID NO 91
<211> LENGTH: 2148
<212> TYPE: DNA
<213> ORGANISM: Artificial Sequence
<220> FEATURE:
<223> OTHER INFORMATION: Codon Optimized

<400> SEQUENCE: 91

```
atgggttcta aatctatttc tgaagttggt gttgatgatt tggttcaagc tggtttgact     60
actgaagaag ctactggttt tcaaagagtt ttgaaagatt ctttgtcttg tactaaaggt    120
tctgatccat ctgaagtttg agacatttg gttgctagaa gagttttgaa accatggtct    180
gtttatgctc attgggatgt ttcttctaaa ggtccaccac atattggtt tccatctttg    240 tatcattcta agatactaa tttgggtaga ttgatggaaa acatggtcc atctttgttg    300 ggtccattgt ataagatcc aattacttct tattctttgt ttcaaaaatt ttctgttgaa    360
catccagaag tttattggtc tattgctttg aaagaattgt ctgtttcttt tcaagaagaa    420
ccaaaatgta ttttggataa atctgataaa tctaaacatg gtggttcttg gttgccaggt    480
gctgttttga atattgctga atgttgttttg ttgccaactt cttatccaag aaaagatgat    540
gattctttgg ctattgtttg agagatgaa ggttctgatg attcttctgt taatttgatt    600
actttgaaac aattgagaga acaagttatt tctgttgcta atctttgga tgctatgttt    660 tctaaaggtg atgctattgc tatggatatg ccaatgactg ctaatgctgt tattatttat    720
ttggctatta ttttgtctgg tttggttgtt gtttctattg ctgattcttt tgctccaaaa    780
gaaattgctt ctagattgca tgtttctcaa gctaaagcta ttttactca agattttatt    840 ttgagaggtg gtagaaaatt tccattgtat tctagagttt tgaagctgc tccagataga    900 gttattgttt tgccagctac tggttctaat attggtattc aattgagaga acaagatatg    960
tcttggggtg attttttgtc ttctgttggt actagatcta gaaaatattc tccatgttat    1020
caaccagttg attctttgat taatattttg ttttcttctg gtactactgg tgaaccaaaa    1080
gctattccat ggactcattt gtctccaatt agatgttctt ctgattttg ggcttatatg    1140 gatattaaag ttggtgatgt tgtttgtggg ccaactaatt ggggttgggc tttgggtcca    1200
tttattttgt ttacttgttt tttgtctggt gctgttttgg cttttgtatca tggttctcca    1260 ttgggtagag ttttggtaa atttgttcaa gatgcttctg ttactaaatt gggtactgtt    1320 ccatcttgg ttaaaacttg gaaaaatact caatgtatga aggtttgga ttggactaaa    1380 attaaatctt tgcttctac tggtgaaact tctaatgttg atgatgattt gtggttgtct    1440
tctcaagctt attataaacc agttattgaa tgttgtggtg gtactgaatt ggcttcttct    1500
```

```
tatattcaag gttctttgtt gcaaccacaa gcttttggtg cttttaatac tgctactatg   1560
actacttctt tgttattat tgatgaacat ggtaatccat atccagatga tcaagcttgt   1620
actggtgaag ttggtttgat tccattgtat ttgggtgctt ctgatagatt gttgaatgct   1680
gatcatgaag aagtttattt taaaggtatg ccattgtata aaggtatgag attgagaaga   1740
catggtgata ttattaatag aactgttggt ggttatttta ttgttcaagg tagagctgat   1800
gatactatga atttgggtgg tattaaaact tcttcttttg aaattgaaca tgtttgtgat   1860
agagctgatg attctatttt ggaaactgct gctgtttctg tttctccaat tggtggtggt   1920
ccagaacaat tggttatgtt tgttgttttg aaaaatggtt atgatgctga agctgaaaat   1980
ttgagaacta aattttctaa agctattcaa tctaatttga atccattgtt taaagttact   2040
gctgttaaaa ttgttcatga atttccaaga actatgtcta ataaattgtt gagaagagtt   2100
ttgagagatc aattgaatag agaattttct attcaatcta aaatttag              2148

<210> SEQ ID NO 92
<211> LENGTH: 303
<212> TYPE: DNA
<213> ORGANISM: Artificial Sequence
<220> FEATURE:
<223> OTHER INFORMATION: Codon Optimized

<400> SEQUENCE: 92
atggctgtta acatttgat tattttgaaa tttaagatg aaattactga agctcaaaaa     60
gaagaatttt ttaaaactta tgttaatttg gttaatatta ttccagctat gaaagatgtt   120
tattggggta agatgttac tcaaaaaaat aaagaagaag gttatactca tattgttgaa   180
gttacttttg aatctgttga aactattcaa gattatatta ttcatccagc tcatgttggt   240
tttggtgatg tttatagatg ttttttgggaa aaattgttga ttttttgatta tactccaaga   300 aaa                                                                 303

<210> SEQ ID NO 93
<211> LENGTH: 330
<212> TYPE: DNA
<213> ORGANISM: Artificial Sequence
<220> FEATURE:
<223> OTHER INFORMATION: Codon Optimized

<400> SEQUENCE: 93
atggaagaag ctaaaggtgt tgttaaacat gttttgttgg ctaaatttaa agaaggtact    60
tctgatgatc aaattcaaca attgattaaa ggttatgcta atttgttgaa tttgattcca   120
tctatgaaat cttttcattg gggtaaagat gtttctttttg aaaatttgca tcaaggtttt   180
actcatattt tgaatctac ttttgaaaat actgaaggtg ttgctgaata tgttgctcat   240
ccagctcatg ttgaatttgc taatgttttt tgtctaatt tggataaagt tgttgttttt   300
gattataaac caactactgt tttgttgcca                                    330

<210> SEQ ID NO 94
<211> LENGTH: 42
<212> TYPE: DNA
<213> ORGANISM: Artificial Sequence
<220> FEATURE:
<223> OTHER INFORMATION: Primer

<400> SEQUENCE: 94
aggaaacgaa gataaatctc gagtttatca ttatcaatac tg                       42
```

```
<210> SEQ ID NO 95
<211> LENGTH: 37
<212> TYPE: DNA
<213> ORGANISM: Artificial Sequence
<220> FEATURE:
<223> OTHER INFORMATION: Primer

<400> SEQUENCE: 95
ggaaaaatca gtcaaggcaa attaaagcct tcgagcg                                   37

<210> SEQ ID NO 96
<211> LENGTH: 27
<212> TYPE: DNA
<213> ORGANISM: Artificial Sequence
<220> FEATURE:
<223> OTHER INFORMATION: Primer

<400> SEQUENCE: 96
gatgggggat ccactagttc tagaatc                                              27

<210> SEQ ID NO 97
<211> LENGTH: 25
<212> TYPE: DNA
<213> ORGANISM: Artificial Sequence
<220> FEATURE:
<223> OTHER INFORMATION: Primer

<400> SEQUENCE: 97
tgatgggctg caggaattcg atatc                                                25

<210> SEQ ID NO 98
<211> LENGTH: 38
<212> TYPE: DNA
<213> ORGANISM: Artificial Sequence
<220> FEATURE:
<223> OTHER INFORMATION: Primer

<400> SEQUENCE: 98
gaactagtgg atcccccatc atgaaccatt tgagagcc                                  38

<210> SEQ ID NO 99
<211> LENGTH: 32
<212> TYPE: DNA
<213> ORGANISM: Artificial Sequence
<220> FEATURE:
<223> OTHER INFORMATION: Primer

<400> SEQUENCE: 99
tattttggct ttaactttct tgggtgtaa tc                                         32

<210> SEQ ID NO 100
<211> LENGTH: 43
<212> TYPE: DNA
<213> ORGANISM: Artificial Sequence
<220> FEATURE:
<223> OTHER INFORMATION: Primer

<400> SEQUENCE: 100
agaaagttaa agccaaaata atgataacga gaataatatc aag                            43

<210> SEQ ID NO 101
<211> LENGTH: 28
<212> TYPE: DNA
<213> ORGANISM: Artificial Sequence
<220> FEATURE:
<223> OTHER INFORMATION: Primer
```

<400> SEQUENCE: 101
ataaacccat ggcgcagacc tgtgagag                                    28

<210> SEQ ID NO 102
<211> LENGTH: 28
<212> TYPE: DNA
<213> ORGANISM: Artificial Sequence
<220> FEATURE:
<223> OTHER INFORMATION: Primer

<400> SEQUENCE: 102
ggtctgcgcc atgggtttat catccgtc                                    28

<210> SEQ ID NO 103
<211> LENGTH: 41
<212> TYPE: DNA
<213> ORGANISM: Artificial Sequence
<220> FEATURE:
<223> OTHER INFORMATION: Primer

<400> SEQUENCE: 103
cgaattcctg cagcccatca gtgtctatgt ctaggtaaag g                     41

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104
tgatgggctg caggaattcg atatc                                       25

<210> SEQ ID NO 105
<211> LENGTH: 27
<212> TYPE: DNA
<213> ORGANISM: Artificial Sequence
<220> FEATURE:
<223> OTHER INFORMATION: Primer

<400> SEQUENCE: 105 gatggggat ccactagttc tagaatc                                      27

<210> SEQ ID NO 106
<211> LENGTH: 33
<212> TYPE: DNA
<213> ORGANISM: Artificial Sequence
<220> FEATURE:
<223> OTHER INFORMATION: Primer

<400> SEQUENCE: 106
caccagaacc gaaggtagag gttctttgtt aac                              33

<210> SEQ ID NO 107
<211> LENGTH: 45
<212> TYPE: DNA
<213> ORGANISM: Artificial Sequence
<220> FEATURE:
<223> OTHER INFORMATION: Primer

<400> SEQUENCE: 107
cgaattcctg cagcccatca ctttgatctc ttgtagacct tattc                 45

<210> SEQ ID NO 108
<211> LENGTH: 42

```
<212> TYPE: DNA
<213> ORGANISM: Artificial Sequence
<220> FEATURE:
<223> OTHER INFORMATION: Primer

<400> SEQUENCE: 108
gaactagtgg atcccccatc atggtttcca atcacttgtt tg                          42

<210> SEQ ID NO 109
<211> LENGTH: 29
<212> TYPE: DNA
<213> ORGANISM: Artificial Sequence
<220> FEATURE:
<223> OTHER INFORMATION: Primer

<400> SEQUENCE: 109
ctctaccttc ggttctggtg tataagtcg                                         29

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110
gatccactag ttctagaatc cg                                                22

<210> SEQ ID NO 111
<211> LENGTH: 35
<212> TYPE: DNA
<213> ORGANISM: Artificial Sequence
<220> FEATURE:
<223> OTHER INFORMATION: Primer

<400> SEQUENCE: 111
tctagaacta gtggatcatg aaccatttga gagcc                                  35

<210> SEQ ID NO 112
<211> LENGTH: 28
<212> TYPE: DNA
<213> ORGANISM: Artificial Sequence
<220> FEATURE:
<223> OTHER INFORMATION: Primer

<400> SEQUENCE: 112
tcgttatcac tttcttgggg tgtaatcg                                          28

<210> SEQ ID NO 113
<211> LENGTH: 36
<212> TYPE: DNA
<213> ORGANISM: Artificial Sequence
<220> FEATURE:
<223> OTHER INFORMATION: Primer

<400> SEQUENCE: 113
ccaagaaagt gataacgaga ataatatcaa gaatac                                 36

<210> SEQ ID NO 114
<211> LENGTH: 44
<212> TYPE: DNA
<213> ORGANISM: Artificial Sequence
<220> FEATURE:
<223> OTHER INFORMATION: Primer

<400> SEQUENCE: 114
```

```
aggtcgacgg tatcgttaaa taaaaacgta taccaaatat tcag          44
```

<210> SEQ ID NO 115
<211> LENGTH: 18
<212> TYPE: DNA
<213> ORGANISM: Artificial Sequence
<220> FEATURE:
<223> OTHER INFORMATION: Primer

<400> SEQUENCE: 115

```
cgataccgtc gacctcga                                       18
```

<210> SEQ ID NO 116
<211> LENGTH: 32
<212> TYPE: DNA
<213> ORGANISM: Artificial Sequence
<220> FEATURE:
<223> OTHER INFORMATION: Primer

<400> SEQUENCE: 116

```
ggttaaacta gtatgggtaa aaactataag tc                       32
```

<210> SEQ ID NO 117
<211> LENGTH: 33
<212> TYPE: DNA
<213> ORGANISM: Artificial Sequence
<220> FEATURE:
<223> OTHER INFORMATION: Primer

<400> SEQUENCE: 117

```
gtgcccgtcg actcattcga aatgactgaa ttg                      33
```

<210> SEQ ID NO 118
<211> LENGTH: 3952
<212> TYPE: DNA
<213> ORGANISM: Artificial Sequence
<220> FEATURE:
<223> OTHER INFORMATION: Codon Optimized

<400> SEQUENCE: 118

```
tcattatcaa tactgccatt tcaaagaata cgtaaataat taatagtagt gattttccta   60 actttatttta gtcaaaaaat tagccttttta attctgctgt aacccgtaca tgcccaaaat  120 aggggggcggg ttacacagaa tatataacat cgtaggtgtc tgggtgaaca gtttattcct  180
ggcatccact aaatataatg gagcccgctt tttaagctgg catccagaaa aaaaaagaat  240
cccagcacca aaatattgtt ttcttcacca accatcagtt cataggtcca ttctcttagc   300
gcaactacag agaacagggg cacaaacagg caaaaaacgg gcacaacctc aatggagtga   360
tgcaacctgc ctggagtaaa tgatgacaca aggcaattga cccacgcatg tatctatctc   420
attttcttac accttctatt accttctgct ctctctgatt tggaaaaagc tgaaaaaaaa   480
ggttgaaacc agttccctga aattattccc ctacttgact aataagtata taagacggt    540 aggtattgat tgtaattctg taaatctatt tcttaaactt cttaaattct acttttatag   600
ttagtctttt ttttagtttt aaaacaccaa gaacttagtt tcgaataaac acacataaac   660
aaacaaaatg aaattgttaa catttccagg tcaaggtact tctatttcta tttctatatt   720
gaaggctata ataagaaaca agtcaagaga atttcaaaca atcttgagtc aaaatggtaa   780
agaatctaac gatttgttgc aatacatctt ccaaaatcca tcttcacctg gttcaatcgc   840
tgtttgttcc aatttgttct atcaattgta ccaaatcttg tctaacccat cagatcctca   900
agaccaagca cctaaaaata tgacaaagat cgatagtcct gacaaaaagg ataacgaaca   960
```

```
atgttatttg ttgggtcatt ctttgggtga attaacttgc ttgtccgtta atagtttatt    1020
ttctttgaag gacttatttg atattgcaaa cttcagaaac aaattaatgg tcacttcaac    1080
agaaaagtac ttggttgccc acaacataaa cagatccaat aagttcgaaa tgtgggcttt    1140
atccagtcca agagcaaccg atttgcctca agaagttcaa aagttgttaa attcaccaaa    1200
cttgttatct tcatcccaaa acactatttc agtagccaat gctaactccg tcaaacaatg    1260
tgttgtaact ggtttagtag atgacttgga atcattaaga acagaattga acttaagatt    1320
ccctagattg agaatcacag aattgaccaa tccatacaac attcctttcc ataattccac    1380
tgtcttaaga ccagttcaag aacctttgta cgactatatt tgggatattt tgaaaaagaa    1440
tggtactcat actttgatgg aattaaacca cccaatcatt gccaatttgg atggtaacat    1500
ctcatactac atccatcacg ctttggatag attcgttaag tgttcttcaa gaactgtaca    1560
attcacaatg tgctatgaca ccattaatag tggtactcca gttgaaatcg ataagtctat    1620
ttgtttcggt cctggtaacg taatatacaa cttaatcaga agaaactgcc ctcaagttga    1680
taccatcgaa tacacttctt tggcaacaat cgatgcctac cataaagctg cagaagaaaa    1740
taaggattaa tcatgtaatt agttatgtca cgcttacatt cacgccctcc ccccacatcc    1800
gctctaaccg aaaaggaagg agttagacaa cctgaagtct aggtccctat ttattttttt    1860
atagttatgt tagtattaag aacgttattt atatttcaaa ttttttcttt ttttctgtac    1920
agacgcgtgt acgcatgtaa cattatactg aaaaccttgc ttgagaaggt tttgggacgc    1980
tcgaaggctt taatttgccc tcagggggg gcccggtacc caattcgccc tatagtgagt    2040
cgtattacgc gcgctcactg gccgtcgttt tacaacgtcg tgactgggaa aaccctggcg    2100
ttacccaact taatcgcctt gcagcacatc cccctttcgc cagctggcgt aatagcgaag    2160
aggcccgcac cgatcgccct tcccaacagt tgcgcagcct gaatggcgaa tggcgcgacg    2220
cgccctgtag cggcgcatta agcgcggcgg gtgtggtggt tacgcgcagc gtgaccgcta    2280
cacttgccag cgccctagcg cccgctcctt tcgctttctt cccttccttt ctcgccacgt    2340
tcgccggctt tccccgtcaa gctctaaatc ggggctccc tttagggttc cgatttagtg    2400
ctttacggca cctcgacccc aaaaaacttg attagggtga tggttcacgt agtgggccat    2460
cgccctgata cggttttt cgccctttga cgttggagtc cacgttcttt aatagtggac    2520
tcttgttcca aactggaaca acactcaacc ctatctcggt ctattctttt gatttataag    2580
ggattttgcc gatttcggcc tattggttaa aaaatgagct gatttaacaa aaatttaacg    2640
cgaattttaa caaaatatta cgtttacaa tttcctgatg cggtattttc tccttacgca    2700
tctgtgcggt atttcacacc gcatagatcc gtcgagttca agagaaaaaa aagaaaaag    2760 caaaagaaa aaggaaagc gcgcctcgtt cagaatgaca cgtatagaat gatgcattac    2820
cttgtcatct tcagtatcat actgttcgta tacatactta ctgacattca taggtataca    2880
tatatacaca tgtatatata tcgtatgctg cagctttaaa taatcggtgt cattagtttt    2940
gctggccgca tcttctcaaa tatgcttccc agcctgcttt tctgtaacgt tcaccctcta    3000
ccttagcatc ccttcccttt gcaaatagtc ctcttccaac aataataatg tcagatcctg    3060
tagagaccac atcatccacg gttctatact gttgacccca tgcgtctccc ttgtcatcta    3120
aacccacacc gggtgtcata atcaaccaat cgtaacctttc atctcttcca cccatgtctc    3180
tttgagcaat aaagccgata acaaaatctt tgtcgctctt cgcaatgtca acagtaccct    3240
tagtatattc tccagtagat agggagccct tgcatgacaa ttctgctaac atcaaaaggc    3300
```

```
ctctaggttc ctttgttact tcttctgccg cctgcttcaa accgctaaca ataccgggc      3360 ccaccacacc gtgtgcattc gtaatgtctg cccattctgc tattctgtat acacccgcag     3420
agtactgcaa tttgactgta ttaccaatgt cagcaaattt tctgtcttcg aagagtaaaa     3480
aattgtactt ggcggataat gcctttagcg gcttaactgt gccctccatg gaaaaatcag    3540
tcaagatatc cacatgtgtt tttagtaaac aaattttggg acctaatgct tcaactaact    3600
ccagtaattc cttggtggta cgaacatcca atgaagcaca caagtttgtt tgcttttcgt    3660
gcatgatatt aaatagcttg gcagcaacag gactaggatg agtagcagca cgttccttat    3720
atgtagcttt cgacatgatt tatcttcgtt tcctgcaggt ttttgttctg tgcagttggg    3780
ttaagaatac tgggcaattt catgtttctt caacactaca tatgcgtata tataccaatc    3840
taagtctgtg ctccttcctt cgttcttcct tctgttcgga gattaccgaa tcaaaaaaat    3900
ttcaaagaaa ccgaaatcaa aaaaaagaat aaaaaaaaaa tgatgaattg aa            3952
```

<210> SEQ ID NO 119
<211> LENGTH: 3718
<212> TYPE: DNA
<213> ORGANISM: Artificial Sequence
<220> FEATURE:
<223> OTHER INFORMATION: Codon Optimized

<400> SEQUENCE: 119

```
tcattatcaa tactgccatt tcaaagaata cgtaaataat taatagtagt gattttccta     60
actttattta gtcaaaaaat tagccttta attctgctgt aacccgtaca tgcccaaaat    120
agggggcggg ttacacagaa tatataacat cgtaggtgtc tgggtgaaca gtttattcct    180
ggcatccact aaatataatg gagcccgctt tttaagctgg catccagaaa aaaaagaat    240 cccagcacca aaatattgtt ttcttcacca accatcagtt cataggtcca ttctcttagc    300
gcaactacag agaacagggg cacaaacagg caaaaacgg gcacaacctc aatggagtga    360
tgcaacctgc ctggagtaaa tgatgacaca aggcaattga cccacgcatg tatctatctc    420 atttcttac accttctatt accttctgct ctctctgatt tggaaaaagc tgaaaaaaaa    480
ggttgaaacc agttccctga aattattccc ctacttgact aataagtata aaagacggt    540 aggtattgat tgtaattctg taaatctatt tcttaaactt cttaaattct acttttatag   600
ttagtctttt ttttagtttt aaaacaccaa gaacttagtt tcgaataaac acacataaac   660
aaacaaaatg aaaaaggttt gtgtcatcgg tgctggtact atgggttctg gtattgctca    720
agcatttgct gcaaaaggtt tcgaagttgt attgagagat ataaaggacg aatttgttga    780
tagaggttta gacttcatca ataagaactt gagtaaattg gttaagaaag gtaaaatcga    840
agaagctact aaggttgaaa tattgacaag aatatctggt actgtagatt tgaacatggc    900
cgctgattgt gacttagtaa ttgaagcagc cgtcgaaaga atggatatta agaaacaaat    960
attcgctgat ttggataata tttgcaagcc agaaactata ttggcatcta acacatcttc   1020
attatcaatt accgaagtcg cctccgctac taagacaaac gataaggtta taggcatgca   1080
tttctttaac ccagcccctg ttatgaaatt ggttgaagta ataagaggta tcgcaaccctc  1140 acaagaaact ttcgatgcag ttaaggaaac atccattgcc attggtaaag atccagtcga   1200
agttgcagaa gcccctggtt tcgtcgttaa cagaatcttg ataccaatga taacgaagc    1260 tgtaggtata ttagctgaag gtatcgcatc cgtcgaagat attgacaaag ccatgaagtt   1320
aggtgctaac catccaatgg gtccttttgga attaggtgac tttataggtt tggacatctg   1380
cttagctatt atggatgttt tgtattccga aactggtgac agtaaataca gacctcacac   1440
```

```
attgttgaag aaatatgtta gagcaggttg gttaggtaga aagagtggta aaggtttcta    1500
cgattactct aaataatcat gtaattagtt atgtcacgct tacattcacg ccctccccccc   1560 acatccgctc taaccgaaaa ggaaggagtt agacaacctg aagtctaggt ccctatttat    1620
ttttttatag ttatgttagt attaagaacg ttatttatat ttcaaatttt tcttttttttt   1680 ctgtacagac gcgtgtacgc atgtaacatt atactgaaaa ccttgcttga aaggttttg     1740 ggacgctcga aggctttaat ttgccctcga gggggggccc ggtacccaat tcgccctata    1800
gtgagtcgta ttacgcgcgc tcactggccg tcgttttaca acgtcgtgac tgggaaaacc    1860
ctggcgttac ccaacttaat cgccttgcag cacatccccc tttcgccagc tggcgtaata    1920
gcgaagaggc ccgcaccgat cgcccttccc aacagttgcg cagcctgaat ggcgaatggc    1980
gcgacgcgcc ctgtagcggc gcattaagcg cggcgggtgt ggtggttacg cgcagcgtga    2040
ccgctacact tgccagcgcc ctagcgcccg ctcctttcgc tttcttccct cctttctcg     2100 ccacgttcgc cggctttccc cgtcaagctc taaatcgggg ctccctttta gggttccgat    2160
ttagtgcttt acggcacctc gaccccaaaa aacttgatta gggtgatggt tcacgtagtg    2220
ggccatcgcc ctgatagacg ttttttcgcc ctttgacgtt ggagtccacg ttctttaata    2280
gtggactctt gttccaaact ggaacaacac tcaaccctat ctcggtctat tcttttgatt    2340
tataagggat tttgccgatt tcggcctatt ggttaaaaaa tgagctgatt taacaaaaat    2400
ttaacgcgaa ttttaacaaa atattaacgt ttacaatttc ctgatgcggt attttctcct    2460
tacgcatctg tgcggtattt cacaccgcat agatccgtcg agttcaagag aaaaaaaaag    2520
aaaaagcaaa aagaaaaaag gaaagcgcgc ctcgttcaga atgacgcgta tagaatgatg    2580
cattaccttg tcatcttcag tatcatactg ttcgtataca tacttactga cattcatagg    2640
tatacatata tacacatgta tatatatcgt atgctgcagc tttaaataat cggtgtcatt    2700
agttttgctg gccgcatctt ctcaaatatg cttcccagcc tgcttttctg taacgttcac    2760
cctctacctt agcatccctt ccctttgcaa atagtcctct tccaacaata ataatgtcag    2820
atcctgtaga gaccacatca tccacggttc tatactgttg acccaatgcg tctcccttgt    2880
catctaaacc cacaccgggt gtcataatca accaatcgta accttcatct cttccaccca    2940
tgtctctttg agcaataaag ccgataacaa aatctttgtc gctcttcgca atgtcaacag    3000
tacccttagt atattctcca gtagatagg agcccttgca tgacaattct gctaacatca    3060
aaaggcctct aggttccttt gttacttctt ctgccgcctg cttcaaaccg ctaacaatac    3120
ctgggcccac cacaccgtgt gcattcgtaa tgtctgccca ttctgctatt ctgtatacac    3180
ccgcagagta ctgcaatttg actgtattac caatgtcagc aaattttctg tcttcgaaga    3240
gtaaaaaatt gtacttggcg gataatgcct ttagcggctt aactgtgccc tccatggaaa    3300
aatcagtcaa gatatccaca tgtgttttta gtaaacaaat tttgggacct aatgcttcaa    3360
ctaactccag taattccttg gtggtacgaa catccaatga agcacacaag tttgtttgct    3420
tttcgtgcat gatattaaat agcttggcag caacaggact aggatgagta gcagcacgtt    3480
ccttatatgt agctttcgac atgatttatc ttcgtttcct gcaggttttt gttctgtgca    3540
gttgggttaa gaatactggg caatttcatg tttcttcaac actacatatg cgtatatata    3600
ccaatctaag tctgtgctcc ttccttcgtt cttccttctg ttcggagatt accgaatcaa    3660
aaaaatttca agaaaccgaa atcaaaaaaa aagaataaaa aaaaaatgat gaattgaa     3718
```

<210> SEQ ID NO 120

<211> LENGTH: 3655
<212> TYPE: DNA
<213> ORGANISM: Artificial Sequence
<220> FEATURE:
<223> OTHER INFORMATION: Codon Optimized

<400> SEQUENCE: 120

| | |
|---|---:|
| tcattatcaa tactgccatt tcaaagaata cgtaaataat taatagtagt gattttccta | 60 |
| actttattta gtcaaaaaat tagccttttta attctgctgt aacccgtaca tgcccaaaat | 120 |
| aggggggcggg ttacacagaa tatataacat cgtaggtgtc tgggtgaaca gtttattcct | 180 |
| ggcatccact aaatataatg gagcccgctt tttaagctgg catccagaaa aaaaagaat | 240 |
| cccagcacca aaatattgtt ttcttcacca accatcagtt cataggtcca ttctcttagc | 300 |
| gcaactacag agaacagggg cacaaacagg caaaaaacgg gcacaacctc aatggagtga | 360 |
| tgcaacctgc ctggagtaaa tgatgacaca aggcaattga cccacgcatg tatctatctc | 420 |
| attttcttac accttctatt accttctgct ctctctgatt tggaaaaagc tgaaaaaaaa | 480 |
| ggttgaaacc agttccctga aattattccc ctacttgact aataagtata taagacggt | 540 |
| aggtattgat tgtaattctg taaatctatt tcttaaactt cttaaattct actttatag | 600 |
| ttagtctttt ttttagtttt aaaacaccaa gaacttagtt tcgaataaac acacataaac | 660 |
| aaacaaaatg gaactaaaca atgtcatcct tgaaaaggaa ggtaaagttg ctgtagttac | 720 |
| cattaacaga cctaaagcat taaatgcgtt aaatagtgat acactaaaag aaatggatta | 780 |
| tgttataggt gaaattgaaa atgatagcga agtacttgca gtaattttaa ctggagcagg | 840 |
| agaaaaatca tttgtagcag gagcagatat ttctgagatg aaggaaatga ataccattga | 900 |
| aggtagaaaa ttcgggatac ttggaaataa agtgtttaga agattagaac ttcttgaaaa | 960 |
| gcctgtaata gcagctgtta atggttttgc tttaggaggc ggatgcgaaa tagctatgtc | 1020 |
| ttgtgatata agaatagctt caagcaacgc aagatttggt caaccagaag taggtctcgg | 1080 |
| aataacacct ggttttggtg gtacacaaag actttcaaga ttagttggaa tgggcatggc | 1140 |
| aaagcagctt atatttactg cacaaaatat aaaggcagat gaagcattaa gaatcggact | 1200 |
| tgtaaataag gtagtagaac ctagtgaatt aatgaataca gcaaaagaaa ttgcaaacaa | 1260 |
| aattgtgagc aatgctccag tagctgttaa gttaagcaaa caggctatta atagaggaat | 1320 |
| gcagtgtgat attgatactg ctttagcatt tgaatcagaa gcatttggag aatgcttttc | 1380 |
| aacagaggat caaaaggatg caatgacagc tttcatagag aaaagaaaaa ttgaaggctt | 1440 |
| caaaaataga tagtcatgta attagttatg tcacgcttac attcacgccc tccccccaca | 1500 |
| tccgctctaa ccgaaaagga aggagttaga caacctgaag tctaggtccc tatttatttt | 1560 |
| tttatagtta tgttagtatt aagaacgtta tttatatttc aaattttttct tttttttctg | 1620 |
| tacagacgcg tgtacgcatg taacattata ctgaaaacct tgcttgagaa ggttttggga | 1680 |
| cgctcgaagg ctttaatttg ccctcgaggg ggggcccggt acccaattcg ccctatagtg | 1740 |
| agtcgtatta cgcgcgctca ctggccgtcg ttttacaacg tcgtgactgg gaaaaccctg | 1800 |
| gcgttaccca acttaatcgc cttgcagcac atccccctt cgccagctgg cgtaatagcg | 1860 |
| aagaggcccg caccgatcgc ccttcccaac agttgcgcag cctgaatggc gaatggcgcg | 1920 |
| acgcgccctg tagcggcgca ttaagcgcgg cgggtgtggt ggttacgcgc agcgtgaccg | 1980 |
| ctacacttgc cagcgcccta gcgcccgctc cttttcgctt tcttcccttcc tttctcgcca | 2040 |
| cgttcgccgg ctttccccgt caagctctaa atcgggggct cccttagggg ttccgattta | 2100 |
| gtgctttacg gcacctcgac cccaaaaaac ttgattaggg tgatggttca cgtagtgggc | 2160 |

```
catcgccctg atagacggtt tttcgcccctt tgacgttgga gtccacgttc tttaatagtg    2220
gactcttgtt ccaaactgga acaacactca accctatctc ggtctattct tttgatttat    2280
aagggatttt gccgatttcg gcctattggt taaaaaatga gctgatttaa caaaaattta    2340
acgcgaattt taacaaaata ttaacgttta caatttcctg atgcggtatt ttctccttac    2400
gcatctgtgc ggtatttcac accgcataga tccgtcgagt tcaagagaaa aaaaagaaa    2460 aagcaaaaag aaaaaaggaa agcgcgcctc gttcagaatg acacgtatag aatgatgcat    2520
taccttgtca tcttcagtat catactgttc gtatacatac ttactgacat tcataggtat    2580
acatatatac acatgtatat atatcgtatg ctgcagcttt aaataatcgg tgtcattagt    2640
tttgctggcc gcatcttctc aaatatgctt cccagcctgc ttttctgtaa cgttcaccct    2700
ctaccttagc atcccttccc tttgcaaata gtcctcttcc aacaataata atgtcagatc    2760
ctgtagagac cacatcatcc acggttctat actgttgacc caatgcgtct cccttgtcat    2820
ctaaacccac accgggtgtc ataatcaacc aatcgtaacc ttcatctctt ccacccatgt    2880
ctctttgagc aataaagccg ataacaaaat ctttgtcgct cttcgcaatg tcaacagtac    2940
ccttagtata ttctccagta gatagggagc ccttgcatga caattctgct aacatcaaaa    3000
ggcctctagg ttcctttgtt acttcttctg ccgcctgctt caaaccgcta acaatacctg    3060
ggcccaccac accgtgtgca ttcgtaatgt ctgcccattc tgctattctg tatacacccg    3120
cagagtactg caatttgact gtattaccaa tgtcagcaaa ttttctgtct tcgaagagta    3180
aaaaattgta cttggcggat aatgccttta gcggcttaac tgtgccctcc atggaaaaat    3240
cagtcaagat atccacatgt gttttttagta acaaattttt gggacctaat gcttcaacta    3300
actccagtaa ttccttggtg gtacgaacat ccaatgaagc acacaagttt gtttgctttt    3360
cgtgcatgat attaaatagc ttggcagcaa caggactagg atgagtagca gcacgttcct    3420
tatatgtagc tttcgacatg atttatcttc gtttcctgca ggttttttgtt ctgtgcagtt    3480 gggttaagaa tactgggcaa tttcatgttt cttcaacact acatatgcgt atatataccaa    3540 atctaagtct gtgctccttc cttcgttctt ccttctgttc ggagattacc gaatcaaaaa    3600
aatttcaaag aaaccgaaat caaaaaaaag aataaaaaaa aaatgatgaa ttgaa         3655
```

<210> SEQ ID NO 121
<211> LENGTH: 4054
<212> TYPE: DNA
<213> ORGANISM: Artificial Sequence
<220> FEATURE:
<223> OTHER INFORMATION: Codon Optimized

<400> SEQUENCE: 121

```
tcattatcaa tactgccatt tcaaagaata cgtaaataat taatagtagt gattttccta      60
actttattta gtcaaaaaat tagcctttta attctgctgt aacccgtaca tgcccaaaat     120 aggggggcggg ttacacagaa tatataacat cgtaggtgtc tgggtgaaca gtttattcct    180
ggcatccact aaatataatg gagcccgctt tttaagctgg catccagaaa aaaaagaat     240 cccagcacca aaatattgtt ttcttcacca accatcagtt cataggtcca ttctcttagc    300
gcaactacag agaacagggg cacaaacagg caaaaaacgg gcacaacctc aatggagtga    360
tgcaacctgc ctggagtaaa tgatgacaca aggcaattga cccacgcatg tatctatctc    420
attttcttac accttctatt accttctgct ctctctgatt tggaaaaagc tgaaaaaaaa    480
ggttgaaacc agttccctga aattattccc ctacttgact aataagtata taagacggt     540
```

```
aggtattgat tgtaattctg taaatctatt tcttaaactt cttaaattct acttttatag    600
ttagtctttt ttttagtttt aaaacaccaa gaacttagtt tcgaataaac acacataaac    660
aaacaaaatg aaaaattgtg tcatagtttc tgccgttaga actgctatcg gttcttttaa    720
cggttcattg gcatctactt cagctatcga tttgggtgct acagtaatca aagctgcaat    780
tgaaagagca aagatagatt ccttgcatat agacgaagtt atcatgggta atgtattgca    840
agctggttta ggtcaaaacc cagctagaca agcattgtta aaatcaggtt tagcagaaac    900
cgtatgtggt ttcactgtca ataaggtttg cggttccggt ttgaagagtg tcgctttagc    960
cgctcaagcc attcaagctg gtcaagcaca atccatagtt gccggtggta tggaaaacat   1020
gagtttggca ccttatttgt tagatgccaa ggctagatct ggttatagat taggtgacgg   1080
tcaagtatac gacgtcattt tgagagatgg tttaatgtgc gctactcatg gttatcacat   1140
gggtataact gctgaaaacg ttgcaaagga atacggtatc acaagagaaa tgcaagatga   1200
attggcttta cactctcaaa gaaaggcagc cgctgcaatc gaatcaggtg cctttaccgc   1260
tgaaattgta ccagtcaacg ttgtaactag aaagaaaact ttcgttttct ctcaagacga   1320
atttccaaaa gctgattcaa ctacagaagc attgggtgcc ttaagacctg ccttcgacaa   1380
ggctggtact gtaactgctg gtaatgcatc cggtataaac gatggtgccg ctgcattggt   1440
catcatggaa gaaagtgccg ctttagcagc cggtttgaca ccttagcta gaattaaatc   1500
ctacgcaagt ggtggtgtcc cacctgcttt gatgggtatg gtccagttc ctgcaacaca   1560
aaagaccttg caattagcag gtttgcaatt agccgatatt gacttaatag aagccaatga   1620
agcatttgct gcacaattct ggctgttgg taaaacttta ggtttcgact ctgaaaaggt   1680
taatgtaaac ggtggtgcaa tcgccttggg tcatccaatt ggtgcatcag gtgccagaat   1740
tttagttaca ttgttacacg ctatgcaagc aagagataaa acattgggtt tagctacctt   1800
gtgtattggt ggtggtcaag gtattgcaat ggttatagaa agattaaatt aatcatgtaa   1860
ttagttatgt cacgcttaca ttcacgcccct ccccccacat ccgctctaac cgaaaaggaa   1920
ggagttagac aacctgaagt ctaggtccct atttattttt ttatagttat gttagtatta   1980
agaacgttat ttatatttca aattttctct tttttttctgt acagacgcgt gtacgcatgt   2040
aacattatac tgaaaacctt gcttgagaag ttttgggac gctcgaaggc tttaatttgc   2100
cctcgagggg gggcccggta cccaattcgc cctatagtga gtcgtattac gcgcgctcac   2160
tggccgtcgt tttacaacgt cgtgactggg aaaaccctgg cgttacccaa cttaatcgcc   2220
ttgcagcaca tccccctttc gccagctggc gtaatagcga agaggcccgc accgatcgcc   2280
cttcccaaca gttgcgcagc ctgaatggcg aatggcgcga cgcgccctgt agcggcgcat   2340
taagcgcggc gggtgtggtg gttacgcgca gcgtgaccgc tacacttgcc agcgccctag   2400
cgcccgctcc tttcgctttc ttcccttcct ttctcgccac gttcgccggc tttccccgtc   2460
aagctctaaa tcggggctc cctttagggt tccgatttag tgctttacgg cacctcgacc   2520
ccaaaaaact tgattagggt gatggttcac gtagtgggcc atcgccctga tagacggttt   2580
ttcgcccttt gacgttggag tccacgttct ttaatagtgg actcttgttc caaactggaa   2640
caacactcaa ccctatctcg gtctattctt ttgatttata agggattttg ccgatttcgg   2700
cctattggtt aaaaaatgag ctgatttaac aaaaatttaa cgcgaatttt aacaaaatat   2760
taacgtttac aatttcctga tgcggtattt tctccttacg catctgtgcg gtatttcaca   2820
ccgcatagat ccgtcgagtt caagagaaaa aaaagaaaa agcaaaaaga aaaaggaaa   2880
gcgcgcctcg ttcagaatga cacgtataga atgatgcatt accttgtcat cttcagtatc   2940
```

| | | |
|---|---|---|
| atactgttcg tatacatact tactgacatt cataggtata catatataca catgtatata | 3000 | |
| tatcgtatgc tgcagcttta aataatcggt gtcattagtt ttgctggccg catcttctca | 3060 | |
| aatatgcttc ccagcctgct tttctgtaac gttcaccctc taccttagca tcccttccct | 3120 | |
| ttgcaaatag tcctcttcca acaataataa tgtcagatcc tgtagagacc acatcatcca | 3180 | |
| cggttctata ctgttgaccc aatgcgtctc ccttgtcatc taaacccaca ccgggtgtca | 3240 | |
| taatcaacca atcgtaacct tcatctcttc cacccatgtc tctttgagca ataaagccga | 3300 | |
| taacaaaatc tttgtcgctc ttcgcaatgt caacagtacc cttagtatat tctccagtag | 3360 | |
| atagggagcc cttgcatgac aattctgcta acatcaaaag gcctctaggt tcctttgtta | 3420 | |
| cttcttctgc cgcctgcttc aaaccgctaa caatacctgg gcccaccaca ccgtgtgcat | 3480 | |
| tcgtaatgtc tgcccattct gctattctgt atacacccgc agagtactgc aatttgactg | 3540 | |
| tattaccaat gtcagcaaat tttctgtctt cgaagagtaa aaaattgtac ttggcggata | 3600 | |
| atgcctttag cggcttaact gtgccctcca tggaaaaatc agtcaagata tccacatgtg | 3660 | |
| ttttttagtaa acaaattttg ggacctaatg cttcaactaa ctccagtaat tccttggtgg | 3720 | |
| tacgaacatc caatgaagca cacaagtttg tttgcttttc gtgcatgata ttaaatagct | 3780 | |
| tggcagcaac aggactagga tgagtagcag cacgttcctt atatgtagct ttcgacatga | 3840 | |
| tttatcttcg tttcctgcag gttttttgttc tgtgcagttg ggttaagaat actgggcaat | 3900 | |
| ttcatgtttc ttcaacacta catatgcgta tatataccaa tctaagtctg tgctccttcc | 3960 | |
| ttcgttcttc cttctgttcg gagattaccg aatcaaaaaa atttcaaaga aaccgaaatc | 4020 | |
| aaaaaaaaga ataaaaaaaa aatgatgaat tgaa | 4054 | |

<210> SEQ ID NO 122
<211> LENGTH: 4054
<212> TYPE: DNA
<213> ORGANISM: Artificial Sequence
<220> FEATURE:
<223> OTHER INFORMATION: Codon Optimized

<400> SEQUENCE: 122

| | | |
|---|---|---|
| tcattatcaa tactgccatt tcaaagaata cgtaaataat taatagtagt gattttccta | 60 | |
| actttattta gtcaaaaaat tagccttttta attctgctgt aacccgtaca tgcccaaaat | 120 | |
| aggggcgggg ttacacagaa tatataacat cgtaggtgtc tgggtgaaca gtttattcct | 180 | |
| ggcatccact aaatataatg gagcccgctt tttaagctgg catccagaaa aaaaaagaat | 240 | |
| cccagcacca aaatattgtt tcttcacca accatcagtt cataggtcca ttctcttagc | 300 | |
| gcaactacag agaacagggg cacaaacagg caaaaaacgg gcacaacctc aatggagtga | 360 | |
| tgcaacctgc ctggagtaaa tgatgacaca aggcaattga cccacgcatg tatctatctc | 420 | |
| attttcttac accttctatt accttctgct ctctctgatt tggaaaaagc tgaaaaaaaa | 480 | |
| ggttgaaacc agttccctga aattattccc ctacttgact aataagtata taagacggt | 540 | |
| aggtattgat tgtaattctg taaatctatt tcttaaactt cttaaattct acttttatag | 600 | |
| ttagtctttt ttttagtttt aaaacaccaa gaacttagtt tcgaataaac acacataaac | 660 | |
| aaacaaaatg actagagaag ttgtagtcgt ttctggtgtt agaacagcta ttggtacttt | 720 | |
| tggtggttca ttaaaagatg ttgctccagc agaattgggt gcattagtag tcagagaagc | 780 | |
| cttggctaga gcacaagtat ccggtgacga cgtcggtcat gttgtattcg gtaatgttat | 840 | |
| ccaaacagaa ccaagagata tgtatttggg tagagtcgct gcagttaatg gtggtgtaac | 900 | |

| | | | | |
|---|---|---|---|---|
| tattaacgcc | cctgctttaa | cagtcaacag | attgtgtggt | tccggtttac aagctatagt | 960 |
| tagtgccgct | caaacaatct | tgttaggtga | caccgacgtt | gctattggtg gtggtgctga | 1020 |
| atctatgtca | agagccccat | acttagctcc | tgcagccaga | tggggtgcca gaatgggtga | 1080 |
| cgctggtttg | gttgacatga | tgtttgggtgc | tttacatgat | cctttccata gaatacacat | 1140 |
| gggtgttact | gcagaaaacg | tagccaagga | atacgatatt | tcaagagcac aacaagacga | 1200 |
| agctgcattg | gaatctcaca | gaagagcatc | agccgctatc | aaagccggtt actttaagga | 1260 |
| tcaaattgtt | ccagtcgttt | caaaaggtag | aaagggtgac | gtcaccttcg atactgacga | 1320 |
| acatgttaga | cacgacgcta | ctattgatga | catgacaaaa | ttgagacctg ttttcgtaaa | 1380 |
| ggaaaatggt | actgttacag | ccggtaatgc | ttccggtttg | aacgatgcag ccgctgcagt | 1440 |
| agtcatgatg | gaaagagcag | aagccgaaag | aagaggtttg | aaaccattag ctagattggt | 1500 |
| ttcttatggt | catgctggtg | ttgatccaaa | agcaatgggt | attggtccag ttcctgctac | 1560 |
| caagatagca | ttggaaagag | ccggtttaca | agtctctgat | ttggacgtta tagaagcaaa | 1620 |
| tgaagccttt | gccgctcaag | catgtgcagt | tacaaaagca | ttgggtttag atccagcaaa | 1680 |
| agtaaatcct | aacggttccg | gtatcagttt | aggtcatcca | attggtgcta ccggtgcatt | 1740 |
| gattactgtt | aaggctttac | acgaattgaa | cagagttcaa | ggtagatacg cattagtaac | 1800 |
| aatgtgcata | ggtggtggtc | aaggtattgc | agccatattc | gaaagaatct aatcatgtaa | 1860 |
| ttagttatgt | cacgcttaca | ttcacgcccct | cccccacat | ccgctctaac cgaaaaggaa | 1920 |
| ggagttagac | aacctgaagt | ctaggtccct | atttattttt | ttatagttat gttagtatta | 1980 |
| agaacgttat | ttatatttca | aattttttctt | tttttctgt | acagacgcgt gtacgcatgt | 2040 |
| aacattatac | tgaaaaccctt | gcttgagaag | gttttgggac | gctcgaaggc tttaatttgc | 2100 |
| cctcgagggg | gggcccggta | cccaattcgc | cctatagtga | gtcgtattac gcgcgctcac | 2160 |
| tggccgtcgt | tttacaacgt | cgtgactggg | aaaaccctgg | cgttacccaa cttaatcgcc | 2220 |
| ttgcagcaca | tccccctttc | gccagctggc | gtaatagcga | agaggcccgc accgatcgcc | 2280 |
| cttcccaaca | gttgcgcagc | ctgaatggcg | aatggcgcga | cgcgccctgt agcggcgcat | 2340 |
| taagcgcggc | gggtgtggtg | gttacgcgca | gcgtgaccgc | tacacttgcc agcgccctag | 2400 |
| cgcccgctcc | tttcgctttc | ttcccttcct | ttctcgccac | gttcgccggc tttccccgtc | 2460 |
| aagctctaaa | tcggggggctc | cctttagggt | tccgatttag | tgctttacgg cacctcgacc | 2520 |
| ccaaaaaact | tgattagggt | gatggttcac | gtagtgggcc | atcgccctga tagacggttt | 2580 |
| ttcgcccttt | gacgttggag | tccacgttct | ttaatagtgg | actcttgttc caaactggaa | 2640 |
| caacactcaa | ccctatctcg | gtctattctt | ttgatttata | agggattttg ccgatttcgg | 2700 |
| cctattggtt | aaaaaatgag | ctgatttaac | aaaaatttaa | cgcgaatttt aacaaaatat | 2760 |
| taacgtttac | aatttcctga | tgcggtattt | tctccttacg | catctgtgcg gtatttcaca | 2820 |
| ccgcatagat | ccgtcgagtt | caagagaaaa | aaaagaaaa | agcaaaaaga aaaaggaaa | 2880 |
| gcgcgcctcg | ttcagaatga | cacgtataga | atgatgcatt | accttgtcat cttcagtatc | 2940 |
| atactgttcg | tatacatact | tactgacatt | cataggtata | catatataca catgtatata | 3000 |
| tatcgtatgc | tgcagcttta | aataatcggt | gtcattagtt | ttgctggccg catcttctca | 3060 |
| aatatgcttc | ccagcctgct | tttctgtaac | gttcaccctc | taccttagca tcccttccct | 3120 |
| ttgcaaatag | tcctcttcca | acaataataa | tgtcagatcc | tgtagagacc acatcatcca | 3180 |
| cggttctata | ctgttgaccc | aatgcgtctc | ccttgtcatc | taaacccaca ccgggtgtca | 3240 |
| taatcaacca | atcgtaacct | tcatctcttc | cacccatgtc | tctttgagca ataaagccga | 3300 |

```
taacaaaatc tttgtcgctc ttcgcaatgt caacagtacc cttagtatat tctccagtag    3360 ataggggagcc cttgcatgac aattctgcta acatcaaaag gcctctaggt tcctttgtta    3420
cttcttctgc cgcctgcttc aaaccgctaa caatacctgg gcccaccaca ccgtgtgcat    3480
tcgtaatgtc tgcccattct gctattctgt atacacccgc agagtactgc aatttgactg    3540
tattaccaat gtcagcaaat tttctgtctt cgaagagtaa aaaattgtac ttggcggata    3600
atgcctttag cggcttaact gtgccctcca tggaaaaatc agtcaagata tccacatgtg    3660
tttttagtaa acaaattttg ggacctaatg cttcaactaa ctccagtaat tccttggtgg    3720
tacgaacatc caatgaagca cacaagtttg tttgcttttc gtgcatgata ttaaatagct    3780
tggcagcaac aggactagga tgagtagcag cacgttcctt atatgtagct ttcgacatga    3840
tttatcttcg tttcctgcag gttttttgttc tgtgcagttg ggttaagaat actgggcaat    3900
ttcatgtttc ttcaacacta catatgcgta tatataccaa tctaagtctg tgctccttcc    3960
ttcgttcttc cttctgttcg gagattaccg aatcaaaaaa atttcaaaga aaccgaaatc    4020
aaaaaaaaga ataaaaaaaa aatgatgaat tgaa                                4054

<210> SEQ ID NO 123
<211> LENGTH: 4063
<212> TYPE: DNA
<213> ORGANISM: Artificial Sequence
<220> FEATURE:
<223> OTHER INFORMATION: Codon Optimized

<400> SEQUENCE: 123
tcattatcaa tactgccatt tcaaagaata cgtaaataat taatagtagt gatttttccta      60 actttatttta gtcaaaaaat tagccttttta attctgctgt aacccgtaca tgcccaaaat    120
agggggcggg ttacacagaa tatataacat cgtaggtgtc tgggtgaaca gtttattcct    180
ggcatccact aaatataatg gagcccgctt tttaagctgg catccagaaa aaaaagaat     240 cccagcacca aaatattgtt ttcttcacca accatcagtt cataggtcca ttctcttagc    300
gcaactacag agaacagggg cacaaacagg caaaaaacgg gcacaacctc aatggagtga    360
tgcaacctgc ctggagtaaa tgatgacaca aggcaattga cccacgcatg tatctatctc    420
attttcttac accttctatt accttctgct ctctctgatt tggaaaaagc tgaaaaaaaa    480
ggttgaaacc agttccctga aattattccc ctacttgact aataagtata taagacggt    540 aggtattgat tgtaattctg taaatctatt tcttaaactt cttaaattct actttttatag    600 ttagtctttt ttttagtttt aaaacaccaa gaacttagtt tcgaataaac acacataaac    660
aaacaaaatg atcgtcaagc caatggttag aaacaacatt tgtttgaacg cccatcctca    720
aggttgcaaa aagggtgttg aagatcaaat cgaatacact aaaaagagaa tcacagcaga    780
agtaaaagct ggtgcaaagg cccctaaaaa tgttttggta ttgggttgtt ccaacggtta    840
tggtttggct agtagaataa ccgctgcatt tggttacggt gccgctacta tcggtgtttc    900
cttcgaaaaa gcaggtagtg aaaccaagta tggtactcca ggttggtaca ataacttggc    960
ctttgatgaa gcagccaaga gagaaggttt gtactctgtc actatagatg gtgacgcttt   1020
ctcagatgaa attaaagcac aagtaataga agaagccaaa aagaaggta tcaagttcga   1080 tttgatcgtt tactctttgg catcaccagt aagaacagat cctgacaccg gtataatgca   1140
caagtcagta ttgaagccat tcggtaaaac tttcacaggg aaaacgtcg atccttcac    1200 tggtgaattg aaggaaatat ctgcagaacc agccaatgat gaagaagctg cagccactgt   1260
```

```
caaagttatg ggtggtgaag actgggaaag atggattaaa caattgtcca aggaaggttt    1320
gttagaagaa ggttgtatca cattggctta ctcttacata ggtcctgaag ctacacaagc    1380
attgtataga aaaggtacta tcggtaaagc taaagaacat ttggaagcta ctgcacacag    1440
attgaataag gaaaacccat ctatcagagc attcgtatca gtcaataagg gtttagttac    1500
aagagcctcc gctgttatcc cagtaattcc tttgtactta gctagtttgt ttaaagttat    1560
gaaggaaaag ggtaaccatg aaggttgcat agaacaaatc acaagattgt acgcagaaag    1620
attgtacaga aaggatggta ctattccagt tgacgaagaa aacagaatta gaatcgatga    1680
ctgggaattg gaagaagacg tacaaaaagc cgtctctgct ttaatggaaa aggttactgg    1740
tgaaaacgct gaatcattga cagatttggc aggttataga cacgactttt tagcctctaa    1800
tggtttcgat gtcgaaggta ttaactacga agctgaagtt gaaagatttg acagaatata    1860
atcatgtaat tagttatgtc acgcttacat tcacgccctc cccccacatc cgctctaacc    1920
gaaaaggaag gagttagaca acctgaagtc taggtcccta tttattttt tatagttatg    1980 ttagtattaa gaacgttatt tatatttcaa atttttcttt ttttctgta cagacgcgtg    2040 tacgcatgta acattatact gaaaaccttg cttgagaagg ttttgggacg ctcgaaggct    2100
ttaatttgcc ctcgaggggg ggcccggtac ccaattcgcc ctatagtgag tcgtattacg    2160
cgcgctcact ggccgtcgtt ttacaacgtc gtgactggga aaaccctggc gttacccaac    2220
ttaatcgcct tgcagcacat cccctttcg ccagctggcg taatagcgaa gaggcccgca    2280
ccgatcgccc ttcccaacag ttgcgcagcc tgaatggcga atggcgcgac gcgcctgta     2340 gcggcgcatt aagcgcggcg ggtgtggtgg ttacgcgcag cgtgaccgct acacttgcca    2400
gcgccctagc gcccgctcct ttcgctttct tcccttcctt tctcgccacg ttcgccggct    2460
ttccccgtca gctctaaat cggggctcc ctttagggtt ccgatttagt gctttacggc      2520
acctcgaccc caaaaaactt gattagggtg atggttcacg tagtgggcca tcgccctgat    2580
agacggtttt tcgccctttg acgttggagt ccacgttctt aatagtgga ctcttgttcc     2640 aaactggaac aacactcaac cctatctcgg tctattcttt tgatttataa gggattttgc    2700
cgatttcggc ctattggtta aaaaatgagc tgatttaaca aaaatttaac gcgaatttta    2760
acaaaatatt aacgtttaca attcctgat gcggtatttt ctccttacgc atctgtgcgg     2820
tatttcacac cgcatagatc cgtcgagttc aagagaaaaa aaagaaaaa gcaaaaagaa     2880 aaaaggaaag cgcgcctcgt tcagaatgac acgtatagaa tgatgcatta ccttgtcatc    2940
ttcagtatca tactgttcgt atacatactt actgacattc ataggtatac atatatacac    3000
atgtatatat atcgtatgct gcagctttaa ataatcggtg tcattagttt tgctggccgc    3060
atcttctcaa atatgcttcc cagcctgctt ttctgtaacg ttcaccctct acctagcat     3120 cccttccctt tgcaaatagt cctcttccaa caataataat gtcagatcct gtagagacca    3180
catcatccac ggttctatac tgttgaccca atgcgtctcc cttgtcatct aaacccacac    3240
cgggtgtcat aatcaaccaa tcgtaacctt catctcttcc acccatgtct ctttgagcaa    3300
taaagccgat aacaaaatct ttgtcgctct tcgcaatgtc aacagtaccc ttagtatatt    3360
ctccagtaga tagggagccc ttgcatgaca attctgctaa catcaaaagg cctctaggtt    3420
cctttgttac ttcttctgcc gcctgcttca aaccgctaac aatacctggg cccaccacac    3480
cgtgtgcatt cgtaatgtct gcccattctg ctattctgta tacacccgca gagtactgca    3540
atttgactgt attaccaatg tcagcaaatt ttctgtcttc gaagagtaaa aaattgtact    3600
tggcggataa tgcctttagc ggcttaactg tgccctccat ggaaaaatca gtcaagatat    3660
```

```
ccacatgtgt tttagtaaa caaattttgg gacctaatgc ttcaactaac tccagtaatt    3720
ccttggtggt acgaacatcc aatgaagcac acaagtttgt ttgcttttcg tgcatgatat    3780
taaatagctt ggcagcaaca ggactaggat gagtagcagc acgttcctta tatgtagctt    3840
tcgacatgat ttatcttcgt ttcctgcagg tttttgttct gtgcagttgg gttaagaata    3900
ctgggcaatt tcatgtttct tcaacactac atatgcgtat atataccaat ctaagtctgt    3960
gctccttcct tcgttcttcc ttctgttcgg agattaccga atcaaaaaaa tttcaaagaa    4020
accgaaatca aaaaaagaa taaaaaaaaa atgatgaatt gaa                      4063
```

<210> SEQ ID NO 124  
<211> LENGTH: 5497  
<212> TYPE: DNA  
<213> ORGANISM: Artificial Sequence  
<220> FEATURE:  
<223> OTHER INFORMATION: Codon Optimized

<400> SEQUENCE: 124

```
tcattatcaa tactgccatt tcaaagaata cgtaaataat taatagtagt gattttccta     60
actttattta gtcaaaaaat tagccttta attctgctgt aacccgtaca tgcccaaaat    120 aggggggcggg ttacacagaa tatataacat cgtaggtgtc tgggtgaaca gtttattcct   180
ggcatccact aaatataatg gagcccgctt tttaagctgg catccagaaa aaaaagaat    240 cccagcacca aaatattgtt ttcttcacca accatcagtt cataggtcca ttctcttagc    300
gcaactacag agaacagggg cacaaacagg caaaaaacgg gcacaacctc aatggagtga    360
tgcaacctgc ctggagtaaa tgatgacaca aggcaattga cccacgcatg tatctatctc    420
attttcttac accttctatt accttctgct ctctctgatt tggaaaaagc tgaaaaaaaa    480
ggttgaaacc agttccctga aattattccc ctacttgact aataagtata taaagacggt    540
aggtattgat tgtaattctg taatctatt tcttaaactt cttaaattct acttttatag    600
ttagtctttt ttttagtttt aaaacaccaa gaacttagtt tcgaataaac acacataaac    660
aaacaaaatg gtttccaatc acttgttga cgcaatgaga gccgctgccc ctggtaacgc    720
ccctttcata agaatagata atactagaac ttggacatac gatgacgcct ttgctttatc    780
tggtagaata gcatcagcta tggatgcttt gggtatcaga ccaggtgaca gagtcgcagt    840
tcaagtagaa aaatccgctg aagcattgat cttgtatttg gcttgtttga gaagtggtgc    900
agtttatttg ccattgaata ctgcctacac attagctgaa ttggattact catagggtga    960
cgcagaacct agattggttg tagtcgcctc ttcagccaga gctggtgtag aaacaattgc    1020
taaaccaaga ggtgcaatag tcgaaacctt agatgctgct ggttctggta gtttgttaga   1080
tttggccaga gacgaacctg ctgattttgt tgacgcttca agatcagccg atgacttagc   1140
cgctattttg tacacctctg gtactacagg tagatcaaag ggtgctatgt tgactcatgg    1200
taatttgttg tcaaacgcat taaccttgag agatttctgg agagttactg ccggtgacag    1260
attaatccac gcttttgccaa ttttttcatac tcacggttta ttcgttgcta ccaacgtaac    1320
tttgttagca ggtgcctcca tgttcttgtt gagtaagttc gatccagaag aaatattatc    1380
tttgatgcct caagctacta tgttgatggg tgtcccaaca ttctacgtta gattgttaca    1440
atcacctaga ttagataagc aagctgttgc aaacatcaga ttgtttatat ccggtagtgc    1500
tccattgtta gcagaaaccc atactgaatt tcaagcaaga acaggtcacg ccatttagga    1560
aagatacggt atgacagaaa ccaatatgaa cacttctaac ccttatgaag gtaaaagaat   1620
```

-continued

```
agctggtaca gttggttttc cattgcctga tgtcacagtt agagtaaccg acccagccac    1680
tggtttagct ttgccacctg aacaaactgg tatgatcgaa attaaaggtc caaacgtttt    1740
taagggttac tggagaatgc ctgaaaagac tgctgctgag tttactgctg atggtttctt    1800
tatctctggt gacttaggta aaattgatag agacggttat gtccatattg ttggtcgtgg    1860
taaagatttg gttatatccg gtggttataa catctaccct aaggaagtag aaggtgaaat    1920
agatcaaatc gaaggtgttg tagaatcagc tgtaataggt gtcccacatc ctgattttgg    1980
tgaaggtgtt acagcagtcg ttgtaagaaa accaggtgct gcattagatg aaaaggcaat    2040
tgtttctgcc ttacaagaca gattggctag atacaagcaa ccaaagagaa taatcttcgc    2100
agaagatttg cctagaaata ctatgggtaa agtacaaaag aacatcttga acaacaata    2160 cgccgactta tacaccagaa ccgaaggtag aggttctttg ttaacatgtg gtgacgttga    2220
agaaaatcca ggtcctatgg cttcagaaaa ggaaataaga agagaaagat tcttgaacgt    2280
attcccaaag ttagttgaag aattgaacgc tagtttgtta gcttatggta tgcctaaaga    2340
agcctgcgat tggtatgctc actctttaaa ctacaatact ccaggtggta aattgaatag    2400
aggtttgagt gtagttgata cttatgctat cttgtctaac aaaaccgttg aacaattagg    2460
tcaagaagaa tacgaaaagg tcgctatctt gggttggtgt attgaattgt tgcaagcata    2520 cttttttggtt gccgatgaca tgatggataa gtctataaca agaagaggtc aaccatgctg    2580
gtacaaagtt ccagaagttg gtgaaatagc cataaatgat gcttttatgt ggaagccgc    2640 tatctataaa ttgttgaagt cacatttcag aaacgaaaag tactacatcg atattaccga    2700
attattccac gaagttactt tccaaacaga attgggtcaa ttgatggatt tgataactgc    2760
acctgaagat aaagttgact tgtcaaagtt ttccttgaag aaacattcat tcatcgtcac    2820 cttttgaaact gcttattact ccttctattt gccagtcgcc ttggctatgt acgtagctgg    2880
tattactgat gaaaaagact tgaagcaagc aagagatgtt ttgatacctt tgggtgaata    2940
cttccaaatc caagatgact acttagactg tttcggtact ccagaacaaa taggtaaaat    3000
cggtacagat attcaagaca ataagtgcag ttgggttatt aacaaggctt tggaattagc    3060
atctgccgaa caaagaaaga cttttggatga aaactacggt aaaaaggact cagttgctga    3120
agcaaagtgt aagaaaattt ttaatgattt gaagattgaa caattgtacc atgaatacga    3180
agaatccatc gctaaagact taaggcaaa gattagtcaa gttgatgaat caagaggttt    3240
taaagccgac gttttgacag cttttcttgaa taaggtctac aagagatcaa agtgatcatg    3300
taattagtta tgtcacgctt acattcacgc cctccccca catccgctct aaccgaaaag    3360
gaaggagtta gacaacctga agtctaggtc cctatttatt tttttatagt tatgttagta    3420
ttaagaacgt tatttatatt tcaaattttt ctttttttc tgtacagacg cgtgtacgca    3480
tgtaacatta tactgaaaac cttgcttgag aaggttttgg gacgctcgaa ggctttaatt    3540
tgccctcgag gggggcccg gtacccaatt cgccctatag tgagtcgtat tacgcgcgct    3600
cactggccgt cgttttacaa cgtcgtgact gggaaaaccc tggcgttacc caacttaatc    3660
gccttgcagc acatccccct ttcgccagct ggcgtaatag cgaagaggcc cgcaccgatc    3720
gcccttccca acagttgcgc agcctgaatg gcgaatggcg cgacgcgccc tgtagcggcg    3780
cattaagcgc ggcgggtgtg gtggttacgc gcagcgtgac cgctacactt gccagcgccc    3840
tagcgcccgc tcctttcgct ttcttccctt cctttctcgc cacgttcgcc ggctttcccc    3900
gtcaagctct aaatcggggg ctccctttag ggttccgatt tagtgcttta cggcacctcg    3960
accccaaaaa acttgattag ggtgatggtt cacgtagtgg gccatcgccc tgatagacgg    4020
```

```
tttttcgccc tttgacgttg gagtccacgt tctttaatag tggactcttg ttccaaactg    4080
gaacaacact caaccctatc tcggtctatt cttttgattt ataagggatt ttgccgattt    4140
cggcctattg gttaaaaaat gagctgattt aacaaaaatt taacgcgaat tttaacaaaa    4200
tattaacgtt tacaatttcc tgatgcggta ttttctcctt acgcatctgt gcggtatttc    4260
acaccgcata gatccgtcga gttcaagaga aaaaaaaga aaaagcaaaa agaaaaaagg    4320
aaagcgcgcc tcgttcagaa tgacacgtat agaatgatgc attaccttgt catcttcagt    4380
atcatactgt tcgtatacat acttactgac attcataggt atacatatat acacatgtat    4440
atatatcgta tgctgcagct ttaaataatc ggtgtcatta gttttgctgg ccgcatcttc    4500
tcaaatatgc ttcccagcct gcttttctgt aacgttcacc ctctaccttg gcatcccttc    4560
cctttgcaaa tagtcctctt ccaacaataa taatgtcaga tcctgtagag accacatcat    4620
ccacggttct atactgttga cccaatgcgt ctcccttgtc atctaaaccc acaccgggtg    4680
tcataatcaa ccaatcgtaa ccttcatctc ttccacccat gtctctttga gcaataaagc    4740
cgataacaaa atctttgtcg ctcttcgcaa tgtcaacagt accctagta tattctccag    4800
tagataggga gcccttgcat gacaattctg ctaacatcaa aaggcctcta ggttcctttg    4860
ttacttcttc tgccgcctgc ttcaaaccgc taacaatacc tgggcccacc acaccgtgtg    4920
cattcgtaat gtctgcccat tctgctattc tgtatacacc cgcagagtac tgcaatttga    4980
ctgtattacc aatgtcagca aattttctgt cttcgaagag taaaaaattg tacttggcgg    5040
ataatgcctt tagcggctta actgtgccct ccatggaaaa atcagtcaag atatccacat    5100
gtgttttag taaacaaatt ttgggaccta atgcttcaac taactccagt aattccttgg    5160
tggtacgaac atccaatgaa gcacacaagt ttgtttgctt ttcgtgcatg atattaaata    5220
gcttggcagc aacaggacta ggatgagtag cagcacgttc cttatatgta gctttcgaca    5280
tgatttatct tcgtttcctg caggttttg ttctgtgcag ttgggttaag aatactgggc    5340
aatttcatgt ttcttcaaca ctacatatgc gtatatatac caatctaagt ctgtgctcct    5400
tccttcgttc ttccttctgt tcggagatta ccgaatcaaa aaaatttcaa agaaaccgaa    5460
atcaaaaaaa agaataaaaa aaaaatgatg aattgaa                             5497
```

PRODUCTION OF CANNABINOIDS IN YEAST

CROSS-REFERENCE TO RELATED APPLICATIONS

This patent application is a continuation-in-part of U.S. Non-Provisional patent application Ser. No. 16/539,436, filed Aug. 13, 2019, titled "Production of Cannabigerolic Acid in Yeast," which is a continuation-in-part of U.S. Non-Provisional patent application Ser. No. 16/122,702, filed Sep. 5, 2018, titled "Production of Tetrahydrocannabinolic Acid in Yeast," which is a continuation of U.S. Non-Provisional patent application Ser. No. 15/815,651, filed Nov. 16, 2017, titled "Production of Cannabidiolic Acid in Yeast," now U.S. Pat. No. 10,093,949, issued on Oct. 9, 2018, which is a continuation of U.S. Non-Provisional patent application Ser. No. 14/795,816, filed Jul. 9, 2015, titled "Production of Cannabinoids in Yeast," now U.S. Pat. No. 9,822,384, issued on Nov. 21, 2017, which in turn claims the benefit and priority of U.S. Provisional Patent Application Ser. No. 62/024,099, filed Jul. 14, 2014, titled "Terpenophenolic Production in Microorganisms." All of the aforementioned disclosures are hereby incorporated by reference herein in their entireties including all references and appendices cited therein.

REFERENCE TO SEQUENCE LISTINGS

The present application is filed with sequence listing(s) attached hereto and incorporated by reference, including Appendix 1A titled "Additional Examples," Appendix 1B titled "Sequence IDs," Appendix 1C titled "Additional Sequence IDs," and Appendix 1D titled "Sequence IDs."

The present application is filed with a ST.25 formatted sequence listing attached hereto and incorporated by reference comprising sequences 1 through 124.

FIELD OF THE INVENTION

This invention relates to molecular biology, and more specifically to the transformation of yeast cells and the production of cannabinoids.

SUMMARY OF THE INVENTION

Exemplary embodiments provided herein include genetically engineering microorganisms, such as yeast or bacteria, to produce cannabinoids by inserting genes that produce the appropriate enzymes for the metabolic production of a desired compound.

DETAILED DESCRIPTION OF EXEMPLARY EMBODIMENTS

Figure 1:
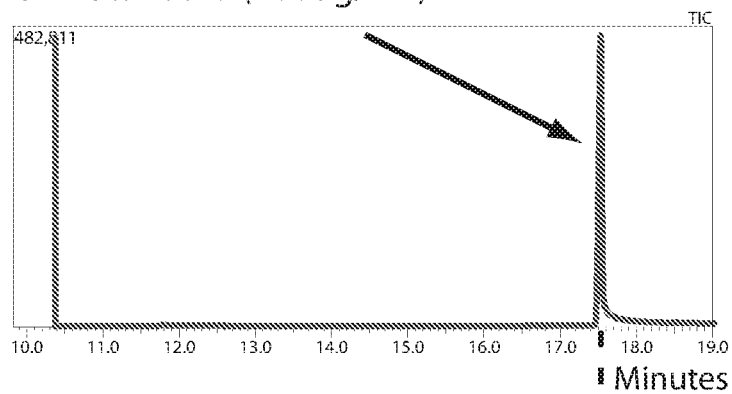
FIG. 1 shows exemplary experimental data achieved in connection with Example 1 of Appendix 1A titled "Additional Examples" for cannabidiol ("CBD")/cannabidiolic acid ("CBDA") production in *S. cerevisiae*.
Figure 1:
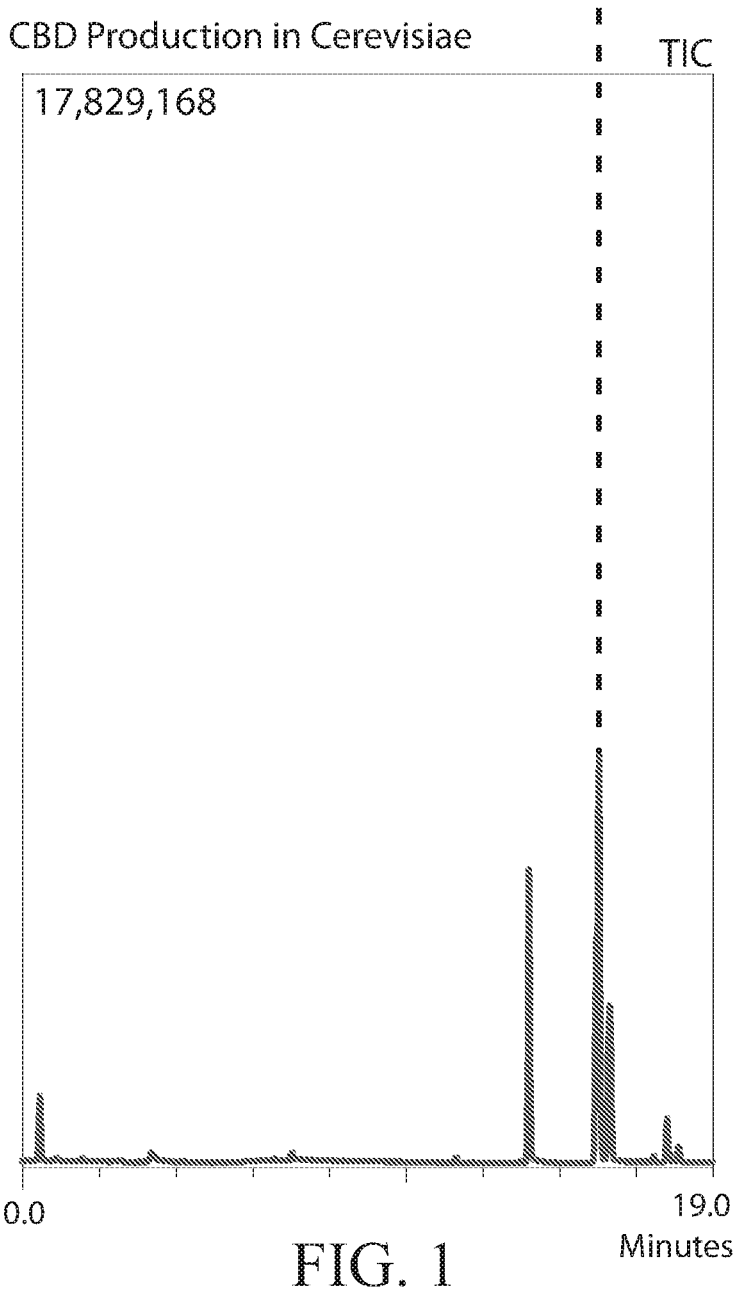

The present application relates to the field of cannabinoid production in yeasts. Cannabinoids are a general class of chemicals that act on cannabinoid receptors and other target molecules to modulate a wide range of physiological behavior such as neurotransmitter release. Cannabinoids are produced naturally in humans (called endocannabinoids) and by several plant species (called phytocannabinoids) including *Cannabis sativa*. Cannabinoids have been shown to have several beneficial medical/therapeutic effects and therefore they are an active area of investigation by the pharmaceutical industry for use as pharmaceutical products for various diseases.

Currently the production of cannabinoids for pharmaceutical or other use is done by chemical synthesis or through the extraction of cannabinoids from plants that are producing these cannabinoids, for example *Cannabis sativa*. There are several drawbacks to the current methods of cannabinoid production. The chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *Cannabis sativa*. Although there are drawbacks to chemically synthesized cannabinoids, the benefit of this production method is that the end product is a highly pure single cannabinoid. This level of purity is preferred for pharmaceutical use. The level of purity required by the pharmaceutical industry is reflected by the fact that no plant extract based cannabinoid production has received FDA approval yet and only synthetic compounds have been approved.

In contrast to the synthetic chemical production of cannabinoids, the other method that is currently used to produce cannabinoids is production of cannabinoids in plants that naturally produce these chemicals; the most used plant for this is *Cannabis sativa*. In this method, the plant *Cannabis sativa* is cultivated and during the flowering cycle various cannabinoids are produced naturally by the plant. The plant can be harvested and the cannabinoids can be ingested for pharmaceutical purposes in various methods directly from the plant itself or the cannabinoids can be extracted from the plant. There are multiple methods to extract the cannabinoids from the plant *Cannabis sativa*. All of these methods typically involve placing the plant, *Cannabis sativa* that contains the cannabinoids, into a chemical solution that selectively solubilizes the cannabinoids into this solution. There are various chemical solutions used to do this such as hexane, cold water extraction methods, CO2 extraction methods, and others. This chemical solution, now containing all the different cannabinoids, can then be removed, leaving behind the excess plant material. The cannabinoid containing solution can then be further processed for use.

There are several drawbacks of the natural production and extraction of cannabinoids in plants such as *Cannabis sativa*. Since there are numerous cannabinoids produced by *Cannabis sativa* it is often difficult to reproduce identical cannabinoid profiles in plants using an extraction process. Furthermore, variations in plant growth will lead to different levels of cannabinoids in the plant itself making reproducible extraction difficult. Different cannabinoid profiles will have different pharmaceutical effects which are not desired for a pharmaceutical product. Furthermore, the extraction of cannabinoids from *Cannabis sativa* extracts produces a mixture of cannabinoids and not a highly pure single pharmaceutical compound. Since many cannabinoids are similar in structure it is difficult to purify these mixtures to a high level resulting in cannabinoid contamination of the end product.

Disclosed herein are strategies for creating cannabinoids in microorganisms such as yeast and methods to produce various cannabinoids in yeast from a simple sugar source. The general methods involve genetically engineering yeast to produce various cannabinoids, where the main carbon source available to the yeast is a sugar (glucose, galactose, fructose, sucrose, honey, molasses, raw sugar, etc.). Genetic engineering of the microorganism involves inserting various genes that produce the appropriate enzymes and/or altering the natural metabolic pathway in the microorganism to achieve the production of a desired compound. Through genetic engineering of microorganisms these metabolic pathways can be introduced into these microorganisms and the same metabolic products that are produced in the plant *Cannabis sativa* can be produced by the microorganisms. The benefit of this method is that once the microorganism is produced, the production of the cannabinoid is low cost and reliable, only a specific cannabinoid is produced or a subset is produced, depending on the organism. The purification of the cannabinoid is straight forward since there is only a single cannabinoid or a selected few cannabinoids present in the microorganism. The process is a sustainable process which is more environmentally friendly than synthetic production.

FIG. 1 shows exemplary experimental data achieved in connection with Example 1 of Appendix 1A titled "Additional Examples" for cannabidiol ("CBD")/cannabidiolic acid ("CBDA") production in *S. cerevisiae*.

FIG. 1 shows gas chromatography-mass spectrometry of cannabidiol (CBD) produced in *S. cerevisiae*. After processing the yeast cells, as described in Example 1 of Appendix 1A, the whole cell ethyl acetate extract is analyzed for the presences of CBD. The samples were prepared in a way similar to that shown in Appendix A1 except that no MSTFA derivatization was used in this sample (therefore CBDA turns into CBD upon heating), the oven protocol was also slightly different than that shown in Appendix 1A. Initially, a standard CBD solution is run (100 ug/mL; TOP). After running the standard the inventors determined the run time of 17.5 minutes. After running the standard the inventors repeated the GC-MS experiment with their whole cell extract (BOTTOM). At a run time of 17.5 minutes, the inventors saw the same peak as in the standard. Mass spectrometry analysis of the peaks showed identical mass for the two samples (standard and extract) indicating the presence of CBD in their whole cell extract.

Figure 2:
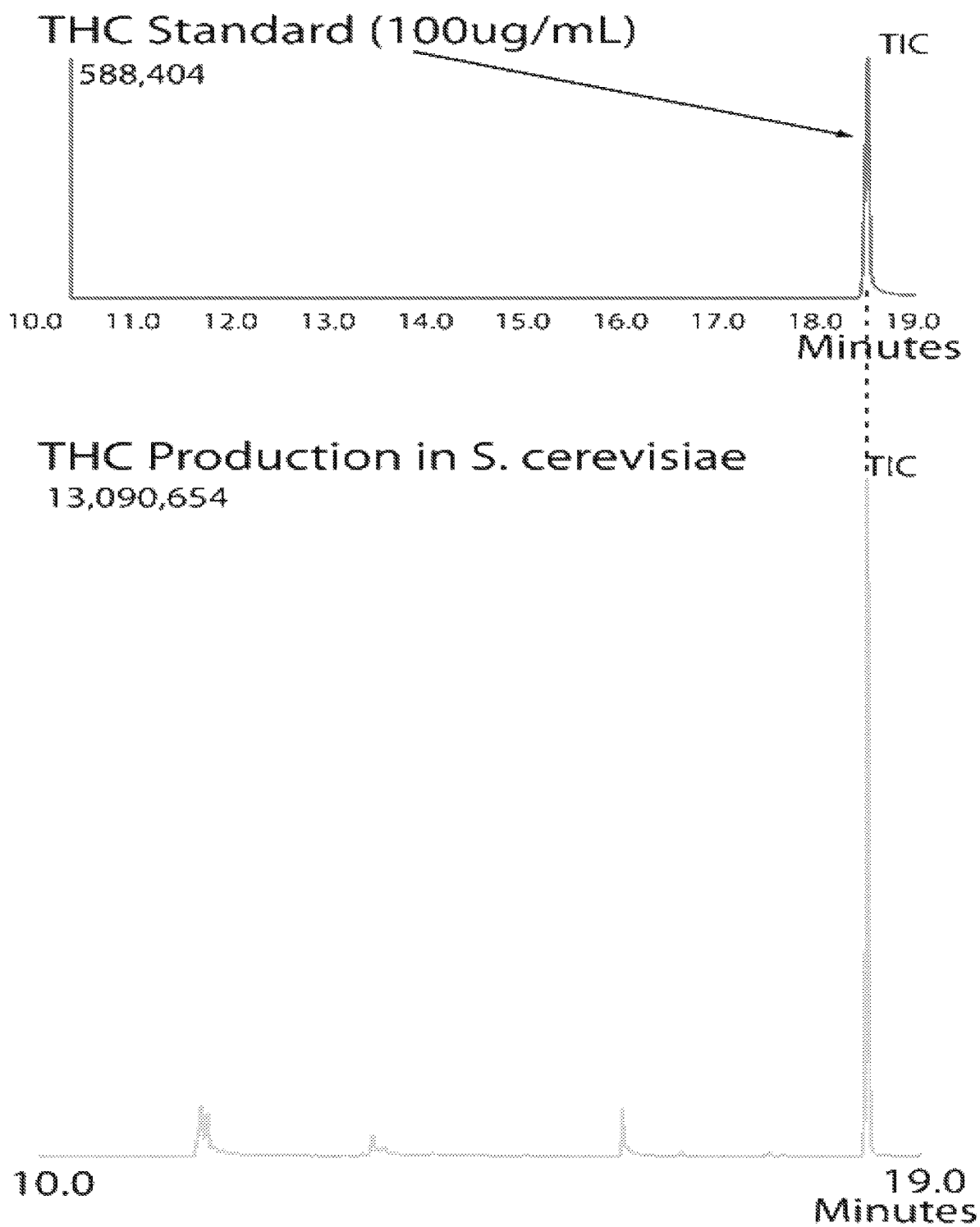
FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae*.

FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae*.

FIG. 2 shows gas chromatography-mass spectrometry of tetrahydrocannabinol (THC) produced in *S. cerevisiae*. After processing the yeast cells, as described in Example 2 of Appendix 1A, the whole cell ethyl acetate extract was analyzed for the presences of THC. The samples were prepared in a way similar to that shown in Appendix 1A except that no MSTFA derivatization was used in this sample (therefore THCA turns into THC upon heating), the oven protocol was also slightly different than that shown in Appendix 1A. Initially, a standard CBD solution was run (100 ug/mL; TOP). After running the standard the inventors determined the run time of 18.5 minutes. After running the standard the inventors repeated the GC-MS experiment with their whole cell extract (BOTTOM). At a run time of 18.5 minutes, the inventors saw the same peak as in the standard. Mass spectrometry analysis of the peaks showed identical mass for the two samples (standard and extract) indicating the presence of THC in their whole cell extract.

Figure 3:
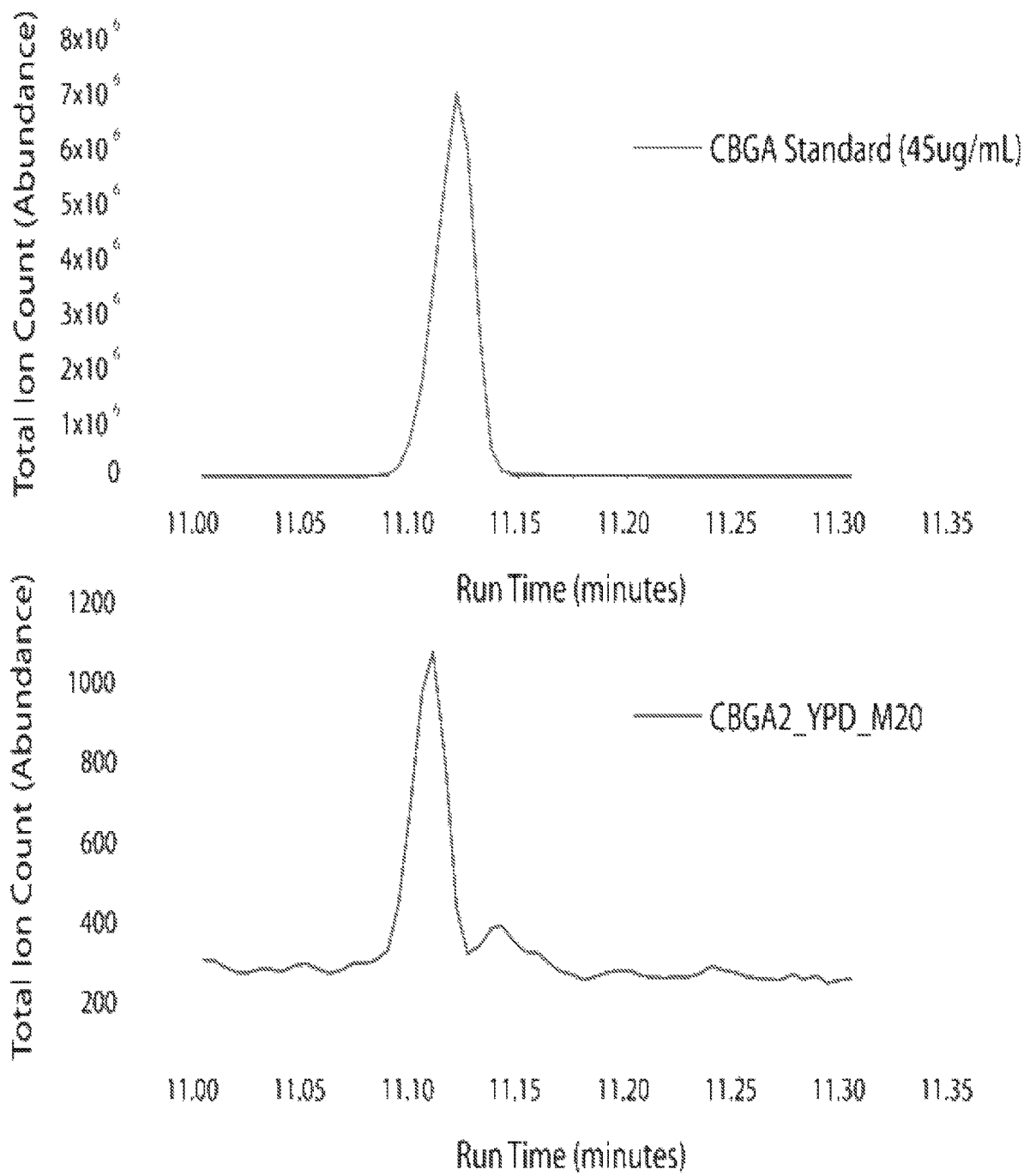
FIG. 3 shows exemplary experimental data achieved in connection with Example 3 of Appendix 1A titled "Additional Examples" for cannabigerol ("CBG")/cannabigerolic acid ("CBGA") production in *S. cerevisiae*.

FIG. 3 shows exemplary experimental data achieved in connection with Example 3 of Appendix 1A titled "Additional Examples" for cannabigerol ("CBG")/cannabigerolic acid ("CBGA") production in *S. cerevisiae*.

FIG. 3 shows gas chromatography-mass spectrometry of cannabigerolic acid (CBGA) produced in *S. cerevisiae*. After processing the yeast cells, as described in Example 3 of Appendix 1A, the whole cell ethyl acetate extract was analyzed for the presences of CBGA. The samples were prepared in a way as described in Appendix 1A, but the oven protocol was also slightly different than that shown in Appendix 1A. Initially, a standard CBGA solution was run (45 ug/mL; TOP). After running the standard, the inventors determined the run time of 11.1 minutes. After running the standard, the inventors repeated the GC-MS experiment with their whole cell extract (BOTTOM). At a run time of 11.1 minutes, the inventors saw the same peak as in the standard. Mass spectrometry analysis of the peaks showed identical mass for the two samples (standard and extract) indicating the presence of CBGA in their whole cell extract.

Figure 4:
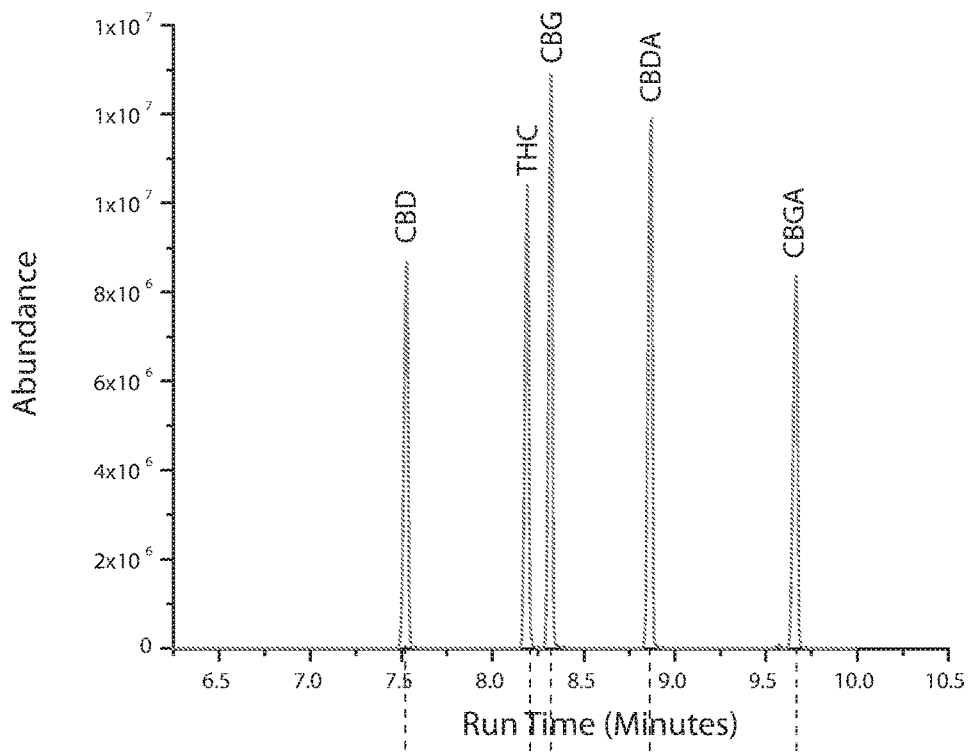
FIG. 4 shows exemplary experimental data achieved in connection with Example 4 of Appendix 1A titled "Additional Examples" for CBGA, CBDA, CBD, CBG and THC production in *K. marxianus*.
Figure 4:
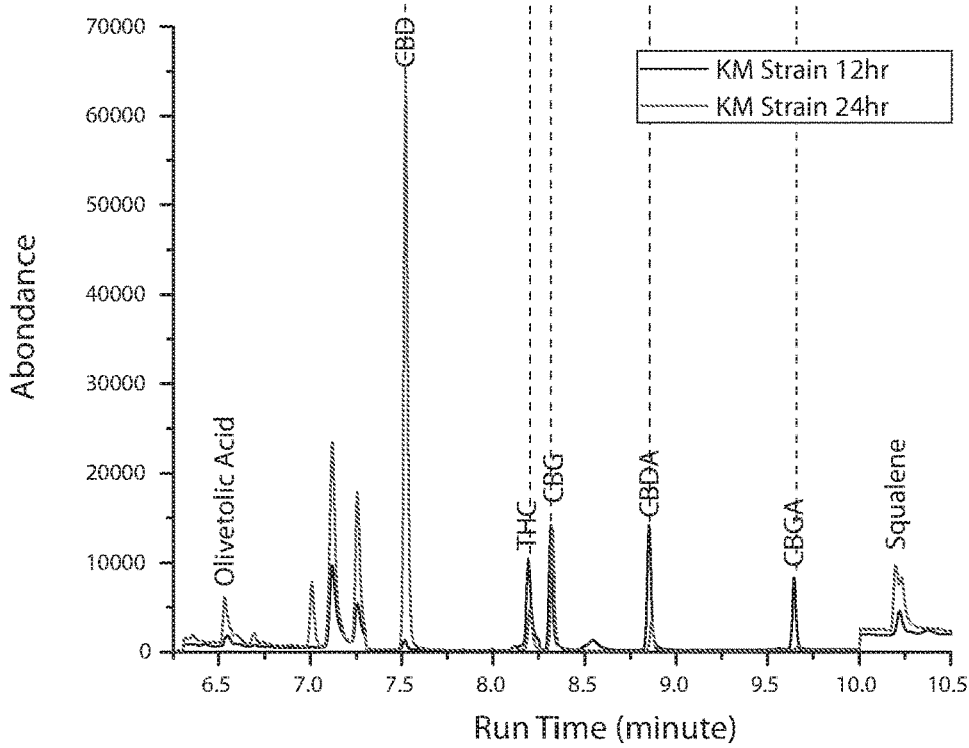

FIG. 4 shows exemplary experimental data achieved in connection with Example 4 of Appendix 1A titled "Additional Examples" for CBGA, CBDA, CBD, CBG and THC production in *K. marxianus*.

FIG. 4 shows gas chromatography-mass spectrometry of cannabinoid production (CBGA, CBDA, CBD, CBG, THC) produced in *K. marxianus*. After processing the yeast cells, as described in Example 4 of Appendix 1A, the whole cell ethyl acetate extract was analyzed for the presence of cannabinoids. The samples were prepared in a way as described in Appendix 1A, but the oven protocol was also slightly different than that shown in Appendix 1A. Initially, a standard solution containing CBD, CBG, THC, CBDA, and CBGA was run (70 ug/mL each; TOP). After running the standard, the inventors determined the run time for each compounds. After running the standard, the inventors repeated the GC-MS experiment with their whole cell extract (BOTTOM). At each run time the inventors saw the same peaks as in the standard. Mass spectrometry analysis of the peaks showed identical mass for the two samples (standard and extract) indicating the presence of cannabinoids in their whole cell extract.

Figure 5:
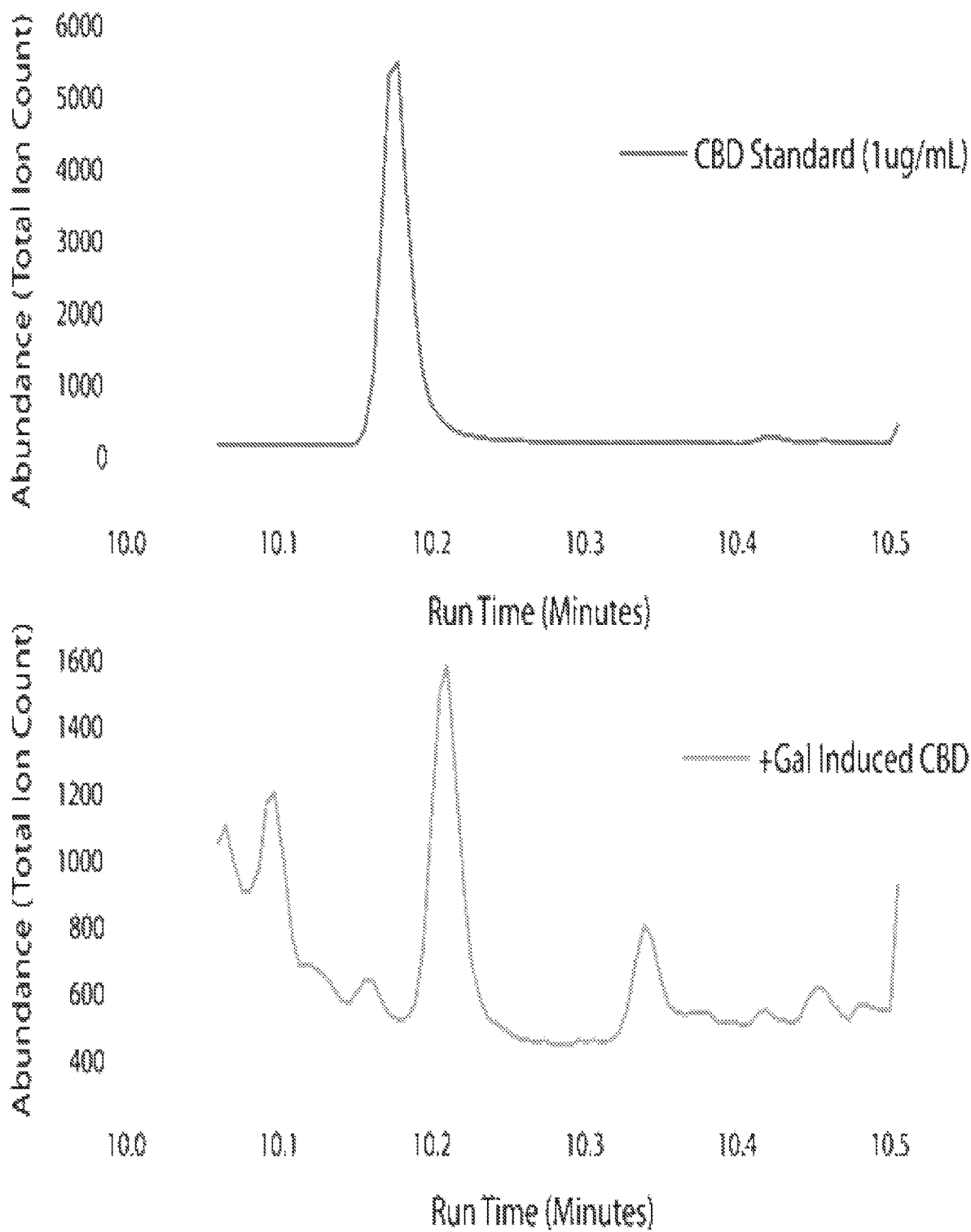
FIG. 5 show exemplary experimental data achieved in connection with Example 5 of Appendix 1A titled "Additional Examples" for galactose induced CBD production in *S. cerevisiae*.

FIG. 5 show exemplary experimental data achieved in connection with Example 5 of Appendix 1A titled "Additional Examples" for galactose induced CBD production in S. cerevisiae.

FIG. 5 shows gas chromatography-mass spectrometry of induced cannabidiol (CBD) production in S. cerevisiae. After processing yeast cells, as described in Example 5 of Appendix 1A, the whole cell ethyl acetate extract was analyzed for the presences of CBD. The samples were prepared in a way as described in Appendix 1A. Initially, a standard solution containing CBD was run (1 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Figure 6:
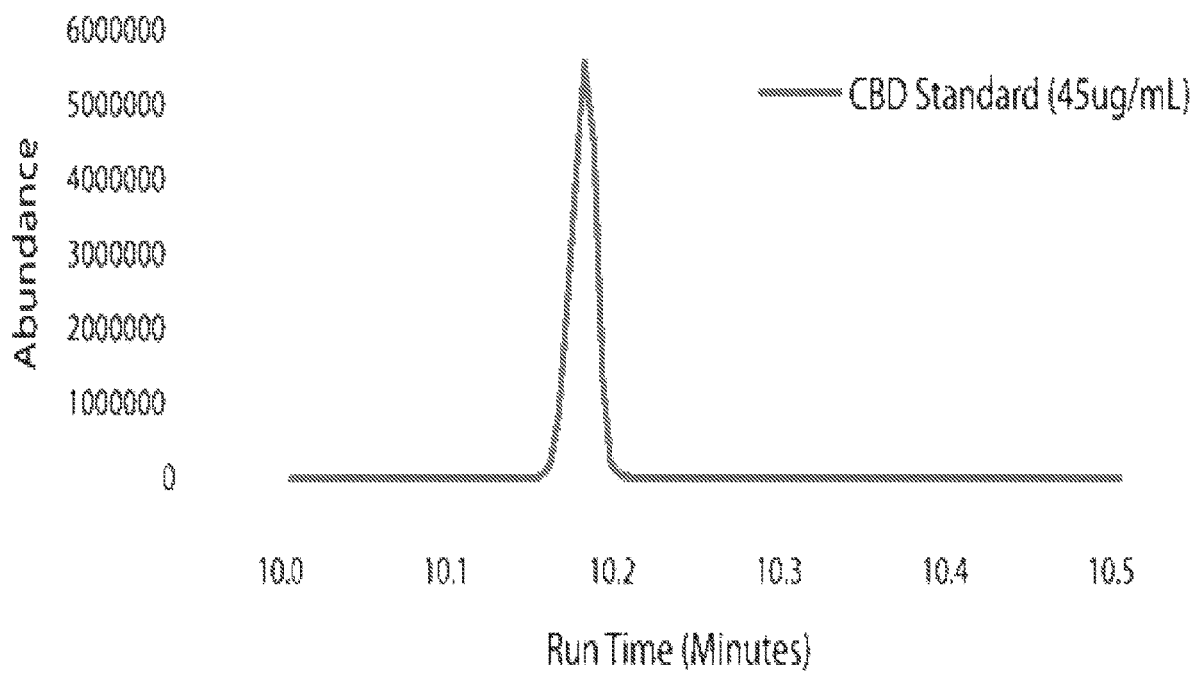
FIG. 6 shows exemplary experimental data achieved in connection with Example 6 of Appendix 1A titled "Additional Examples" for secretion of CBD into media by *S. cerevisiae*.
Figure 6:
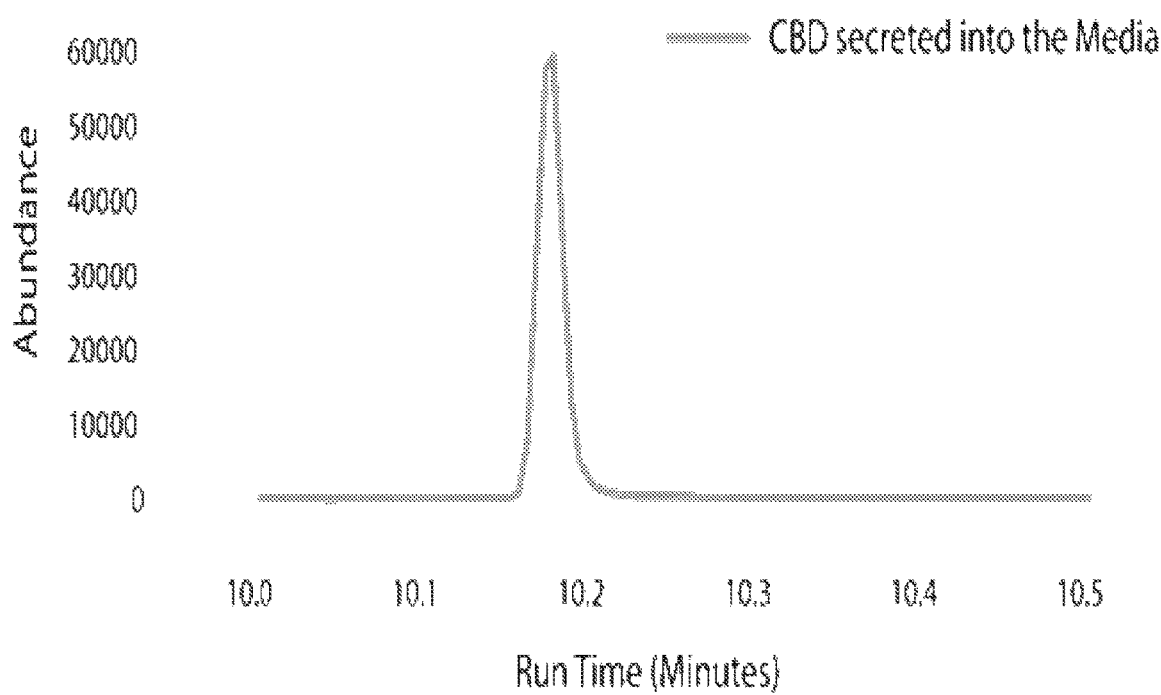

FIG. 6 shows exemplary experimental data achieved in connection with Example 6 of Appendix 1A titled "Additional Examples" for secretion of CBD into media by S. cerevisiae.

FIG. 6 shows gas chromatography-mass spectrometry of induced cannabidiol production (CBD) produced in S. cerevisiae and secreted into the media. After processing the growth media, as described in Example 6 of Appendix 1A, the media ethyl acetate extract was analyzed for the presence of CBD. The samples were prepared in a way as described in Appendix 1A. Initially, a standard solution containing CBD was run (45 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Biosynthetic Production of Cannabidiolic Acid (CBDA) in S. cerevisiae.

Through genetic engineering the inventors have reconstituted the cannabidiolic acid (CBDA) metabolic pathway found in Cannabis sativa into S. cerevisiae (a species of yeast).

Producing CBGA is an initial step in producing many cannabinoids from Cannabis sativa in S. cerevisiae. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Figure 7:
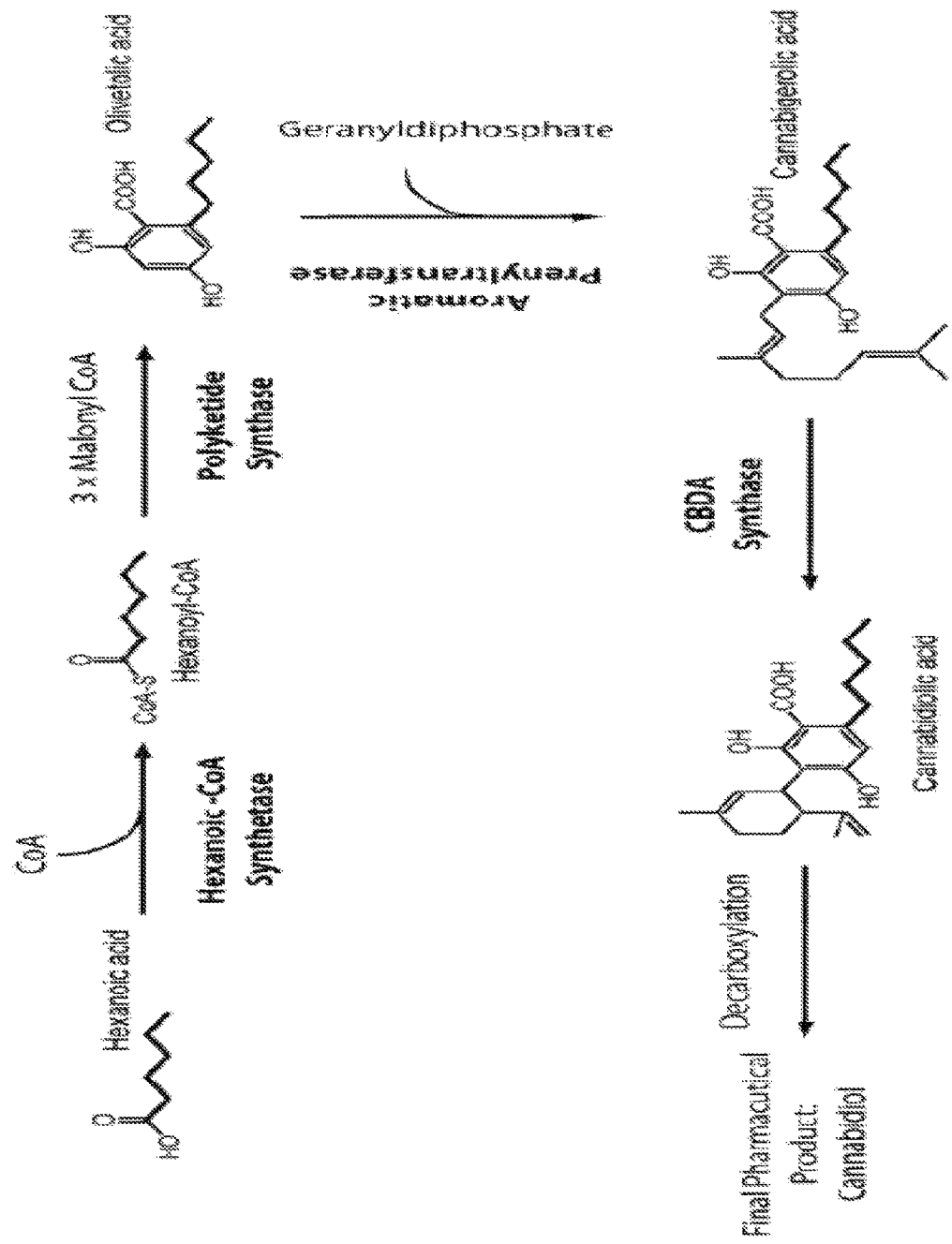
FIG. 7 shows an exemplary metabolic pathway for the production of cannabinoids by *Cannabis sativa*.

FIG. 7 shows an exemplary metabolic pathway for the production of cannabinoids by Cannabis sativa.

The biosynthetic route for the production of cannabidiolic acid in Cannabis sativa is shown in FIG. 7. The pathway begins with the conversion of Hexanoic acid (a simple fatty acid) to Hexanoyl-CoA by Hexanoyl-CoA Synthetase. Hexanoyl-CoA is converted to Oleviolic acid (OA), a polyketide, by a Polyketide synthase. OA is then prenylated with the monoterpene geranyl diphosphate to cannabigerolic acid by an Aromatic prenyltransferase. Finally, cannabidiolic acid (CBDA) is produced by cyclizing cannabigerolic acid via CBDA synthase (CBDAs). In summary, it takes four enzymatic steps to produce CBDA from Hexanoic acid. The inventors have engineered this metabolic pathway into S. cerevisiae (a species of yeast) for the production of CBDA.

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, through genetic engineering many of the required enzymes can be added and the production of GPP can be increased. In order to add the required enzymes for CBDA production in yeast the inventors created plasmids that contain the essential genes in the CBDA biosynthetic pathway. The inventors have transformed these genes into S. cerevisiae.

Synthesis of Fusion Genes Required for CBDA Production in S. cerevisiae.

The genome of Cannabis sativa has been investigated and the acyl-activating enzymes CsAAE1 was determined to convert hexanoic acid to hexanoyl-CoA (Step 1 in FIG. 7). The inventors have overexpressed CsAAE1 in yeast while simultaneously supplementing the growth media with Hexanoic acid. By supplementing the media with hexanoic acid, the inventors ensured that the yeast have the required starting materials for the production of hexanoyl-CoA. In addition to CsEE1, the cannabis plant has several other acyl-activating enzymes with sequences that are similar to CsEE1. These enzymes can also be used for the conversation of hexanoic acid to hexanoyl-CoA. These are listed in Appendix 1C.

The next enzymatic step that was engineered into the yeast strain was for the production of Olivetolic acid (OA) from hexanoyl-CoA. This step requires the substrates hexanoyl-CoA and 3 malonyl-CoA molecules, with the malonyl-CoA molecule produced by yeast naturally. Olivetolic acid production requires two enzymes for the condensation and subsequent cyclization of malonyl-CoA with hexanoyl-CoA. This process requires the tetraketide synthase, olivetolic synthase (OS), and the polyketide cyclase, olivetolic acid cyclase (OAC). In some embodiments, stoichiometric amounts of both of these enzymes are preferred; as it has been experimentally determined that OAC binds a chemical intermediate made by OS. In various embodiments, in order to ensure the proper amounts of OS and OAC the inventors have created a single gene that is a fusion of OS, a self cleaving T2A peptide, and the OAC gene (OS-T2A-OAC) and in certain cases an HA tag was inserted at the C-terminus of OAC to verify protein expression. This entire fusion protein was produced in yeast and the self cleaving peptide is spliced in vivo to produce OS and OAC. In addition to the tetraketide synthase, olivetolic synthase (OS), and the polyketide cyclase, olivetolic acid cyclase (OAC), the cannabis plant has several other enzymes with sequences that are similar to the tetraketide synthase, olivetolic synthase (OS), and the polyketide cyclase, olivetolic acid cyclase (OAC). These enzymes can also be used for the conversation of hexanoyl-CoA to olivetolic acid. These are listed in Appendix 1C.

The next enzymatic step requires the production of geranyl pyrophosphate (GPP). In yeast the prenyltransferace Erg20 condenses isopentenyl diphosphate (IPP) and dimethylallyl diphosphate (DMAP) to geranyl pyrophosphate (GPP) and feranyl pyrophosphate (FPP) naturally. While only these two products are produced in yeast, a greater quantity of FPP when compared to GPP is produced. More GPP is required for the production of CBDA. In order to increase the production of GPP compared to FPP the inventors inserted a mutant prenyltransferase, Erg20(K179E) in the yeast strain. This mutant has been shown to shift the ratio of GPP:FPP to 70:30. This Erg20(K179E) mutant was placed on a fusion gene with CsAAE1, the enzyme for hexanoyl-CoA, and a self-cleaving peptide, T2A (CsAAE1-T2A-Erg20(K179E). We also added a FLAG tag to the C-terminus of the Erg20p (K197E) enzyme (CsAAE1-T2A-Erg20(K179E)-FLAG) to verify expression of this fusion protein in yeast in certain yeast strains. After production in yeast the self-cleaving peptide was cut producing CsAAE1 and Erg20(K179E).

Once the inventors verified that they had enough GPP to prenylate Olivetolic acid to cannabigerolic acid the inventors inserted the aromatic prenyltransferase (CsPt1) gene into the yeast. In this final enzymatic step the inventors placed the cannabidiolic acid synthase (CBDAs) gene into yeast for the conversion of cannabigerolic acid to CBDA. Similar to the inventors' previous approach, they introduced a single gene containing CsPt1, a self-cleaving peptide T2A, CBDs, and in certain cases a MYC tag was inserted at the C-terminus of CBDs in order to verify production of each enzyme (CsPt1-T2A-CBDs-MYC). In addition to the aromatic prenyltransferase (CsPt1) the cannabis plant has several other enzymes with sequences that are similar to the aromatic prenyltransferase (CsPt1). These enzymes can also be used for the conversation of olivetolic acid to CBGA. These are listed in Appendix 1C.

Creation of a Stable Yeast Strain Producing the Metabolic Pathway for CBDA.

Three stable transformations of *S. cerevesaie* where created utilizing selection for leucine, uracil and tryptophan. The inventors first transformed an auxotrophic yeast strain (his3D1/leu2/trp1-289/ura3-52) with the CsAAE1-T2A-Erg20(K197E)-FLAG gene in an integrating vector; other sequences listed in Appendix 1C number 85-91 can replace CsAAE1. 5 µg of CsAAE1-T2A-Erg20(K197E)-FLAG in a vector containing a gene for tryptophan depletion resistance was linearized with the restriction enzyme EcoRV, transformed into chemically competent InVSc1, and grown on Yeast Nitrogen Base without amino acids and 0.5% ammonium sulfate (YNBA) agar plates supplemented with histidine, leucine, tryptophan, 1% glucose and 2% lactic acid are grown at 30° C. until colonies are formed. Any yeast colonies that did not incorporate the plasmid, that contains the CsAAE1-T2A-Erg20(K197E)-FLAG gene died since the starting yeast strain is a tryptophan auxotroph. All colonies, with successful plasmid incorporation, where picked and grown in YNBA supplemented with histidine, leucine and uracil, 1% glucose and 2% lactic acid. All colonies were screened for protein production by taking whole cell extracts of each induced clone and the total protein was subjected to SDS-PAGE followed by western blotting against the c-terminal tag of Erg20(K197E). Positive clones where stored at −80° C. in glycerol stocks. The highest expressing clone was taken for the second transformation and was designated as VscGPHA.

Using the VscGPHA strains the inventors added 5 µg of OS-T2A-OAC-HA in the a vector containing a gene for leucine depletion resistance; other sequences listed in Appendix 1C number 60-84 can replace OS and OAC. This plasmid was linearized with the restriction enzyme AseI and transformed into chemically competent VscGPHA and grown on YNBA agar plates supplemented with histidine and uracil, 1% glucose and 2% lactic acid and grown at 30° C. until colonies were formed. Any yeast colonies that did not incorporate the plasmid that contains the OS-T2A-OAC-HA gene died since the VscGPHA is a leucine auxotroph. All colonies, with successful plasmid incorporation, were picked and grown in YNBA supplemented with histidine, and leucine. All colonies were screened for protein production by taking whole cell extracts of each induced clone and subjected the total protein to SDS-PAGE followed by western blotting against the c-terminal HA tag of OAC. Positive clones were stored at −80° C. in glycerol stocks. The highest expressing clone was taken for the second stable transformation and was designated VscGPHOA.

The final stable transformation was done in a similar way as the previous transformation. The CsPT-T2A-CBDAs-MYC gene was placed in the vector containing a gene for uracil depletion resistance 5 µg of this plasmid was linearized with EcorV and transformed into chemically competent VscGPHOA; other sequences listed in Appendix 1C number 30-59 can replace CsPT. Transformed VscGPHOA was grown in YNBA supplemented with histidine, 1% glucose and 2% lactic acid. Any yeast colonies that did not incorporate the plasmid that contains the CsPT-T2A-CBDAs-MYC gene died since they lacked leucine. All colonies were picked and grown in YNBA supplemented with histidine, 1% glucose and 2% lactic acid. All colonies were screened for protein production by taking whole cell extracts of each induced clone and subjecting the total protein to SDS-PAGE followed by western blotting against the c-terminal Myc tag of CBDAs. Positive clones are stored at −80° C. in glycerol stocks. The highest expressing CBDAs was taken for the final strain and designated VscCBDA.

Production of CBDA in Yeast.

To initiate the reconstituted metabolic pathway of CBDA a colony of VscCBDA was freshly streaked on a plate of a frozen glycerol stock of VscCBDA. A small culture of VscCBDA was grown in YNBA supplemented with 0.05% histidine, 1% glucose, 2% lactic acid, and 0.03% hexanoic acid overnight at 30° C. The overnight culture was transferred to 1 L of YNBA supplemented with 0.05% histidine, 1% glucose, 2% lactic acid, and 0.03% hexanoic acid and was grown at 30° C. until mid-log phase. Cells were pelleted by centrifugation then washed with 200 ml of phosphate buffered saline (PBS) and repelleted. Pelleted cells were resuspended with 1 L of YNBA supplemented with 0.05% histidine, 2% galactose, and 0.03% hexanoic acid and grown at 30° C. overnight.

Overnight 1 L cultures were pelleted by centrifugation, resuspended, washed one time in PBS and pelleted. Cell pellets were resuspended in 40% (wt/vol) KOH and 50% (vol/vol) ethanol solution and boiled for 10 minutes. Metabolite extraction was done by extracting from the boiled extracts 3 times with hexane, then 3 times with ethyl acetate. The spent supernatant broth was extracted in a similar fashion as described above. Organic phases of extracts of each sample were pooled then dried by a rotary evaporator and stored for liquid chromatography mass spectrometry (LC-MS) and gas chromatography mass spectrometry (GC-MS) analysis to confirm and quantitate how much CBDA is produced from strain VscCBDA.

Biosynthetic Production of Cannabidiolic Acid (CBDA) in *K. marxianus*.

Through genetic engineering the inventors have reconstituted the cannabidiolic acid (CBDA) metabolic pathway found in *Cannabis sativa* into *K. marxianus* (a species of yeast). Producing CBGA is an initial step in producing many cannabinoids from *Cannabis sativa* in *K. marxianus*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Synthesis of Fusion Genes Required for CBDA Production in *K. Marxianus*.

Figure 8:
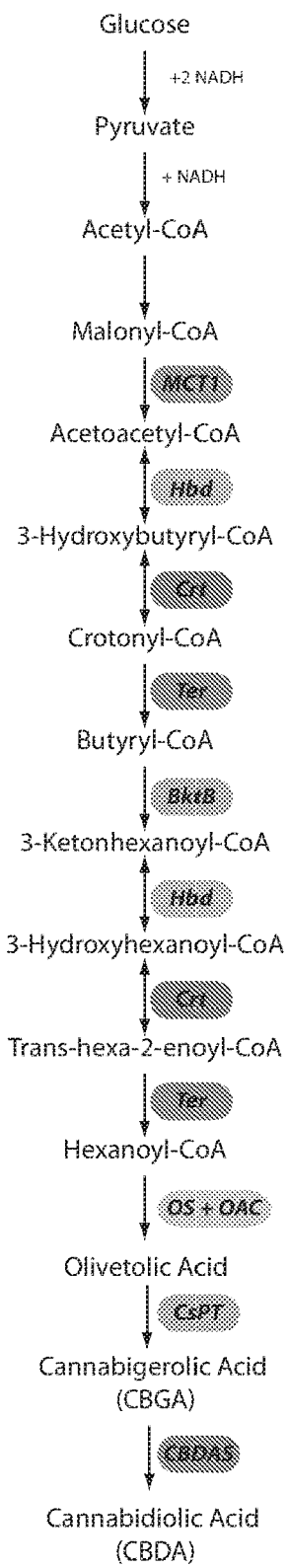
FIG. 8 shows an exemplary biosynthetic route for the production of CBDA from glucose.

FIG. 8 shows an exemplary biosynthetic route for the production of CBDA from glucose. The biosynthetic route for the production of cannabidiolic acid in *Cannabis sativa*, from glucose to CBDA is shown in FIG. 8. The pathway begins with the conversion of glucose to malonyl-CoA through a series of steps that are common to many strains of yeast. The conversion of malonyl-CoA to Acetoacetyl-CoA is conducted by the enzyme MCT1, an acyl-carrier-protein. Acetoacetyl-CoA is converted to 3-Hydroxybutyryl-CoA by the enzyme 3-hydroxybutyryl-CoA dehydrogenase (Hbd) from *Clostridium acetobutylicum*. Next, 3-Hydroxybutyryl-CoA is converted into Crotonyl-CoA by the enzyme crotonase (Crt) from *Clostridium acetobutylicum* and the conversion of Crotonyl-CoA to Butyryl-CoA is controlled by the enzyme trans-enoyl-CoA reductatase (Ter) from *Treponema denticola*. The Butyryl-CoA is converted to 3-Ketonhexanoyl-CoA by the enzyme β-ketothiolase (Bktb) from *Ralstonia Eutropha*. 3-Ketonhexanoyl-CoA is converted to 3-Hydroxyhexanoyl-CoA by the enzyme Hbd. Hydroxyhexanoyl-CoA is converted to Trans-hexa-2-enoyl-CoA by the enzyme Crt. Trans-hexa-2-enoyl-CoA is converted to Hexanoyl-CoA by the enzyme Ter. Hexanoyl-CoA, with 3 malonyl-CoAs, is converted to Oleviolic acid (OA) by a Polyketide synthase and cyclase, OA and OAC respectively. OA is then prenylated with the monoterpene geranyl diphosphate to cannabigerolic acid by an Aromatic prenyltransferase, CsPT. Finally, cannabidiolic acid (CBDA) is produced by cyclizing cannabigerolic acid via CBDA synthase (CBDAS). We have engineered this metabolic pathway into *K. marxianus* (a species of yeast) for the production of CBDA (FIG. 8).

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, the inventors through genetic engineering created many of the required enzymes that can be added so the production of GPP was increased. In order to add the required enzymes for CBDA production in yeast the inventors created plasmids that contain the essential genes in the CBDA biosynthetic pathway. The inventors have transformed these genes into *K. marxianus*.

Creation of a Stable *K. marxianus* Strain Producing the Metabolic Pathways for Hexonyl-coA and CBDA.

Two stable transformations of *K. marxianus* were created utilizing selection for uracil and G418 (Genenticin). The inventors first transformed an auxotrophic *K. marxianus* strain (ATCC 17555 KM5) with 5 different genes needed to produce high levels of hexanoyl-CoA. After functional conformation of the genes required for hexanoyl-CoA the inventors did a second transformation with the genes responsible for CBDA production. The molecular biology methods required for biosynthetic production of CBDA in *K. marxianus* are outlined below.

Gene names Crt, Bktb, MCT1, TeR, Hbd, Erg20p(K179E) were codon optimized, synthesized and subclonned into puc57 and p426 ATCC with the restriction enzymes SpeI and SalI.

Genes Crt, Bktb, MCT1, TeR, Hbd, and Erg20p(K179E) were amplified via PCR using the primers GPD_F and URA_R and all 6 amplicons were electroporated into *K. marxianus* ATCC 17555 KM5 at a concentration of 200 nM and selected onto yeast nitrogen base (YNB) supplemented with amino acid dropout mix (DO supplement—Ura Clonetech 630416) 2% glucose, and 2% Agar plates.

Gene integration and functional gene expression of Crt, Bktb, MCT1, TeR, Hbd, and Erg20p(K179E) was validated by genomic PCR and RT-PCR methods respectively. The final strain produced containing the functional expression of Crt, Bktb, MCT1, TeR, Hbd, and Erg20p(K179E) was labeled kMarxHex1.

Gene names CBDAs, CsPt, OS, and OAC were codon optimized and synthesized by Genscript. The codon optimized gene sequences of CBDAs and CsPt were cloned in frame with a nucleotide sequence containing a self cleaving T2A peptide and designated as CstTCbds. The codon optimized gene sequences of OS and OAC were cloned in frame with a nucleotide sequence containing a self cleaving T2A peptide and designated as OSTOc. CsTCbds and OSTOc were cloned in frame with an *S. cerevisiae* internal ribosomal entry site (TRES), Ure2, into a galactose inducible vector and the final gene sequence pcen/arsGal-OSTOc-IRES-CsTCbds plasmid can be seen below. The plasmid pcen/arsGal-OSTOc-IRES-CstTCbds was used to synthesize a functional gene fragment that expresses the enzymes CBDAs, CsPt, OS, and OAC by using the primers GalIRES_F, GalIRES_R.

The Gibson Assembly method (from the following paragraph above: "Genes Crt, Bktb, MCT1, TeR, Hbd, and Erg20p(K179E) were amplified via PCR using the Primers GPD F and RURA R and all 6 amplicons were electroporated into K. marxianus ATCC 17555 KM5 at a concentration of 200 nM and selected onto yeast nitrogen base (YNB) supplemented with amino acid dropout mix (DO supplement—Ura Clontech 630416) 2% glucose, and 2% Agar plates") was used to subclone the PCR fragment into the plasmid HO-polyKanMx4-HO (ATCC 87804) using the primers KmXIRES_F and KmXIRES_R to create the plasmid pHOOSCstKnMxHO.

The plasmid pHOOSCstKnMxHO was digested with NotI and transformed into kMarxHex1 using standard electroporation methods. The selection of stable integrants was done with yeast nitrogen base (YNB) supplemented with amino acid dropout mix (DO supplement—Ura Clonetech 630416) 2% glucose, 1 mg/ml G418 (Gibco) and 2% Agar plates.

Gene integration and functional gene expression of pHOOSCstKnMxHO validated by genomic PCR and RT-PCR methods respectively. The final strain produced containing the functional expression of Crt, Bktb, MCT1, TeR, Hbd, Erg20p(K179E) CBDAs, CsPt, OS, and OAC was labeled k.MarxCBDA.

Production of CBDA in *K. marxianus*.

To initiate the reconstituted metabolic pathway of CBDA, a colony from k.Marx CBDA was freshly streaked onto an agar plate from a frozen glycerol stock of k.Marx CBDA. A small culture of VscCBDA was grown in YNBA base (YNB) supplemented with amino acid dropout mix (DO supplement—Ura Clonetech 630416) 2% glucose, 1 mg/ml G418 (Gibco) and 2% Agar plates was grown overnight at 30° C. The overnight culture was transferred to 1 L of YNBA supplemented with base (YNB) supplemented with amino acid dropout mix (DO supplement—Ura Clonetech 630416) 2% glucose, and 1 mg/ml G418 (Gibco) and was grown at 30° C. until mid-log phase. Cells were pelleted by centrifugation then washed with 200 ml of phosphate buffered saline (PBS) and repelleted. Pelleted cells were resuspended with 1 L of YNBA supplemented with base (YNB) supplemented with amino acid dropout mix (DO supplement—Ura Clonetech 630416) 2% galactose, and 1 mg/ml G418 (Gibco) and grown at 30° C. overnight.

Processing CBDA for Analysis of Cannabinoid Production.

Overnight 1 L cultures were pelleted by centrifugation, re-suspended, washed one time in PBS and pelleted. The process for extracting cannabinoids from the yeast generally follows the following basic steps:
1. Remove the yeast cells from the media by centrifugation or filtration.
2. Lysis the cells using either chemical or mechanical methods or a combination of methods. Mechanical methods can include a French Press or glass bead milling or other standard methods. Chemical methods can include enzymatic cell lysis, solvent cell lysis, or detergent based cell lysis.
3. Perform a liquid-liquid extraction of the cannabinoids form the cell lysate using the appropriate chemical solvent. An appropriate solvent is any solvent where the cannabinoids are highly soluble in this solvent and the solvent is not miscible in water. Examples of this are hexane, ethyl acetate, and cyclohexane. Preferred solvents can be straight or branched alkane chains (C5-C8) work well; mixtures of these solvents can also be use.

Protocol used for Cannabinoid Extraction from Yeast Cell Lysate
1. After lysising the cells using any mechanical technique, add 1 mL of 4M KCl, pH2.0 to each 1 mL of cell lysate.
2. Add 1-2 mLs of ethyl acetate for each 1 mL of cell lysate.
3. Rigorously mix for 1 min.
4. Centrifuge the mixture for 5 min at 1000×g.
5. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for Cannabinoid Extraction from Growth Media (for Secreted Cannabinoid Samples)
1. Add 1 mL of ethyl acetate for every 1 mL of growth media.
2. Rigorously mix for 1 min.
3. Centrifuge the mixture for 5 min at 1000×g.
4. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for GC-MS Analysis of Cannabinoid Extracts for k.Marx CBDA
1. Remove solvent from samples under vacuum.
2. Re-suspend dry samples in either 100 uL of dry hexane or dry ethyl acetate
3. Add 20 uL of N-Methyl-N-(trimethylsilyl) trifluoroacetamide (MSTFA)
4. Briefly mix
5. Heat solution to 60° C. for 10-15 minutes
6. GC-MS Method
   a. Instrument Agilent 6890-5975 GC-MS (Model Number: Agilent 19091S-433)
   b. Column HP-5MS 5% Phenyl Methyl Siloxane
   c. OVEN:
      i. Initial temp: 100° C. (On) Maximum temp: 300° C.
      ii. Initial time: 3.00 min Equilibration time: 0.50 min
      iii. Ramps:

| # | Rate  | Final temp | Final time |
|---|-------|------------|------------|
| 1 | 30.00 | 280        | 1.00       |
| 2 | 70.00 | 300        | 5.00       |
| 3 | 0.0 (Off) |        |            | iv. Post temp: 0° C.
   v. Post time: 0.00 min
   vi. Run time: 15.29 min

---

What is claimed is:

1. A method for making Cannabigerovarinic Acid in *S. cerevisiae*, the method comprising:
   - converting glucose to malonyl-CoA with a first nucleotide sequence comprising the nucleotide sequence of SEQ. ID. NO.124 expressing Meningitis associated and temperature regulated Fimbria (MatB);
   - converting malonyl-CoA to Acetoacetyl-CoA with a second nucleotide sequence comprising the nucleotide sequence of SEQ. ID. NO.118 expressing Monocarboxylate Transporter 1 (MCT1);
   - converting Acetoacetyl-CoA to 3-Hydroxybutyryl-CoA with a third nucleotide sequence comprising the nucleotide sequence of SEQ. ID. NO. 119 expressing 3-hydroxybutyryl-CoA dehydrogenase (Hbd);
   - converting 3-Hydroxybutyryl-CoA to Crotonyl-CoA with a fourth nucleotide sequence comprising the nucleotide sequence of SEQ. ID. NO. 120 expressing crotonase (Crt);
   - converting Crotonyl-CoA to Butyryl-CoA with a fifth nucleotide sequence comprising the nucleotide sequence of SEQ. ID. NO.123 expressing trans-enoyl-CoA reductase (Ter);
   - converting Butyryl-CoA to divarinic acid with a sixth nucleotide sequence comprising the nucleotide sequence of SEQ. ID. NO. 60 expressing Polyketide synthase and with a seventh nucleotide sequence of SEQ. ID. NO. 92 or SEQ. ID. NO. 93 expressing olivetolic acid cyclase;
   - converting divarinic acid to Cannabigerovarinic Acid with an eighth nucleotide sequence comprising the nucleotide sequence of SEQ. ID. NO. 30 expressing an Aromatic prenyltransferase.

* * * * *

UNITED STATES PATENT AND TRADEMARK OFFICE
CERTIFICATE OF CORRECTION

PATENT NO. : 11,293,038 B2
APPLICATION NO. : 16/679637
DATED : April 5, 2022
INVENTOR(S) : Jason L. Poulos and Anthony N. Farina It is certified that error appears in the above-identified patent and that said Letters Patent is hereby corrected as shown below:

In the Specification

In Column 1, Line 10, the portion reading: ""Production of Cannabigerolic Acid in Yeast," which is a continuation-in-part of U.S. Non-Provisional Patent Application" should read: ""Production of Cannabigerolic Acid in Yeast," now U.S. Patent No. 10,954,534, issued on March 23, 2021, which is a continuation-in-part of U.S. Non-Provisional Patent Application"

In Column 1, Line 13, the portion reading: ""Production of Tetrahydrocannabinolic Acid in Yeast," which is a continuation of U.S. Non-Provisional Patent Application" should read: ""Production of Tetrahydrocannabinolic Acid in Yeast," now U.S. Patent No. 10,392,635, issued on August 27, 2019, which is a continuation of U.S. Non-Provisional Patent Application"

In Column 10, Line 36, the term "Primers" should read: "primers"

In Column 10, Line 37, the term "RURA" should read: "URA"

In the Claims

In Claim 1 at Column 408, Line 56, the portion reading "olivetolic acid cyclase;" should read: "olivetolic acid cyclase; and"

Signed and Sealed this
Thirty-first Day of May, 2022

Katherine Kelly Vidal
*Director of the United States Patent and Trademark Office*